US012552798B2

(12) United States Patent
Jiang et al.

(10) Patent No.: US 12,552,798 B2
(45) Date of Patent: Feb. 17, 2026

(54) SUBSTITUTED IMIDAZOLECARBOXAMIDE AS BRUTON'S TYROSINE KINASE INHIBITORS

(71) Applicant: Henan Zhiwei Biomedicine Co., Ltd., Xinxiang (CN)

(72) Inventors: Yuqin Jiang, Xinxiang (CN); Qingjie Ding, Xinxiang (CN); Chunhua Ma, Xinxiang (CN); Guiqing Xu, Xinxiang (CN); Dandan Zhang, Xinxiang (CN); Yang Li, Xinxiang (CN); Pengfei Li, Xinxiang (CN); Wei Li, Xinxiang (CN); Shouning Yang, Xinxiang (CN); Xin Shi, Xinxiang (CN); Peipei Shi, Xinxiang (CN)

(73) Assignee: Henan Zhiwei Biomedicine Co., Ltd., Xinxiang (CN)

( * ) Notice: Subject to any disclaimer, the term of this patent is extended or adjusted under 35 U.S.C. 154(b) by 856 days.

(21) Appl. No.: 17/781,806

(22) PCT Filed: Dec. 4, 2020

(86) PCT No.: PCT/CN2020/133938

§ 371 (c)(1),
(2) Date: Jun. 2, 2022

(87) PCT Pub. No.: WO2021/110142

PCT Pub. Date: Jun. 10, 2021

(65) Prior Publication Data

US 2022/0411430 A1 Dec. 29, 2022

(30) Foreign Application Priority Data

Dec. 4, 2019 (CN) ........................ 201911229830.0
Jun. 5, 2020 (CN) ........................ 202010504361.5

(51) Int. Cl.

| | |
|---|---|
| ***A61K 31/4184*** | (2006.01) |
| ***A61K 31/4188*** | (2006.01) |
| ***C07D 235/00*** | (2006.01) |
| ***C07D 487/04*** | (2006.01) |

(52) U.S. Cl.

CPC .................................. *C07D 487/04* (2013.01)

(58) Field of Classification Search

CPC ............ A61K 31/4184; A61K 31/4188; C07D 235/00
USPC ....................................... 514/393; 548/302.7
See application file for complete search history.

(56) References Cited

U.S. PATENT DOCUMENTS

2012/0040949 A1 2/2012 Berthel et al.
2015/0005277 A1 1/2015 Wang et al.

FOREIGN PATENT DOCUMENTS

| | | | | |
|---|---|---|---|---|
| CN | 104884458 A | 9/2015 | | |
| CN | 106317057 A | 1/2017 | | |
| CN | 106588914 A | 4/2017 | | |
| CN | 106661035 A | 5/2017 | | |
| CN | 106831787 A | 6/2017 | | |
| CN | 107056789 A | 8/2017 | | |
| JP | 2016-521273 A | 7/2016 | | |
| WO | 2007/026720 A1 | 3/2007 | | |
| WO | 2015/189620 A1 | 12/2015 | | |
| WO | 2016/081364 A1 | 5/2016 | | |
| WO | 2016/161248 A1 | 10/2016 | | |
| WO | 2018/033853 A2 | 2/2018 | | |
| WO | 2018/137681 A1 | 8/2018 | | |
| WO | 2019/034009 A1 | 2/2019 | | |
| WO | WO-2021110142 A1 * | 6/2021 | ......... | A61K 31/5025 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Wolff, Manfred E., Ed. Burger's Medicinal Chemistry and Drug Discovery—Fifth Edition, vol. 1: Principles and Practice, New York: John Wiley & Sons, 1994, 975-977.*
Office Action issued in corresponding Chinese Patent Application No. 202080084402.8 dated Sep. 23, 2023.
Medicinal Chemistry 2nd Edition, Ed. Mayon, Hionan Scientific Press, pp. 6-7, Aug. 31, 2012.
Extended European Search Report issued in corresponding European Patent Application No. 20896650.7 dated Nov. 21, 2023.
Office Action issued in corresponding Japanese Patent Application No. 2022-534249 dated Jul. 4, 2023.
International Search Report issued in corresponding International Patent Application No. PCT/CN2020/133938 dated Mar. 5, 2021.
Written Opinion issued in corresponding International Patent Application No. PCT/CN2020/133938 dated Mar. 5, 2021.

* cited by examiner

*Primary Examiner* — Douglas M Willis
(74) *Attorney, Agent, or Firm* — Morgan, Lewis & Bockius LLP

(57) ABSTRACT

The disclosure relates to a series of substituted imidazolecarboxamide compounds of formula I as BTK (Bruton's Tyrosine Kinase) inhibitors, and the methods of using the same for the treatment of autoimmune disease, inflammatory disease, cancer and potentially allergies.

(I)

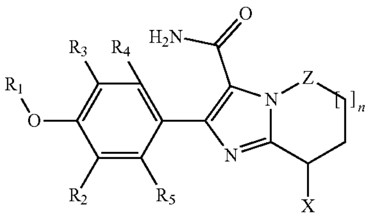

23 Claims, No Drawings

SUBSTITUTED IMIDAZOLECARBOXAMIDE AS BRUTON'S TYROSINE KINASE INHIBITORS

TECHNICAL FIELD

The application relates to a series of substituted imidazolecarboxamide compounds of formula I as BTK (Bruton's Tyrosine Kinase) inhibitors, and the methods of making and using the same for the treatment of autoimmune disease, inflammatory disease, cancer and potentially allergies.

I

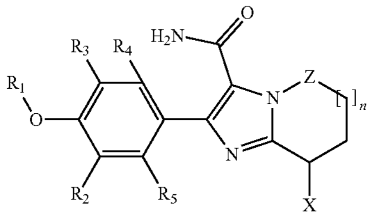

BACKGROUND ART

BTK (Bruton's Tyrosine Kinase) is a non-receptor tyrosine kinase of the Tec family (Bradshaw et al, *Cell Signal,* 2010, 22, 1175-1184.). It plays an important role in the maturation of B cells and the activation of mast cells. It is primarily expressed in hematopoietic cells such as B cell, mast cell and microphages and exists in tissues including bone marrow, lymph nodes and spleens. They participate in signal transduction in response to virtually all types of extracellular stimuli which are transmitted by growth factor receptors, cytokine receptors, G-protein coupled receptors, antigen-receptors and integrins (Qiu et al, *Oncogene,* 2000, 19, 5651-5661.) Structurally it features a pleckstrin homology domain, a Src homology 3 domain, a Srchomology 2 domain, and a Src homology 1 domain (kinase domain). The pleckstrin homology domain binds phosphatidylinositol (3,4,5)-triphosphate (PIP3) and induces BTK to phosphorylate phospholipase C gamma which then hydrolyzes phosphatidylinositol 4,5 biphosphate (PIP2) into two secondary messengers, inositol triphosphate (IP3) and diacylglycerol (DAG) which in turn modulate downstream B cell signaling. Dysfunctional BTK activation has been the culprit of autoimmune disease such as rheumatoid arthritis, osteoporosis, lupus and implicated in many cancers. Mutations of BTK gene are directly implicated in the immunodeficiency disease X-linked agammaglobulinemia (XLA). Patients with this disease have premature B cells in their bone marrow but they never mature and enter into circulation.

BTK inhibitors such as Ibrutinib (Structure A. Pan et al, *Chem Med Chem.,* 2007, 2, 58-61; Lee A. Honigberg et al, *PNAS,* 2010, 107, 13075-13080.), Acalabrutinib (Structure B, Barf et al, *J Pharmacol Exp Ther.,* 2017, 363, 240-252; Robert B. Kargbo, *ACS Med Chem Lett.,* 2017, 8, 911-913.) have demonstrated their effectiveness in the treatment of various cancers.

A

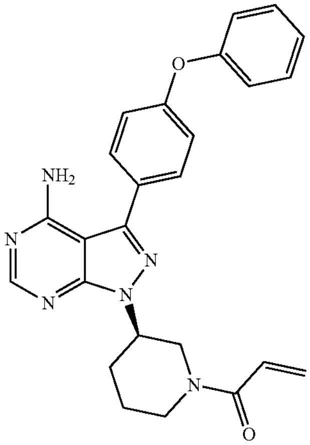

B

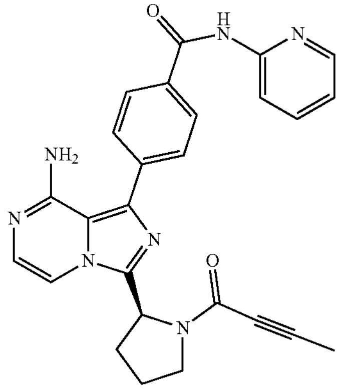

Several other candidates (Bradshaw et al. *Nat Chem Biol.,* 2015, 11, 525-531; U.S. Pat. No. 9,447,106 B2; CN103848810 A1) in different stages of clinical trials are being tested for various diseases including cancer and autoimmune diseases. All these point to the potential application of BTK inhibition in the treatment of various diseases in the area of cancer, allergy and auto-immune diseases.

SUMMARY

The present application discloses compounds as protein kinase BTK inhibitors which may be used for the treatment of autoimmune disease, inflammatory disease, cancer and potentially allergies.

In one aspect, the present application provides a compound represented by Formula I, or a pharmaceutically acceptable salt, active metabolite, tautomer, stereoisomer, or prodrug thereof.

I

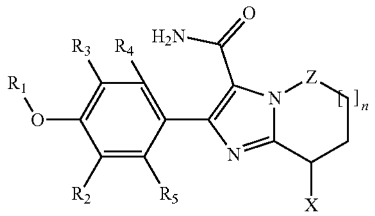

wherein $R_1$ is selected from aryl, $C_{1-6}$ alkyl, $C_{1-6}$ alkyl substituted with halogen, $C_{1-6}$ alkoxy, $C_{3-6}$ cycloalkyl; aryl independently substituted with halogen, cyano, $C_{1-6}$ alkoxy, ($C_{1-4}$) fluoroalkyl; n is an integer that is selected from 0, 1, 2, 3;

$R_2$, $R_3$, $R_4$, $R_5$ are independently selected from the groups consisting of hydrogen, halogen, $C_{1-4}$ fluoroalkyls, cyano, $C_{1-6}$ alkyl, $C_{3-6}$ cycloalkyls and $C_{1-6}$ alkoxy;

X is selected from a 4-8 membered nitrogen-containing heterocyclyl where the said nitrogen atom is substituted with Y; an aryl that is substituted with —$NR_6$Y, or an aryl that may be independently substituted with halogen, cyano, $C_{1-6}$ alkoxy, ($C_{1-4}$) fluoroalkyl along with —$NR_6$Y; an heteroaryl that is substituted with —$NR_6$Y, or a heteroaryl that may be independently substituted with halogen, cyano, $C_{1-6}$ alkoxy, ($C_{1-4}$) fluoroalkyls along with —$NR_6$Y; a group of —$(CH_2)_m NR_6$Y and m is an integer selected from any of from 1 to 3; a nitrogen-containing spiral heterocyclyl where the said nitrogen is substituted with Y;

$R_6$ is selected from the group consisting of hydrogen, $C_{1-6}$ alkyl and $C_{1-6}$ alkyl substituted with halogen and $C_{1-6}$ alkoxys;

Y is selected from the group consisting of —CN, —C(═O)P, —S(═O)P and —S(═O)$_2$P;

P is selected from

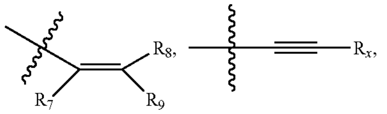

and

Rx is selected from the group consisting of H, cyano, halogen, $C_{1-6}$ alkyl, $C_{1-6}$ alkoxy, $C_{3-6}$ cycloalkyl, phenyl, —$(CH_2)_m NR_{10}R_{11}$, $C_{1-6}$ alkyl substituted with halogen, hydroxy;

$R_7$ is selected from hydrogen, halogen, cyano, $C_{1-6}$ alkyl, $C_{1-6}$ alkyl substituted with groups selected from F, hydroxyl and $C_{1-6}$ alkoxy; $C_{3-6}$ cycloalkyl, $C_{3-6}$ cycloalkyl substituted with F;

$R_8$ and $R_9$ are independently selected from hydrogen; halogen; cyano; $CF_3$; aryl; aryl substituted with halogen, cyano, $C_{1-6}$ alkyl, $C_{1-6}$ alkoxy; heteroaryl; heteroaryl substituted with halogen, cyano, $C_{1-6}$ alkyl, $C_{1-6}$ alkoxy; $C_{1-6}$ alkyl; $C_{1-6}$ alkyl substituted with $C_{1-6}$ alkoxy, —$NR_{10}R_{11}$, halogen, hydroxyl, $C_6$ or $C_{10}$ aryl, and heteroaryl; $C_{3-6}$ cycloalkyl; $C_{3-6}$ cycloalkyl substituted with halogen; $C_{2-6}$ alkenyl; $C_{2-6}$ alkenyl substituted with $C_{1-6}$ alkoxy, —$NR_{10}R_{11}$, halogen, hydroxyl, aryl and heteroaryl;

$R_{10}$ and $R_{11}$ are each independently selected from hydrogen, $C_{1-6}$ alkyl, $C_{3-6}$ cycloalkyl; or together with the nitrogen they substitute form a 4-6 membered heterocycloalkyl;

m is an integer selected from 1, 2 or 3; and

Z is selected from NH or $CH_2$.

In some embodiments, the above mentioned aryl may be $C_6$ or $C_{10}$ aryl; the above mentioned heteroaryl may be heteroaryl having one cycle with 5 to 10, 5 to 8, or 5 to 6 ring atoms at least one of which is a heteroatom selected from O, N, and S (excluding the circumstance of two O atoms and/or S atoms are adjacent); the above said spiral heterocyclyl may have two cycles at least one of which is 4-8 membered heterocyclyl containing N atom.

In one embodiment of formula I, X is selected from the group consisting of

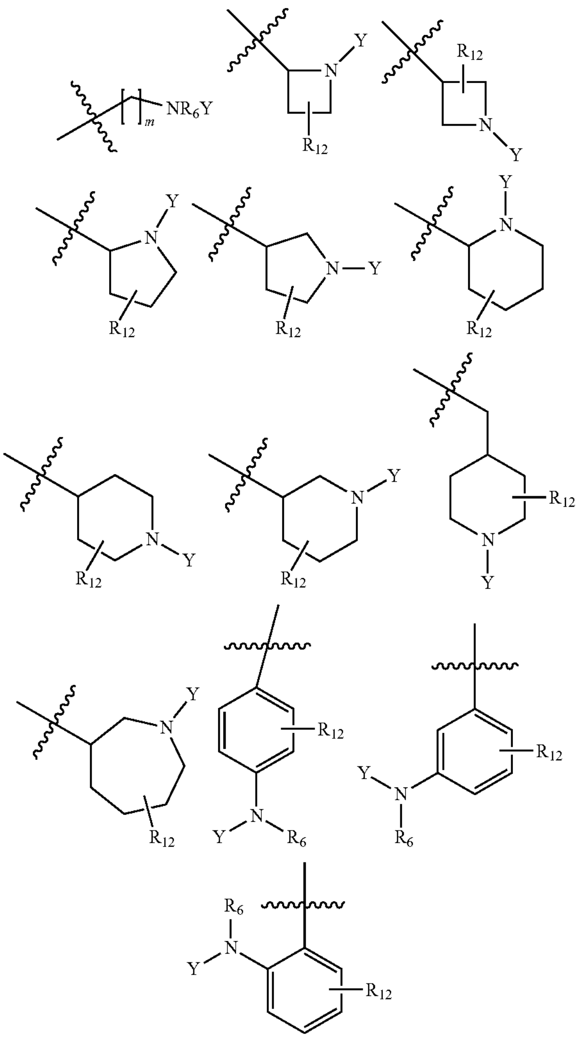

wherein $R_{12}$ is selected from H, F, $C_{1-6}$ alkyl, $C_{1-6}$ alkyl substituted with halogen, $C_{1-6}$-alkoxy; and $R_{12}$ may substitute more than one position; or in the above heterocyclyls, $R_{12}$ may form a double bond in the ring it attaches to, or form a 3-6 membered ring fused or spiraled with the ring it attaches to.

In another embodiment of formula I, $R_6$ is hydrogen; $R_{12}$ is hydrogen; $R_2$, $R_3$, $R_4$, and $R_5$ are H; and n is selected from 0, 1.

In another embodiment of formula I, X is selected from

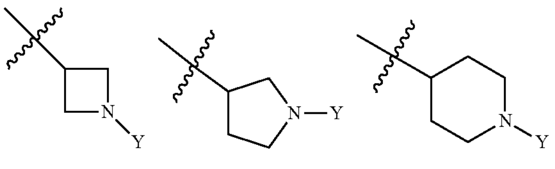

-continued

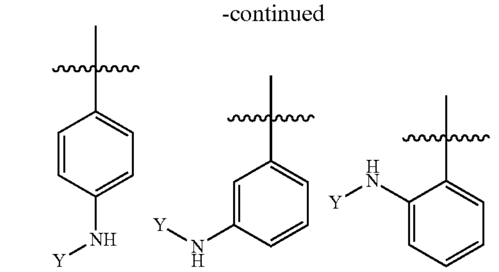

wherein Y is —C(=O)P or CN;

P is selected from

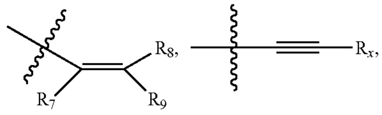

and

Rx is selected from the group consisting of H, $C_{1-6}$ alkyl, $C_{1-6}$ alkyl substituted with halogen, and $C_{1-6}$ cycloalkyl;

$R_7$ is selected from hydrogen, halogen, cyano, $C_{1-6}$ alkyl, $C_{1-6}$ alkyl substituted with halogen; and $R_8$ and $R_9$ are independently selected from the group consisting of hydrogen, halogen, $C_{1-6}$ alkyl, $C_{1-6}$ alkyl substituted with halogen or —$NR_{10}R_{11}$; and $C_{1-6}$ cycloalkyl;

$R_{10}$ and $R_{11}$ are independently selected from $C_{1-6}$ alkyl.

In another embodiment of formula I, X is selected from

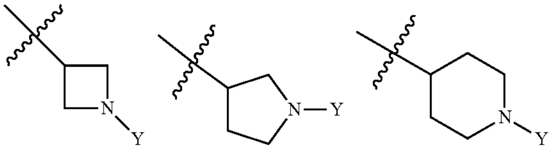

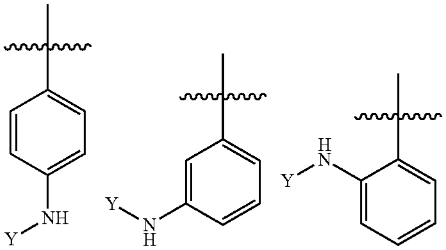

Wherein Y is —C(=O)P or CN;

P is selected from

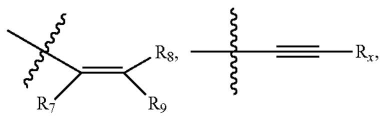

and

Rx is selected H, $CH_3$, $CF_3$ or cyclopropyl;

$R_7$ is selected from hydrogen, methyl, halogen or cyano;

$R_8$ and $R_9$ are independently selected from hydrogen, $CF_3$, $CH_3$, $C_2H_5$, isobutyl, cyclopropyl or —$(CH_2)_mN(CH_3)_2$ and m is an integer selected from any of from 1 to 3.

In another embodiment of formula I, X is selected from

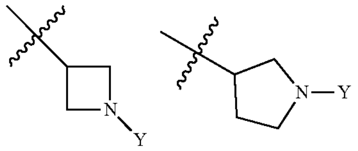

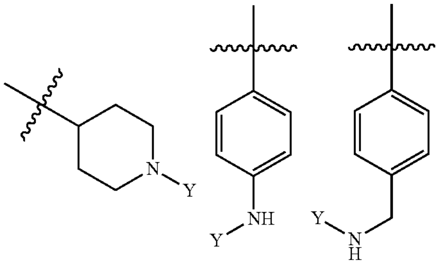

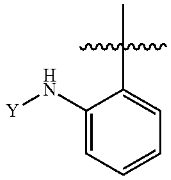

Y is —C(=O)P;

P is selected from

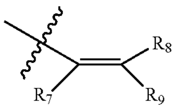

or

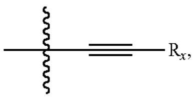

and

Rx is selected from H or $CH_3$;

$R_7$ is selected from hydrogen, F, or cyano;

$R_8$ and $R_9$ are independently selected from hydrogen or $CF_3$.

In another embodiment of formula I, $R_1$ is selected from the group consisting of $C_{1-6}$ alkyl, $C_{1-6}$ alkoxy, $C_{3-6}$ cycloalkyl, and

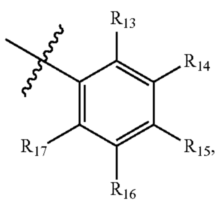

wherein $R_{13}$, $R_{14}$, $R_{15}$, $R_{16}$, $R_{17}$ are independently selected from the group consisting of H; cyano; $C_{1-6}$ alkyl; $C_{1-6}$ alkyl substituted with halogen, particularly $C_{1-6}$ alkyl substituted with F; $C_{1-6}$ alkoxy; halogen; $C_6$ or $C_{10}$ aryl; $C_6$ or $C_{10}$ aryl independently substituted with halogen, $C_{1-6}$ alkyl, $C_{1-6}$ alkoxy, cyano, or trifluoromethyl; heteroaryl, particularly a five-membered or six-membered heteroaryl, or a bicycle heteroaryl where the five-membered or six-membered ring fused with each other.

In another embodiment of formula I, $R_1$ is

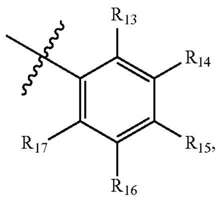

wherein, $R_{13}$, $R_{14}$, $R_{15}$, $R_{16}$ and $R_{17}$ are independently selected from H, halogen, cyano, $C_{1-6}$ alkoxy, $C_{1-6}$ alkyl substituted by halogen.

In another embodiment of formula I, $R_1$ is

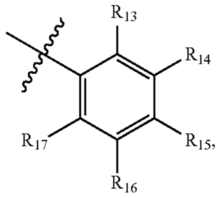

wherein, $R_{15}$ is selected from H, halogen, $C_{1-6}$ alkoxy, cyano, $C_{1-6}$ alkyl substituted by halogen, and $R_{13}$, $R_{14}$, $R_{16}$ and $R_{17}$ are H.

In another embodiment of formula I, $R_{15}$ is selected from the group consisting of H, $CH_3$, $CH_2CH_3$, $OCH_3$, F, Cl, Br, CN and $CF_3$; and $R_{13}$, $R_{14}$, $R_{16}$ and $R_{17}$ are H. For example, in formula I, $R_{13}$, $R_{14}$, $R_{15}$, $R_{16}$ and $R_{17}$ are H.

In another embodiment of formula I, $R_{15}$ is selected from the group consisting of H, $CH_3$, $CH_2CH_3$, $OCH_3$, F, Cl, Br, CN and $CF_3$; $R_2$ or $R_3$ is $C_{1-6}$ alkoxy; and $R_{13}$, $R_{14}$, $R_{16}$ and $R_{17}$ are H.

In another embodiment of formula I, X is selected from

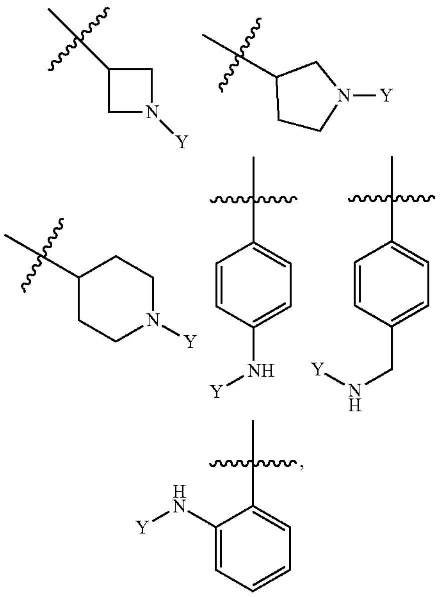

wherein Y is —C(=O)P, where

P is selected from

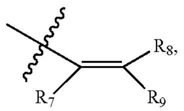

or

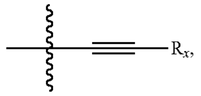

and

Rx is selected from the group consisting of H, $CH_3$, $CF_3$ and cyclopropyl, $—(CH_2)_mNR_{10}R_{11}$ wherein m is an integer selected from 1, 2, 3;

n is 0;

Z is $CH_2$;

$R_1$ is:

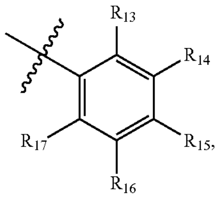

wherein $R_{13}$, $R_{14}$, $R_{15}$, $R_{16}$ and $R_{17}$ are independently selected from H, $OCH_3$, F, Cl, Br, $CF_3$ and CN;

$R_2$ is H or methoxy, $R_3$, $R_4$, $R_5$ are H;

$R_7$ is selected from hydrogen, cyano, and halogen;

$R_8$ and $R_9$ are independently selected from hydrogen, $CF_3$, $CH_3$, cyclopropyl and $C_{1-6}$ alkyl substituted with $—NR_{10}R_{11}$; and $R_{10}$, $R_{11}$ are independently selected from $C_{1-6}$ alkyl.

In another embodiment of formula I, X is selected from

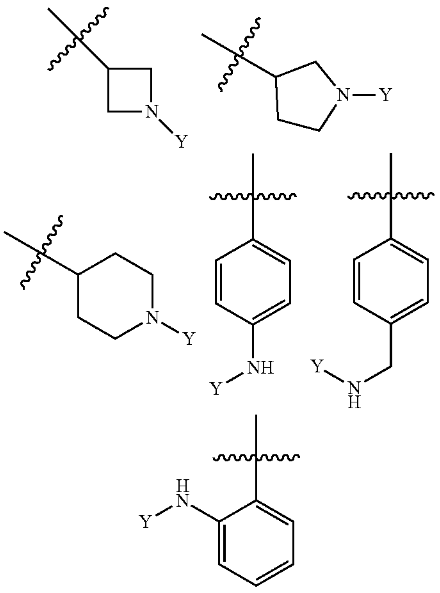

Wherein Y is —C(═O)P where

P is selected from

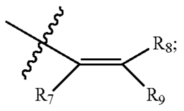

n is 0;

Z is $CH_2$;

$R_1$ is phenyl;

$R_2$ is H or methoxy, $R_3$, $R_4$, $R_5$ are H;

$R_7$ is selected from hydrogen, cyano, and halogen;

$R_8$ and $R_9$ are independently selected from hydrogen, $CF_3$, $CH_3$, cyclopropyl.

In another embodiment of formula I, X is selected from

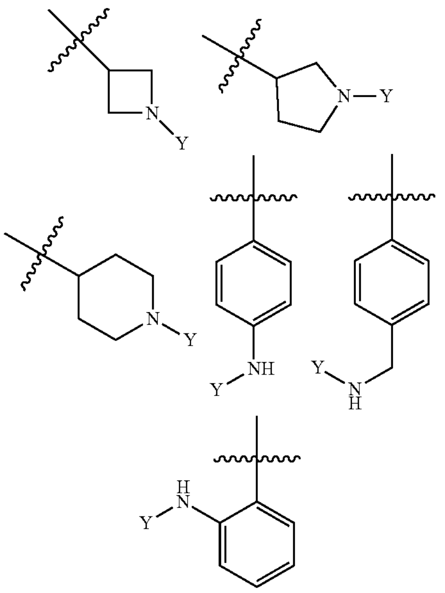

Wherein Y is —C(═O)P where

P is selected from

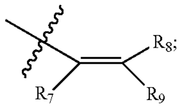

n is 1

Z is NH;

$R_1$ is phenyl;

$R_2$ is H or methoxy, $R_3$, $R_4$, $R_5$ are H;

$R_7$ is selected from hydrogen, cyano, and halogen;

$R_8$ and $R_9$ are independently selected from hydrogen, $CF_3$, $CH_3$, cyclopropyl.

In some embodiments, some specific compounds within formula I are selected from the followings:

8-(1-acryloylpiperidin-4-yl)-2-(4-phenoxyphenyl)-5,6,7,8-tetrahydroimidazo[1,2-b]pyridazine-3-carboxamide 8-(1-(but-2-ynoyl)piperidin-4-yl)-2-(4-phenoxyphenyl)-5,6,7,8-tetrahydroimidazo[1,2-b]pyridazine-3-carboxamide 8-(1-(3-methylbut-2-enoyl)piperidin-4-yl)-2-(4-phenoxyphenyl)-5,6,7,8-tetrahydroimidazo[1,2-b]pyridazine-3-carboxamide 8-(1-methacryloylpiperidin-4-yl)-2-(4-phenoxyphenyl)-5,6,7,8-tetrahydroimidazo[1,2-b]pyridazine-3-carboxamide (E)-8-(1-(but-2-enoyl)piperidin-4-yl)-2-(4-phenoxyphenyl)-5,6,7,8-tetrahydroimidazo[1,2-b]pyridazine-3-carboxamide (E)-8-(1-(pent-2-enoyl)piperidin-4-yl)-2-(4-phenoxyphenyl)-5,6,7,8-tetrahydroimidazo[1,2-b]pyridazine-3-carboxamide (E)-8-(1-(2-cyano-4-methylpent-2-enoyl)piperidin-4-yl)-2-(4-phenoxyphenyl)-5,6,7,8-tetrahydroimidazo[1,2-b]pyridazine-3-carboxamide 2-(4-phenoxyphenyl)-8-(1-propioloylpiperidin-4-yl)-5,6,7,8-tetrahydroimidazo[1,2-b]pyridazine-3-carboxamide (E)-8-(1-(2-cyano-3-cyclopropylacryloyl)piperidin-4-yl)-2-(4-phenoxyphenyl)-5,6,7,8-tetrahydroimidazo[1,2-b]pyridazine-3-carboxamide 8-(1-acryloylpiperidin-4-yl)-2-(4-(4-fluorophenoxy)phenyl)-5,6,7,8-tetrahydroimidazo[1,2-b]pyridazine-3-carboxamide 8-(1-(but-2-ynoyl)piperidin-4-yl)-2-(4-(4-fluorophenoxy)phenyl)-5,6,7,8-tetrahydroimidazo[1,2-b]pyridazine-3-carboxamide (E)-2-(4-(4-fluorophenoxy)phenyl)-8-(1-(4,4,4-trifluorobut-2-enoyl)piperidin-4-yl)-5,6,7,8-tetrahydroimidazo[1,2-b]pyridazine-3-carboxamide 8-(1-acryloylpiperidin-4-yl)-2-(4-(4-methoxyphenoxy)phenyl)-5,6,7,8-tetrahydroimidazo[1,2-b]pyridazine-3-carboxamide 8-(1-(but-2-ynoyl)piperidin-4-yl)-2-(4-(4-methoxyphenoxy)phenyl)-5,6,7,8-tetrahydroimidazo[1,2-b]pyridazine-3-carboxamide (E)-2-(4-(4-methoxyphenoxy)phenyl)-8-(1-(4,4,4-trifluorobut-2-enoyl)piperidin-4-yl)-5,6,7,8-tetrahydroimidazo[1,2-b]pyridazine-3-carboxamide 8-(1-(2-fluoroacryloyl)piperidin-4-yl)-2-(4-phenoxyphenyl)-5,6,7,8-tetrahydroimidazo[1,2-b]pyridazine-3-carboxamide (E)-2-(4-phenoxyphenyl)-8-(1-(4,4,4-trifluorobut-2-enoyl)piperidin-4-yl)-5,6,7,8-tetrahydroimidazo[1,2-b]pyridazine-3-carboxamide 2-(4-phenoxyphenyl)-8-(1-propioloylpiperidin-4-yl)-5,6,7,8-tetrahydroimidazo[1,2-b]pyridazine-3-carboxamide 8-(2-acrylamidophenyl)-2-(4-phenoxyphenyl)-5,6,7,8-tetrahydroimidazo[1,2-b]pyridazine-3-carboxamide 8-(1-acryloylazetidin-3-yl)-2-(4-phenoxyphenyl)-5,6,7,8-tetrahydroimidazo[1,2-b]pyridazine-3-carboxamide 8-(1-(but-2-ynoyl)azetidin-3-yl)-2-(4-phenoxyphenyl)-5,6,7,8-tetrahydroimidazo[1,2-b]pyridazine-3-carboxamide (E)-2-(4-phenoxyphenyl)-8-(1-(4,4,4-trifluorobut-2-enoyl)azetidin-3-yl)-5,6,7,8-tetrahydroimidazo[1,2-b]pyridazine-3-carboxamide 8-(4-acrylamidophenyl)-2-(4-phenoxyphenyl)-5,6,7,8-tetrahydroimidazo[1,2-b]pyridazine-3-carboxamide 8-(1-cyanopiperidin-4-yl)-2-(4-phenoxyphenyl)-5,6,7,8-tetrahydroimidazo[1,2-b]pyridazine-3-carboxamide (E)-8-(1-(4-(dimethylamino)but-2-enoyl)piperidin-4-yl)-2-(4-phenoxyphenyl)-5,6,7,8-tetrahydroimidazo[1,2-b]pyridazine-3-carboxamide 7-(1-acryloylpiperidin-4-yl)-2-(4-phenoxyphenyl)-6,7-dihydro-5H-pyrrolo[1,2-a]imidazole-3-carboxamide 8-(1-acryloylpiperidin-4-yl)-2-(4-methoxyphenyl)-5,6,7,8-tetrahydroimidazo[1,2-b]pyridazine-3-carboxamide 7-(1-acryloylpiperidin-4-yl)-2-(3-methoxy-4-phenoxyphenyl)-6,7-dihydro-5H-pyrrolo[1,2-a]imidazole-3-carboxamide 8-(1-acryloylpiperidin-4-yl)-2-(3-methoxy-4-phenoxyphenyl)-5,6,7,8-tetrahydroimidazo[1,2-b]pyridazine-3-carboxamide.

In a further aspect, the application provides a pharmaceutical composition which includes an effective amount of a compound of the application, or a pharmaceutically acceptable salt, active metabolite, tautomer, stereoisomer, or prodrug thereof, and a pharmaceutically acceptable carrier.

In some embodiments, the pharmaceutical composition is in a form suitable for administration including but not limited to oral administration, parenteral administration, topical administration and rectal administration. In further or additional embodiments, the pharmaceutical composition is in the form of a tablet, capsule, pill, powder, sustained release formulation, solution and suspension, for parenteral injection as a sterile solution, suspension or emulsion, for topical administration as an ointment or cream or for rectal administration as a suppository. In further or additional embodiments, the pharmaceutical composition is in unit dosage forms suitable for single administration of precise dosages. In further or additional embodiments, the amount of compound of formula I is in the range of about 0.001 to about 1000 mg/kg body weight/day. In further or additional embodiments, the amount of compound of formula I is about 0.001 to about 7 g/day. In further or additional embodiments, dosage levels below the lower limit of the aforesaid range may be more than adequate. In further or additional embodiments, dosage levels above the upper limit of the aforesaid range may be required. In further or additional embodiments, the compound of formula I is administered in a single dose, once daily. In further or additional embodiments, the compound of formula I is administered in multiple doses, more than once per day. In further or additional embodiments, the pharmaceutical composition further comprises at least one therapeutic agent.

In another aspect, the application provides a method for preventing or treating a subject suffering from or at risk of BTK mediated disease or condition, comprising administering to said subject an effective amount of a compound of this application or a pharmaceutically acceptable salt, active metabolite, tautomer, stereoisomer, or prodrug thereof, or a pharmaceutical composition of this application.

In another aspect, the application provides a method for preventing or treating a subject suffering from or at risk of a disease or disorder selected from the group consisting of an autoimmune disease, inflammatory disease, cancer, allergy, diffused large B cell lymphoma, follicular lymphoma, chronic lymphocytic leukemia, mantel cell lymphoma, splenic marginal zone lymphoma, large B cell lymphoma, lupus erythematosus, rheumatoid arthritis, Crohn's disease, psoriasis, multiple sclerosis, asthma etc., comprising administering to said subject an effective amount of a compound of this application or a pharmaceutically acceptable salt, active metabolite, tautomer, stereoisomer, or prodrug thereof, or a pharmaceutical composition of this application.

In a further aspect, the application provides a use of a compound of the application, or a pharmaceutically acceptable salt, active metabolite, tautomer, stereoisomer, or prodrug thereof, in the preparation of a medicament for inhibiting the activity of BTK.

In another aspect, the application provides a use of a compound of the application, or a pharmaceutically acceptable salt, active metabolite, tautomer, stereoisomer, or prodrug thereof, in the preparation of a medicament for treating a disease or disorder that may benefit from the inhibition of BTK.

In another aspect, the application provides a use of a compound of the application, or a pharmaceutically acceptable salt, active metabolite, tautomer, stereoisomer, or prodrug thereof, in the preparation of a medicament for treating a disease or disorder selected from the group consisting of an autoimmune disease, inflammatory disease, cancer, allergy, diffused large B cell lymphoma, follicular lymphoma, chronic lymphocytic leukemia, mantel cell lymphoma, splenic marginal zone lymphoma, large B cell lymphoma, lupus erythematosus, rheumatoid arthritis, Crohn's disease, psoriasis, multiple sclerosis, asthma etc.

In another aspect, the application provides a compound of the application, or a pharmaceutically acceptable salt, active metabolite, tautomer, stereoisomer, or prodrug thereof, for inhibiting BTK.

In another aspect, the application provides a compound of the application, or a pharmaceutically acceptable salt, active metabolite, tautomer, stereoisomer, or prodrug thereof, for the treatment of a disease or disorder that may benefit from the inhibition of BTK.

In another aspect, the application provides a compound of the application, or a pharmaceutically acceptable salt, active metabolite, tautomer, stereoisomer, or prodrug thereof, for treating a disease or disorder selected from the group consisting of an autoimmune disease, inflammatory disease, cancer, allergy, diffused large B cell lymphoma, follicular lymphoma, chronic lymphocytic leukemia, mantel cell lymphoma, splenic marginal zone lymphoma, large B cell lymphoma, lupus erythematosus, rheumatoid arthritis, Crohn's disease, psoriasis, multiple sclerosis, asthma etc.

In some embodiments, the subject is a mammal, such as human.

In some embodiments, the foregoing disease or condition, for example BTK mediated disease or condition, includes but not limit to cancer, autoimmune disease, inflammatory disease and allergy. Such diseases include but not limit to diffused large B cell lymphoma, follicular lymphoma, chronic lymphocytic leukemia, mantel cell lymphoma, splenic marginal zone lymphoma, large B cell lymphoma, lupus erythematosus, rheumatoid arthritis, Crohn's disease, psoriasis, multiple sclerosis, asthma etc.

DETAILED DESCRIPTION

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Certain Chemical Terminology

The present application also intended to include isotopically labeled compounds. The commonly seen isotopic atoms include but not limited to $^{2}H$, $^{3}H$, $^{13}C$, $^{14}C$, $^{17}O$, $^{18}O$, $^{15}N$ etc. These atoms are the same as their naturally richest atom but have a different mass number. Applications of isotopically labeling in drug discovery are reported (Elmore, Charles S., *Annu Rep Med Chem.,* 2009, 44, 515-534.).

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated by reference in their entirety. In the event that there is a plurality of definitions for terms herein, those in this section prevail.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms “a”, “an” and “the” include plural referents unless the context clearly dictates otherwise. It should also be noted that use of “or” means “and/or” unless stated otherwise. Furthermore, use of the term “including” as well as other forms, such as “include”, “includes”, and “included” is not limiting. Likewise, use of the term “comprising” as well as other forms, such as “comprise”, “comprises”, and “comprised” is not limiting.

Definition of standard chemistry terms may be found in reference works, including Carey and Sundberg “ADVANCED ORGANIC CHEMISTRY $4^{TH}$ ED”. Vols. A (2000) and B (2001), Plenum Press, New York. Unless otherwise indicated, conventional methods of mass spectroscopy, NMR, HPLC, IR and UV/Vis spectroscopy and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Reactions and purification techniques can be performed e.g., using kits of manufacturer’s specifications or as commonly accomplished in the art or as described herein. The foregoing techniques and procedures can be generally performed of conventional methods well known in the art and as described in various general and more specific references that are cited and discussed throughout the present specification.

Where substituent groups are specified by their conventional chemical formulas, written from left to right, they equally encompass the chemically identical substituents that would result from writing the structure from right to left. As a non-limiting example, $CH_2O$ is equivalent to $OCH_2$.

Unless otherwise noted, the use of general chemical terms, such as though not limited to “alkyl”, “aryl” are equivalent to their optionally substituted forms. For example, “alkyl” as used herein, includes optionally substituted alkyl.

The compounds presented herein may possess one or more stereocenters and each center may exist in the R or S configuration, or combinations thereof. Likewise, the compounds presented herein may possess one or more double bonds and each may exist in the E (trans) or Z (cis) configuration, or combinations thereof. Presentation of one particular stereoisomer should be understood to include all possible stereoisomers, including regioisomers, diastereomers, enantiomers or epimers and mixtures thereof. Thus, the compounds presented herein include all separate configurational stereoisomeric, regioisomeric, diastereomeric, enantiomeric, and epimeric forms as well as the corresponding mixtures thereof. A racemate (a mixture of S and R form), diastereomers and single isomers of either S or R can exist. It is the intention of the application that compounds claimed here could be a mixture of diastereomers, a racemate or a single isomer of either S or R.

The term “optional” or “optionally” means that the subsequently described event or circumstance may or may not occur, and that the description includes instances where said event or circumstance occurs and instances in which it does not. For example, “alkyl optionally substituted with . . . ” means either “alkyl” or “substituted alkyl with . . . ” as defined below.

As used herein, a group designated as “$C_{1-6}$” indicates that there are one to six carbon atoms in the moiety, i.e. groups containing 1 carbon atom, 2 carbon atoms, 3 carbon atoms, 4 carbon atoms, 5 carbon atoms, and 6 carbon atoms. Thus, by way of example only, “$C_{1-6}$ alkyl” indicates that there are one to six carbon atoms in the alkyl group, i.e., the alkyl group is selected from among methyl, ethyl, propyl, iso-propyl, n-butyl, iso-butyl, sec-butyl, and t-butyl, n-pentyl, isopentyl, neopentyl, n-hexyl and the isomers thereof.

The terms “cycle”, “cyclic”, “ring” and “membered ring” as used herein, alone or in combination, refer to any covalently closed structure, including alicyclic, heterocyclic, aromatic, heteroaromatic and polycyclic fused or nonfused ring systems as described herein. Rings can be optionally substituted. Rings can form part of a fused ring system. The term “membered” is meant to denote the number of skeletal atoms that constitute the ring. Thus, by way of example only, cyclohexane, pyridine, pyran and pyrimidine are six-membered rings.

The term “fused” as used herein, alone or in combination, refers to cyclic structures in which two or more rings share one or more bonds.

The term “heterocyclyl” as used herein, alone or in combination, refers to heteroalicyclyl groups having one cycle. Herein, whenever the number of carbon atoms in a heterocycle is indicated (e.g., $C_{3-6}$ heterocycle), at least one non-carbon atom (the heteroatom) must be present in the ring. Designations such as “$C_{3-6}$ heterocycle” refer only to the number of carbon atoms in the ring and do not refer to the total number of atoms in the ring. Designations such as “4-8 membered heterocycle” refer to the total number of atoms that are contained in the ring (i.e., a four, five, six, seven, or eight membered ring, in which at least one atom is a carbon atom, at least one atom is a heteroatom and the remaining two to six atoms are either carbon atoms or heteroatoms). For heterocycles having two or more heteroatoms, those two or more heteroatoms can be the same or different from one another. Heterocycles can be optionally substituted. Bonding (i.e. attachment to a parent molecule or further substitution) to a heterocycle can be via a heteroatom or a carbon atom. The “heterocycle” includes heterocycloalkyl.

The term “spiral heterocyclyl” as used herein, alone or in combination, refers to a polycyclyl wherein two rings share a carbon atom and at least one ring atom is a heteroatom. The spiral heterocyclyl may have two or more cycles, each of them may be 4-8 membered cycles. Spiral heterocyclyl can be optionally substituted. Bonding (i.e. attachment to a parent molecule or further substitution) to a spiral heterocycle can be via a heteroatom or a carbon atom. The “spiral heterocycle” includes heterocycloalkyl.

The term “cycloalkyl” as used herein, alone or in combination, refers to an optionally substituted, saturated, hydrocarbon monoradical ring which may include additional, non-ring carbon atoms as substituents (e.g. methylcyclopropyl). The cycloalkyl may have three to about ten, or three to about eight, or three to about six, or three to five ring atoms. The examples include but not limited to cyclopropyl, cyclobutyl, cyclopentyl, and cyclohexyl.

The term "aryl" as used herein, alone or in combination, refers to an optionally substituted aromatic hydrocarbon radical of six to about twenty ring carbon atoms, and includes fused and nonfused aryl rings. A fused aryl ring radical contains from two to four fused rings where the ring of attachment is an aryl ring, and the other individual rings may be alicyclic, heterocyclic, aromatic, heteroaromatic or any combination thereof. Further, the term aryl includes fused and non-fused rings. Moreover, the term aryl includes but not limited to monocycle, bicycle and tricycle or more cycles. The aryl (for example monocyclic aryl) contains, for example, from six to about twelve, or six to about ten, or six to about eight ring carbon atoms. A nonlimiting example of a single ring aryl group includes phenyl; a fused ring aryl group includes naphthyl, phenanthrenyl, anthracenyl, azulenyl; and a nonfused biaryl group includes biphenyl.

The term "heteroaryl" as used herein, alone or in combination, refers to optionally substituted aromatic mono-radicals containing from about five to about twenty, for example, five to twelve, five to ten, five or six skeletal ring atoms, where one or more, for example one to four, one to three, or one to two of the ring atoms is a heteroatom independently selected from among oxygen, nitrogen, sulfur, phosphorous, silicon, selenium and tin but not limited to these atoms and with the proviso that the ring of said group does not contain two adjacent O or S atoms. Heteroaryl includes monocyclic heteroaryl (having one ring), bicyclic heteroaryl (having two rings), or polycyclic heteroaryl (having more than two rings). In embodiments in which two or more heteroatoms are present in the ring, the two or more heteroatoms can be the same as each another, or some or all of the two or more heteroatoms can each be different from the others. Individual rings may be alicyclic, heterocyclic, aromatic, heteroaromatic or any combination thereof. A single ring heteroaryl (monocyclic heteroaryl) includes but not limited to those having five to about twelve, or five to about ten, or five to seven, or six ring atoms. A non-limiting example of a single ring heteroaryl group includes pyridyl; fused ring heteroaryl groups include benzimidazolyl, quinolinyl, acridinyl; and a non-fused bi-heteroaryl group includes bipyridinyl. Further examples of heteroaryls include, without limitation, furanyl, thienyl, oxazolyl, acridinyl, phenazinyl, benzimidazolyl, benzofuranyl, benzoxazolyl, benzothiazolyl, benzothiadiazolyl, benzothiophenyl, benzoxadiazolyl, benzotriazolyl, imidazolyl, indolyl, isoxazolyl, isoquinolinyl, indolizinyl, isothiazolyl, isoindolyloxadiazolyl, indazolyl, pyridyl, pyridazyl, pyrimidyl, pyrazinyl, pyrrolyl, pyrazolyl, purinyl, phthalazinyl, pteridinyl, quinolinyl, quinazolinyl, quinoxalinyl, triazolyl, tetrazolyl, thiazolyl, triazinyl, thiadiazolyl and the like, and their oxides, such as for example pyridyl-N-oxide and the like.

The term "alkyl" as used herein, alone or in combination, refers to an optionally substituted straight chain, or optionally substituted branched chain saturated hydrocarbon monoradical having, for example, from one to about eighteen, or one to about ten carbon atoms, or one to six carbon atoms. Examples of alkyl include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and the like.

The "alkyl" as used in combination includes but not limited to the "alkyl" included in "alkoxy".

The term "alkoxy" as used herein, alone or in combination, refers to an alkyl ether radical, O-alkyl. Non-limiting examples of alkoxy radicals include methoxy, ethoxy, n-propoxy, isopropoxy, n-butoxy, iso-butoxy, sec-butoxy, tert-butoxy and the like.

The term "alkenyl" as used herein, alone or in combination, refers to an optionally substituted straight-chain, or optionally substituted branched chain hydrocarbon monoradical having one or more carbon-carbon double-bonds and having, for example, from two to about eighteen or two to about ten carbon atoms, or two to about six carbon atoms, or two to about four carbon atoms. The group may be in either the cis or trans conformation about the double bond(s), and should be understood to include both isomers. Examples include, but are not limited to ethenyl ($-CH=CH_2$), 1-propenyl ($-CH_2CH=CH_2$), isopropenyl [$-C(CH_3)=CH_2$], butenyl, 1,3-butadienyl and the like.

The present definition also covers the occurrence of the term "alkenyl" where no numerical range is designated.

The terms "halogen", "halo" or "halide" as used herein, alone or in combination refer to fluoro, chloro, bromo and iodo.

Hydroxy or hydroxyl refers to a group of —OH.

Cyano refers to a group of —CN.

In the molecular structures shown in the application, when asymmetric centers appear, a solid wedge means the bond is pointing to the top of the paper while a dotted wedge means the bond is pointing to the back of the paper. A solid bond line usually means all possible isomers.

Certain Pharmaceutical Terminology

The term "subject", "patient" or "individual" as used herein in reference to individuals suffering from a disease, a disorder, a condition, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat", "treating" or "treatment", and other grammatical equivalents as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The terms "effective amount", "therapeutically effective amount" or "pharmaceutically effective amount" as used herein, refer to a sufficient amount of at least one agent or compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case may be determined using techniques, such as a dose escalation study.

The terms "administer", "administering", "administration", and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein, e.g., as discussed in Goodman and Gilman, The Pharmacological Basis of Therapeutics, current ed.; Pergamon; and Remington's, Pharmaceutical Sciences (current edition), Mack Publishing Co., Easton, Pa. In preferred embodiments, the compounds and compositions described herein are administered orally.

The term "acceptable" as used herein, with respect to a formulation, composition or ingredient, means having no persistent detrimental effect on the general health of the subject being treated.

The term "pharmaceutically acceptable" as used herein, refers to a material, such as a carrier or diluent, which does not abrogate the biological activity or properties of the compounds described herein, and is relatively nontoxic, i.e., the material may be administered to an individual without causing undesirable biological effects or interacting in a deleterious manner with any of the components of the composition in which it is contained.

The term "pharmaceutical composition", as used herein, refers to a biologically active compound, optionally mixed with at least one pharmaceutically acceptable chemical component, such as, though not limited to carriers, stabilizers, diluents, dispersing agents, suspending agents, thickening agents, and/or excipients.

The term "carrier" as used herein, refers to relatively nontoxic chemical compounds or agents that facilitate the incorporation of a compound into cells or tissues.

The term "pharmaceutically acceptable salt" as used herein, refers to salts that retain the biological effectiveness of the free acids and bases of the specified compound and that are not biologically or otherwise undesirable. Compounds described herein may possess acidic or basic groups and therefore may react with any of a number of inorganic or organic bases, and inorganic and organic acids, to form a pharmaceutically acceptable salt. These salts can be prepared in situ during the final isolation and purification of the compounds of the application, or by separately reacting a purified compound in its free base form with a suitable organic or inorganic acid, and isolating the salt thus formed. Examples of pharmaceutically acceptable salts include those salts prepared by reaction of the compounds described herein with a mineral or organic acid or an inorganic or organic base.

The term "tautomer" as used herein refers to an isomer readily interconverted from a compound of this application by e.g., migration of a hydrogen atom or proton.

The term "prodrug" as used herein, refers to any pharmaceutically acceptable salt, ester, salt of an ester or other derivative of a compound of this application, which, upon administration to a recipient, is capable of providing, either directly or indirectly, a compound of this application or a pharmaceutically active metabolite or residue thereof. Particularly favored derivatives or prodrugs are those that increase the bioavailability of the compounds of this application when such compounds are administered to a patient (e.g., by allowing orally administered compound to be more readily absorbed into blood) or which enhance delivery of the parent compound to a biological compartment (e.g., the brain or lymphatic system).

The term "active metabolite", as used herein, refers to a biologically active derivative of a compound that is formed when the compound is metabolized.

The term "metabolized", as used herein, refers to the sum of the processes (including, but not limited to, hydrolysis reactions and reactions catalyzed by enzymes) by which a particular substance is changed by an organism.

$IC_{50}$ means the concentration of a particular compound that inhibits 50% of a specific measured activity.

Embodiment

The novel features of the application are set forth with particularity in the appended claims. A better understanding of the features and advantages of the present application will be obtained by reference to the following detailed description that sets forth illustrative embodiments, in which the principles of the application are utilized.

Some embodiments of the present application have been shown and described herein by way of example only. It should be understood that various alternatives to the embodiments of the application described herein may be employed in practicing the application. Those ordinary skilled in the art will appreciate that numerous variations, changes, and substitutions are possible without departing from the application. It is intended that the following claims define the scope of aspects of the application and that methods and structures within the scope of these claims and their equivalents be covered thereby.

Description of Scheme I.

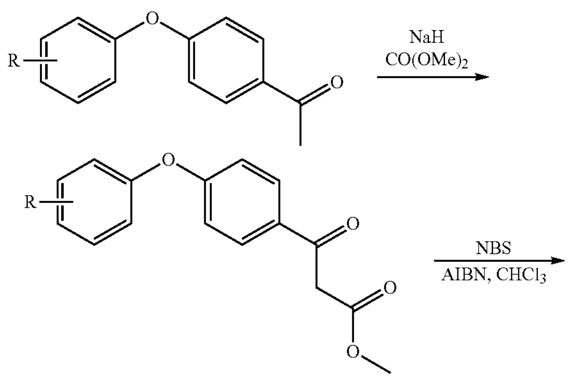

-continued
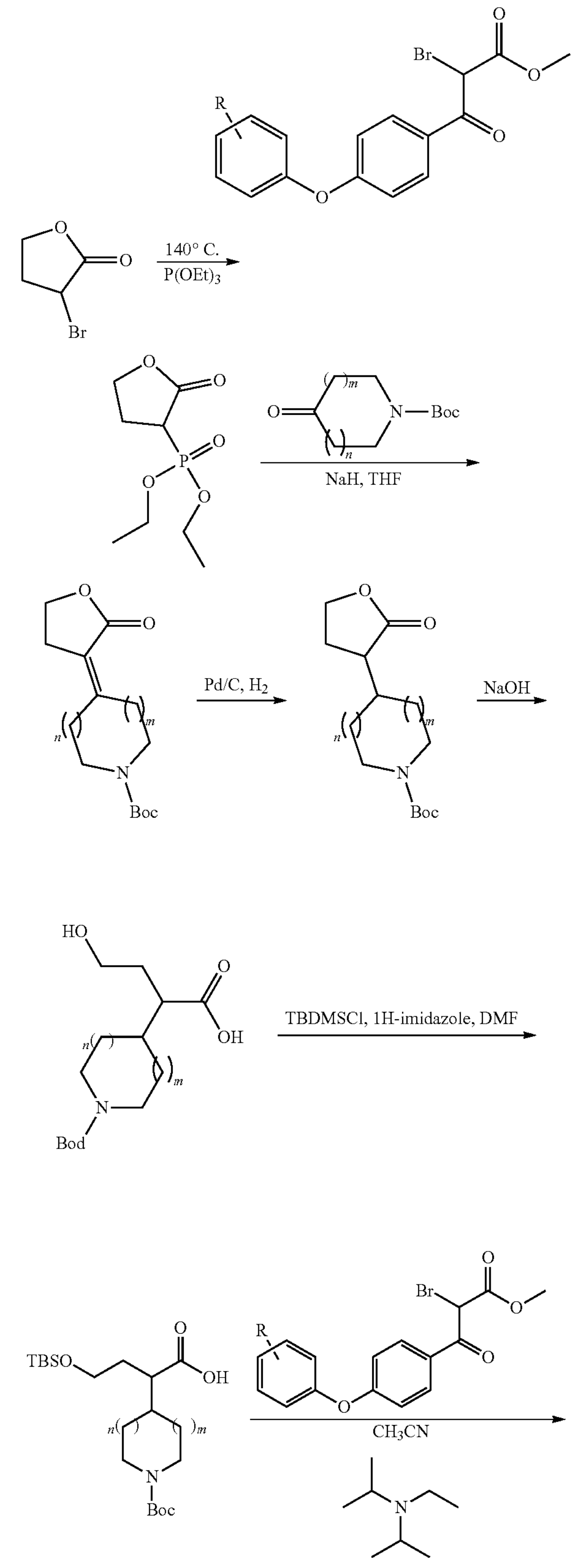
-continued
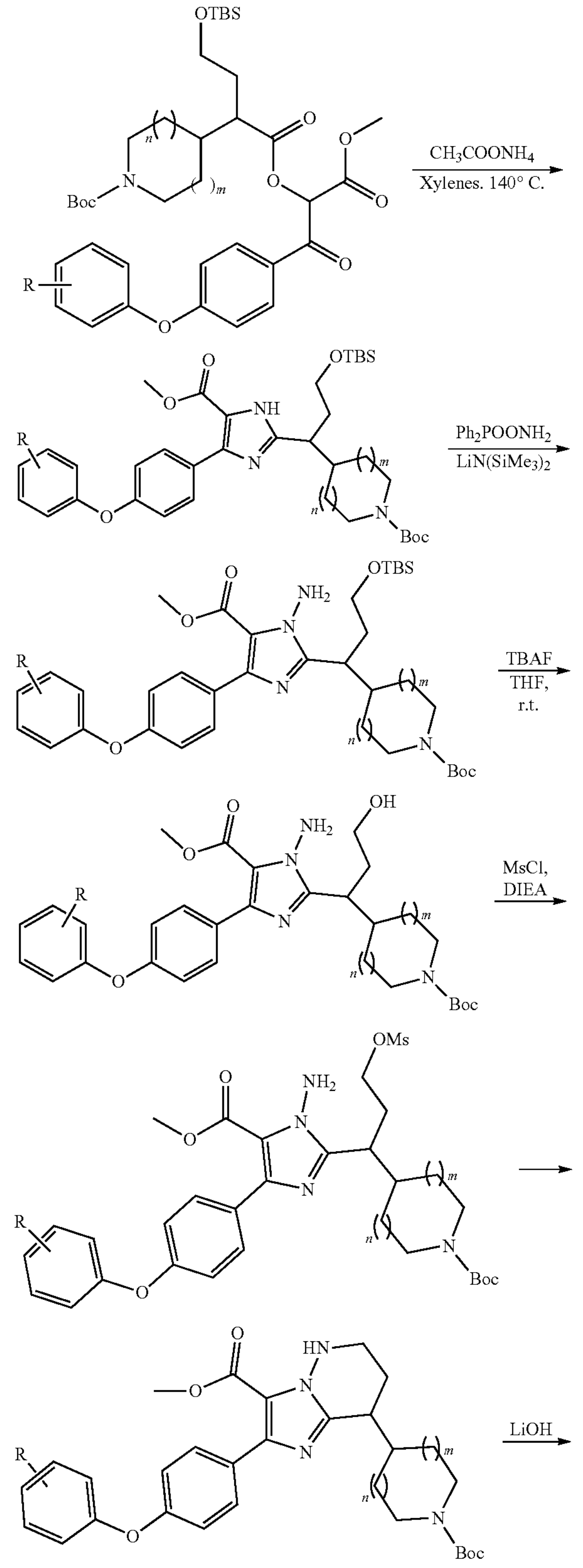

-continued
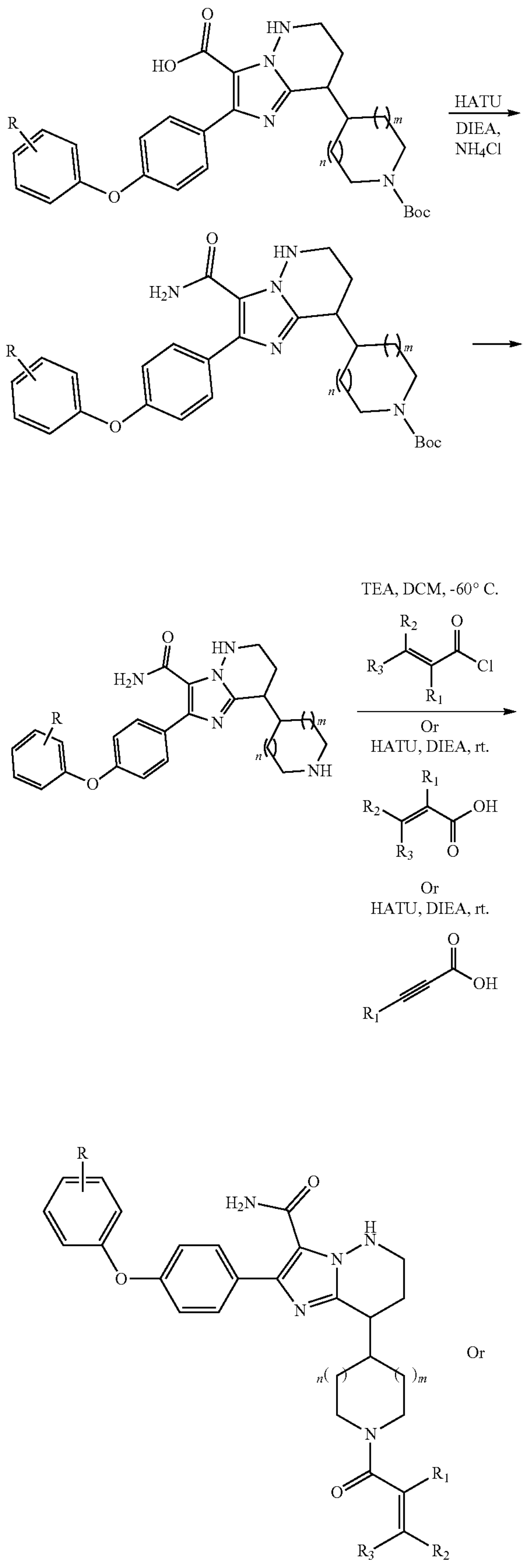
-continued
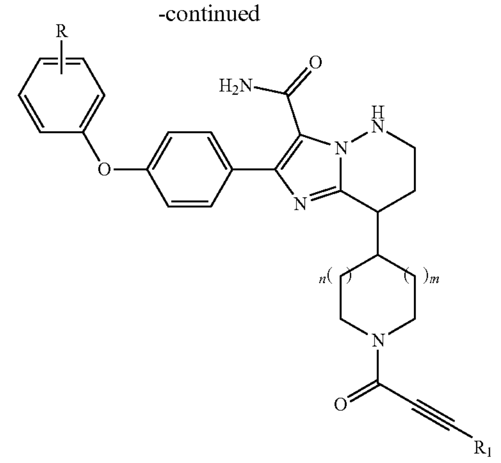
In Scheme I, m or n is a number selected from 0 or 1.
EXAMPLES
Example 1: 8-(1-acryloylpiperidin-4-yl)-2-(4-phenoxyphenyl)-5,6,7,8-tetrahydroimidazo[1,2-b]pyridazine-3-carboxamide
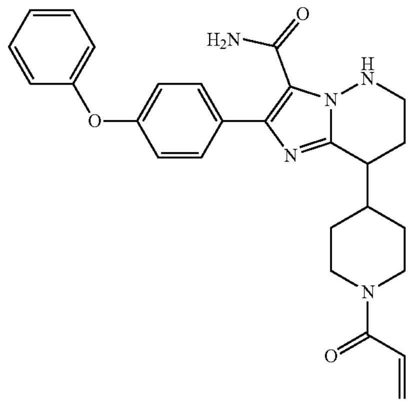 [SMILES: C=CC(=O)N1CCC(C2CCNn3c2nc(-c2ccc(Oc4ccccc4)cc2)c3C(N)=O)CC1]
Step A: Preparation of methyl 3-oxo-3-(4-phenoxyphenyl)propanoate
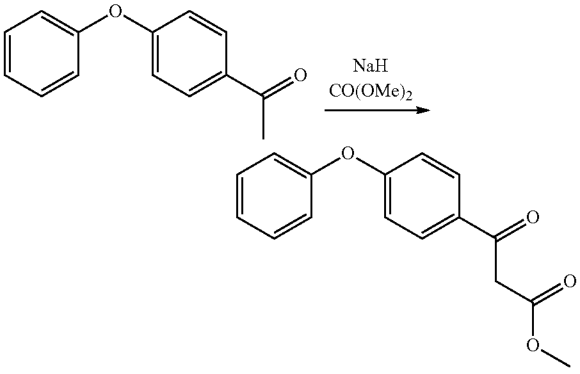

To a stirred suspension of NaH (60% dispersion in mineral oil; 565.3 g, 14.13 mol) in N, N-dimethylformamide (DMF) (3 L) at 0° C. was added dropwise the solution of 1-(4-phenoxyphenyl)ethanone (2.0 kg, 9.42 mol) in N, N-dimethylformamide (2 L). After 30 minutes, dimethylcarbonate (4.2 kg, 47.11 mol) was added next. The mixture was allowed to warm to room temperature over a 2 hs period, then poured into 1:1 water/saturated sodium bicarbonate. 1 mol/L cooled glacial acetic acid was added dropwise until pH 6-7, then extracted with ethyl acetate (3×2000 mL). The combined organic layer was washed with saturated brine, dried over anhydrous $Na_2SO_4$, filtered and concentrated. The residue was purified by chromatography with petroleum ether and ethyl acetate (20:1) to afford product as a yellow oil (2.3 kg, 90%). $^1$H NMR (600 MHz, DMSO-d6) δ 8.00-7.96 (m, 2H), 7.47 (t, J=8.0 Hz, 2H), 7.26 (t, J=7.4 Hz, 1H), 7.16-7.12 (m, 2H), 7.05 (d, J=8.8 Hz, 2H), 4.16 (s, 2H), 3.65 (s, 3H). MS (ESI, m/z): 271.1 $[M+H]^+$.

Step B: Preparation of methyl 2-bromo-3-oxo-3-(4-phenoxyphenyl)propanoate

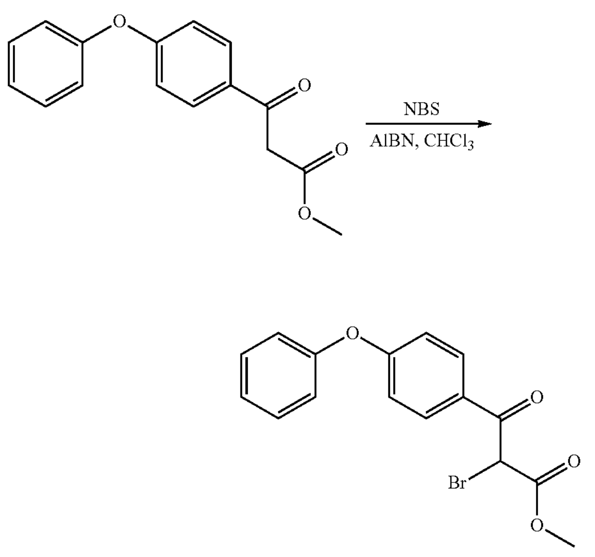 [SMILES: COC(=O)CC(=O)c1ccc(Oc2ccccc2)cc1 ; "NBS" ; COC(=O)C(Br)C(=O)c1ccc(Oc2ccccc2)cc1]

To a solution of the product of Step A (1.0 kg, 3.70 mol) in $CHCl_3$ (5 L) was added N-bromosuccinimide (NBS) (231.5 g, 4.07 mol) and azobisisobutyronitrile (AIBN) (303.7 g, 1.85 mol). The reaction mixture was refluxing for 6 hs. Then the $CHCl_3$ was evaporated. The residue was diluted with 1500 mL ethyl acetate. The mixture was washed with aqueous 5% HCl (2×1000 mL) and 500 mL water, then dried over anhydrous sodium sulfate. Evaporation of the solvent gave the crude product as oil, the crude residue was flash chromatographed with ethyl acetate and petroleum ether (1:10) to get desired product as yellow oil (1.1 kg, 85%). $^1$H NMR (400 MHz, DMSO-d6) δ 8.10-8.03 (m, 2H), 7.53-7.46 (m, 2H), 7.33-7.26 (m, 1H), 7.20-7.15 (m, 2H), 7.11-7.06 (m, 2H), 6.63 (s, 1H), 3.75 (s, 3H). MS (ESI, m/z): 349.9 $[M+H]^+$.

Step C: Preparation of diethyl (2-oxotetrahydrofuran-3-yl)phosphonate

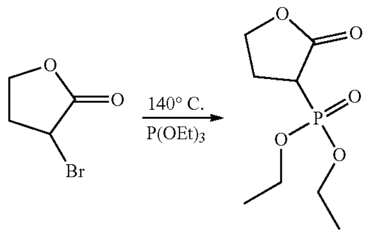

A mixture of triethylphosphite (3.3 kg, 20.01 mol) and α-bromo-γ-butyrolactone (3.0 kg, 18.21 mol) was heated to reflux. After 4 h the mixture was allowed to cool to room temperature, then rotorary evaporated to remove ethyl bromide. The resulting mixture was then purified by flash chromatography on silica gel with ethyl acetate and dichloromethane (1:1) to get product as colorless oil (3.5 kg, 86%). $^1$H NMR (400 MHz, $CDCl_3$) δ 4.45-4.37 (m, 1H), 4.35-4.27 (m, 1H), 4.25-4.11 (m, 4H), 3.11-2.96 (m, 1H), 2.62-2.49 (m, 2H), 1.32 (td, J=7.1, 3.4 Hz, 6H). MS (ESI, m/z): 233.1 $[M+H]^+$.

Step D: Preparation of tert-butyl 4-(2-oxodihydrofuran-3(2H)-ylidene)piperidine-1-carboxylate

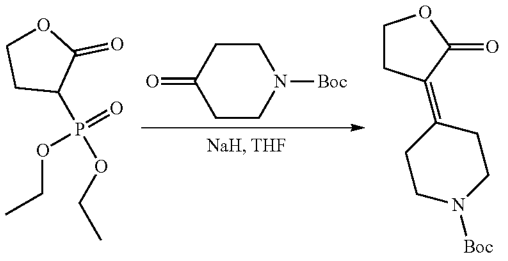

To a slurry of tetrahydrofuran-washed sodium hydride (60% dispersion in mineral oil; 602.2 g, 15.06 mol) was added diethyl (2-oxotetrahydrofuran-3-yl)phosphonate (3.3 kg, 15.06 mol) as a solution in dry tetrahydrofuran (3 L) dropwise over 70 min at 10° C. The mixture was stirred for 30 min before the addition of tert-butyl 4-oxopiperidine-1-carboxylate (2.0 kg, 10.01 mol) as a solution in tetrahydrofuran (2 L). The mixture was then stirred for 2 hs before the addition of dichloromethane (2 L) followed by water (5 L). The tetrahydrofuran was then removed under reduced pressure, the aqueous residue extracted with dichloromethane (3×1000 ml), then washed with water (2×1000 ml) and dried over anhydrous $Na_2SO_4$. Then residue was evaporated, and purified by column chromatography on silica gel with ethyl acetate and petroleum ether (1:2) to give product as a white solid (1.5 kg, 56%). $^1$H NMR (400 MHz, $CDCl_3$) δ 4.33 (t, J=7.5 Hz, 2H), 3.54 (t, J=5.9 Hz, 2H), 3.47 (t, J=5.9 Hz, 2H), 3.12-3.05 (m, 2H), 2.91 (t, J=7.5 Hz, 2H), 2.33 (t, J=5.8 Hz, 2H), 1.48 (s, 9H). MS (ESI, m/z): 268.1 $[M+H]^+$.

Step E: Preparation of tert-butyl 4-(2-oxotetrahydrofuran-3-yl)piperidine-1-carboxylate

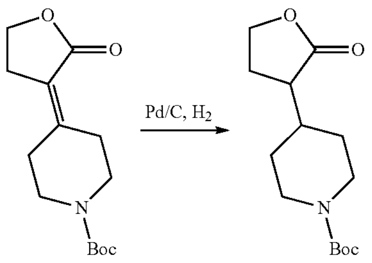

To a solution of the product of step D (1.5 kg, 5.61 mol) in ethyl acetate (4 L) was added 10% Pd/C (300.0 g, 20%) at room temperature. The mixture was stirred for 3 hs under $H_2$. The mixture was passed through Celite, and the solid was washed with ethyl acetate, and filtrate was concentrated under vacuum to get desired product (1.5 kg, 99%). $^1$H NMR (400 MHz, $CDCl_3$) δ 4.37-4.29 (m, 1H), 4.25-4.08 (m, 3H), 2.79-2.64 (m, 2H), 2.59-2.44 (m, 1H), 2.33-2.19 (m, 1H), 2.12-2.02 (m, 1H), 2.01-1.84 (m, 2H), 1.59-1.51 (m, 1H), 1.46 (s, 9H), 1.37-1.21 (m, 2H). MS (ESI, m/z): 270.1 $[M+H]^+$.

Step F: Preparation of 2-(1-(tert-butoxycarbonyl)piperidin-4-yl)-4-hydroxybutanoic acid

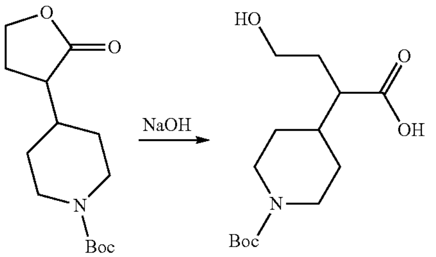

The product of step E (1.0 kg, 3.71 mmol), $H_2O$ (2 L), and sodium hydroxide (297.1 g, 7.4 mol) were added in a round bottom flask. This reaction mixture was stirred at room temperature overnight. The clear reaction mixture was then extracted with ethyl acetate. The aqueous layer was isolated and acidified to pH 3-4 with concentrated HCl, then extracted with 3×1000 mL of dichloromethane. The organic phase was washed with saturated brine and then dried over anhydrous $Na_2SO_4$. The organic phase was concentrated in vacuo to get product as a white solid (1.0 kg, 93%). $^1$H NMR (600 MHz, DMSO-d6) δ 12.12 (s, 1H), 4.45 (s, 1H), 3.94 (s, 2H), 3.40 (s, 1H), 3.30 (s, 1H), 2.65 (s, 2H), 2.20 (s, 1H), 1.69-1.56 (m, 4H), 1.55-1.48 (m, 1H), 1.38 (s, 9H), 1.14-0.99 (m, 2H). MS (ESI, m/z): 288.2 $[M+H]^+$.

Step G: Preparation of 2-(1-(tert-butoxycarbonyl)piperidin-4-yl)-4-((tert-butyldimethylsilyl)oxy)butanoic Acid

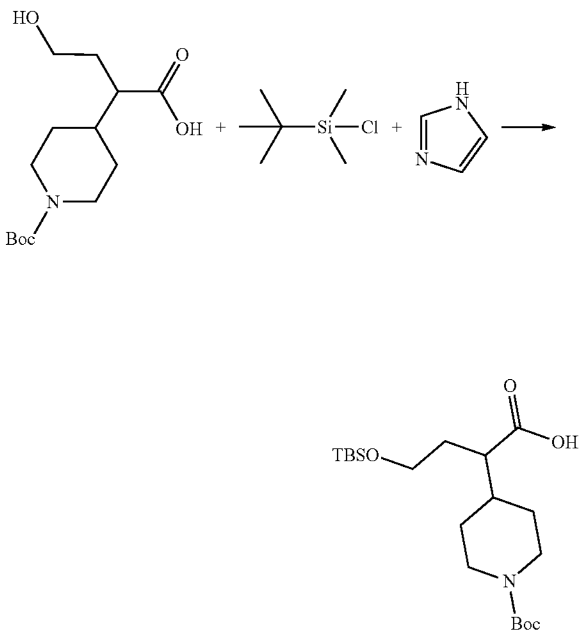

The tert-butyldimethylsilylchloride (597.9 g, 3.97 mol) was added to a mixture of the product of step F (950.1 g, 3.31 mmol) and Imidazole (450.0 g, 6.6 mol) in N, N-dimethylformamide (3 L). The reaction mixture was stirred at 30° C. for 5 hs under Argon atmosphere, then poured into a separatory funnel containing 1000 mL of brine and extracted 4 times with 2 L of dichloromethane. The organic fractions were combined, dried over anhydrous $Na_2SO_4$, filtered, and concentrated under reduced pressure to give the crude product, the residue was purified via flash chromatography eluting with dichloromethane and methanol (20:1) to give the product as a clear colorless oil (4.4 g, 78%). $^1$H NMR (400 MHz, $CDCl_3$) δ 4.12 (t, J=8.0 Hz, 1H), 3.58-3.69 (m, 2H), 2.66 (t, J=12.0 Hz, 2H), 2.39-2.41 (m, 1H), 1.81-1.90 (m, 1H), 1.68-1.77 (m, 3H), 1.61 (d, J=16.0 Hz, 1H), 1.44 (s, 9H), 1.16-1.35 (m, 3H), 0.87 (s, 9H), 0.03 (s, 6H). MS (ESI, m/z): 402.2 $[M+H]^+$.

Step H: Preparation of tert-butyl 4-(11,11,12,12-tetramethyl-3,6-dioxo-4-(4-phenoxybenzoyl)-2,5,10-trioxa-11-silatridecan-7-yl)piperidine-1-carboxylate

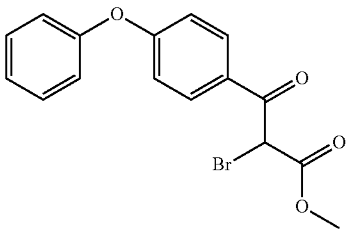

+

-continued

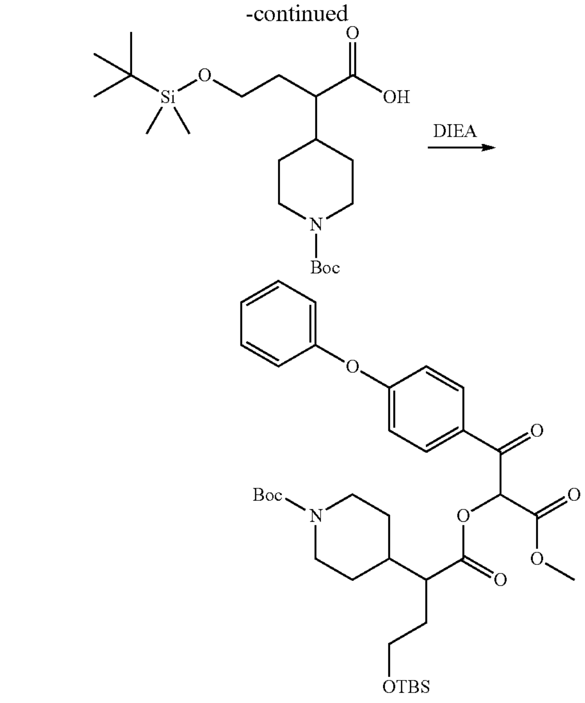

To a solution of the product of step G (138.0 g, 343.71 mmol) and N, N-diisopropylethylamine (DIEA) (55.5 g, 429.61 mmol) in acetonitrile (500 mL) was added the product of step B (100.0 g, 286.41 mmol). The mixture was stirred at 30° C. for 3 hs. The solvent was removed by rotorary evaporation and the residue taken up in EA, washed with 0.1 N HCl, and brine. The organic fractions were dried over anhydrous $Na_2SO_4$, filtered, and concentrated under reduced pressure to give the crude product, the residue was purified via flash chromatography eluting with ethyl acetate and petroleum ether (1:10) to give the product as a clear colorless oil (150 g, 78%). $^1H$ NMR (400 MHz, $CDCl_3$) δ 7.97 (dd, J=12.0, 4.0 Hz, 2H), 7.41 (t, J=8.0 Hz, 2H), 7.23 (t, J=8.0 Hz, 1H), 7.08 (d, J=8.0 Hz, 2H), 7.00 (d, J=8.0 Hz, 2H), 6.25 (s, 1H), 4.12 (s, 2H), 3.78 (s, 3H), 3.65 (dt, J=12.0, 8.0, 4.0 Hz, 1H), 3.51-3.60 (m, 1H), 2.56-2.65 (m, 3H), 1.73-1.87 (m, 3H), 1.60-1.69 (m, 2H), 1.44 (d, J=1.3 Hz, 9H), 1.12-1.36 (m, 3H), 0.85 (d, J=12.0 Hz, 9H), 0.02 (s, 3H), −0.02 (d, J=8.0 Hz, 3H). MS (ESI, m/z): 670.3 $[M+H]^+$.

Step I: Preparation of tert-butyl 4-(3-((tert-butyldimethylsilyl)oxy)-1-(5-(methoxycarbonyl)-4-4-phenoxyphenyl-1H-imidazol-2-yl)propyl)piperidine-1-carboxylate

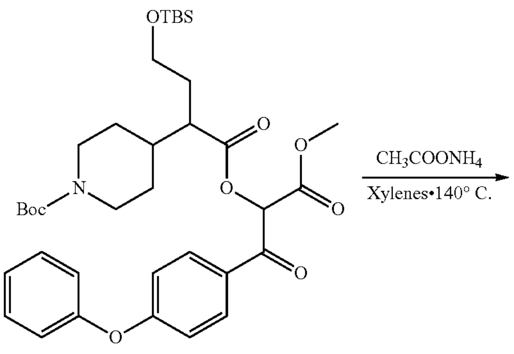

-continued

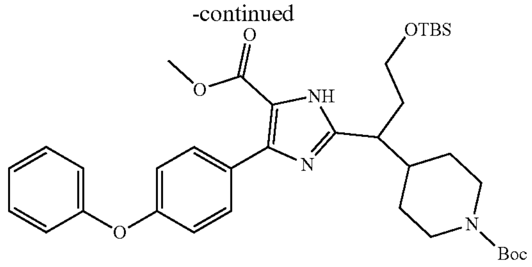

To a slurry of ammonium acetate (132.6 g, 1.72 mol) in xylenes (400 mL) was added the product of step H (96.0 g, 143.31 mmol). The mixture was stirred at 140° C. for 4 hs. The solution was cooled to room temperature and evaporated. The residue was dissolved in ethyl acetate and washed with saturated brine. The organic phase was dried over anhydrous $Na_2SO_4$, filtered and concentrated. The residue was purified by silica gel column chromatography with ethyl acetate and petroleum ether (1:5) to give the product as a clear colorless oil (37 g, 39%). $^1H$ NMR (400 MHz, $CDCl_3$) δ 9.71 (s, 1H), 7.93 (d, J=8.0 Hz, 2H), 7.34 (t, J=8.0 Hz, 2H), 7.11 (t, J=8.0 Hz, 1H), 7.02-7.06 (m, 4H), 4.12 (dd, J=16.0, 8.0 Hz, 2H), 3.84 (s, 3H), 3.65 (dt, J=8.0, 4.0 Hz, 1H), 3.44-3.49 (m, 1H), 2.79-2.84 (m, 1H), 2.67-2.63 (m, 2H), 1.90-2.09 (m, 3H), 1.85 (d, J=12.0 Hz, 1H), 1.44 (s, 9H), 1.26 (t, J=8.0 Hz, 1H), 1.20 (dt, J=8.0, 4.0 Hz, 2H), 0.89 (s, 9H), 0.03 (d, J=4.0 Hz, 6H). MS (ESI, m/z): 650.3 $[M+H]^+$.

Step J: Preparation of tert-butyl 4-(1-(1-amino-5-(methoxycarbonyl)-4-(4-phenoxyphenyl)-1H-imidazol-2-yl)-3-((tert-butyldimethylsilyl)oxy)propyl) piperidine-1-carboxylate

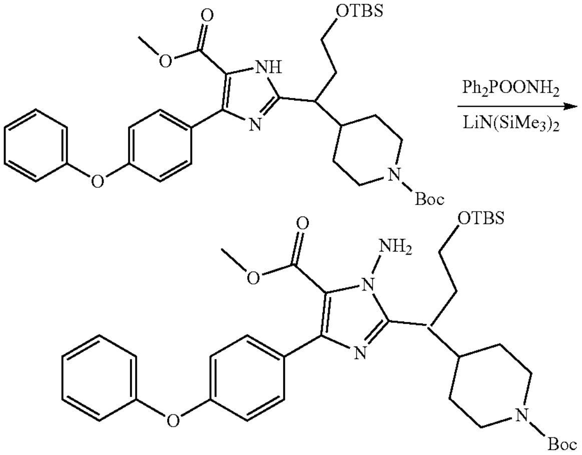

Lithium hexamethyldisilazane (85 mL of a 1 M solution in tetrahydrofuran, 85.31 mmol) was slowly added to the product of step I (37.0 g, 56.91 mmol) in anhydrous N, N-dimethylformamide (500 mL) at 0° C. After the mixture was stirred for 30 min, O-(diphenylphosphinyl) hydroxylamine (26.5 g, 113.86 mmol) was added, followed by stirring at room temperature for 4 hs (in cases where the reaction mixture became too viscous, additional N, N-dimethylformamide was added). The reaction was quenched with water until a clear solution was formed, then concentrated to dryness under reduced pressure. The residue was washed several times with ethyl acetate or dichloromethane.

The combined organic fractions were concentrated in vacuo and purified by flash chromatography on silica gel with ethyl acetate and petroleum ether (1:3) to give the product as a clear colorless oil (29 g, 76%). $^{1}H$ NMR (400 MHz, $CDCl_3$) δ 7.63-7.58 (m, 2H), 7.37-7.30 (m, 2H), 7.10 (t, J=7.4 Hz, 1H), 7.06-6.98 (m, 4H), 5.58 (s, 2H), 4.18-3.97 (m, 2H), 3.77 (s, 3H), 3.66-3.57 (m, 1H), 3.38-3.28 (m, 2H), 2.75-2.57 (m, 2H), 2.03-1.98 (m, 2H), 1.97-1.87 (m, 2H), 1.43 (s, 9H), 1.28-1.18 (m, 3H), 0.85 (s, 9H), 0.01-(−0.04) (m, 6H). MS (ESI, m/z): 665.3 $[M+H]^+$.

Step K: Preparation of tert-butyl 4-(1-(1-amino-5-(methoxycarbonyl)-4-(4-phenoxyphenyl)-1H-imidazol-2-yl)-3-hydroxypropyl)piperidine-1-carboxylate

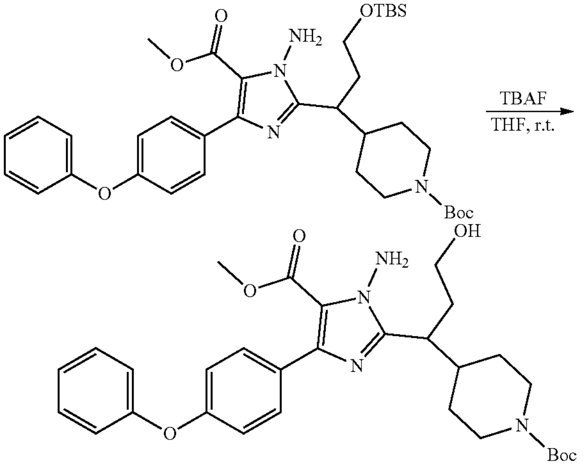

To a solution of the product of step J (29.0 g, 43.61 mmol) in tetrahydrofuran (150 mL) was added a 1M solution of tetrabutylammonium fluoride in tetrahydrofuran (66 mL, 65.41 mmol) at RT. The solution was stirred for 2 hs and diluted with 100 mL ethyl acetate solution. The organic layer was separated and washed with $H_2O$ (3×200 mL). The water extract was washed with ethyl acetate solution (2×150 mL), and the organic layers were combined and dried over anhydrous $Na_2SO_4$. The solvent was evaporated in vacuo, and purified by flash chromatography on silica gel with dichloromethane and methanol (30:1) to give the product as a clear colorless oil (22 g, 91%). $^{1}H$ NMR (400 MHz, $CDCl_3$) δ 7.64-7.59 (m, 2H), 7.37-7.32 (m, 2H), 7.12 (t, J=7.4 Hz, 1H), 7.07-6.99 (m, 4H), 5.52 (s, 2H), 4.24-3.95 (m, 2H), 3.79 (s, 3H), 3.69-3.59 (m, 1H), 3.51-3.40 (m, 1H), 3.38-3.28 (m, 1H), 2.76-2.56 (m, 2H), 2.12-1.98 (m, 3H), 1.96-1.86 (m, 1H), 1.44 (s, 9H), 1.38-1.29 (m, 1H), 1.26-1.14 (m, 2H). MS (ESI, m/z): 551.2 $[M+H]^+$.

Step L: Preparation of tert-butyl 4-(1-(1-amino-5-(methoxycarbonyl)-4-(4-phenoxyphenyl)-1H-imidazol-2-yl)-3-((methylsulfonyl)oxy)propyl)piperidine-1-carboxylate

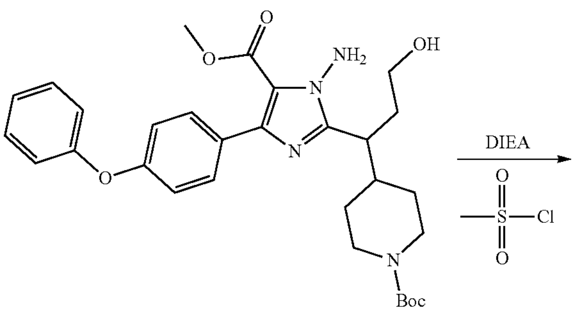

-continued

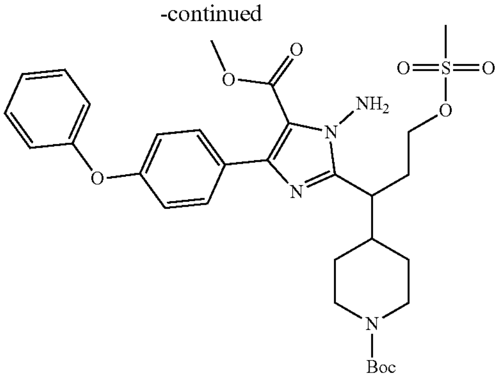

Methanesulfonyl chloride (6.0 g, 51.94 mmol) was added via syringe into a stirred mixture of the product of step K (22.1 g, 39.95 mmol) and N, N-diisopropylethylamine (7.8 g, 59.93 mmol) in dichloromethane (100 ml) maintained at 0° C. The mixture was stirred at room temperature for 3 h (TLC monitoring) and then partitioned between dichloromethane and water. The organic phase was dried, then evaporated to afford a white solid, the crude product was passed through a column of silica gel with dichloromethane and methanol (20:1) to afford the desired product as a colorless oil (21 g, 83%). $^{1}H$ NMR (400 MHz, $CDCl_3$) δ 7.65-7.61 (m, 2H), 7.36-7.32 (m, 2H), 7.12 (s, 1H), 7.06-7.01 (m, 4H), 5.36 (s, 2H), 4.25-4.14 (m, 2H), 4.01 (td, J=9.8, 3.9 Hz, 2H), 3.79 (s, 3H), 3.47 (dd, J=13.7, 5.9 Hz, 1H), 2.94 (s, 3H), 2.66 (s, 1H), 2.45-2.32 (m, 1H), 2.25 (dt, J=14.6, 4.9 Hz, 1H), 1.89 (d, J=12.3 Hz, 2H), 1.44 (s, 9H), 1.35-1.25 (m, 4H). MS (ESI, m/z): 629.3 $[M+H]^+$.

Step M: Preparation of methyl 8-(1-(tert-butoxycarbonyl)piperidin-4-yl)-2-(4-phenoxyphenyl)-5,6,7,8-tetrahydroimidazo[1,2-b]pyridazine-3-carboxylate

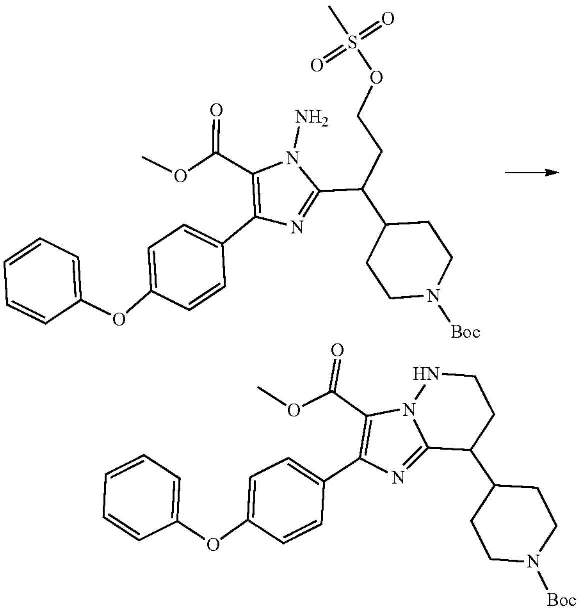

N, N-diisopropylethylamine (8.2 g, 63.61 mmol) and 1 M solution of tetrabutylammonium fluoride in tetrahydrofuran (32 mL, 31.81 mmol) were added to the solution of the product of step L (20.0 g, 31.81 mmol) in anhydrous tetrahydrofuran (100 mL), the mixture was heated to 50° C. for 2 hs, then cooled to r.t., concentrated and purified by flash column chromatography with dichloromethane and methanol (10:1) to give the desired product (11 g, 64%). $^1H$ NMR (600 MHz, $CDCl_3$) δ 7.64 (d, J=7.9 Hz, 2H), 7.34 (t, J=7.4 Hz, 2H), 7.11 (t, J=7.4 Hz, 1H), 7.07-7.02 (m, 4H), 7.01 (s, 1H), 4.17 (s, 2H), 3.78 (s, 3H), 3.50-3.44 (m, 1H), 3.38-3.31 (m, 1H), 3.09 (s, 1H), 2.71 (s, 2H), 2.41 (s, 1H), 2.12-2.02 (m, 1H), 1.98-1.89 (m, 1H), 1.77-1.71 (m, 1H), 1.61 (s, 1H), 1.45 (s, 9H), 1.42-1.32 (m, 2H). MS (ESI, m/z): 533.2 $[M+H]^+$.

Step N: Preparation of 8-(1-(tert-butoxycarbonyl) piperidin-4-yl)-2-(4-phenoxyphenyl)-5,6,7,8-tetrahydroimidazo[1,2-b]pyridazine-3-carboxylic Acid

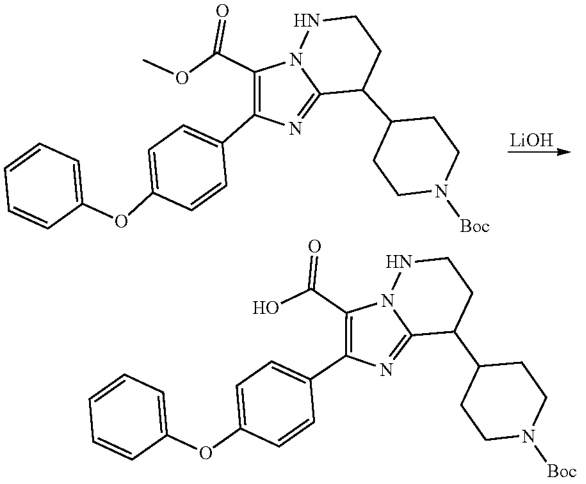

To a solution of the product of step M (10.0 g, 18.77 mmol) in tetrahydrofuran (60 mL) was added LiOH (2.25 g, 93.87 mmol) in water (10 mL), the mixture was heated at 50'C for 3 hs. After cooled to r.t., the mixture was acidified to pH 3-4 with concentrated HCl and then extracted with 3×100 mL of dichloromethane. The organic phase was washed with saturated brine and then dried over anhydrous $Na_2SO_4$. The organic phase was concentrated in vacuo to afford 11 g crude product. The residue was used to next step without further purification. MS (ESI, m/z): 519.3 $[M+H]^+$.

Step O: Preparation of tert-butyl 4-(3-carbamoyl-2-(4-phenoxyphenyl)-5,6,7,8-tetrahydroimidazo[1,2-b] pyridazin-8-yl)piperidine-1-carboxylate

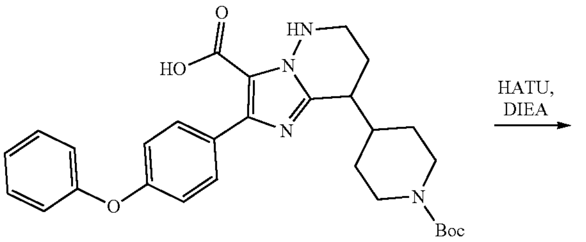

-continued

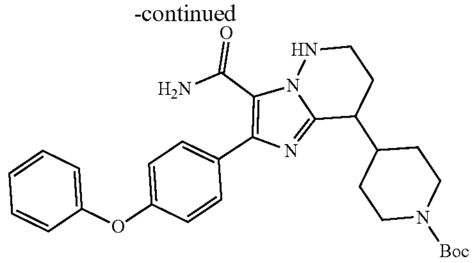

To the solution of the product of step N (11.0 g, 21.21 mmol) in dichloromethane (60 mL) was added N, N-diisopropylethylamine (11.0 g, 84.84 mmol). After 5 min, $NH_4Cl$ (4.54 g, 84.84 mmol) and HATU (12.1 g, 31.82 mmol) was added. The reaction mixture was continued to stir at room temperature for 2 hs. Dichloromethane and water were added. The layers were separated, and the aqueous phase was extracted with dichloromethane. The combined organic phases were washed three times (3×100 mL) with brine solution. The organic phase was dried over anhydrous $Na_2SO_4$, filtered and concentrated. The residue was purified by chromatography with dichloromethane and methanol (40:1) to give product as an off-white solid (7 g, 64%). $^1H$ NMR (600 MHz, $CDCl_3$) δ 7.63-7.55 (m, 2H), 7.38-7.29 (m, 2H), 7.15-7.07 (m, 1H), 7.00 (dt, J=16.0, 8.0 Hz, 4H), 6.88 (dd, J=13.0, 6.2 Hz, 1H), 6.26 (s, 1H), 5.70 (s, 1H), 4.14 (s, 2H), 3.66-3.57 (m, 2H), 3.47-3.39 (m, 1H), 3.34-3.24 (m, 1H), 3.11 (dd, J=14.8, 7.4 Hz, 2H), 2.73 (d, J=57.5 Hz, 2H), 2.38-2.34 (m, 1H), 2.05-2.00 (m, 1H), 1.92-1.86 (m, 1H), 1.71 (d, J=12.3 Hz, 1H), 1.43 (s, 9H). MS (ESI, m/z): 518.3 $[M+H]^+$.

Step P: Preparation of 2-(4-phenoxyphenyl)-8-(piperidin-4-yl)-5,6,7,8-tetrahydroimidazo[1,2-b] pyridazine-3-carboxamide

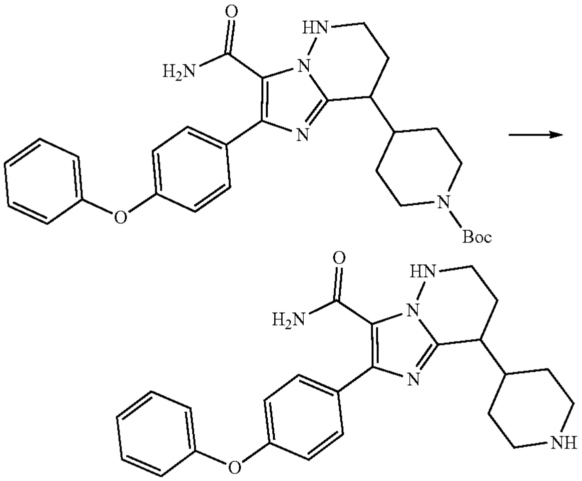

To a solution of the product of step O (5.0 g, crude) in EtOH (2 mL) was added 33% HCl/EtOH (20 mL) at room temperature. The mixture was stirred for 3 hs, then concentrated under vacuum to get 6.5 g crude product. The residue was used to next step without further purification. $^1H$ NMR (600 MHz, DMSO-d6) δ 8.46 (s, 1H), 7.98 (s, 1H), 7.84 (d, J=8.7 Hz, 2H), 7.51 (s, 1H), 7.40 (dd, J=8.2, 7.6 Hz, 2H), 7.14 (t, J=7.4 Hz, 11H), 7.04 (d, J=7.8 Hz, 2H), 6.99 (d, J=8.7 Hz, 2H), 6.70 (s, 1H), 3.38-3.30 (m, 1H), 3.27-3.16 (m, 2H), 3.12 (s, 1H), 3.04-2.97 (m, 1H), 2.86-2.77 (m, 1H), 2.76-2.68 (m, 1H), 2.26-2.17 (m, 1H), 1.96-1.86 (m, 2H), 1.78-1.65 (m, 2H), 1.62-1.47 (m, 2H). MS (ESI, m/z): 418.2 $[M+H]^+$.

Step Q: Preparation of 8-(1-acryloylpiperidin-4-yl)-2-(4-phenoxyphenyl)-5,6,7,8-tetrahydroimidazo[1,2-b]pyridazine-3-carboxamide

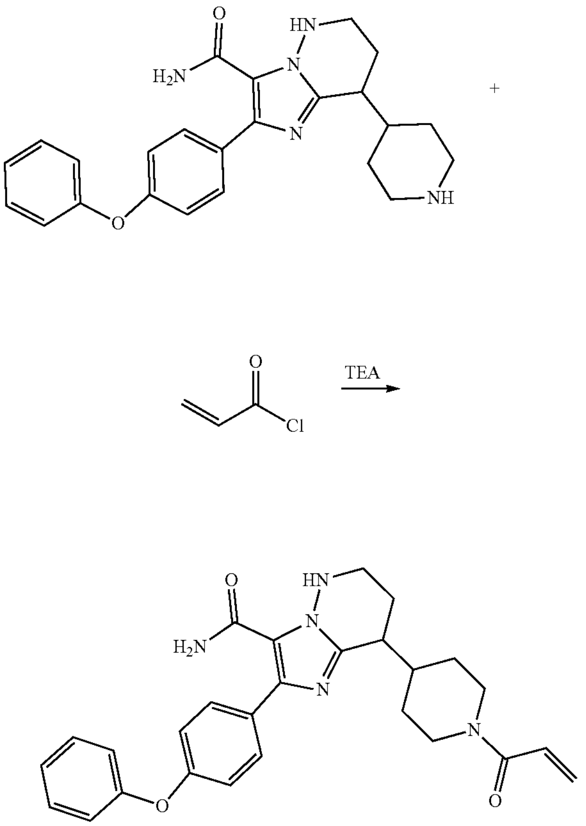

The mixture of the product of step P (200.0 mg, 0.48 mmol) and triethylamine (290.88 mg, 2.88 mmol) in dichloromethane (10 mL) was cooled to −60° C., then the solution of propenoyl chloride (52.1 mg, 0.57 mmol) in dichloromethane (1 mL) was added slowly, LC-MS was tracking, at the end of the reaction, 1 mL MeOH was added, the mixture was concentrated under vacuum to get crude product. The residue was purified by flash chromatography on silica gel with dichloromethane and methanol (40:1) to get product as a white solid (38 mg, 19%). $^1$H NMR (400 MHz, MeOD) δ 8.48 (s, 1H), 7.62-7.54 (m, 2H), 7.46-7.39 (m, 2H), 7.26-7.18 (m, 1H), 7.16-7.04 (m, 4H), 6.81-6.73 (m, 1H), 6.23-6.14 (m, 1H), 5.77-5.70 (m, 1H), 4.75-4.60 (m, 1H), 4.35-4.13 (m, 3H), 3.79 (d, J=4.2 Hz, 1H), 3.32-3.13 (m, 1H), 2.86-2.68 (m, 2H), 2.66-2.58 (m, 2H), 1.95-1.82 (m, 1H), 1.58-1.31 (m, 3H). MS (ESI, m/z): 418.2 $[M+H]^+$.

1a

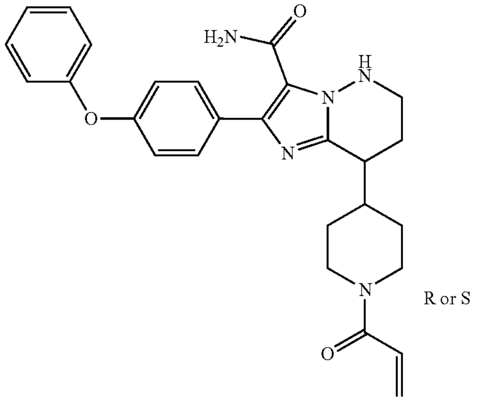

1a $^1$H NMR (600 MHz, $CDCl_3$) δ 7.56 (s, 2H), 7.42 (s, 1H), 7.36 (t, J=7.9 Hz, 2H), 7.14 (t, J=7.4 Hz, 1H), 7.07-7.04 (m, 4H), 6.60-6.54 (m, 1H), 6.26 (d, J=16.9 Hz, 1H), 5.99 (s, 1H), 5.67 (d, J=10.5 Hz, 1H), 5.30 (s, 1H), 4.79-4.72 (dd, J=32.3, 12.8 Hz, 1H), 4.08-4.00 (m, 1H), 3.46-3.44 (m, 1H), 3.15-3.05 (m, 2H), 2.67-2.50 (m, 2H), 2.08-2.05 (m, 1H), 1.91-1.78 (m, 2H), 1.55-1.53 (m, 1H), 1.50-1.46 (m, 1H), 1.42-1.40 (m, 1H).

1b

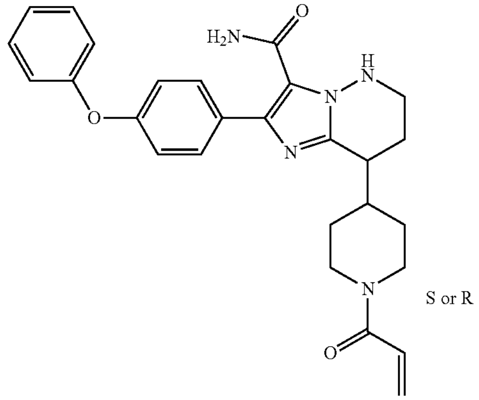

1b H NMR (600 MHz, $CDCl_3$) δ 7.56 (s, 2H), 7.36 (t, J=7.8 Hz, 2H), 7.14 (t, J=7.4 Hz, 1H), 7.06 (dd, J=11.6, 8.3 Hz, 4H), 6.63-6.52 (m, 1H), 6.26 (d, J=16.8 Hz, 1H), 5.99 (s, 1H), 5.67 (d, J=10.5 Hz, 1H), 5.30 (s, 1H), 4.75 (dd, J=33.1, 12.1 Hz, 1H), 4.08-4.00 (m, 1H), 3.44 (s, 1H), 3.35 (t, J=11.4 Hz, 1H), 3.15-3.05 (m, 2H), 2.68-2.45 (m, 2H), 2.06 (s, 1H), 1.96-1.75 (m, 2H), 1.53 (s, 1H), 1.49 (d, J=6.7 Hz, 1H), 1.41 (d, J=14.1 Hz, 1H).

Compound example 1 was separated into two enantiomeric stereoisomers compound 1a (peak 1, levoisomer, retention time at 7.9 min in chiral analysis), and compound 1b (peak 2, dextroisomer, retention time at 9.12 min in chiral analysis) by chiral prep-HPLC.

The chiral separation conditions are shown below.

| | |
|---|---|
| Column | CHIRALCEL AS-H |
| Column size | 250 × 4.6 mm |
| Injection | 10 μL |
| Mobile phase | MeOH/$CH_3CN$ = 60/40 |
| Flow rate | 1 mL/min |

-continued

| | |
|---|---|
| Wave length | UV 254 nm |
| Tempetature | 35° C. |
| Sample solution | 5 mg/mL |

The chiral-analysis conditions are shown below.

| | |
|---|---|
| Column | CHIRALPAK AD-H |
| Column size | 250 x 10 mm |
| Injection | 50 μL |
| Mobile phase | $MeOH/CH_3CN$ = 60/40 |
| Flow rate | 2.5 mL/min |
| Wave length | UV 254 nm |

The specific rotation of compound 1a and compound 1b was measured by polarimeter.

Specific rotation measurement conditions are shown below.

| | |
|---|---|
| Polarimeter | IP-digi300FD |
| Sample solution | 20 mg/ml |
| Solvent | Methanol |
| Tempetature | 20° C. |

Specific rotation results are shown below.

| Sample number | Specific rotation |
|---|---|
| 1a | −133.87 |
| 1b | 141.05 |

Example 2

8-[1-(1-Oxo-but-2-ynyl)-piperidin-4-yl]-2-(4-phenoxy-phenyl)-5,6,7,8-tetrahydro-imidazo[1,2-b]pyridazine-3-carboxamide

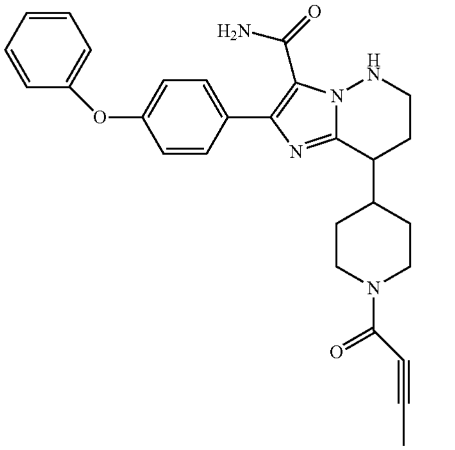 [SMILES: CC#CC(=O)N1CCC(C2CCNn3c2nc(-c2ccc(Oc4ccccc4)cc2)c3C(N)=O)CC1]

Preparation of 8-[1-(1-Oxo-but-2-ynyl)-piperidin-4-yl]-2-(4-phenoxy-phenyl)-5,6,7,8-tetrahydro-imidazo[1,2-b]pyridazine-3-carboxamide

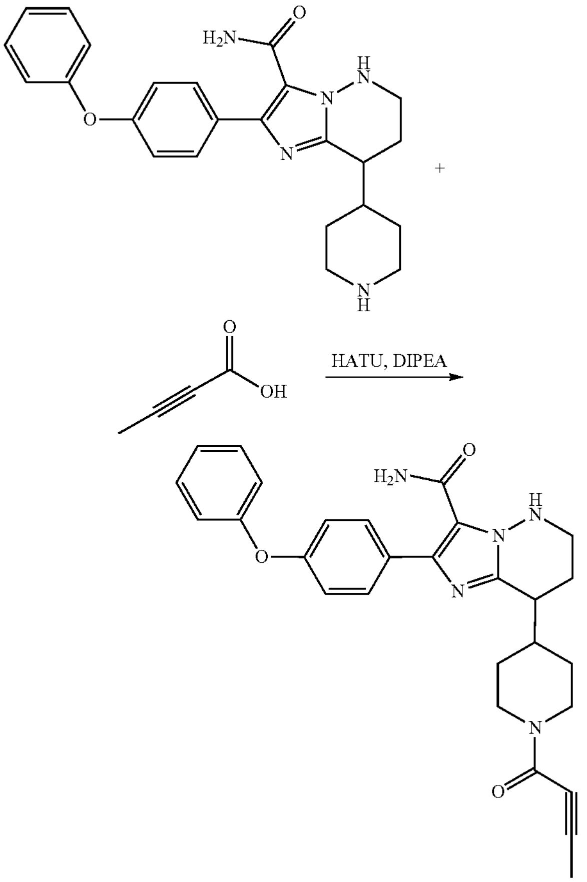

To the solution of the product (200.0 mg, 0.48 mmol) of step P of example 1 in dry N, N-dimethylformamide (10 mL) was added N, N-diisopropylethylamine (371.5 mg, 2.88 mmol). After 5 min, but-2-ynoic acid (47.8 mg, 0.57 mmol) and HATU (273.1 mg, 0.72 mmol) was added. The reaction mixture was continued to stir at room temperature for 2 hs. Dichloromethane and water were added. The layers were separated, the aqueous phase was extracted with dichloromethane. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give product as an off-white solid (54 mg, 23%). $^1H$ NMR (400 MHz, DMSO-d6) δ 8.24 (s, 1H), 7.95 (s, 1H), 7.87 (dd, J=8.8, 1.3 Hz, 2H), 7.52 (s, 1H), 7.46 (dd, J=8.4, 7.6 Hz, 2H), 7.20 (t, J=7.4 Hz, 1H), 7.10 (d, J=7.8 Hz, 2H), 7.07-7.01 (m, 2H), 6.63-6.55 (m, 1H), 4.51-4.27 (m, 2H), 3.81-3.60 (m, 2H), 3.20 (dd, J=12.9, 5.7 Hz, 3H), 3.12-3.00 (m, 1H), 2.34 (s, 1H), 2.07 (t, J=6.1 Hz, 3H), 1.98-1.95 (m, 2H), 1.86-1.70 (m, 1H), 1.63-1.46 (m, 2H). MS (ESI, m/z): 484.2 $[M+H]^+$.

Example 3

8-(1-(3-methylbut-2-enoyl)piperidin-4-yl)-2-(4-phenoxyphenyl)-5,6,7,8-tetrahydroimidazo[1,2-b]pyridazine-3-carboxamide

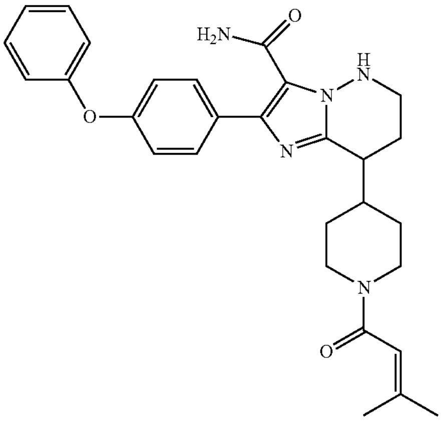 [SMILES: CC(C)=CC(=O)N1CCC(C2CCNn3c2nc(-c2ccc(Oc4ccccc4)cc2)c3C(N)=O)CC1]

Preparation of 8-(1-(3-methylbut-2-enoyl)piperidin-4-yl)-2-(4-phenoxyphenyl)-5,6,7,8-tetrahydroimidazo[1,2-b]pyridazine-3-carboxamide

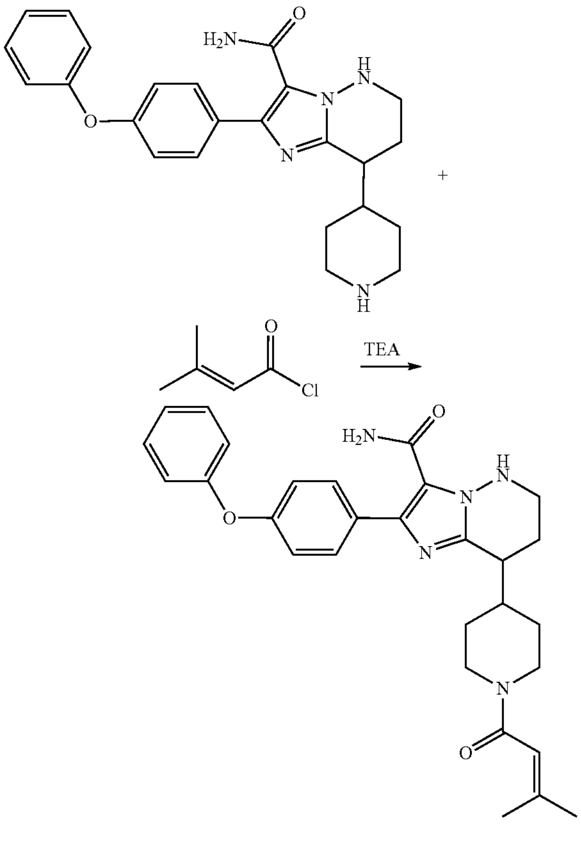

The mixture of the product (200.0 mg, 0.48 mmol) of step P of example land triethylamine (290.88 mg, 2.88 mmol) in dichloromethane (10 mL) was cooled to −60° C., then the solution of 3-methylbut-2-enoyl chloride (62.47 mg, 0.53 mmol) in dichloromethane (1 mL) was added slowly, LC-MS was tracking, at the end of the reaction, 1 mL MeOH was added, the mixture was concentrated under vacuum to get crude product. The residue was purified by flash chromatography on silica gel with dichloromethane and methanol (25:1) to get product as a white solid (43 mg, 18%). $^1$H NMR (400 MHz, MeOD) δ 7.54 (dd, J=8.7, 1.9 Hz, 2H), 7.30-7.21 (m, 2H), 7.02 (dd, J=10.6, 4.2 Hz, 1H), 6.95-6.85 (m, 4H), 5.75 (d, J=8.1 Hz, 11H), 4.51 (dd, J=24.3, 13.1 Hz, 1H), 3.94 (dd, J=24.1, 13.0 Hz, 1H), 3.34 (dt, J=13.6, 4.0 Hz, 11H), 3.13 (t, J=11.2 Hz, 1H), 3.05 (t, J=9.6 Hz, 1H), 3.02-2.88 (m, 1H), 2.65-2.47 (m, 1H), 2.44-2.26 (m, 1H), 1.92 (dd, J=10.1, 3.7 Hz, 1H), 1.77-1.67 (m, 8H), 1.43-1.26 (m, 3H). MS (ESI, m/z): 500.3 [M+H]$^+$.

Example 4

8-[1-(2-Methyl-acryloyl)-piperidin-4-yl]-2-(4-phenoxy-phenyl)-5,6,7,8-tetrahydro-imidazo[1,2-b]pyridazine-3-carboxamide

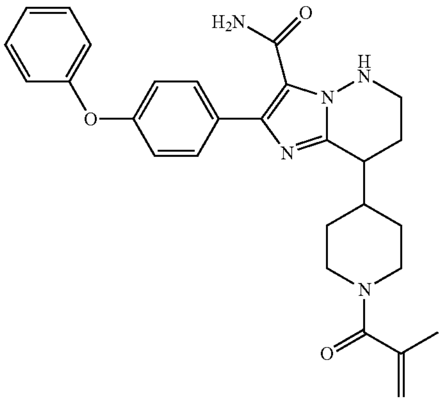 [SMILES: C=C(C)C(=O)N1CCC(C2CCNn3c2nc(-c2ccc(Oc4ccccc4)cc2)c3C(N)=O)CC1]

Preparation of 8-[1-(2-Methyl-acryloyl)-piperidin-4-yl]-2-(4-phenoxy-phenyl)-5,6,7,8-tetrahydro-imidazo[1,2-b]pyridazine-3-carboxamide

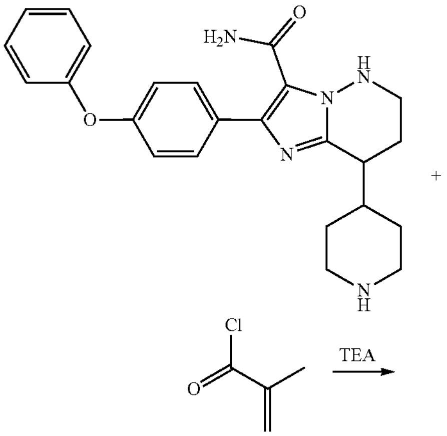

-continued

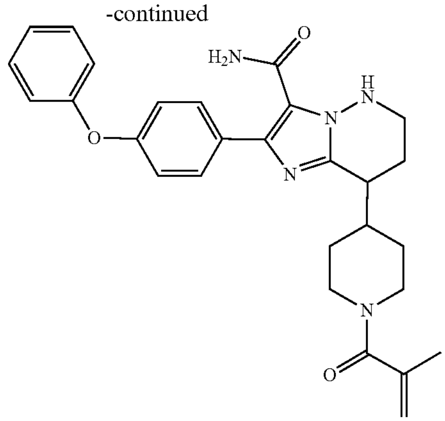

The mixture of the product (200.0 mg, 0.48 mmol) of step P of example 1 and triethylamine (290.8 mg, 2.88 mmol) in dichloromethane (10 mL) was cooled to −60° C., then the solution of methacryloyl chloride (55 mg, 0.53 mmol) in dichloromethane (1 mL) was added slowly, LC-MS was tracking, at the end of the reaction, 1 mL MeOH was added, the mixture was concentrated under vacuum to get 420 mg crude. The crude was purified by flash chromatography on silica gel with dichloromethane and methanol (25:1) to get product as a white solid (38 mg, 16%). $^{1}$H NMR (400 MHz, MeOD) δ 7.57-7.51 (m, 2H), 7.28-7.21 (m, 2H), 7.05-6.98 (m, 1H), 6.95-6.84 (m, 4H), 5.09 (s, 1H), 4.92 (s, 1H), 4.44 (d, J=12.3 Hz, 1H), 3.95 (dd, J=22.7, 13.7 Hz, 1H), 3.35-3.30 (m, 1H), 3.15-3.09 (m, 1H), 3.03 (d, J=11.5 Hz, 2H), 2.63-2.61 (m, 1H), 2.41-2.34 (m, 1H), 1.96-1.86 (m, 1H), 1.82 (s, 3H), 1.76-1.66 (m, 2H), 1.39-1.28 (m, 3H). MS (ESI, m/z): 486.3 [M+H]$^{+}$.

Example 5

8-(1-But-2-enoyl-piperidin-4-yl)-2-(4-phenoxy-phenyl)-5,6,7,8-tetrahydro-imidazo[1,2-b]pyridazine-3-carboxamide

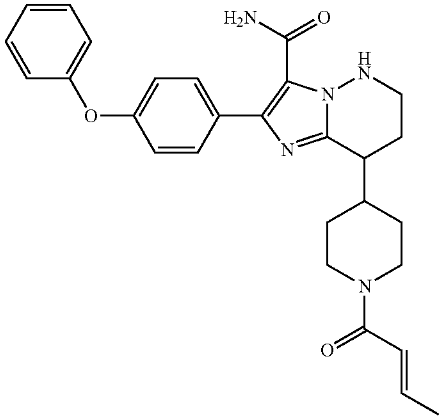 [SMILES: C/C=C/C(=O)N1CCC(C2CCNn3c2nc(-c2ccc(Oc4ccccc4)cc2)c3C(N)=O)CC1]

Preparation of (E)-8-(1-(but-2-enoyl)piperidin-4-yl)-2-(4-phenoxyphenyl)-5,6,7,8-tetrahydroimidazo[1,2-b]pyridazine-3-carboxamide

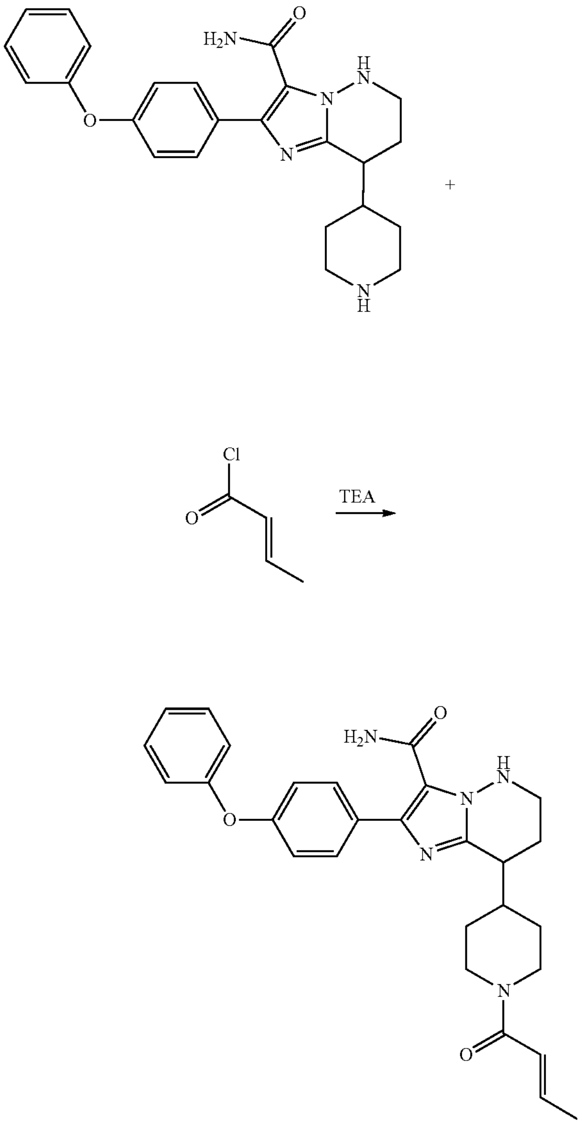

The mixture of the product of step P of example 1 (200.0 mg, 0.48 mmol) and triethylamine (290.8 mg, 2.88 mmol) in dichloromethane (10 mL) was cooled to −60° C., then the solution of (E)-but-2-enoyl chloride (55 mg, 0.53 mmol) in dichloromethane (1 mL) was added slowly, LC-MS was tracking, at the end of the reaction, 1 mL MeOH was added, the mixture was concentrated under vacuum to get crude product. The residue was purified by flash chromatography on silica gel with dichloromethane and methanol (25:1) to get product as a white solid (41 mg, 17.6%). $^{1}$H NMR (400 MHz, MeOD) δ 7.60-7.49 (m, 2H), 7.32-7.22 (m, 2H), 7.02 (t, J=7.4 Hz, 1H), 6.96-6.86 (m, 4H), 6.73-6.64 (m, 1H), 6.42-6.31 (m, 1H), 4.59-4.49 (m, 1H), 4.14-4.04 (m, 1H), 3.36-3.33 (m, 1H), 3.14 (t, J=11.3 Hz, 1H), 3.0-2.94 (m, 2H), 2.68-2.49 (m, 1H), 2.40 (s, 1H), 1.92 (d, J=4.6 Hz, 1H), 1.82-1.72 (m, 5H), 1.44-1.27 (m, 3H). MS (ESI, m/z): 486.3 [M+H]$^{+}$.

Example 6

(E)-8-(1-(pent-2-enoyl)piperidin-4-yl)-2-(4-phenoxyphenyl)-5,6,7,8-tetrahydroimidazo[1,2-b]pyridazine-3-carboxamide

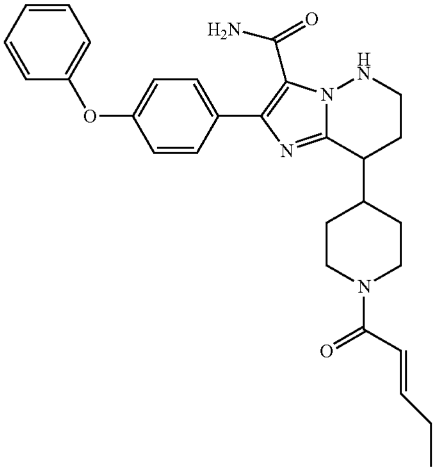 [SMILES: CC/C=C/C(=O)N1CCC(C2CCNn3c2nc(-c2ccc(Oc4ccccc4)cc2)c3C(N)=O)CC1]

Preparation of (E)-8-(1-(pent-2-enoyl)piperidin-4-yl)-2-(4-phenoxyphenyl)-5,6,7,8-tetrahydroimidazo[1,2-b]pyridazine-3-carboxamide

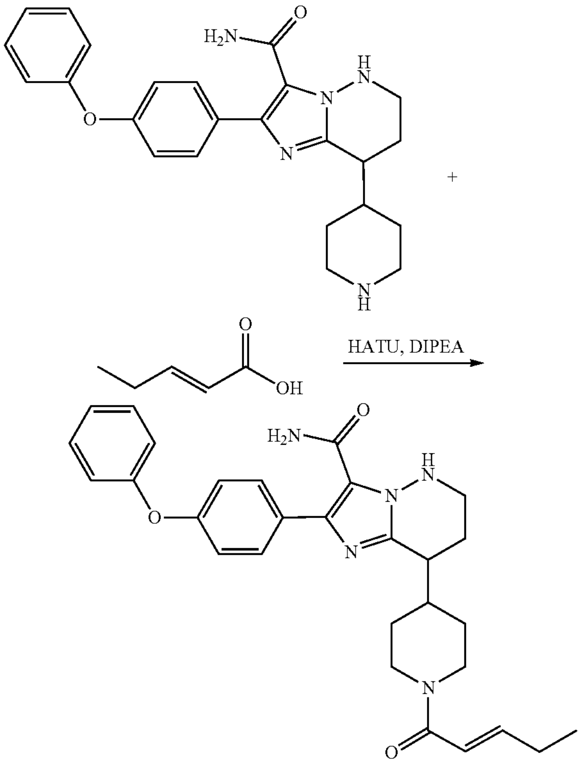

To the solution of the product (200.0 mg, 0.48 mmol) of step P of example 1 in dry N, N-dimethylformamide (10 mL) was added N, N-diisopropylethylamine (371.5 mg, 2.88 mmol). After 5 min, (E)-pent-2-enoic acid (34 mg, 0.34 mmol) and HATU (273 mg, 0.72 mmol) was added. The reaction mixture was continued to stir at room temperature for 2 hS. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give product as an off-white solid (32 mg, 22%). $^1$H NMR (400 MHz, MeOD) δ 7.54 (d, J=8.7 Hz, 2H), 7.30-7.22 (m, 2H), 7.02 (t, J=7.4 Hz, 1H), 6.97-6.85 (m, 4H), 6.74-6.67 (m, 1H), 6.35-6.28 (m, 1H), 4.60-4.50 (m, 1H), 4.14-4.01 (m, 1H), 3.37-3.32 (m, 1H), 3.19-3.11 (m, 1H), 3.10-2.93 (m, 2H), 2.70-2.49 (m, 1H), 2.40 (s, 1H), 2.15 (dd, J=12.3, 6.5 Hz, 2H), 1.92 (d, J=5.3 Hz, 1H), 1.76 (d, J=11.5 Hz, 2H), 1.45-1.27 (m, 3H), 0.98 (dd, J=11.1, 7.2 Hz, 3H). MS (ESI, m/z): 500.3 [M+H]$^+$.

Example 7

8-[1-(2-Cyano-4-methyl-pent-2-enoyl)-piperidin-4-yl]-2-(4-phenoxy-phenyl)-5,6,7,8-tetrahydro-imidazo[1,2-b]pyridazine-3-carboxamide

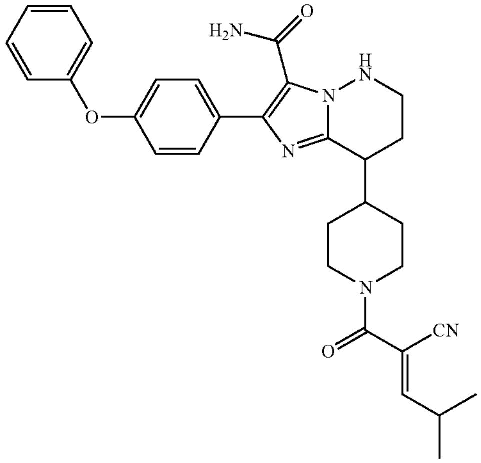 [SMILES: CC(C)/C=C(\C#N)C(=O)N1CCC(C2CCNn3c2nc(-c2ccc(Oc4ccccc4)cc2)c3C(N)=O)CC1]

Step A: Preparation of 8-(1-(2-cyanoacetyl)piperidin-4-yl)-2-(4-phenoxyphenyl)-5,6,7,8-tetrahydroimidazo[1,2-b]pyridazine-3-carboxamide

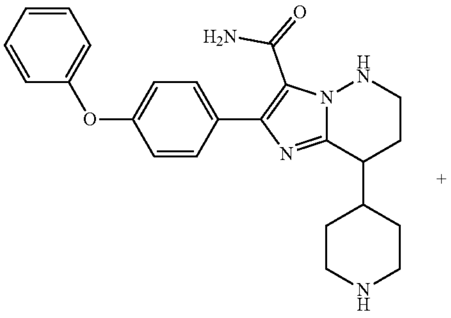

-continued

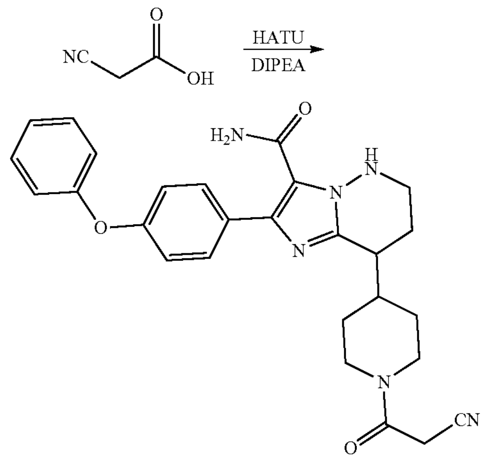

To the solution of 1.0 g (2.41 mmol) of the product of step P of example 1 in dry N, N-dimethylformamide (20 mL) was added N, N-diisopropylethylamine (1.8 g, 14.41 mmol). After 5 min, 2-cyanoacetic acid (244.5 mg, 2.87 mmol) and HATU (1.4 g, 3.61 mmol) was added. The reaction mixture was continued to stir at room temperature for 2 hs. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give product as an off-white solid (950 mg, crude).

Step B: Preparation of 8-[1-(2-cyano-4-methyl-pent-2-enoyl)-piperidin-4-yl]-2-(4-phenoxy-phenyl)-5,6,7,8-tetrahydro-imidazo[1,2-b]pyridazine-3-carboxamide

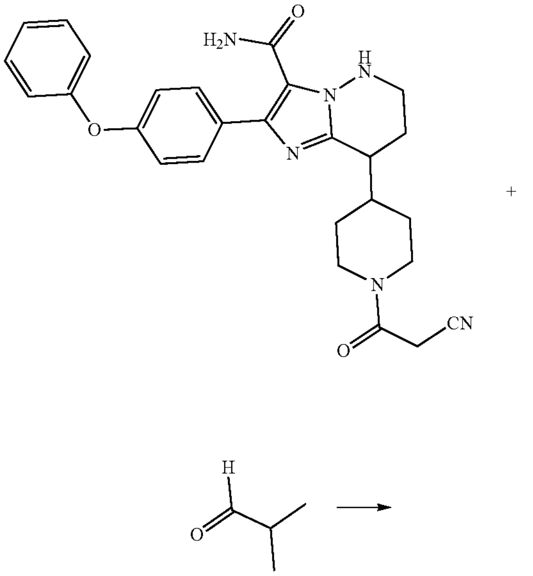

-continued

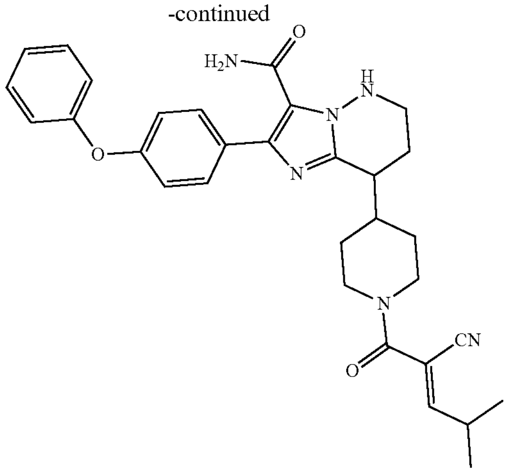

To the solution of isobutyraldehyde (29.7 mg, 0.41 mmol) in dry dichloromethane (10 mL) at 0° C. was added pyrrolidine (180 μL, 2.01 mmol) and then trimethyl chlorosilane (280 μL, 2.01 mmol). The ice bath was removed and the reaction mixture was stirred for 10 min followed by the additions of 200 mg (0.41 mmol) of the product of step A of example 7. The reaction solution was stirred for 1 h. Ethyl acetate and water was added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (27:1) to afford product as a white solid (45 mg, 20%). $^1$H NMR (400 MHz, MeOD) δ 7.60-7.50 (m, 2H), 7.31-7.21 (m, 2H), 7.02 (t, J=7.4 Hz, 1H), 6.96-6.85 (m, 4H), 6.70 (d, J=10.2 Hz, 1H), 4.41 (s, 1H), 3.99 (dd, J=19.5, 12.4 Hz, 1H), 3.38-3.32 (m, 1H), 3.19-3.02 (m, 3H), 2.41 (d, J=3.5 Hz, 1H), 2.00-1.89 (m, 1H), 1.76 (dd, J=10.1, 3.5 Hz, 2H), 1.42 (d, J=7.3 Hz, 3H), 1.30-1.24 (m, 1H), 1.04 (d, J=6.6 Hz, 6H). MS (ESI, m/z): 539.3 $[M+H]^+$.

Example 8

8-[1-(2-Cyano-3-cyclopropyl-acryloyl)-piperidin-4-yl]-2-(4-phenoxy-phenyl)-5,6,7,8-tetrahydro-imidazo[1,2-b]pyridazine-3-carboxamide

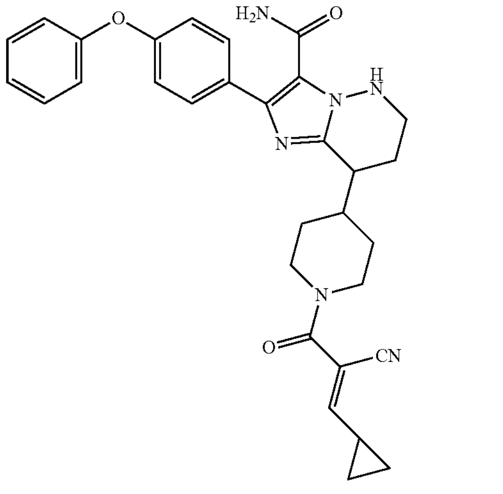 [SMILES: N#C/C(=C\C1CC1)C(=O)N1CCC(C2CCNn3c2nc(-c2ccc(Oc4ccccc4)cc2)c3C(N)=O)CC1]

Preparation of 8-[1-(2-cyano-3-cyclopropyl-acryloyl)-piperidin-4-yl]-2-(4-phenoxy-phenyl)-5,6,7,8-tetrahydro-imidazo[1,2-b]pyridazine-3-carboxamide

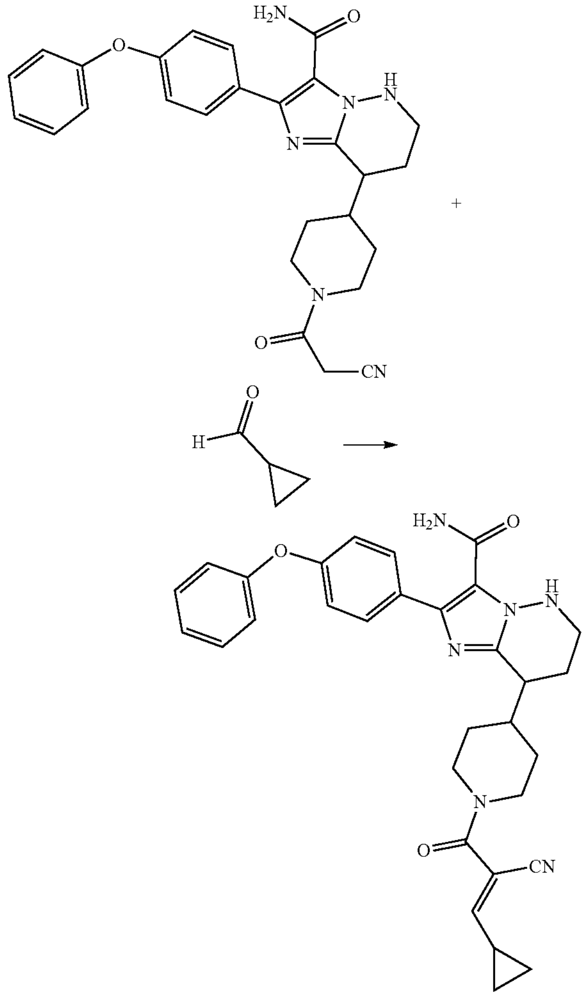

To the solution of cyclopropanecarbaldehyde (29.1 mg, 0.41 mmol) in dry dichloromethane (10 mL) at 0° C. was added pyrrolidine (180 μL, 2.01 mmol) and then trimethyl chlorosilane (280 μL, 2.01 mmol). The ice bath was removed and the reaction mixture was stirred for 10 min followed by the additions of the product (200 mg, 0.41 mmol) of step A of example 7. The reaction solution was stirred for 1 h. Ethyl acetate and water was added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (27:1) to afford product as a white solid (42 mg, 19%). $^1H$ NMR (400 MHz, MeOD) δ 7.58-7.50 (m, 2H), 7.26 (dd, J=10.7, 5.3 Hz, 2H), 7.05-6.98 (m, 1H), 6.96-6.85 (m, 4H), 6.39 (d, J=11.0 Hz, 1H), 4.49-4.47 (m, 1H), 4.19-3.85 (m, 1H), 3.33 (dd, J=9.6, 4.1 Hz, 1H), 3.19-2.96 (m, 3H), 2.80-2.59 (m, 1H), 2.40 (s, 1H), 2.03-1.86 (m, 2H), 1.82-1.67 (m, 2H), 1.50-1.30 (m, 3H), 1.11 (dd, J=7.7, 2.3 Hz, 2H), 0.85-0.72 (m, 2H). MS (ESI, m/z): 537.3 $[M+H]^+$.

Example 9

8-[1-(2-Fluoro-acryloyl)-piperidin-4-yl]-2-(4-phenoxy-phenyl)-5,6,7,8-tetrahydro-imidazo[1,2-b]pyridazine-3-carboxamide

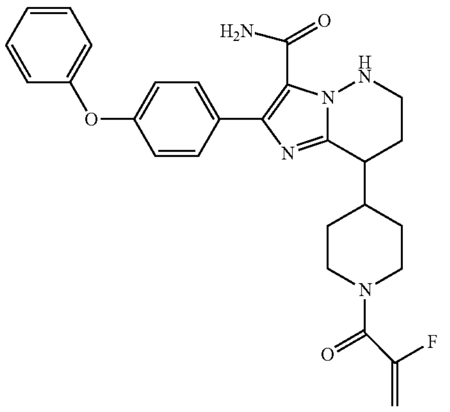 [SMILES: C=C(F)C(=O)N1CCC(C2CCNn3c2nc(-c2ccc(Oc4ccccc4)cc2)c3C(N)=O)CC1]

Preparation of 8-[1-(2-fluoro-acryloyl)-piperidin-4-yl]-2-(4-phenoxy-phenyl)-5,6,7,8-tetrahydro-imidazo[1,2-b]pyridazine-3-carboxamide

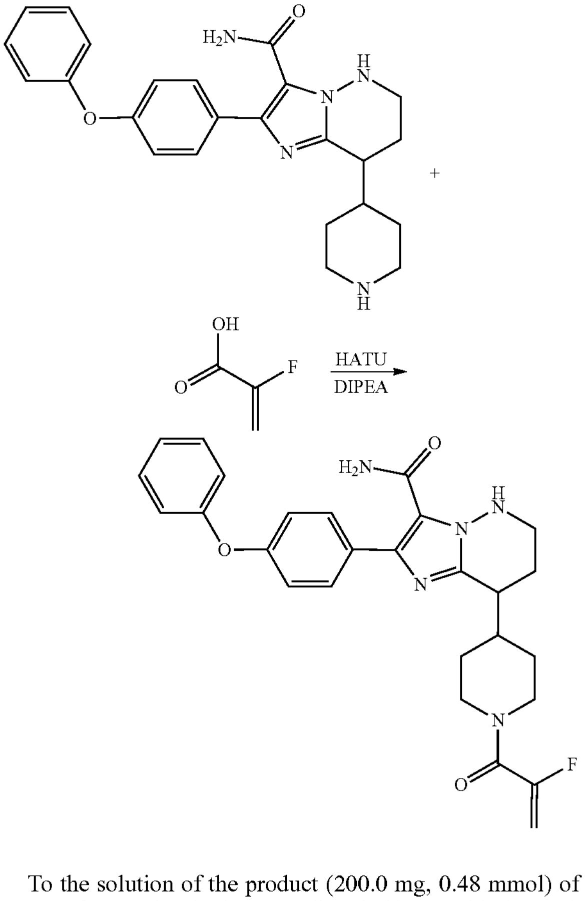

To the solution of the product (200.0 mg, 0.48 mmol) of step P of example 1 in dry N, N-dimethylformamide (10 mL) was added N, N-diisopropylethylamine (371.5 mg, 2.88 mmol). After 5 min, 2-fluoroacrylic acid (51.8 mg, 0.57 mmol) and HATU (273.1 mg, 0.72 mmol) was added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give product as an off-white solid (37 mg, 16%). $^1H$ NMR (400 MHz, MeOD) δ 7.59-7.49 (m, 2H), 7.30-7.20 (m, 2H), 7.01 (t, J=7.4 Hz, 1H), 6.96-6.84 (m, 4H), 5.09 (s, 1H), 5.05 (d, J=3.7 Hz, 1H), 4.97 (d, J=3.8 Hz, 1H), 4.40 (s, 1H), 3.99 (dd, J=14.3, 7.1 Hz, 1H), 3.32 (s, 1H), 3.13 (s, 3H), 2.80-2.55 (m, 1H), 2.45-2.38 (M, 1H), 1.93-1.90 (M, 1H), 1.82-1.66 (m, 2H), 1.52-1.25 (m, 4H). MS (ESI, m/z): 490.2 $[M+H]^+$.

Example 10

2-(4-Phenoxy-phenyl)-8-[1-(4,4,4-trifluoro-but-2-enoyl)-piperidin-4-yl]-5,6,7,8-tetrahydro-imidazo[1,2-b]pyridazine-3-carboxamide

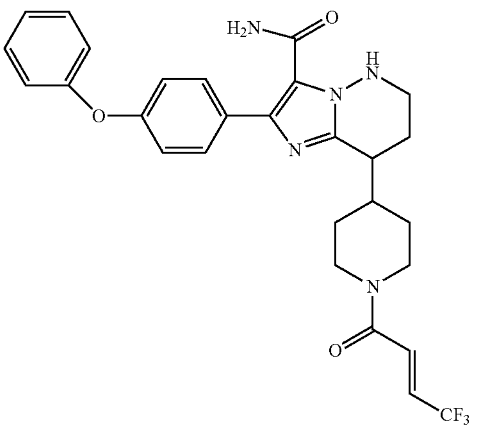 [SMILES: NC(=O)c1c(-c2ccc(Oc3ccccc3)cc2)nc2n1NCCC2C1CCN(C(=O)/C=C/C(F)(F)F)CC1]

Preparation of 2-(4-phenoxy-phenyl-8-[1-(4,4,4-trifluoro-but-2-enoyl)-piperidin-4-yl]-5,6,7,8-tetrahydro-imidazo[1,2-b]pyridazine-3-carboxamide

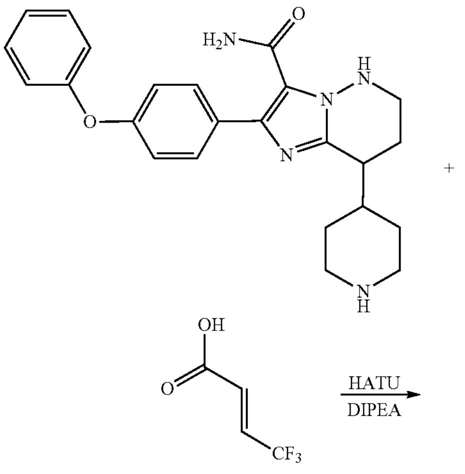

-continued

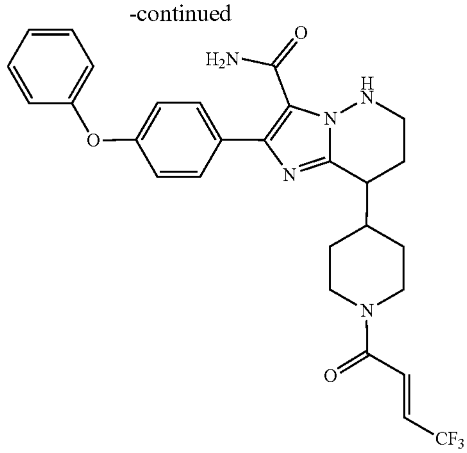

To the solution of the product (200.0 mg, 0.48 mmol) of step P of example 1 in dry N, N-dimethylformamide (10 mL) was added N, N-diisopropylethylamine (371.5 mg, 2.88 mmol). After 5 min, (E)-4,4,4-trifluorobut-2-enoic acid (80.5 mg, 0.57 mmol) and HATU (273.1 mg, 0.72 mmol) was added. The reaction mixture was continued to stir at room temperature for 2 hs. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give product as an off-white solid (54 mg, 21%). $^1H$ NM/R (400 MHz, MeOD) δ 7.58-7.50 (m, 2H), 7.29-7.21 (m, 2H), 7.20-7.11 (m, 1H), 7.05-6.97 (m, 1H), 6.94-6.84 (m, 4H), 6.62-6.51 (m, 1H), 4.53 (dd, J=25.1, 13.2 Hz, 1H), 3.98 (dd, J=24.9, 13.6 Hz, 1H), 3.34-3.29 (M, 1H), 3.14-2.88 (m, 3H), 2.71-2.53 (m, 1H), 2.42-2.36 (m, 1H), 2.00-1.85 (m, 1H), 1.83-1.66 (m, 2H), 1.47-1.26 (m, 3H). MS (ESI, m/z): 540.2 $[M+H]^+$.

10a

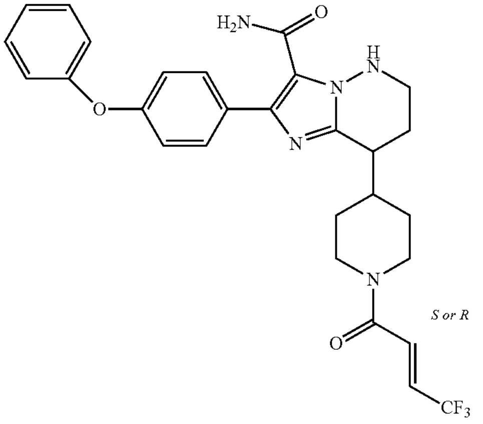

10a $^1H$ NMR (600 MHz, $CDCl_3$) δ 7.55 (t, J=8.4 Hz, 2H), 7.44 (d, J=22.0 Hz, 1H), 7.36 (t, J=7.7 Hz, 2H), 7.15 (t, J=7.4 Hz, 1H), 7.06 (dd, J=11.1, 8.3 Hz, 4H), 6.97 (t, J=14.1 Hz, 1H), 6.72-6.66 (m, 1H), 5.98 (s, 1H), 5.36 (s, 1H), 4.77-4.70 (m, 1H), 4.00-3.91 (m, 1H), 3.47 (dd, J=15.7, 8.2 Hz, 2H), 3.35 (t, J=11.2 Hz, 1H), 3.23-3.07 (m, 2H), 2.68 (q, J=13.2

Hz, 1H), 2.54 (dd, J=26.3, 13.5 Hz, 1H), 2.07 (s, 1H), 1.97-1.83 (m, 2H), 1.55-1.38 (m, 2H).

10b

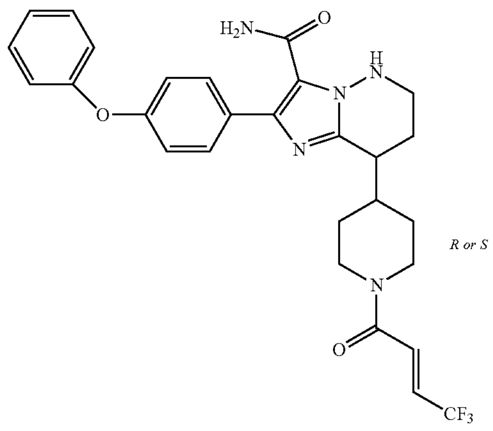

10b $^1$H NMR (600 MHz, $CDCl_3$) δ 7.55 (t, J=8.4 Hz, 2H), 7.45 (d, J=21.4 Hz, 1H), 7.37 (t, J=7.8 Hz, 2H), 7.15 (t, J=7.4 Hz, 1H), 7.06 (dd, J=11.6, 8.5 Hz, 4H), 6.96 (d, J=13.8 Hz, 1H), 6.74-6.65 (m, 1H), 5.97 (s, 1H), 5.35 (s, 1H), 4.77-4.70 (m, 1H), 4.00-3.91 (m, 1H), 3.47 (dd, J=16.4, 8.2 Hz, 2H), 3.35 (t, J=11.2 Hz, 1H), 3.19-3.10 (m, 2H), 2.68 (q, J=13.1 Hz, 1H), 2.63-2.45 (m, 1H), 2.07 (s, 1H), 1.99-1.79 (m, 2H), 1.56-1.39 (m, 2H).

Compound example 10 was separated into two enantiomeric stereoisomers compound 10a (peak 1, levoisomer, retention time at 7.8 min in chiral analysis), and compound 10b (peak 2, dextroisomer, retention time at 8.9 min in chiral analysis) by chiral prep-HPLC. The chiral separation conditions are shown below.

| | |
|---|---|
| Column | CHIRALCEL AS-H |
| Column size | 250 × 4.6 mm |
| Injection | 10 μL |
| Mobile phase | MeOH/$CH_3CN$ = 60/40 |
| Flow rate | 1 mL/min |
| Wave length | UV 254 nm |
| Tempetature | 35° C. |
| Sample solution | 5 mg/mL |

The chiral analysis condition is shown below.

| | |
|---|---|
| Column | CHIRALPAK AD-H |
| Column size | 250 × 10 mm |
| Injection | 50 μL |
| Mobile phase | MeOH/$CH_3CN$ = 60/40 |
| Flow rate | 2.5 mL/min |
| Wave length | UV 254 nm |

The specific rotation of compound 10a and compound 10b was measured by polarimeter.

Specific rotation measurement conditions are shown below.

-continued

| | |
|---|---|
| Polarimeter | IP-digi300FD |
| Sample solution | 20 mg/ml |
| Solvent | Methanol |
| Tempetature | 20° C. |

Specific rotation results are shown below.

| Sample number | Specific rotation |
|---|---|
| 10a | −129.85 |
| 10b | 105.29 |

Example 11

2-(4-phenoxyphenyl)-8-(1-propioloylpiperidin-4-yl)-5,6,7,8-tetrahydroimidazo[1,2-b]pyridazine-3-carboxamide

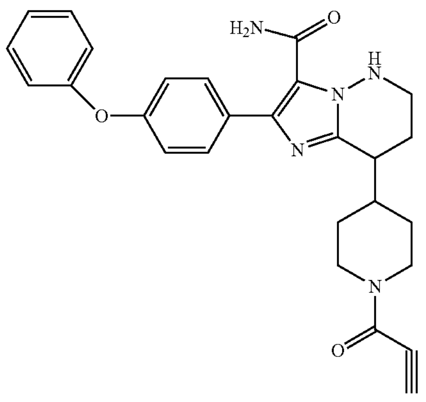 [SMILES: C#CC(=O)N1CCC(C2CCNn3c2nc(-c2ccc(Oc4ccccc4)cc2)c3C(N)=O)CC1]

Preparation of 2-(4-phenoxyphenyl)-8-(1-propioloylpiperidin-4-yl)-5,6,7,8-tetrahydroimidazo[1,2-b]pyridazine-3-carboxamide

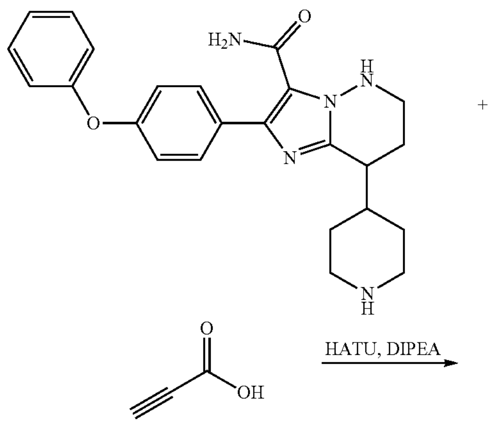

-continued

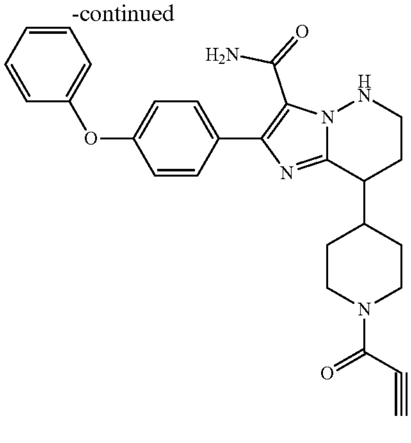

To the solution of the product (200.0 mg, 0.48 mmol) of step P of example 1 in dry N, N-dimethylformamide (10 mL) was added N, N-diisopropylethylamine (371.5 mg, 2.88 mmol). After 5 min, propiolic acid (167.3 mg, 0.57 mmol) and HATU (273 mg, 0.72 mmol) was added. The reaction mixture was continued to stir at room temperature for 2 hs. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give product as an off-white solid (54 mg, 23%). $^1H$ NMR (600 MHz, MeOD) δ 7.64 (d, J=8.2 Hz, 2H), 7.36 (t, J=7.6 Hz, 2H), 7.13 (t, J=7.4 Hz, 1H), 7.01 (dd, J=17.4, 8.1 Hz, 4H), 4.62-4.42 (m, 2H), 3.97 (d, J=10.9 Hz, 1H), 3.46 (d, J=13.8 Hz, 1H), 3.28-3.14 (m, 3H), 2.79-2.67 (m, 1H), 2.50 (s, 1H), 2.04 (d, J=10.5 Hz, 1H), 1.93-1.80 (m, 2H), 1.55 (d, J=12.0 Hz, 1H), 1.52-1.31 (m, 2H). MS (ESI, m/z): 470.2 $[M+H]^+$.

Examples 12

8-(1-acryloylpiperidin-4-yl)-2-(4-(4-fluorophenoxy)phenyl)-5,6,7,8-tetrahydroimidazo[1,2-b]pyridazine-3-carboxamide

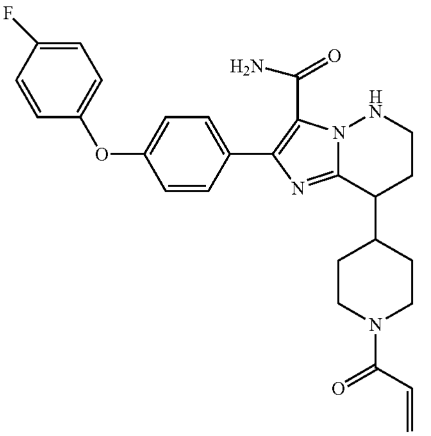 [SMILES: C=CC(=O)N1CCC(C2CCNn3c2nc(-c2ccc(Oc4ccc(F)cc4)cc2)c3C(N)=O)CC1]

Step A: Preparation of methyl 3-(4-(4-fluorophenoxy)phenyl)-3-oxopropanoate

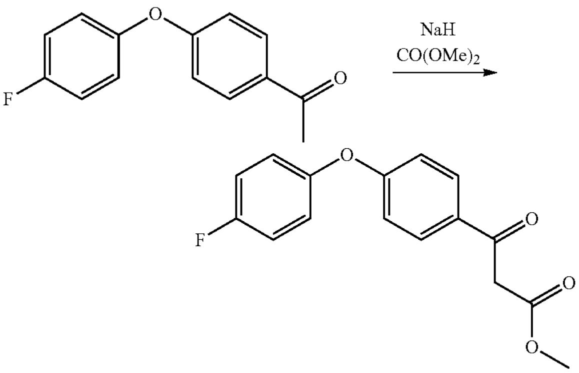

To a stirred suspension of NaH (60% dispersion in mineral oil; 469.0 g, 11.73 mol) in N, N-dimethylformamide (3 L) at 0° C. was added dropwise 1-(4-(4-fluorophenoxy)phenyl)ethan-1-one (1.8 kg, 7.82 mol) dissolved in N, N-dimethylformamide (2 L). After 30 minutes, the mixture was cooled to 0° C. and dimethylcarbonate (3.5 kg, 39.01 mol) was added. The mixture was allowed to warm to room temperature over a 2-hour period and then poured into water/saturated sodium bicarbonate (1:1). The aqueous layer was extracted with ethyl acetate, and 1 mol/L cooled glacial acetic acid was added dropwise until pH 6-7. The residue was extracted with ethyl acetate (3×1500 mL), the combined organic layer was washed with saturated brine, dried over anhydrous $Na_2SO_4$, filtered and concentrated. The residue was purified by chromatography with petroleum ether and ethyl acetate (12:1) to afford product as a yellow oil (2.1 kg, 93%). $^1H$ NMR (400 MHz, DMSO-d6) δ 7.99 (d, J=8.9 Hz, 2H), 7.34-7.28 (m, 2H), 7.24-7.18 (m, 2H), 7.07-7.02 (m, 2H), 4.17 (s, 2H), 3.66 (s, 3H). MS (ESI, m/z): 289.1 $[M+H]^+$.

Step B: Preparation of methyl 2-bromo-3-(4-(4-fluorophenoxy)phenyl)-3-oxopropanoate

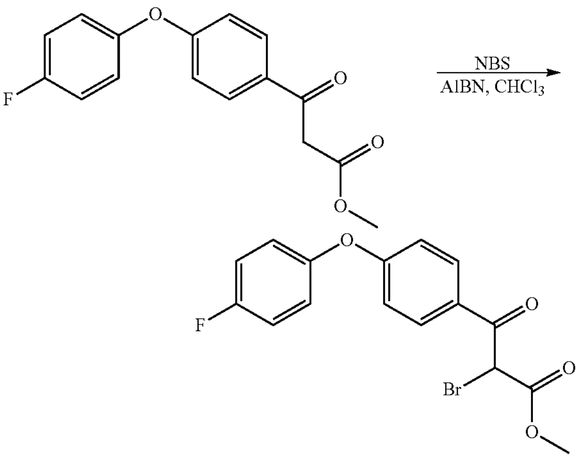

To a solution of the product of step A of example 12 (1.0 kg, 3.47 mol) in $CHCl_3$ (5 L) was added N-bromosuccinimide (217.0 g, 3.82 mol) and azobisisobutyronitrile (284.8 g, 1.73 mol). The reaction mixture was refluxing for 6 hs. Then the $CHCl_3$ was evaporated. The residue was diluted with 100 mL ethyl acetate. The mixture was washed with aqueous 5% HCl (2×1000 mL) and 500 mL water and then dried over anhydrous sodium sulfate. Evaporation of the solvent gave the crude product as oil, the crude residue was flash chromatographed with ethyl acetate and petroleum ether (1:10) to get the product as yellow oil (1.0 kg, 78%). $^1$H NMR (600 MHz, $CDCl_3$) δ 7.97 (d, J=7.8 Hz, 2H), 7.13-7.09 (m, 2H), 7.08-7.04 (m, 2H), 6.98 (d, J=7.8 Hz, 2H), 5.63 (s, 1H), 3.83 (s, 3H). MS (ESI, m/z): 367.9 $[M+H]^+$.

Step C: Preparation of tert-butyl 4-(4-(4-(4-fluoro-phenoxy)benzoyl)-11,11,12,12-tetramethyl-3,6-di-oxo-2,5,10-trioxa-11-silatridecan-7-yl)piperidine-1-carboxylate

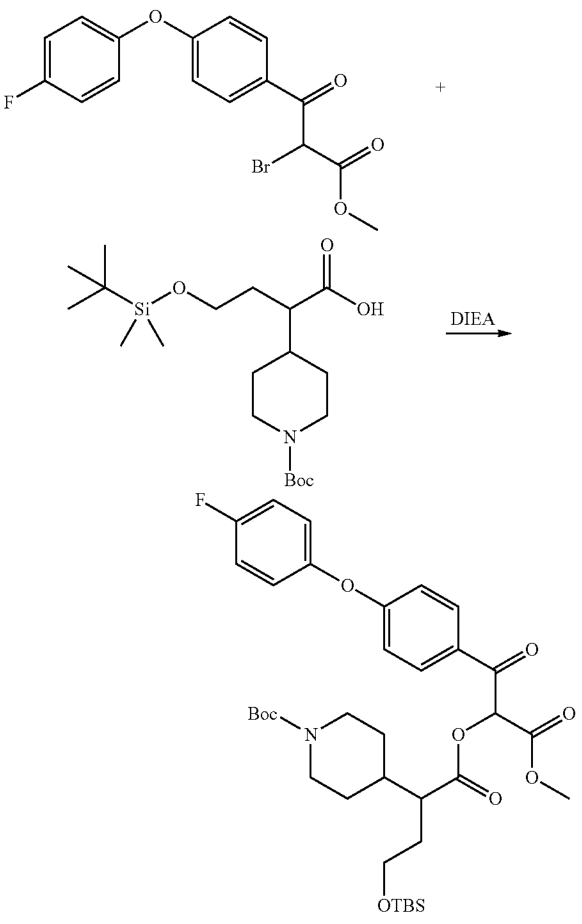

To a solution of the product of step G of example 1 (39.4 g, 98.05 mmol) and N, N-diisopropylethylamine (15.8 g, 122.56 mmol) in acetonitrile (500 ml) was added the product of step B of example 12 (30.0 g, 81.71 mmol). The mixture was stirred at 30° C. for 3 hs. The solvent was removed by rotorary evaporation and the residue taken up methyl acetate, washed with 0.1 N HCl, and brine. The organic fractions were dried over anhydrous $Na_2SO_4$, filtered, and concentrated under reduced pressure to give the crude product which was purified via flash chromatography eluting with ethyl acetate and petroleum ether (1:10) to give the product as a clear colorless oil (46 g, 81.8%). $^1$H NMR (400 MHz, $CDCl_3$) δ 8.00-7.91 (m, 2H), 7.12-7.02 (m, 4H), 6.95 (d, J=8.9 Hz, 2H), 6.23 (s, 1H), 4.16-4.02 (m, 2H), 3.76 (s, 3H), 3.68-3.58 (m, 1H), 3.58-3.48 (m, 1H), 2.70-2.51 (m, 3H), 1.90-1.78 (m, 2H), 1.74-1.65 (m, 1H), 1.61 (d, J=8.5 Hz, 2H), 1.43 (d, J=1.4 Hz, 9H), 1.28-1.21 (m, 2H), 0.83 (d, J=13.4 Hz, 9H), 0-(−0.05) (m, 6H). MS (ESI, m/z): 574.2 $[M+H]^+$.

Step D: Preparation of tert-butyl 4-(3-((tert-butyldi-methylsilyl)oxy)-1-(4-(4-(4-fluorophenoxy)phenyl)-5-(methoxycarbonyl)-1H-imidazol-2-yl)propyl)pip-eridine-1-carboxylate

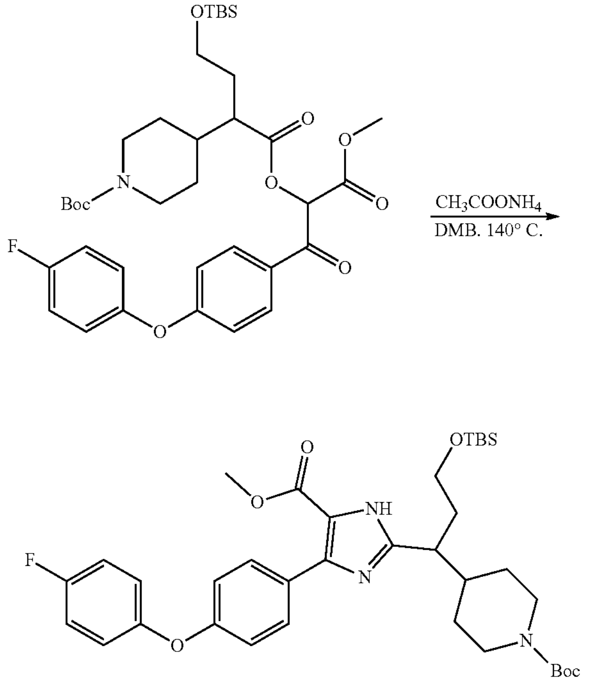

To a slurry of ammonium acetate (49.7 g, 1.72 mol) in xylenes (150 mL) was added the product of step C of example 12 (36.0 g, 52.33 mmol). The mixture was stirred at 140° C. for 4 hs. The solution was cooled to room temperature and the solvent was evaporated. The residue was dissolved in EA and washed with saturated brine. The organic phase was dried over anhydrous $Na_2SO_4$, filtered and concentrated. The residue was purified by silica gel column chromatography with ethyl acetate and petroleum ether (1:5) to give the product as a clear colorless oil (14 g, 33%). $^1$H NMR (600 MHz, $CDCl_3$) δ 10.06 (s, 1H), 7.88 (d, J=6.7 Hz, 2H), 7.02-6.97 (m, 6H), 4.11-4.04 (m, 2H), 3.81 (s, 3H), 3.64-3.60 (m, 1H), 2.80 (s, 1H), 2.64 (s, 2H), 2.02-1.95 (m, 4H), 1.83 (d, J=12.0 Hz, 1H), 1.66 (s, 1H), 1.42 (s, 9H), 1.16 (d, J=9.3 Hz, 2H), 0.86 (s, 9H), 0.00 (s, 6H). MS (ESI, m/z): 668.4 $[M+H]^+$.

Step E: Preparation of tert-butyl 4-(1-(1-amino-4-(4-(4-fluorophenoxy)phenyl)-5-(methoxycarbonyl)-1H-imidazol-2-yl)-3-((tert-butyldimethylsilyl)oxy)propyl)piperidine-1-carboxylate

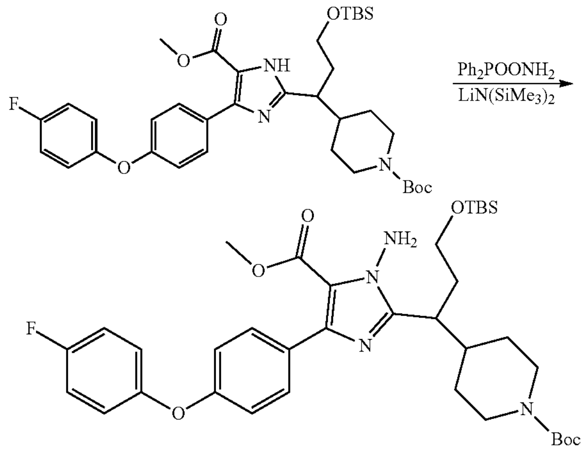

Lithium hexamethyldisilazane (18 mL of a 1 M solution in tetrahydrofuran, 17.97 mmol) was slowly added to the product of step D of example 12 (8.0 g, 11.98 mmol) in anhydrous N, N-dimethylformamide (100 mL) at 0° C. After the mixture was stirred for 30 min, O-(diphenylphosphinyl) hydroxylamine (5.6 g, 23.96 mmol) was added at 0° C., followed by stirring at room temperature for 4 hs (in cases where the reaction mixture became too viscous, additional N, N-dimethylformamide was added). The reaction was quenched with water until a clear solution was formed and concentrated to dryness under reduced pressure. The residue was washed several times with ethyl acetate or dichloromethane. The combined organic fractions were concentrated in vacuo and purified by flash chromatography on silica gel with ethyl acetate and petroleum ether (1:3) to give the product as a clear colorless oil (6.4 g, 78%). $^1H$ NMR (600 MHz, $CDCl_3$) δ 7.60 (d, J=7.9 Hz, 2H), 7.04-6.98 (m, 4H), 6.96 (d, J=7.9 Hz, 2H), 5.58 (s, 2H), 4.18-3.95 (m, 2H), 3.77 (s, 3H), 3.66-3.56 (m, 1H), 3.34 (d, J=6.3 Hz, 2H), 2.72-2.57 (m, 2H), 2.04-1.99 (m, 2H), 1.98-1.88 (m, 2H), 1.43 (s, 9H), 1.38-1.34 (m, 1H), 1.27-1.16 (m, 2H), 0.85 (s, 9H), −0.01 (d, J=17.7 Hz, 6H). MS (ESI, m/z): 683.4 $[M+H]^+$.

Step F: Preparation of tert-butyl 4-(1-(1-amino-4-(4-(4-fluorophenoxy)phenyl)-5-(methoxycarbonyl)-1H-imidazol-2-yl)-3-hydroxypropyl)piperidine-1-carboxylate

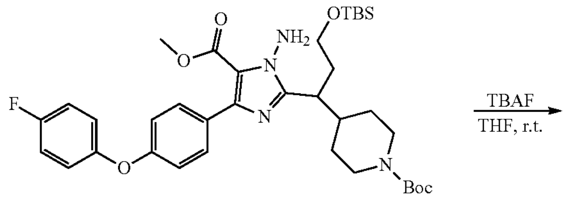

-continued

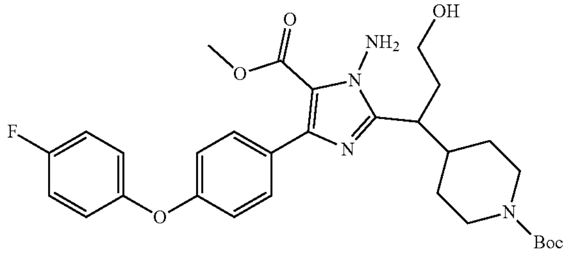

To a solution of the product of step E of example 12 (6.4 g, 9.37 mmol) in tetrahydrofuran (50 mL) was added a 1 M solution of tetrabutylammonium fluoride in tetrahydrofuran (14 mL, 14.05 mmol) at RT. The solution was stirred for 2 hs and diluted with 100 mL ethyl acetate solution. The organic layer was separated and washed with $H_2O$ (3×200 mL). The water extract was washed with ethyl acetate solution (2×150 mL), and the organic layers were combined and dried over anhydrous $Na_2SO_4$. The solvent was evaporated in vacuo, and purified by flash chromatography on silica gel with dichloromethane and methanol (35:1) to give the product as a clear colorless oil (5.1 g, 95%). $^1H$ NMR (600 MHz, $CDCl_3$) δ 7.61 (d, J=7.9 Hz, 2H), 7.06-6.99 (m, 4H), 6.97 (d, J=7.8 Hz, 2H), 5.52 (s, 2H), 4.20-3.98 (m, 2H), 3.79 (s, 3H), 3.68-3.60 (m, 1H), 3.50-3.42 (m, 1H), 3.36-3.30 (m, 1H), 2.76-2.58 (m, 2H), 2.11-1.98 (m, 3H), 1.94-1.86 (m, 1H), 1.63 (s, 1H), 1.44 (s, 9H), 1.35-1.30 (m, 1H), 1.26-1.16 (m, 2H). MS (ESI, m/z): 569.3 $[M+H]^+$.

Step G: Preparation of methyl 8-(1-(tert-butoxycarbonyl)piperidin-4-yl)-2-(4-(4-fluorophenoxy)phenyl)-5,6,7,8-tetrahydroimidazo[1,2-b]pyridazine-3-carboxylate

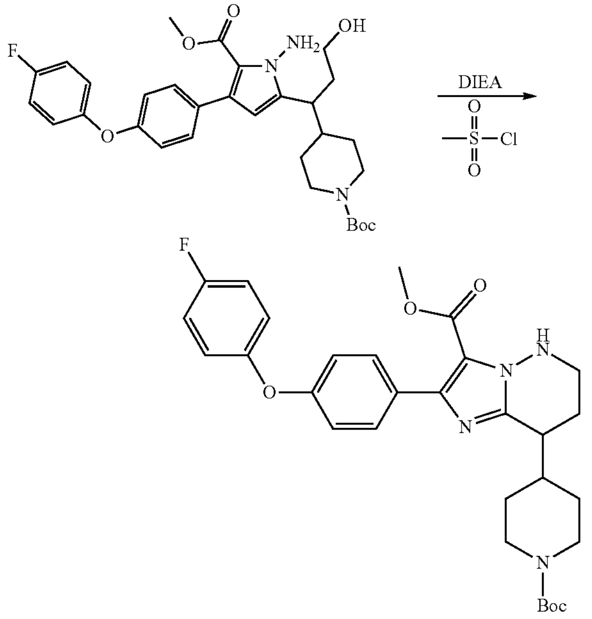

Methanesulfonyl chloride (1.3 g, 11.43 mmol) was added via syringe into a stirred mixture of the product of step F of example 12 (5.0 g, 8.79 mmol) and N, N-diisopropylethylamine (3.4 g, 26.38 mmol) in dichloromethane (100 ml)

maintained at 0° C. Then the mixture was stirred at room temperature overnight (TLC monitoring) and then partitioned between dichloromethane and water. The organic phase was dried and evaporated to afford a white solid. The crude intermediate was dissolved in tetrahydrofuran (20 mL), 1 M solution of tetrabutylammonium fluoride in tetrahydrofuran (11 mL, 11.48 mmol) and N, N-diisopropylethylamine (2.0 g, 15.31 mmol) was added to the mixture, which was stirred 3 hs, then partitioned between dichloromethane and water. The organic phase was dried and evaporated to afford a white solid, then passed through a column of silica gel with dichloromethane and methanol (30:1) to afford the desired product as a colorless oil (3.5 g, 72%). $^1$H NMR (600 MHz, $CDCl_3$) δ 7.65-7.61 (m, 2H), 7.06-7.01 (m, 4H), 6.99-6.95 (m, 2H), 4.17 (s, 2H), 3.78 (s, 3H), 3.51-3.43 (m, 1H), 3.38-3.32 (m, 1H), 3.11 (s, 1H), 2.71 (s, 2H), 2.42 (s, 1H), 2.10-2.02 (m, 1H), 1.98-1.90 (m, 1H), 1.77-1.71 (m, 1H), 1.45 (s, 9H), 1.42-1.24 (m, 3H). MS (ESI, m/z): 551.3 $[M+H]^+$.

Step H: Preparation of tert-butyl 4-(3-carbamoyl-2-(4-(4-fluorophenoxy)phenyl)-5,6,7,8-tetrahydroimidazo[1,2-b]pyridazin-8-yl)piperidine-1-carboxylate

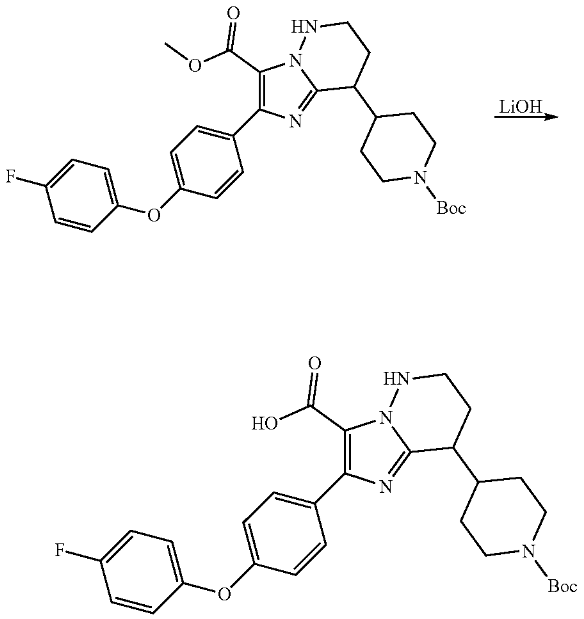

To a solution of the product of step G of example 12 (3.4 g, 6.17 mmol) in tetrahydrofuran (20 mL) was added LiOH (739.3 mg, 30.87 mmol) in water (5 mL), the mixture was heated at 50° C. for 3 hs, then cooled to r.t. The mixture acidified to pH 3-4 with concentrated HCl and then extracted with 3×100 mL of dichloromethane. The organic phase was washed with saturated brine and then dried over anhydrous $Na_2SO_4$. The organic phase was concentrated in vacuo to afford 3.7 g crude product. The residue was used to next step without further purification.

Step I: Preparation of 8-(1-(tert-butoxycarbonyl)piperidin-4-yl)-2-(4-(4-fluorophenoxy)phenyl)-5,6,7,8-tetrahydroimidazo[1,2-b]pyridazine-3-carboxylic Acid

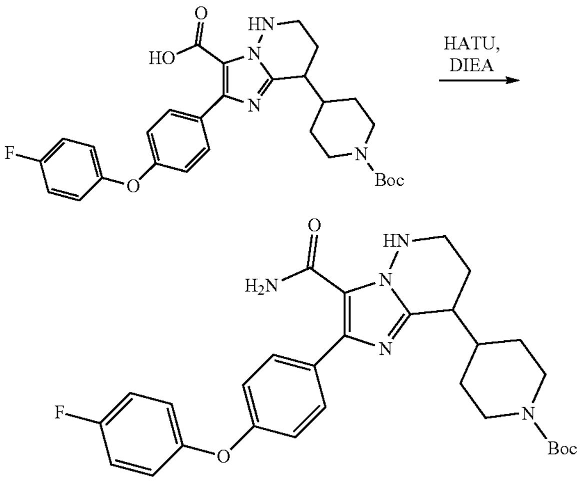

To the solution of the product of step H of example 12 (3.5 g, 6.52 mmol) in dichloromethane (30 mL) was added N, N-diisopropylethylamine (3.4 g, 26.09 mmol). After 5 min, $NH_4Cl$ (1.4 g, 26.09 mmol) and HATU (3.72 g, 9.78 mmol) was added. The reaction mixture was continued to stir at room temperature for 2 hs. Dichloromethane and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (40:1) to give product as an off-white solid (2.3 g, 65%). $^1$H NMR (400 MHz, $CDCl_3$) δ 7.59-7.55 (m, 2H), 7.26 (s, 1H), 7.07-7.00 (m, 6H), 6.09 (s, 1H), 5.42 (s, 1H), 4.17 (s, 2H), 3.50-3.41 (m, 1H), 3.39-3.29 (m, 1H), 3.15-3.06 (m, 1H), 2.76-2.64 (m, 2H), 2.44-2.34 (m, 1H), 2.11-2.02 (m, 1H), 1.99-1.87 (m, 1H), 1.76-1.68 (m, 2H), 1.45 (s, 9H), 1.42-1.25 (m, 2H). MS (ESI, m/z): 536.3 $[M+H]^+$.

Step J: Preparation of 2-(4-(4-fluorophenoxy)phenyl)-8-(piperidin-4-yl)-5,6,7,8-tetrahydroimidazo[1,2-b]pyridazine-3-carboxamide

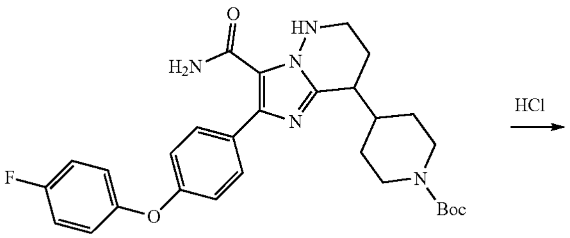

-continued

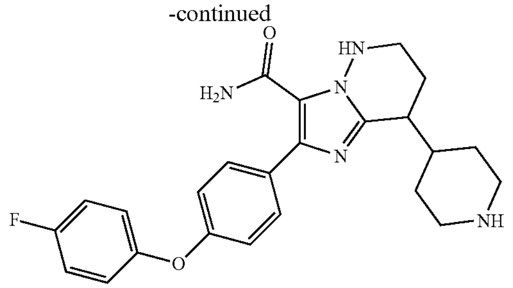

To a solution of the product of step I of example 12 (2.3 g, 4.29 mmol) in EtOH 15 mL) was added 33% HCl/EtOH (10 mL) at room temperature in reaction still. The mixture was stirred for 3 hs. the mixture was concentrated under vacuum to get 3.5 g crude product. The residue was used to next step without further purification. MS (ESI, m/z): 436.2 $[M+H]^+$.

Step K: Preparation of 8-(1-acryloylpiperidin-4-yl)-2-(4-(4-fluorophenoxy)phenyl)-5,6,7,8-tetrahydro-imidazo[1,2-b]pyridazine-3-carboxamide

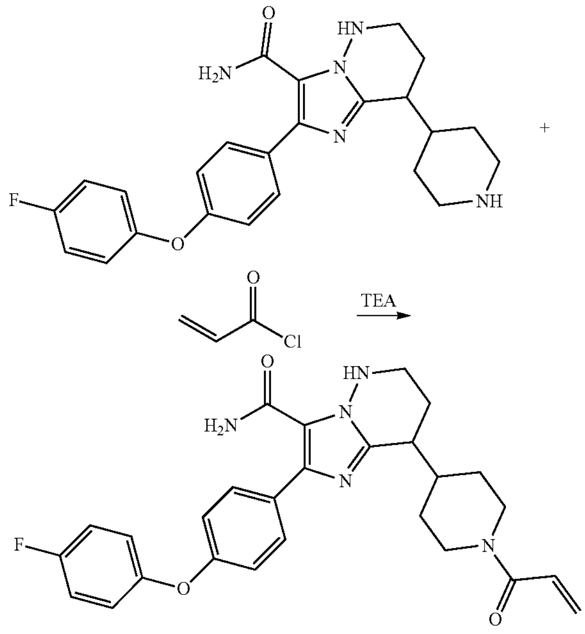

The mixture of the product of step J of example 12 (200.0 mg, 0.46 mmol) and triethylamine (278.7 mg, 2.76 mmol) in dichloromethane (5 mL) was cooled to −60° C. Then the solution of propenoyl chloride (45.0 mg, 0.51 mmol) in dichloromethane (3 mL) was added slowly, LC-MS was tracking, at the end of the reaction, 1 mL MeOH was added, the mixture was concentrated under vacuum to get 700 mg crude, and purified by flash chromatography on silica gel with dichloromethane and methanol (40:1) to get product as a white solid (41 mg, 30%). $^1$H NMR (400 MHz, MeOD) δ 7.54 (d, J=8.4 Hz, 2H), 7.05-6.92 (m, 4H), 6.86 (d, J=8.7 Hz, 2H), 6.71-6.61 (m, 1H), 6.10-6.03 (m, 1H), 5.65-5.58 (m, 1H), 4.60-4.51 (m, 1H), 4.12-4.03 (m, 1H), 3.37-3.31 (m, 1H), 3.19-2.97 (m, 3H), 2.70-2.52 (m, 1H), 2.46-2.34 (m, 1H), 1.91 (d, J=4.4 Hz, 1H), 1.78-1.72 (m, 2H), 1.42-1.30 (m, 3H). MS (ESI, m/z): 490.2 $[M+H]^+$.

Example 13

8-(1-(but-2-ynoyl)piperidin-4-yl)-2-(4-(4-fluorophenoxy)phenyl)-5,6,7,8-tetrahydroimidazo[1,2-b]pyridazine-3-carboxamide

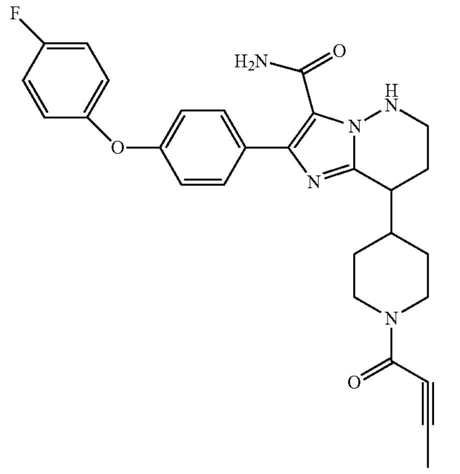 [SMILES: CC#CC(=O)N1CCC(C2CCNn3c2nc(-c2ccc(Oc4ccc(F)cc4)cc2)c3C(N)=O)CC1]

Preparation of 8-(1-(but-2-ynoyl)piperidin-4-yl)-2-(4-(4-fluorophenoxy)phenyl)-5,6,7,8-tetrahydroimidazo[1,2-b]pyridazine-3-carboxamide

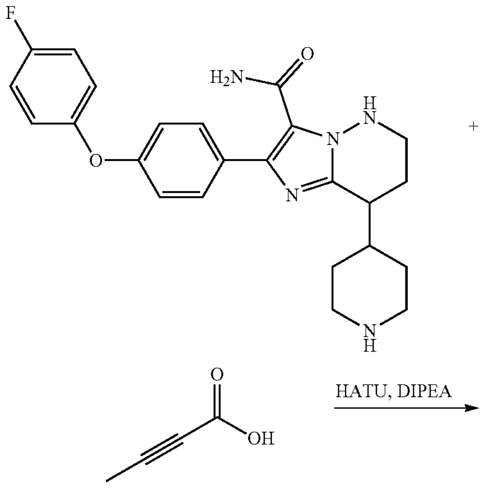

-continued

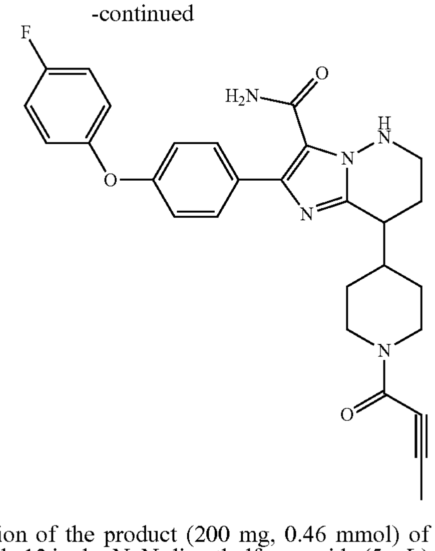

To the solution of the product (200 mg, 0.46 mmol) of step J of example 12 in dry N, N-dimethylformamide (5 mL) was added N, N-diisopropylethylamine (356.0 mg, 2.76 mmol). After 5 min, but-2-ynoic acid (46.3 mg, 0.55 mmol) and HATU (262.2 mg, 0.69 mmol) was added. The reaction mixture was continued to stir at room temperature for 2 hs. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give product as an off-white solid (56 mg, 24%). $^1H$ NMR (400 MHz, DMSO-d6) δ 7.89 (s, 1H), 7.83-7.76 (m, 2H), 7.46 (s, 1H), 7.27-7.21 (m, 2H), 7.12-7.06 (m, 2H), 6.96 (d, J=8.7 Hz, 2H), 6.55 (d, J=9.6 Hz, 1H), 4.42-4.25 (m, 2H), 3.16-3.08 (m, 2H), 3.03 (d, J=9.3 Hz, 1H), 2.70-2.56 (m, 1H), 2.27 (s, 1H), 2.01 (d, J=4.6 Hz, 3H), 1.97-1.84 (m, 2H), 1.75-1.64 (m, 1H), 1.51-1.43 (m, 1H), 1.34-1.21 (m, 3H). MS (ESI, m/z): 502.2 $[M+H]^+$.

Example 14

(E)-2-(4-(4-fluorophenoxy)phenyl)-8-(1-(4,4,4-trifluorobut-2-enoyl)piperidin-4-yl)-5,6,7,8-tetrahydroimidazo[1,2-b]pyridazine-3-carboxamide

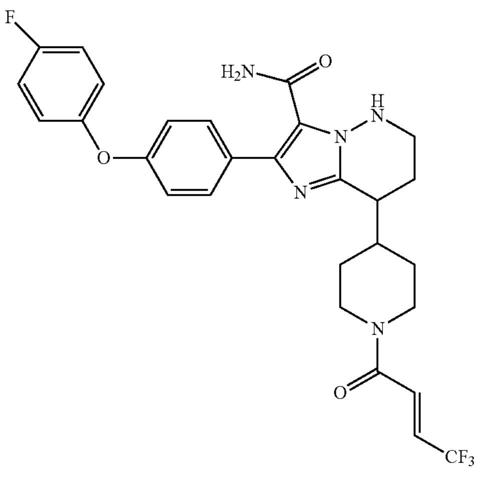 [SMILES: NC(=O)c1c(-c2ccc(Oc3ccc(F)cc3)cc2)nc2n1NCCC2C1CCN(C(=O)/C=C/C(F)(F)F)CC1]

Preparation of (E)-2-(4-(4-fluorophenoxy)phenyl)-8-(1-(4,4,4-trifluorobut-2-enoyl)piperidin-4-yl)-5,6,7,8-tetrahydroimidazo[1,2-b]pyridazine-3-carboxamide

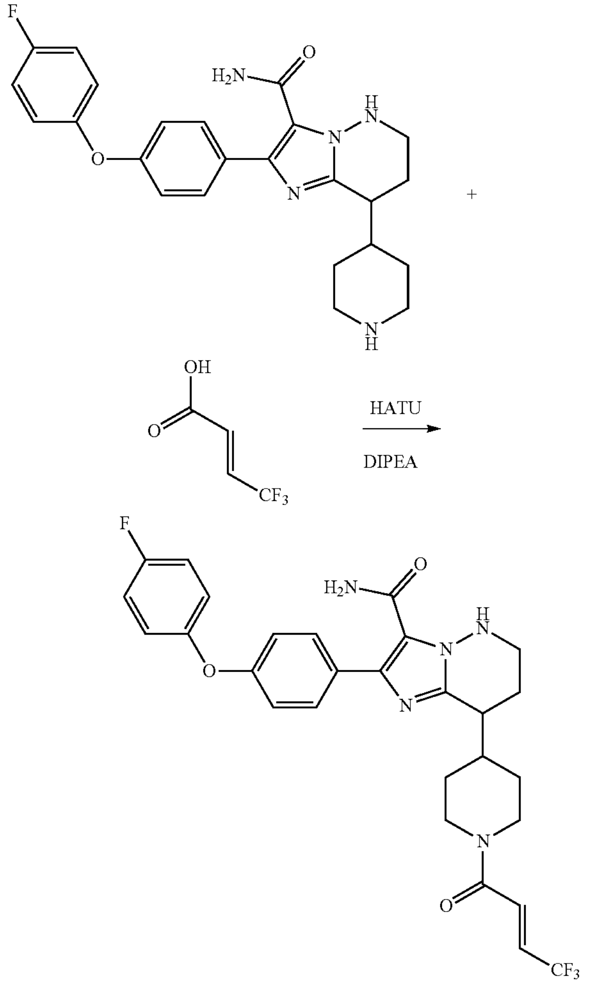

To the solution of the product of step J of example 12 (200 mg, 0.46 mmol) in dry N, N-dimethylformamide (5 mL) was added N, N-diisopropylethylamine (356.0 mg, 2.76 mmol). After 5 min, (E)-4,4,4-trifluorobut-2-enoic acid (83.6 mg, 0.60 mmol) and HATU (262.2 mg, 0.69 mmol) was added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give product as an off-white solid (56 mg, 24%). $^1H$ NMR (400 MHz, $CDCl_3$) δ 7.58-7.55 (m, 2H), 7.28-7.22 (m, 1H), 7.06-6.96 (m, 6H), 6.72-6.64 (m, 1H), 6.16 (s, 1H), 5.58 (s, 1H), 4.82-4.65 (m, 1H), 4.06-3.98 (m, 1H), 3.40 (s, 1H), 3.39-3.29 (m, 1H), 3.18-3.08 (m, 2H), 2.74-2.61 (m, 1H), 2.59-2.45 (m, 1H), 2.12-2.02 (m, 1H), 1.98-1.76 (m, 3H), 1.65-1.57 (m, 1H), 1.55-1.41 (m, 2H). MS (ESI, m/z): 558.2 $[M+H]^+$.

Example 15

8-(1-acryloylpiperidin-4-yl)-2-(4-(4-methoxyphenoxy)phenyl)-5,6,7,8-tetrahydroimidazo[1,2-b]pyridazine-3-carboxamide

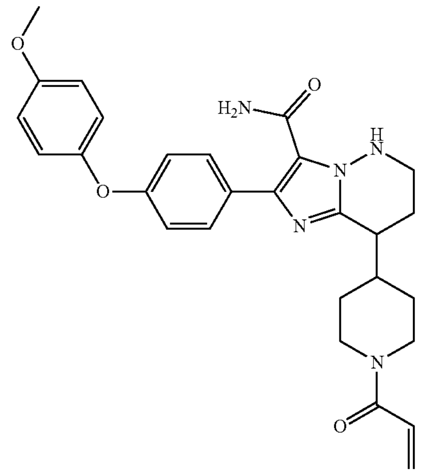 [SMILES: C=CC(=O)N1CCC(C2CCNn3c2nc(-c2ccc(Oc4ccc(OC)cc4)cc2)c3C(N)=O)CC1]

Step A: Preparation of methyl 3-(4-(4-methoxyphenoxy)phenyl)-3-oxopropanoate

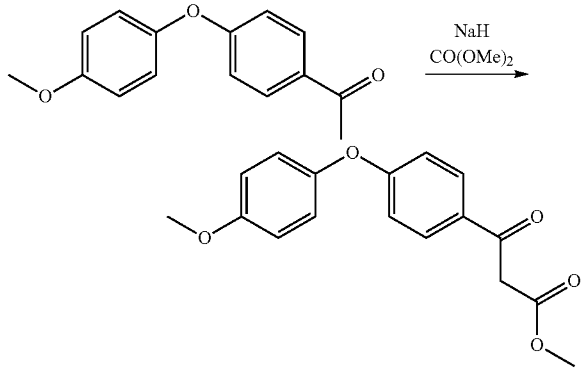

To a stirred suspension of NaH (60% dispersion in mineral oil; 495.3 g, 12.38 mol) in N, N-dimethylformamide (3 L) at 0° C. was added dropwise 1-(4-phenoxyphenyl)ethanone (2.0 kg, 8.26 mol) dissolved in N, N-dimethylformamide (2 L). After 30 minutes, the mixture was cooled to 0° C. and dimethylcarbonate (3.7 kg, 41.28 mol) was added. The mixture was allowed to warm to room temperature over a 2 hs period and then poured into water/saturated sodium bicarbonate (1:1). The aqueous layer was extracted with ethyl acetate, and after removal of the solvent under vacuum, the crude residue was flash chromatographed with ethyl acetate and petroleum ether (1:10) to give product as yellow oil (2.2 kg, 88%). $^1H$ NMR (400 MHz, DMSO-d6) δ 7.95 (d, J=8.9 Hz, 2H), 7.14-7.07 (m, 2H), 7.05-6.93 (m, 4H), 4.15 (s, 2H), 3.78 (s, 3H), 3.64 (s, 3H). MS (ESI, m/z): 301.1 $[M+H]^+$.

Step B: Preparation of methyl 2-bromo-3-(4-(4-methoxyphenoxy)phenyl)-3-oxopropanoate

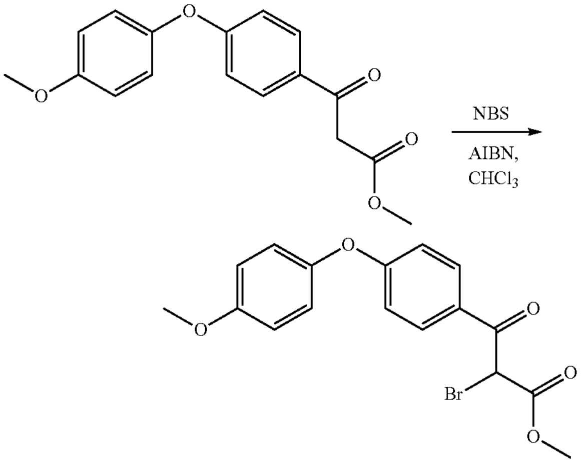

To a solution of the product of step A of example 15 (1.0 kg, 3.33 mol) in $CHCl_3$ (5 L) was added N-bromosuccinimide (651.9 g, 3.66 mol) and azobisisobutyronitrile (273.4 g, 1.66 mol). The reaction mixture was refluxing for 6 hs. Then the $CHCl_3$ was evaporated. The residue was diluted with 100 mL ethyl acetate. The mixture was washed with aqueous 5% HCl (2×1000 mL) and 500 mL water and then dried over anhydrous sodium sulfate. Evaporation of the solvent gave the crude product as oil, the crude residue was flash chromatographed with ethyl acetate and petroleum ether (1:10) to give product as yellow oil (980 g, 77%). $^1H$ NMR (400 MHz, $CDCl_3$) δ 7.99-7.91 (m, 2H), 7.04-6.99 (m, 2H), 6.97-6.92 (m, 4H), 5.64 (s, 1H), 3.82 (d, J=1.3 Hz, 6H). MS (ESI, m/z): 380.0 $[M+H]^+$.

Step C: Preparation of tert-butyl 4-(4-(4-(4-methoxyphenoxy)benzoyl)-11,11,12,12-tetramethyl-3,6-dioxo-2,5,10-trioxa-11-silatridecan-7-yl)piperidine-1-carboxylate

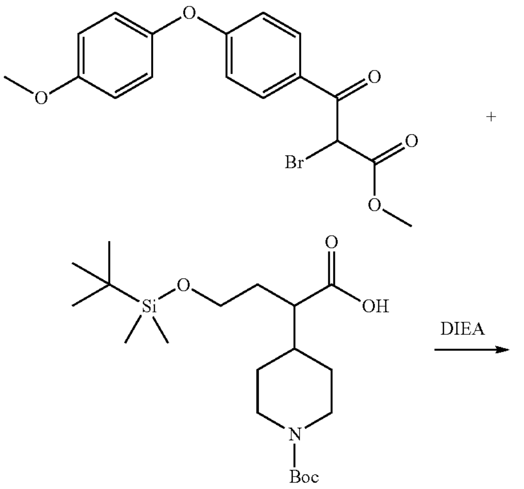

-continued

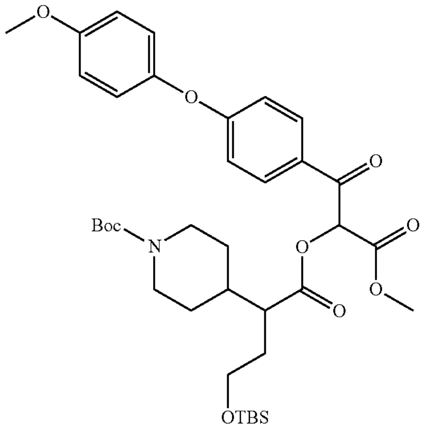

The product of step G (38.1 g, 94.94 mmol) of example 1 and The product of step B of example 15 (30.0 g, 79.11 mmol) were taken up in acetonitrile (250 mL), then N, N-diisopropylethylamine (15.3 g, 118.66 mmol) was added and the solution stirred at 30° C. for 3 hs. The solvent was removed by rotorary evaporation and the residue taken up in ethyl acetate, washed with 0.1 N HCl, and brine. The organic fractions were dried over anhydrous $Na_2SO_4$, filtered, and concentrated under reduced pressure to give the crude product which was purified via flash chromatography eluting with ethyl acetate and petroleum ether (1:10) to give the product as a clear colorless oil (48 g, 87%). $^1$H NMR (400 MHz, $CDCl_3$) δ 7.93 (d, J=8.7 Hz, 2H), 7.00 (d, J=8.7 Hz, 2H), 6.92 (dd, J=10.1, 5.2 Hz, 4H), 6.23 (s, 1H), 4.09 (d, J=4.9 Hz, 2H), 3.87-3.72 (m, 6H), 3.65-3.60 (m, 1H), 3.58-3.46 (m, 1H), 2.62 (d, J=11.0 Hz, 1H), 2.59-2.48 (m, 1H), 1.92-1.77 (m, 2H), 1.77-1.67 (m, 2H), 1.68-1.55 (m, 2H), 1.42 (s, 9H), 1.34-1.18 (m, 2H), 0.86-0.80 (m, 9H), −0.01 (dd, J=17.6, 6.6 Hz, 6H). MS (ESI, m/z): 700.3 $[M+H]^+$.

Step D: Preparation of tert-butyl 4-(3-((tert-butyldimethylsilyl)oxy)-1-(5-(methoxycarbonyl)-4-(4-(4-methoxyphenoxy)phenyl)-1H-imidazol-2-yl)propyl) piperidine-1-carboxylate

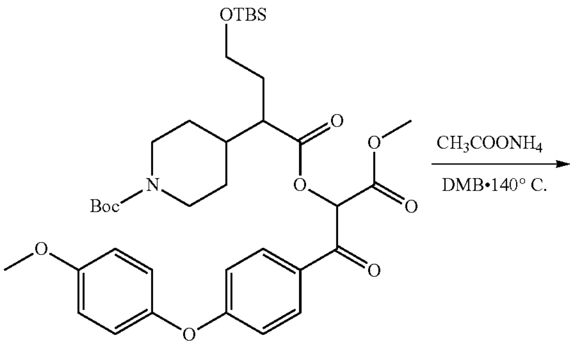

-continued

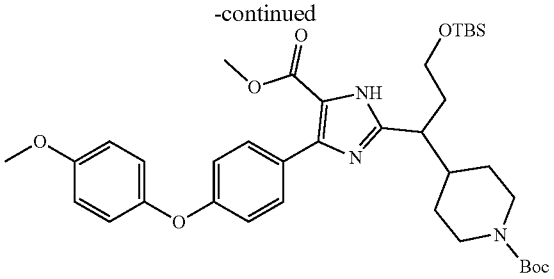

To a slurry of ammonium acetate (37.9 g, 491.76 mmol) in xylenes (150 mL) was added the product of step C of example 15 (24.0 g, 40.98 mmol). The mixture was stirred at 140° C. for 4 hours. The solution was cooled to room temperature and the solvent was evaporated. The residue was dissolved in EA and washed with saturated brine. The organic phase was dried over anhydrous $Na_2SO_4$, filtered and concentrated. The residue was purified by silica gel column chromatography with ethyl acetate and petroleum ether (1:5) to give the product as a clear colorless oil (8 g, 28%). $^1$H NMR (400 MHz, $CDCl_3$) δ 10.09 (s, 1H), 7.86 (d, J=8.6 Hz, 2H), 7.01-6.95 (m, 4H), 6.87 (d, J=9.0 Hz, 2H), 4.14-4.00 (m, 2H), 3.80 (d, J=5.2 Hz, 6H), 3.64-3.58 (m, 1H), 3.48-3.42 (m, 1H), 2.83-2.78 (m, 1H), 2.69-2.59 (m, 2H), 2.08-1.89 (m, 4H), 1.87-1.80 (m, 1H), 1.42 (s, 9H), 1.21-1.12 (m, 2H), 0.87 (s, 9H), −0.00 (t, J=4.2 Hz, 6H). MS (ESI, m/z): 650.3 $[M+H]^+$.

Step E: Preparation of tert-butyl 4-(1-(1-amino-5-(methoxycarbonyl)-4-(4-(4-methoxyphenoxy)phenyl)-1H-imidazol-2-yl)-3-((tert-butyldimethylsilyl)oxy)propyl)piperidine-1-carboxylate

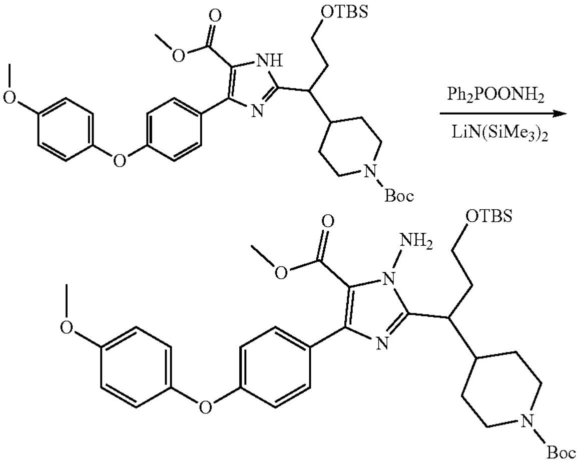

Lithium hexamethyldisilazane (17 mL of a 1 M solution in tetrahydrofuran, 16.98 mmol) was slowly added to the product of step D of example 15 (7.7 g, 11.32 mmol) in anhydrous N, N-dimethylformamide (150 mL) at 0° C. After the mixture was stirred for 30 min, O-(diphenylphosphinyl) hydroxylamine (5.3 g, 22.65 mmol) was added at 0° C., followed by stirring at room temperature for 4-6 h (in cases where the reaction mixture became too viscous, additional N, N-dimethylformamide was added). The reaction was quenched with water until a clear solution was formed and concentrated to dryness under reduced pressure. The residue was washed several times with ethyl acetate or dichloromethane. The combined organic fractions were concentrated in vacuo and purified by flash chromatography on silica gel with ethyl acetate and petroleum ether (1:3) to give the product as a clear colorless oil (7 g, 89%). $^1$H NMR (400 MHz, $CDCl_3$) δ 7.63-7.57 (m, 2H), 7.06-7.01 (m, 2H), 7.00-6.95 (m, 2H), 6.94-6.88 (m, 2H), 5.60 (s, 2H), 4.24-3.96 (m, 2H), 3.86-3.78 (m, 6H), 3.68-3.60 (m, 1H), 3.41-3.31 (m, 2H), 2.78-2.58 (m, 2H), 2.08-2.01 (m, 2H), 2.00-1.90 (m, 2H), 1.46 (s, 9H), 1.42-1.35 (m, 1H), 1.31-1.18 (m, 2H), 0.88 (s, 9H), 0.04-(−0.01) (m, 6H). MS (ESI, m/z): 695.4 [M+H]$^+$.

Step F: Preparation of tert-butyl 4-(1-(1-amino-5-(methoxycarbonyl)-4-(4-(4-methoxyphenoxy)phenyl)-1H-imidazol-2-yl)-3-hydroxypropyl)piperidine-1-carboxylate

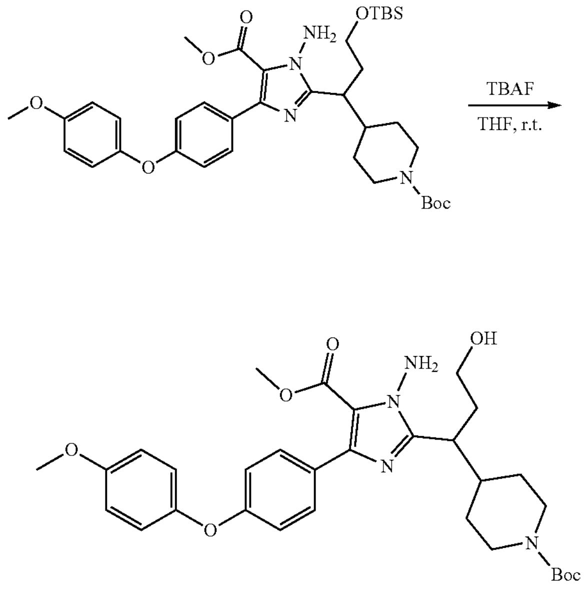 [SMILES: COC(=O)c1c(-c2ccc(Oc3ccc(OC)cc3)cc2)nc(C(CCO[Si](C)(C)C(C)(C)C)C2CCN(C(=O)OC(C)(C)C)CC2)n1N ; "TBAF" ; COC(=O)c1c(-c2ccc(Oc3ccc(OC)cc3)cc2)nc(C(CCO)C2CCN(C(=O)OC(C)(C)C)CC2)n1N]

To a solution of the product of step E of example 15 (6.0 g, 8.63 mmol) in tetrahydrofuran (50 mL) was added a 1 M solution of tetrabutylammonium fluoride in tetrahydrofuran (13 mL, 12.94 mmol) at RT. The solution was stirred for 2 hs and diluted with 100 mL ethyl acetate solution. The organic layer was separated and washed with $H_2O$ (3×200 mL). The water extract was washed with ethyl acetate solution (2×150 mL), and the organic layers were combined and dried over anhydrous $Na_2SO_4$. The solvent was evaporated in vacuo, and purified by flash chromatography on silica gel with dichloromethane and methanol (25:1) to give the product as a clear colorless oil (4.5 g, 89%). $^1$H NMR (400 MHz, $CDCl_3$) δ 7.58 (d, J=8.7 Hz, 2H), 7.04-6.98 (m, 2H), 6.95 (d, J=8.7 Hz, 2H), 6.92-6.87 (m, 2H), 5.52 (s, 2H), 4.20-4.09 (m, 1H), 4.08-3.96 (m, 1H), 3.83-3.76 (m, 6H), 3.66-3.60 (m, 1H), 3.49-3.41 (m, 1H), 3.35-3.29 (m, 1H), 2.73-2.58 (m, 2H), 2.09-1.99 (m, 3H), 1.94-1.87 (m, 1H), 1.44 (s, 9H), 1.34-1.19 (m, 3H). MS (ESI, m/z): 581.3 [M+H]$^+$.

Step G: Preparation of methyl 8-(1-(tert-butoxycarbonyl)piperidin-4-yl)-2-(4-(4-methoxyphenoxy)phenyl)-5,6,7,8-tetrahydroimidazo[1,2-b]pyridazine-3-carboxylate

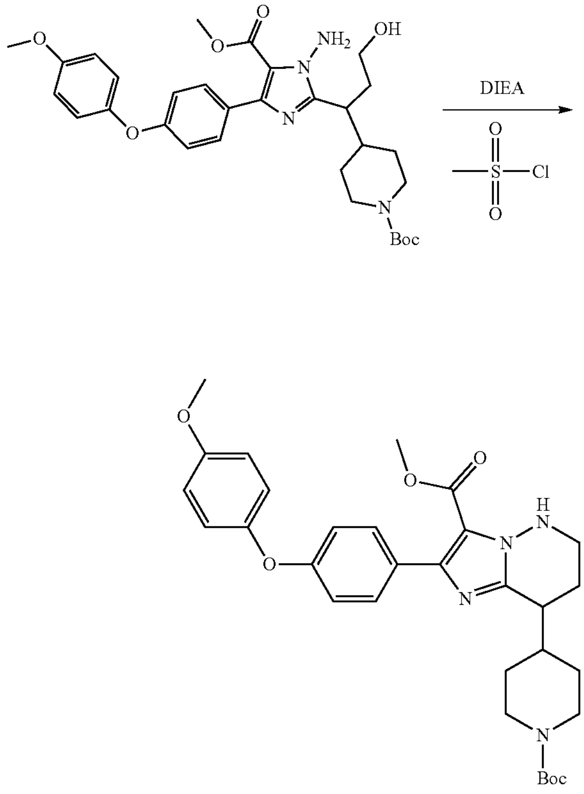

Methanesulfonyl chloride (1.2 g, 10.33 mmol) was added via syringe into a stirred mixture of the product of step F of example 15 (4.0 g, 6.89 mmol) and N, N-diisopropylethylamine (3.5 g, 27.55 mmol) in dichloromethane (30 ml) maintained at 0° C. The mixture was stirred at room temperature for 3 hs (TLC monitoring) and then partitioned between dichloromethane and water. The organic phase was dried and evaporated to afford an oil. The crude intermediate was dissolved in tetrahydrofuran (20 mL), 1 M solution of tetrabutylammonium fluoride in tetrahydrofuran (10 mL, 10.33 mmol) and N, N-diisopropylethylamine (3.5 g, 27.55 mmol) was added to the mixture, which was stirred 3 hs, then partitioned between dichloromethane and water. The organic phase was dried and evaporated to afford a white solid, then passed through a column of silica gel with dichloromethane and methanol (25:1) to afford the desired product as a colorless oil (2.3 g, 59%). $^1$H NMR (400 MHz, $CDCl_3$) δ 7.60 (d, J=8.7 Hz, 2H), 7.03-6.99 (m, 2H), 6.96-6.93 (m, 2H), 6.91-6.87 (m, 2H), 4.16 (s, 2H), 3.81 (s, 3H), 3.77 (s, 3H), 3.51-3.42 (m, 1H), 3.38-3.29 (m, 1H), 3.10 (d, J=3.8 Hz, 1H), 2.78-2.62 (m, 2H), 2.41 (s, 1H), 2.08-2.02 (m, 1H), 1.99-1.90 (m, 1H), 1.77-1.70 (m, 1H), 1.45 (s, 9H), 1.36-1.23 (m, 3H). MS (ESI, m/z): 563.3 [M+H]$^+$.

Step H: Preparation of 8-(1-(tert-butoxycarbonyl) piperidin-4-yl)-2-(4-(4-methoxyphenoxy)phenyl)-5, 6,7,8-tetrahydroimidazo[1,2-b]pyridazine-3-carboxylic Acid

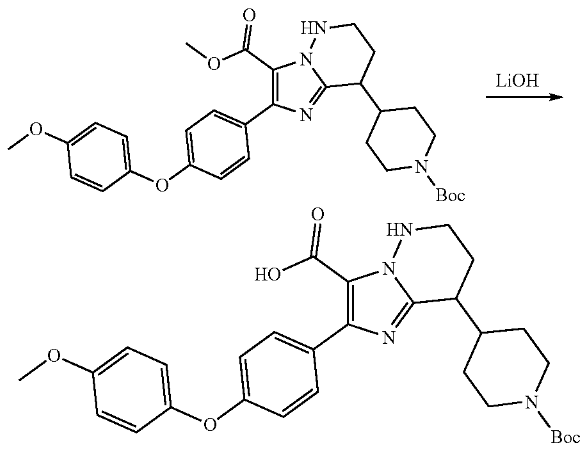

To a solution of the product of step G of example 15 (2.3 g, 4.09 mmol) in tetrahydrofuran (10 mL) was added LiOH (489.4 mg, 20.44 mmol) in water (5 mL), the mixture was heated at 50° C. for 3 hs. Then cooled to r.t. The mixture acidified to pH 3-4 with concentrated HCl and then extracted with 3×100 mL of dichloromethane. The organic phase was washed with saturated brine and then dried over anhydrous $Na_2SO_4$. The organic phase was concentrated in vacuo to afford 2.5 g crude product. The residue was used to next step without further purification. MS (ESI, m/z): 549.3 $[M+H]^+$.

Step I: Preparation of tert-butyl 4-(3-carbamoyl-2-(4-(4-methoxyphenoxy)phenyl)-5,6,7,8-tetrahydroimidazo[1,2-b]pyridazin-8-yl)piperidine-1-carboxylate

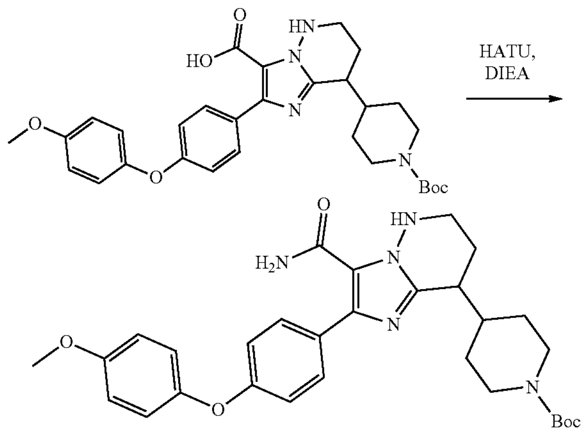

To the solution of the product of step H of example 15 (2.5 g, 4.56 mmol) in dichloromethane (30 mL) was added N, N-diisopropylethylamine (2.4 g, 18.23 mmol). After 5 min, $NH_4Cl$ (975.0 mg, 18.23 mmol) and HATU (2.6 g, 6.84 mmol) was added. The reaction mixture was continued to stir at room temperature for 2 h. Dichloromethane and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (40:1) to give product as an off-white solid (2.1 g, 95%). $^1$H NMR (400 MHz, $CDCl_3$) δ 7.55-7.49 (m, 2H), 7.38 (s, 1H), 7.02-6.97 (m, 4H), 6.93-6.87 (m, 2H), 5.99 (s, 1H), 5.38 (s, 1H), 4.16 (s, 2H), 3.82 (s, 3H), 3.48-3.40 (m, 1H), 3.39-3.29 (m, 1H), 3.14-3.04 (m, 1H), 2.76-2.62 (m, 2H), 2.46-2.32 (m, 1H), 2.12-2.01 (m, 1H), 1.99-1.87 (m, 1H), 1.75-1.64 (m, 2H), 1.45 (s, 9H), 1.44-1.41 (m, 1H), 1.40-1.32 (m, 1H). MS (ESI, m/z): 548.3 $[M+H]^+$.

Step J: Preparation of 8-(1-acryloylpiperidin-4-yl)-2-(4-(4-methoxyphenoxy)phenyl)-5,6,7,8-tetrahydroimidazo[1,2-b]pyridazine-3-carboxamide

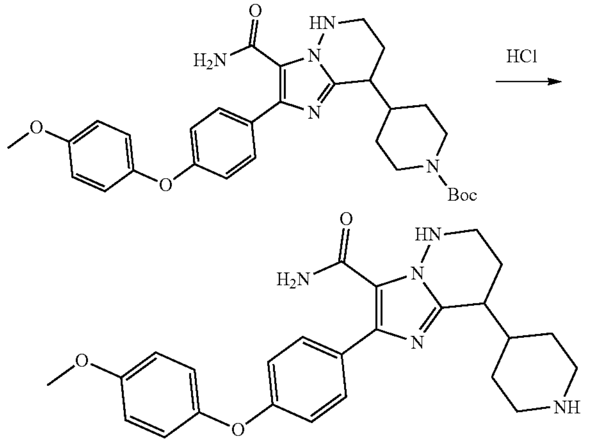

To a solution of the product of step I of example 15 (5.0 g, crude) in EtOH (2 mL) was added 33% HCl/EtOH (10 mL) at room temperature in reaction still. The mixture was stirred for 3 hs. the mixture was concentrated under vacuum to get 6.5 g crude. The residue was used to next step without further purification. MS (ESI, m/z): 448.2 $[M+H]^+$.

Step K: Preparation of 8-(1-acryloylpiperidin-4-yl)-2-(4-(4-methoxyphenoxy)phenyl)-5,6,7,8-tetrahydroimidazo[1,2-b]pyridazine-3-carboxamide

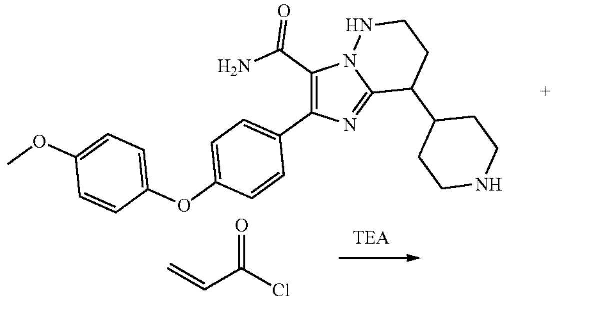

-continued

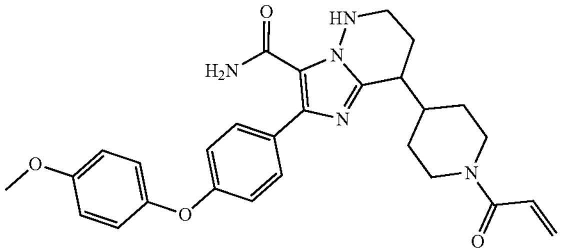

The mixture of the product of step J of example 15 (200 mg, 0.45 mmol) and triethylamine (271.3 mg, 2.68 mmol) in dichloromethane (5 mL) was cooled to −60° C. Then the solution of propenoyl chloride (40.4 mg, 0.45 mmol) in dichloromethane (1 mL) was added slowly, LC-MS was tracking, at the end of the reaction, 1 mL MeOH was added, the mixture was concentrated under vacuum to get crude product, and purified by flash chromatography on silica gel with dichloromethane and methanol (40:1) to get white solid (53 mg, 23%). $^1$H NMR (400 MHz, $CDCl_3$) δ 7.52 (d, J=6.1 Hz, 2H), 7.00-6.94 (m, 4H), 6.92-6.86 (m, 2H), 6.0-6.51 (m, 1H), 6.27-6.19 (m, 1H), 5.68-5.62 (m, 1H), 4.79-4.63 (m, 1H), 4.10-3.94 (m, 1H), 3.80 (s, 3H), 3.40 (s, 1H), 3.36-3.26 (m, 1H), 3.14-3.01 (m, 2H), 2.65-2.55 (m, 1H), 2.53-2.41 (m, 1H), 2.08-1.96 (m, 1H), 1.91-1.85 (m, 1H), 1.85-1.73 (m, 1H), 1.48-1.42 (m, 1H), 1.42-1.35 (m, 2H). MS (ESI, m/z): 502.2 [M+H]$^+$.

Example 16

8-(1-(but-2-ynoyl)piperidin-4-yl)-2-(4-(4-methoxyphenoxy)phenyl)-5,6,7,8-tetrahydroimidazo[1,2-b]pyridazine-3-carboxamide

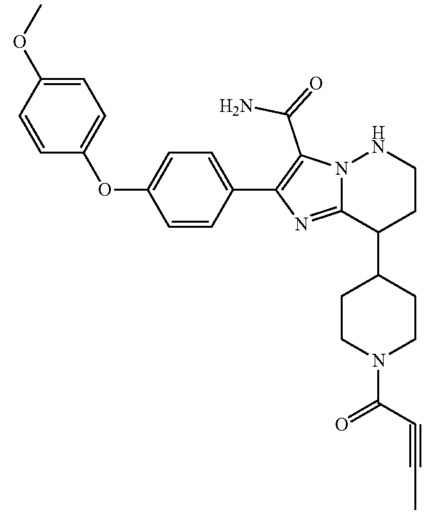 [SMILES: CC#CC(=O)N1CCC(C2CCNn3c2nc(-c2ccc(Oc4ccc(OC)cc4)cc2)c3C(N)=O)CC1]

Preparation of 8-(1-(but-2-ynoyl)piperidin-4-yl)-2-(4-(4-methoxyphenoxy)phenyl)-5,6,7,8-tetrahydroimidazo[1,2-b]pyridazine-3-carboxamide

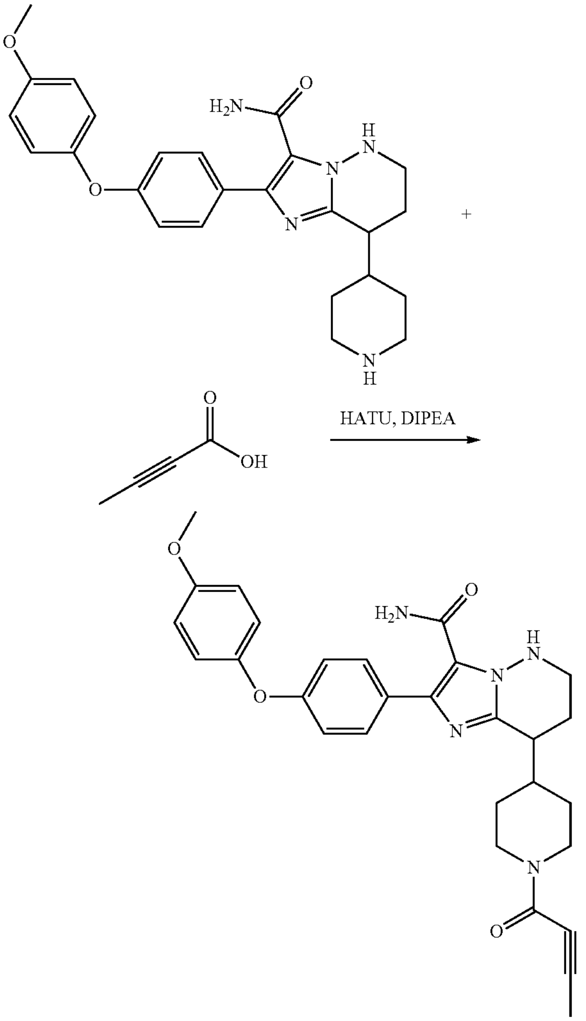

To the solution of the product (200 mg, 0.45 mmol) of step J of example 15 in dry N, N-dimethylformamide (5 mL) was added N, N-diisopropylethylamine (346.5 mg, 2.68 mmol). After 5 min, but-2-ynoic acid (45.0 mg, 0.54 mmol) and HATU (256.5 mg, 0.67 mmol) was added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give product as an off-white solid (58 mg, 25%). $^1$H NMR (400 MHz, $CDCl_3$) δ 7.55-7.48 (m, 2H), 7.40-7.30 (m, 1H), 6.99 (t, J=8.0 Hz, 4H), 6.94-6.87 (m, 2H), 6.09 (s, 1H), 5.49 (s, 1H), 4.70-4.55 (m, 1H), 4.50-4.36 (m, 1H), 3.82 (s, 3H), 3.44 (s, 1H), 3.38-3.28 (m, 1H), 3.19-3.03 (m, 2H), 2.66-2.58 (m, 1H), 2.55-2.46 (m, 1H), 2.05-1.97 (m, 4H), 1.96-1.84 (m, 2H), 1.51 (s, 1H), 1.45-1.39 (m, 2H). MS (ESI, m/z): 514.2 [M+H]$^+$.

Example 17

(E)-2-(4-(4-methoxyphenoxy)phenyl)-8-(1-(4,4,4-trifluorobut-2-enoyl)piperidin-4-yl)-5,6,7,8-tetrahydroimidazo[1,2-b]pyridazine-3-carboxamide

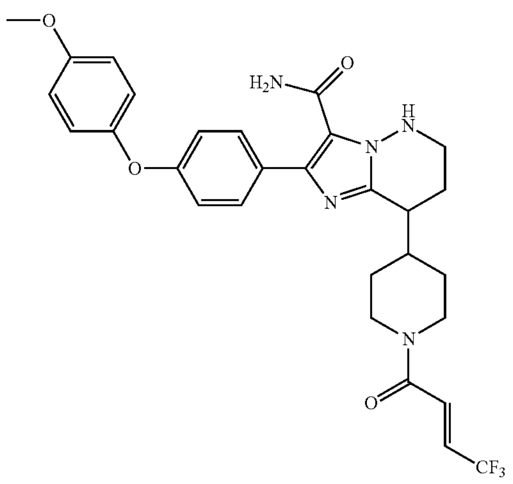 [SMILES: COc1ccc(Oc2ccc(-c3nc4n(c3C(N)=O)NCCC4C3CCN(C(=O)/C=C/C(F)(F)F)CC3)cc2)cc1]

Preparation of (E)-2-(4-(4-methoxyphenoxy)phenyl)-8-(1-(4,4,4-trifluorobut-2-enoyl)piperidin-4-yl)-5,6,7,8-tetrahydroimidazo[1,2-b]pyridazine-3-carboxamide

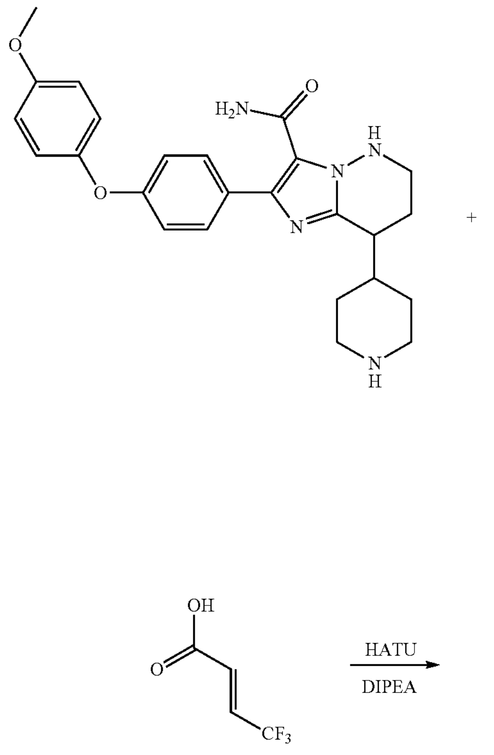

-continued

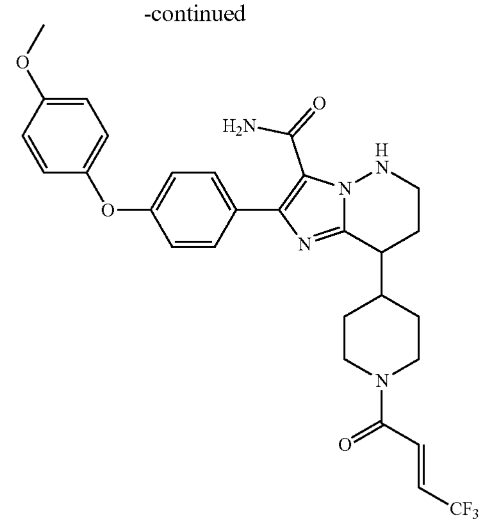

To the solution of the product (200 mg, 0.45 mmol) of step J of example 15 in dry N, N-dimethylformamide (10 mL) was added N, N-diisopropylethylamine (346.5 mg, 2.68 mmol). After 5 min, (E)-4,4,4-trifluorobut-2-enoic acid (75.1 mg, 0.54 mmol) and HATU (256.5 mg, 0.67 mmol) was added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give product as an off-white solid (63 mg, 24%). $^1H$ NMR (400 MHz, $CDCl_3$) δ 7.56-7.48 (m, 2H), 6.99-6.94 (m, 4H), 6.91-6.87 (m, 2H), 6.68-6.60 (m, 2H), 6.34 (s, 1H), 5.61 (s, 1H), 4.76-4.62 (m, 1H), 4.00-3.87 (m, 1H), 3.80 (s, 3H), 3.69-3.63 (m, 2H), 3.44 (s, 1H), 3.31 (s, 1H), 3.17-3.12 (m, 3H), 2.70-2.63 (m, 1H), 2.54-2.46 (m, 1H), 2.08-2.00 (m, 1H), 1.96-1.83 (m, 2H), 1.62-1.56 (m, 1H). MS (ESI, m/z): 570.2 $[M+H]^+$.

Example 18

8-(1-acryloylazetidin-3-yl)-2-(4-phenoxyphenyl)-5,6,7,8-tetrahydroimidazo[1,2-b]pyridazine-3-carboxamide

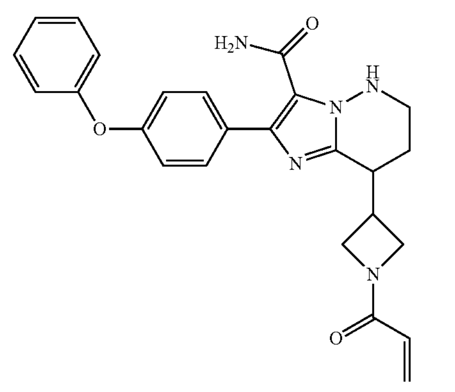 [SMILES: C=CC(=O)N1CC(C2CCNn3c2nc(-c2ccc(Oc4ccccc4)cc2)c3C(N)=O)C1]

Step A: Preparation of tert-butyl 3-(2-oxodihydrofuran-3(2H)-ylidene)azetidine-1-carboxylate

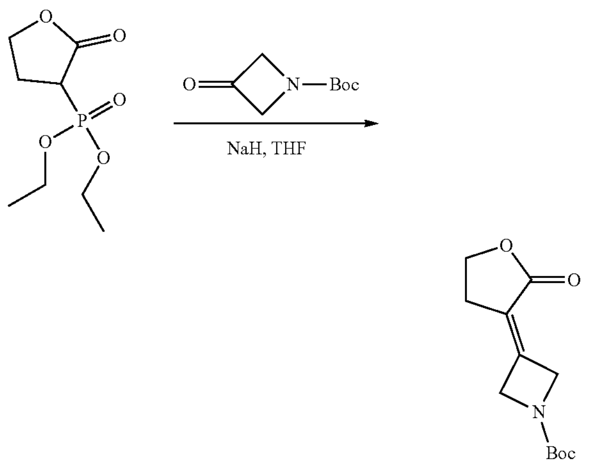

To a slurry of tetrahydrofuran-washed sodium hydride (60% dispersion in mineral oil; 385.5 g, 9.64 mol) was added diethyl (2-oxotetrahydrofuran-3-yl)phosphonate (2.2 kg, 9.64 mol) as a solution in dry tetrahydrofuran (3 L) dropwise over 70 min at 10° C. The mixture was stirred for 30 min before the addition of tert-butyl 3-oxoazetidine-1-carboxylate (1.1 kg, 6.43 mol) as a solution in tetrahydrofuran (2 L). The mixture was then stirred for 2 h before the addition of dichloromethane (2 L) followed by water (5 L). The tetrahydrofuran was then removed under reduced pressure, the aqueous residue extracted with dichloromethane (3×1000 ml), then washed with water (2×1000 ml) and dried (anhydrous $Na_2SO_4$) before evaporating to dryness to give a yellow oil, then purified by column chromatography on silica gel with ethyl acetate and petroleum ether (1:2) to give product as a white solid (920 g, 59%). $^1H$ NMR (400 MHz, $CDCl_3$) δ 4.91-4.82 (m, 2H), 4.59-4.56 (m, 2H), 4.40 (t, J=7.4 Hz, 2H), 2.85-2.80 (m, 2H), 1.45 (s, 9H). MS (ESI, m/z): 240.1 $[M+H]^+$.

Step B: Preparation of tert-butyl 3-(2-oxotetrahydrofuran-3-yl)azetidine-1-carboxylate

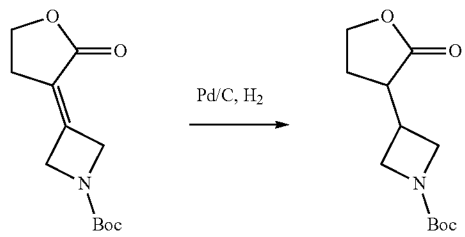 [SMILES: CC(C)(C)OC(=O)N1CC(=C2CCOC2=O)C1 ; CC(C)(C)OC(=O)N1CC(C2CCOC2=O)C1]

To a solution of the product of step A of example 18 (800 g, 3.34 mol) in ethyl acetate (4 L) was added 10% Pd/C (160.3 g, 20%) at room temperature. The mixture was stirred for 3 hs under $H_2$. The mixture was passed through Celite, and the solid was washed with ethyl acetate, and filtrate was concentrated under vacuum to get desired product (800 g, 99%). $^1H$ NMR (400 MHz, $CDCl_3$) δ 4.34-4.27 (m, 1H), 4.20-4.13 (m, 1H), 4.07 (t, J=8.6 Hz, 1H), 3.98 (t, J=8.4 Hz, 1H), 3.87-3.75 (m, 1H), 3.64-3.57 (m, 1H), 2.84-2.67 (m, 2H), 2.43-2.31 (m, 1H), 2.01-1.89 (m, 1H), 1.35 (s, 9H). MS (ESI, m/z): 242.1 $[M+H]^+$.

Step C: Preparation of 2-(1-(tert-butoxycarbonyl)azetidin-3-yl)-4-hydroxybutanoic Acid

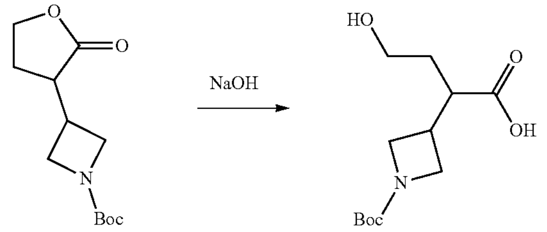 [SMILES: CC(C)(C)OC(=O)N1CC(C2CCOC2=O)C1 ; "NaOH" ; CC(C)(C)OC(=O)N1CC(C(CCO)C(=O)O)C1]

The product of step B of example 18 (350 g, 1.45 mmol), $H_2O$ (500 mL), and sodium hydroxide (116.1 g, 2.90 mol) were added in a round bottom flask. This reaction mixture was stirred at room temperature overnight. The clear reaction mixture was then extracted with ethyl acetate, the aqueous layer was isolated and acidified to pH 3-4 with concentrated HCl and then extracted with 100 mL of dichloromethane. The organic phase was washed with saturated brine and then dried over anhydrous $Na_2SO_4$. The organic phase was concentrated in vacuo to get product as a White solid (345 g, 91%). MS (ESI, m/z): 260.2 $[M+H]^+$.

Step D: Preparation of 2-(1-(tert-butoxycarbonyl)azetidin-3-yl)-4-((tert-butyldimethylsilyl)oxy)butanoic Acid

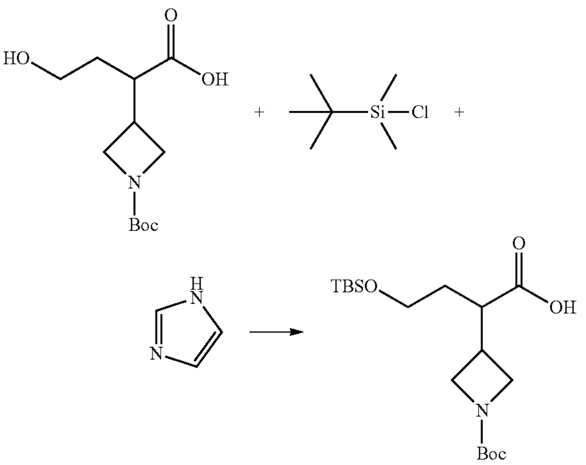

Tert-butyldimethylsilylchloride (273.2 g, 1.57 mol) was added to a mixture of the product of step C of example 18 (340 g, 1.31 mmol) and imidazole (178.5 g, 2.62 mol) in N, N-dimethylformamide (3 L). The reaction mixture was stirred at 30° C. for 5 h under argon atmosphere and poured into a separatory funnel containing 400 mL of brine and extracted 4 times with 2 L dichloromethane. The organic fractions were combined, dried over anhydrous $Na_2SO_4$, filtered, and concentrated under reduced pressure to give the crude product which was purified via flash chromatography eluting with ethyl acetate and petroleum ether (1:2) to give the product as a clear colorless oil (crude 400 g). MS (ESI, m/z): 374.2 $[M+H]^+$.

Step E: Preparation of tert-butyl 3-(11,11,12,12-tetramethyl-3,6-dioxo-4-(4-phenoxybenzoyl)-2,5,10-trioxa-11-silatridecan-7-yl)azetidine-1-carboxylate

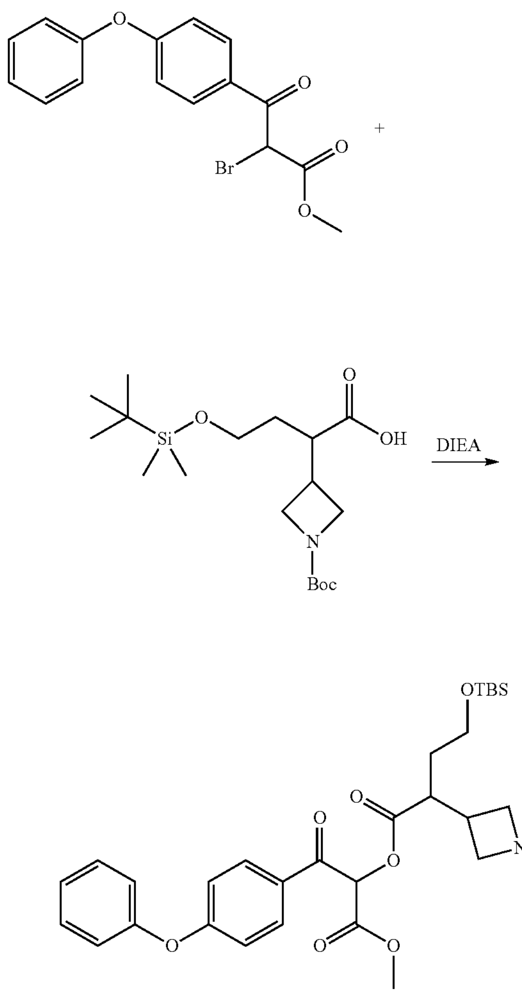

The product of step B (30.0 g, 85.92 mmol) of example 1 and the product of step D of example 18 (38.5 g, 103.10 mmol) were taken up in acetonitrile (250 mL), then N, N-diisopropylethylamine (16.7 g, 128.87 mmol) was added and the solution stirred at 30° C. for 3 hs. The solvent was removed by rotorary evaporation and the residue taken up in ethyl acetate, washed with 0.1 N HCl, and brine. The organic fractions were dried over anhydrous $Na_2SO_4$, filtered, and concentrated under reduced pressure to give the crude product which was purified via flash chromatography eluting with ethyl acetate and petroleum ether (1:20) to give the product as a clear colorless oil (46.3 g, 83%). $^1$H NMR (400 MHz, $CDCl_3$) δ 7.93 (d, J=8.8 Hz, 2H), 7.37 (t, J=7.9 Hz, 2H), 7.19 (t, J=7.4 Hz, 1H), 7.05 (d, J=8.0 Hz, 2H), 6.97 (d, J=8.9 Hz, 2H), 6.22 (s, 1H), 4.03-3.94 (m, 2H), 3.68-3.59 (m, 3H), 2.94-2.86 (m, 1H), 2.83-2.75 (m, 1H), 1.93-1.80 (m, 1H), 1.71-1.59 (m, 1H), 1.39 (s, 9H), 0.83 (d, J=7.3 Hz, 9H), 0.01-(−0.04) (m, 6H). MS (ESI, m/z): 642.3 $[M+H]^+$.

Step F: Preparation of methyl 2-(1-(1-(tert-butoxy-carbonyl)azetidin-3-yl)-3-((tert-butyldimethylsilyl)oxy)propyl)-4-(4-phenoxyphenyl)-1H-imidazole-5-carboxylate

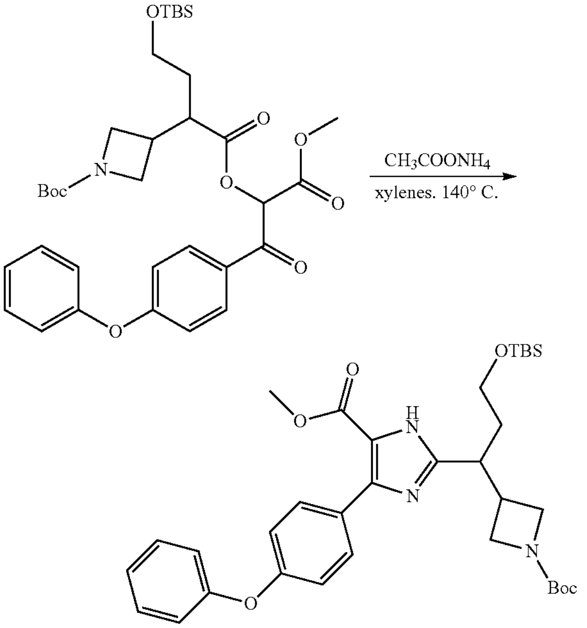

To a slurry of ammonium acetate (57.6 g, 747.86 mmol) in xylenes (400 mL) was added the product of step E of example 18 (40.0 g, 62.32 mmol). The mixture was stirred at 140° C. for 4 hours. The solution was cooled to room temperature and evaporated. The residue was dissolved in ethyl acetate and washed with saturated brine. The organic phase was dried over anhydrous $Na_2SO_4$, filtered and concentrated. The residue was purified by silica gel column chromatography with ethyl acetate and petroleum ether (1:5) to give the product as a clear colorless oil (18 g, 46%). $^1$H NMR (400 MHz, $CDCl_3$) δ 10.15 (s, 1H), 7.98-7.91 (m, 2H), 7.38-7.31 (m, 2H), 7.16-7.08 (m, 1H), 7.07-7.01 (m, 4H), 4.14-3.97 (m, 2H), 3.84 (d, J=5.2 Hz, 3H), 3.77-3.65 (m, 3H), 3.63-3.54 (m, 1H), 3.27-3.16 (m, 1H), 3.14-3.01 (m, 1H), 1.96-1.74 (m, 2H), 1.43 (s, 9H), 0.98-0.82 (m, 9H), 0.19-0.05 (m, 7H). MS (ESI, m/z): 622.3 $[M+H]^+$.

Step G: Preparation of methyl 1-amino-2-(1-(1-(tert-butoxycarbonyl)azetidin-3-yl)-3-((tert-butyldimethylsilyloxy)propyl)-4-(4-phenoxyphenyl)-1H-imidazole-5-carboxylate

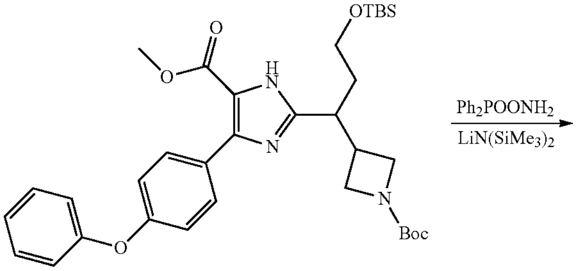

-continued

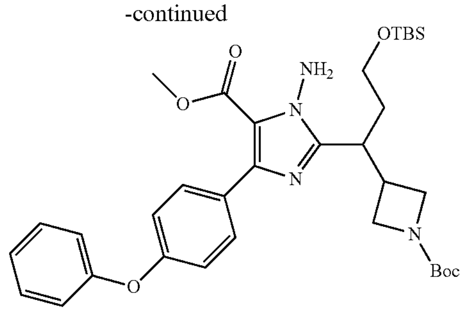

Lithium hexamethyldisilazane (20 mL of a 1 M solution in tetrahydrofuran, 19.29 mmol) was slowly added to the product of step F of example 18 (8.0 g, 12.86 mmol) in anhydrous N, N-dimethylformamide (60 mL) at 0° C. After the mixture was stirred for 30 min, O-(diphenylphosphinyl) hydroxylamine (6.0 g, 25.73 mmol) was added at 0° C., followed by stirring at room temperature for 4-6 hs (in cases where the reaction mixture became too viscous, additional N, N-dimethylformamide was added). The reaction was quenched with water until a clear solution was formed and concentrated to dryness under reduced pressure. The residue was washed several times with ethyl acetate or dichloromethane. The combined organic fractions were concentrated in vacuo and purified by flash chromatography on silica gel with ethyl acetate and petroleum ether (1:3) to give the product as a clear colorless oil (6.4 g, 78%). $^1$H NMR (400 MHz, $CDCl_3$) δ 7.63-7.54 (m, 2H), 7.38-7.29 (m, 2H), 7.11 (t, J=7.4 Hz, 1H), 7.06-6.97 (m, 4H), 5.66 (s, 2H), 4.07 (t, J=7.7 Hz, 1H), 3.88 (t, J=8.5 Hz, 1H), 3.82-3.75 (m, 3H), 3.73-3.64 (m, 3H), 3.58-3.53 (m, 1H), 3.52-3.43 (m, 1H), 3.12 (s, 1H), 1.87-1.80 (m, 2H), 1.42 (s, 9H), 0.88-0.75 (m, 9H), 0.03-(−0.05) (m, 6H). MS (ESI, m/z): 637.3 [M+H].

Step H: Preparation of methyl 1-amino-2-(1-(1-(tert-butoxycarbonyl)azetidin-3-yl)-3-hydroxypropyl)-4-(4-phenoxyphenyl)-1H-imidazole-5-carboxylate

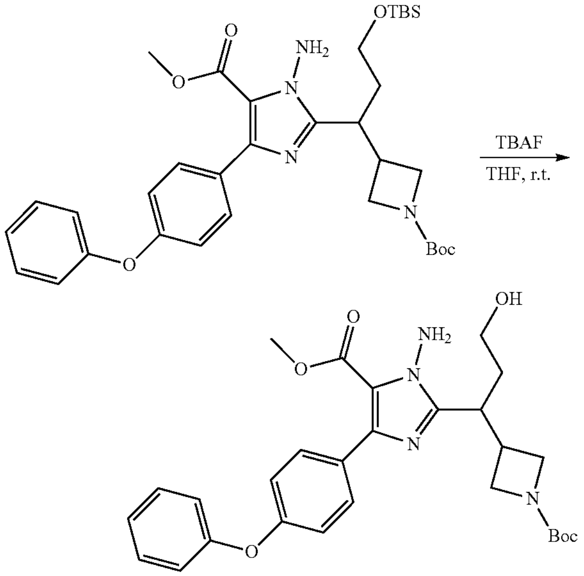

To a solution of the product of step G of example 18 (6.0 g, 9.24 mmol) in tetrahydrofuran (50 mL) was added a 1 M solution of tetrabutylammonium fluoride in tetrahydrofuran (11 mL, 11.08 mmol) at RT. The solution was stirred for 2 hs and diluted with 100 mL ethyl acetate solution. The organic layer was separated and washed with $H_2O$ (3×200 mL). The water extract was washed with ethyl acetate solution (2×150 mL), and the organic layers were combined and dried over anhydrous $Na_2SO_4$. The solvent was evaporated in vacuo, and purified by flash chromatography on silica gel with dichloromethane and methanol (40:1) to give the product as a clear colorless oil (4 g, 81%). $^1$H NMR (400 MHz, $CDCl_3$) δ 7.63-7.56 (m, 2H), 7.38-7.31 (m, 2H), 7.12 (t, J=7.4 Hz, 1H), 7.07-6.96 (m, 4H), 5.75 (s, 2H), 4.08 (t, J=8.4 Hz, 1H), 3.90 (t, J=8.4 Hz, 1H), 3.78 (s, 3H), 3.75-3.66 (m, 2H), 3.64-3.58 (m, 1H), 3.56-3.50 (m, 1H), 3.45-3.36 (m, 1H), 3.19-3.12 (m, 1H), 1.93-1.80 (m, 2H), 1.41 (s, 9H). MS (ESI, m/z): 523.2 $[M+H]^+$.

Step I: Preparation of methyl 8-(1-(tert-butoxycarbonyl)azetidin-3-yl)-2-(4-phenoxyphenyl)-5,6,7,8-tetrahydroimidazo[1,2-b]pyridazine-3-carboxylate

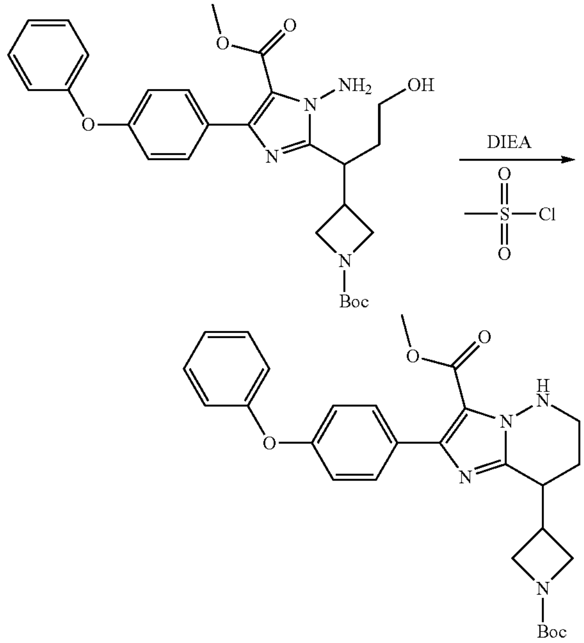

Methanesulfonyl chloride (1.3 g, 11.48 mmol) was added via syringe into a stirred mixture of the product of step H of example 18 (4.0 g, 7.65 mmol) and N, N-diisopropylethylamine (2.0 g, 15.31 mmol) in dichloromethane (70 ml) maintained at 0° C. The mixture was stirred at room temperature for 3 hs (TLC monitoring) and then partitioned between dichloromethane and water. The organic phase was dried and evaporated to afford a white oil, The crude intermediate was dissolved in tetrahydrofuran (20 mL), 1 M solution of tetrabutylammonium fluoride in tetrahydrofuran (11 mL, 11.48 mmol) and N, N-diisopropylethylamine (2.0 g, 15.31 mmol) was added to the mixture, which was stirred 3 hs, then partitioned between dichloromethane and water. The organic phase was dried and evaporated to afford a white solid, then passed through a column of silica gel with dichloromethane and methanol (30:1) to afford the desired product as a colorless oil (3.4 g, 88%). $^1$H NMR (600 MHz, $CDCl_3$) δ 7.65 (d, J=7.8 Hz, 2H), 7.34 (t, J=7.4 Hz, 2H), 7.11 (t, J=7.4 Hz, 1H), 7.05 (d, J=8.1 Hz, 2H), 7.01 (d, J=7.8 Hz, 2H), 4.23 (s, 1H), 4.16 (d, J=8.4 Hz, 1H), 4.02 (t, J=8.4 Hz, 1H), 3.82 (t, J=6.8 Hz, 1H), 3.78 (s, 3H), 3.47 (s, 1H), 3.42-3.36 (m, 1H), 3.31-3.24 (m, 1H), 2.90 (s, 1H), 2.21 (d, J=6.7 Hz, 1H), 1.78 (s, 1H), 1.44 (s, 9H). MS (ESI, m/z): 505.2 $[M+H]^+$.

Step J: Preparation of 8-(1-(tert-butoxycarbonyl) azetidin-3-yl)-2-(4-phenoxyphenyl)-5,6,7,8-tetrahydroimidazo[1,2-b]pyridazine-3-carboxylic Acid

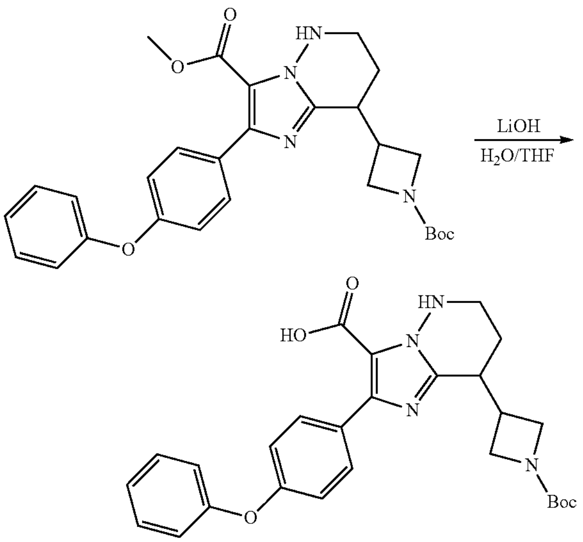

To a solution of the product of step I of example 18 (2.0 g, 3.96 mmol) in tetrahydrofuran (10 mL) was added LiOH (474.6 mg, 19.82 mmol) in water (5 mL), the mixture was heated at 50'C for 3 hs, then cooled to r.t. The mixture acidified to pH 3-4 with concentrated HCl and then extracted with dichloromethane (3×100 mL). The organic phase was washed with saturated brine and then dried over anhydrous $Na_2SO_4$. The organic phase was concentrated in vacuo to afford 2.4 g crude product. The residue was used to next step without further purification. MS (ESI, m/z): 505.2 $[M+H]^+$.

Step K: Preparation of tert-butyl 3-(3-carbamoyl-2-(4-phenoxyphenyl)-5,6,7,8-tetrahydroimidazo[1,2-b] pyridazin-8-yl)azetidine-1-carboxylate

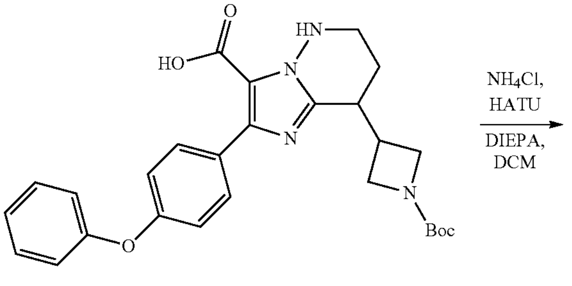

-continued

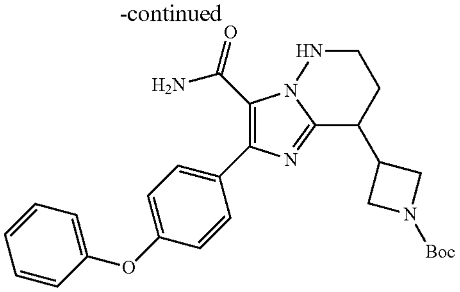

To the solution of the product of step J of example 18 (2.4 g, 4.89 mmol) in dichloromethane (30 mL) was added N, N-diisopropylethylamine (2.5 g, 19.57 mmol). After 5 min, $NH_4Cl$ (1.1 g, 19.57 mmol) and HATU (2.8 g, 7.34 mmol) was added. The reaction mixture was continued to stir at room temperature for 2 hs. Dichloromethane and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (40:1) to give product as an off-white solid (1.7 g, 71%). $^1$H NMR (400 MHz, MeOD) δ 7.70-7.63 (m, 2H), 7.39-7.31 (m, 2H), 7.15-7.07 (m, 1H), 7.06-6.99 (m, 2H), 6.99-6.94 (m, 2H), 4.09 (d, J=6.5 Hz, 2H), 4.00 (t, J=8.5 Hz, 1H), 3.89 (s, 1H), 3.46-3.40 (m, 1H), 3.30-3.17 (m, 2H), 3.08-2.96 (m, 1H), 2.22-2.15 (m, 1H), 1.80-1.65 (m, 1H), 1.42 (s, 9H). MS (ESI, m/z): 288.2 $[M+H]^+$.

Step L: Preparation of 2-(4-phenoxyphenyl)-8-(piperidin-4-yl)-5,6,7,8-tetrahydroimidazo[1,2-b] pyridazine-3-carboxamide

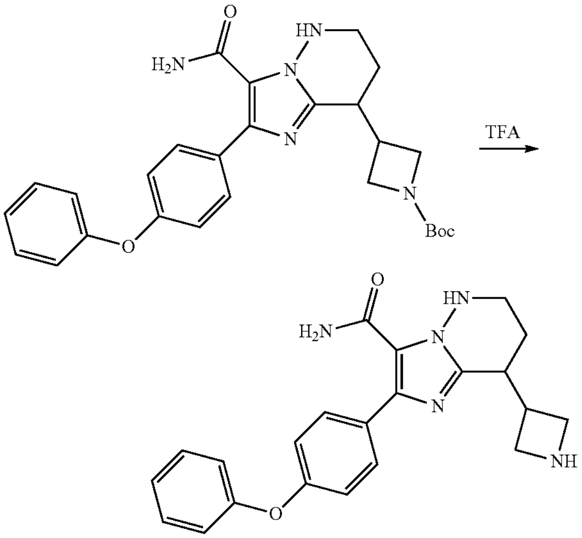

To a solution of the product of step K of example 18 (1.5 g, 3.06 mmol) in dichloromethane (10 mL) was added $CF_3COOH$ (2 mL) at room temperature in reaction still. The mixture was stirred for 30 min, and concentrated under vacuum to get 2.3 g crude. The residue was used to next step without further purification. $^1$H NMR (600 MHz, MeOD) δ 8.58 (s, 1H), 7.71 (d, J=8.1 Hz, 2H), 7.37 (t, J=7.6 Hz, 2H), 7.14 (t, J=7.3 Hz, 1H), 7.03 (d, J=7.9 Hz, 2H), 6.99 (d, J=8.1 Hz, 2H), 4.37 (t, J=9.3 Hz, 1H), 4.22 (t, J=7.9 Hz, 2H), 4.13 (t, J=9.2 Hz, 1H), 3.47-3.39 (m, 2H), 3.31-3.25 (m, 1H), 2.23-2.13 (m, 1H), 1.71-1.63 (m, 1H). MS (ESI, m/z): 390.2 $[M+H]^+$.

Step M: Preparation of 8-(1-acryloylazetidin-3-yl)-2-(4-phenoxyphenyl)-5,6,7,8-tetrahydroimidazo[1,2-b]pyridazine-3-carboxamide

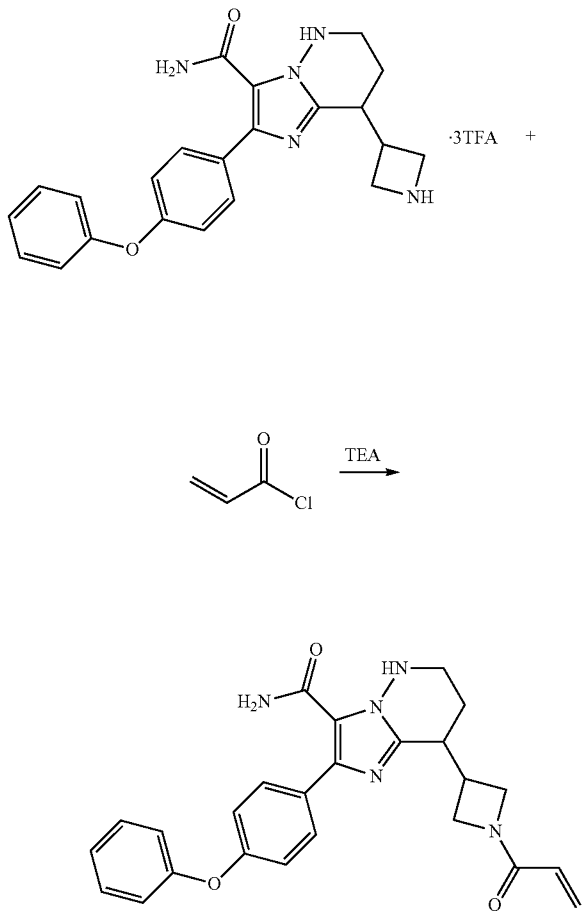

The mixture of the product of step L of example 18 (200.0 mg, 0.51 mmol) and triethylamine (207.8 mg, 2.05 mmol) in dichloromethane (5 mL) was cooled to −60° C. Then the solution of propenoyl chloride (46.5 mg, 0.51 mmol) in dichloromethane (1 mL) was added slowly, LC-MS was tracking, at the end of the reaction, 1 mL MeOH was added, the mixture was concentrated under vacuum to get crude product. And the residue was purified by flash chromatography on silica gel with dichloromethane and methanol (30:1) to get product (48 mg, 21%) as a white solid. $^1$H NMR (600 MHz, DMSO-d6) δ 7.84-7.80 (m, 2H), 7.41 (t, J=7.8 Hz, 2H), 7.15 (t, J=7.3 Hz, 1H), 7.04 (d, J=8.0 Hz, 2H), 6.99 (d, J=8.0 Hz, 2H), 6.39-6.31 (m, 1H), 6.13-6.08 (m, 1H), 5.69-5.62 (m, 1H), 4.48-4.40 (m, 1H), 4.32-4.21 (m, 1H), 4.19-4.06 (m, 1H), 4.06 (s, 1H), 4.04-3.84 (m, 1H), 3.32-3.28 (m, 1H), 3.21-3.15 (m, 1H), 2.92 (s, 1H), 2.14-2.01 (m, 1H), 1.61-1.50 (m, 1H). MS (ESI, m/z): 444.2 $[M+H]^+$.

Example 19

8-(1-(but-2-ynoyl)azetidin-3-yl)-2-(4-phenoxyphenyl)-5,6,7,8-tetrahydroimidazo[1,2-b]pyridazine-3-carboxamide

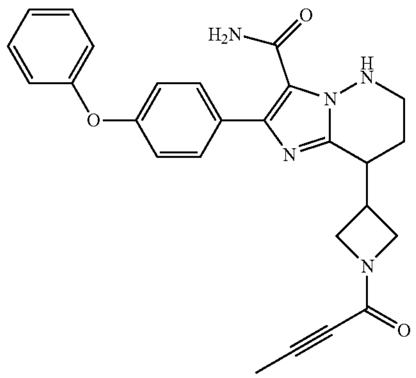 [SMILES: CC#CC(=O)N1CC(C2CCNn3c2nc(-c2ccc(Oc4ccccc4)cc2)c3C(N)=O)C1]

Preparation of 8-(1-(but-2-ynoyl)azetidin-3-yl)-2-(4-phenoxyphenyl)-5,6,7,8-tetrahydroimidazo[1,2-b]pyridazine-3-carboxamide

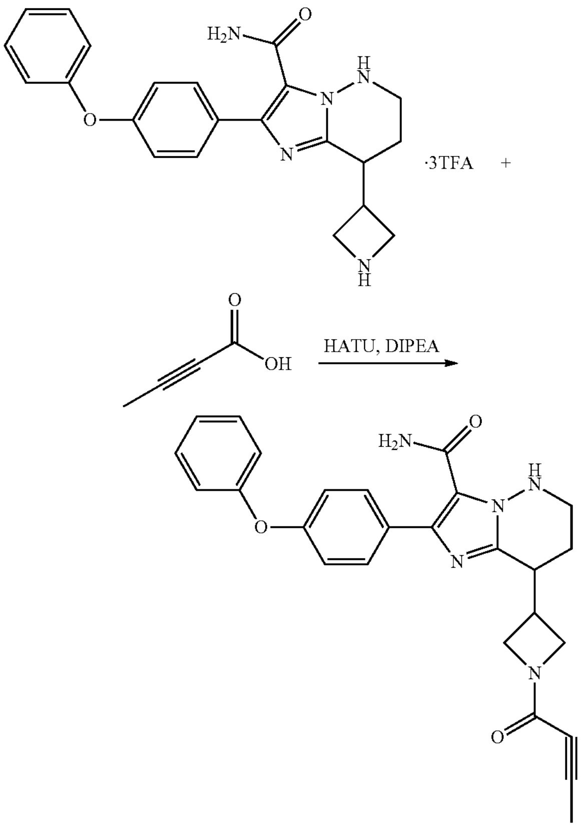

To the solution of the product of step L of example 18 (350.1 mg, 0.89 mmol) in dry N, N-dimethylformamide (5 mL) was added N, N-diisopropylethylamine (464.6 mg, 3.59 mmol). After 5 min, but-2-ynoic acid (83.1 mg, 0.98 mmol)

and HATU (512.5 mg, 1.35 mmol) was added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (40:1) to give product as an off-white solid (64 mg, 15%). $^1H$ NMR (400 MHz, $CDCl_3$) δ 7.65-7.56 (m, 2H), 7.40-7.32 (m, 2H), 7.17-7.10 (m, 1H), 7.08-7.01 (m, 4H), 5.83 (s, 1H), 4.53-4.35 (m, 1H), 4.33-4.21 (m, 1H), 4.18-4.07 (m, 2H), 3.88 (dd, J=10.4, 6.0 Hz, 1H), 3.47-3.22 (m, 3H), 3.10-2.87 (m, 1H), 2.26-2.10 (m, 1H), 1.96 (d, J=1.7 Hz, 3H), 1.79-1.64 (m, 1H). MS (ESI, m/z): 514.2 $[M+H]^+$.

Example 20

(E)-2-(4-phenoxyphenyl)-8-(1-(4,4,4-trifluorobut-2-enoyl)azetidin-3-yl)-5,6,7,8-tetrahydroimidazo[1,2-b]pyridazine-3-carboxamide

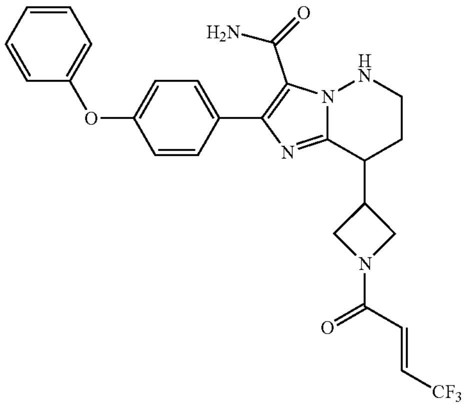 [SMILES: NC(=O)c1c(-c2ccc(Oc3ccccc3)cc2)nc2n1NCCC2C1CN(C(=O)/C=C/C(F)(F)F)C1]

Preparation of (E)-2-(4-phenoxyphenyl)-8-(1-(4,4,4-trifluorobut-2-enoyl)azetidin-3-yl)-5,6,7,8-tetrahydroimidazo[1,2-b]pyridazine-3-carboxamide

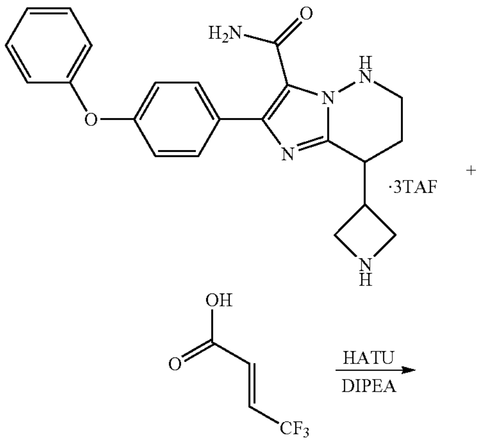

-continued

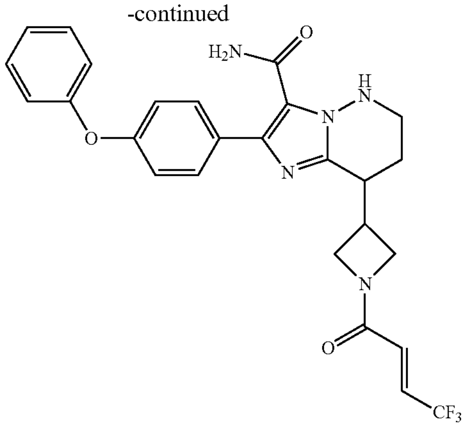

To the solution of the product of step L of example 18 (350 mg, 0.89 mmol) in dry N, N-dimethylformamide (5 mL) was added N, N-diisopropylethylamine (464.5 mg, 3.59 mmol). After 5 min, (E)-4,4,4-trifluorobut-2-enoic acid (138.5 mg, 0.98 mmol) and HATU (512.5 mg, 1.35 mmol) was added. The reaction mixture was continued to stir at room temperature for 2 hs. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (40:1) to give product as an off-white solid (67 mg, 14%). $^1H$ NMR (400 MHz, $CDCl_3$) δ 7.55-7.46 (m, 2H), 7.32-7.24 (m, 2H), 7.10-7.03 (m, 1H), 7.00-6.89 (m, 5H), 6.70-6.59 (m, 2H), 6.55-6.49 (m, 1H), 5.82 (s, 1H), 4.57 (dd, J=9.4, 5.9 Hz, 1H), 4.47-4.39 (m, 1H), 4.30 (t, J=8.6 Hz, 1H), 4.14 (dd, J=13.7, 6.0 Hz, 1H), 3.91 (dd, J=10.8, 6.0 Hz, 1H), 3.52-3.48 (m, 1H), 3.40-3.29 (m, 1H), 3.25-3.19 (m, 1H), 2.99 (p, J=7.5 Hz, 1H), 2.93-2.75 (m, 1H), 2.16-2.08 (m, 1H), 1.69-1.58 (m, 1H). MS (ESI, m/z): 570.2 $[M+H]^+$.

Example 21

8-(1-acryloylpyrrolidin-3-yl)-2-(4-phenoxyphenyl)-5,6,7,8-tetrahydroimidazo[1,2-b]pyridazine-3-carboxamide

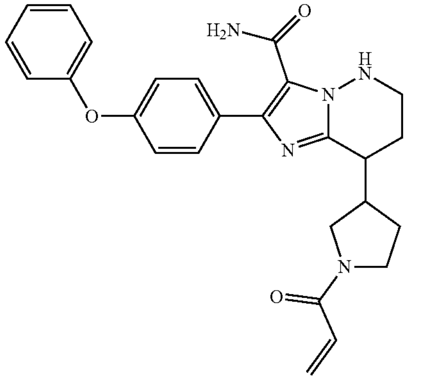 [SMILES: C=CC(=O)N1CCC(C2CCNn3c2nc(-c2ccc(Oc4ccccc4)cc2)c3C(N)=O)C1]

Step A: Preparation of tert-butyl (E)-3-(2-oxodihydrofuran-3(2H)-ylidene)pyrrolidine-1-carboxylate

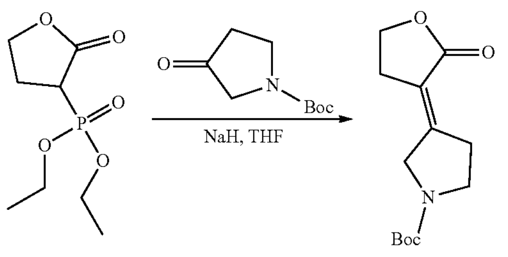

To a slurry of tetrahydrofuran-washed sodium hydride (60% dispersion in mineral oil; 32.4 g, 809.83 mmol) was added diethyl (2-oxotetrahydrofuran-3-yl)phosphonate (180 g, 809.83 mmol) as a solution in dry tetrahydrofuran (3 L) dropwise over 70 min at 10° C. The mixture was stirred for 30 min before the addition of tert-butyl 3-oxopyrrolidine-1-carboxylate (100 g, 539.89 mol) as a solution in tetrahydrofuran (2 L). The mixture was then stirred for 2 h before the addition of dichloromethane (2 L) followed by water (5 L). The tetrahydrofuran was then removed under reduced pressure, the aqueous residue extracted with dichloromethane (3×1000 ml), then washed with water (2×1000 ml) and dried (anhydrous $Na_2SO_4$) before evaporating to dryness to give a yellow oil, then purified by column chromatography on silica gel with ethyl acetate and petroleum ether (1:2) to give product as a white solid (34 g, 24%). $^1H$ NMR (400 MHz, $CDCl_3$) δ 4.49 (s, 2H), 4.41 (t, J=7.5 Hz, 2H), 3.59 (t, J=7.0 Hz, 2H), 2.89-2.85 (m, 2H), 2.70-2.62 (m, 2H), 1.48 (s, 9H). MS (ESI, m/z): 254.1 $[M+H]^+$.

Step B: Preparation of tert-butyl 3-(2-oxotetrahydrofuran-3-yl)pyrrolidine-1-carboxylate

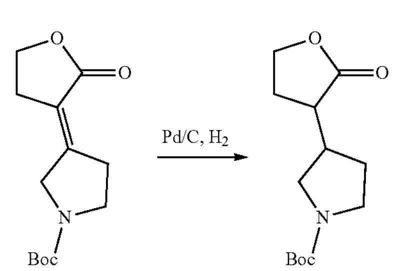 [SMILES: CC(C)(C)OC(=O)N1CC/C(=C2/CCOC2=O)C1 ; CC(C)(C)OC(=O)N1CCC(C2CCOC2=O)C1]

To a solution of the product of step A of example 21 (34 g, 3.34 mol) in ethyl acetate (4 L) was added 10% Pd/C (3.4 g, 10%) at room temperature. The mixture was stirred for 3 hs under $H_2$. The mixture was passed through Celite, and the solid was washed with ethyl acetate, and filtrate was concentrated under vacuum to get desired product (32.5 g, 94%). $^1H$ NMR (600 MHz, $CDCl_3$) δ 4.26 (s, 1H), 4.12 (d, J=7.9 Hz, 1H), 3.50-3.36 (m, 2H), 3.25-3.14 (m, 1H), 2.93 (t, J=9.3 Hz, 1H), 2.47-2.34 (m, 1H), 2.27 (d, J=6.1 Hz, 2H), 2.20 (s, 1H), 2.00-1.90 (m, 1H), 1.77-1.61 (m, 1H), 1.35 (s, 9H). MS (ESI, m/z): 256.1 $[M+H]^+$.

Step C: Preparation of 2-(1-(tert-butoxycarbonyl)pyrrolidin-3-yl)-4-hydroxybutanoic Acid

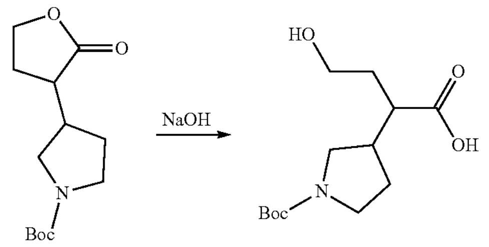

The product of step B of example 21 (16.5 g, 64.63 mmol), $H_2O$ (100 mL), and sodium hydroxide (5.7 g, 129.25 mol) were added in a round bottom flask. This reaction mixture was stirred at room temperature overnight. The clear reaction mixture was then extracted with ethyl acetate, the aqueous layer was isolated and acidified to pH 3-4 with concentrated HCl and then extracted with 100 mL of dichloromethane. The organic phase was washed with saturated brine and then dried over anhydrous $Na_2SO_4$. The organic phase was concentrated in vacuo to give product as an oil (17.5 g, 91%). $^1H$ NMR (400 MHz, $CDCl_3$) δ 4.36 (d, J=5.2 Hz, 1H), 4.25-4.17 (m, 1H), 3.86-3.70 (m, 2H), 3.53-3.48 (m, 2H), 3.29 (d, J=8.6 Hz, 1H), 3.04 (d, J=8.0 Hz, 1H), 2.53-2.49 (m, 1H), 2.44-2.37 (m, 2H), 1.90-1.83 (m, 1H), 1.46 (s, 9H). MS (ESI, m/z): 274.2 $[M+H]^+$.

Step D: Preparation of 2-(1-(tert-butoxycarbonyl)pyrrolidin-3-yl)-4-((tert-butyldimethylsilyl)oxy)butanoic acid

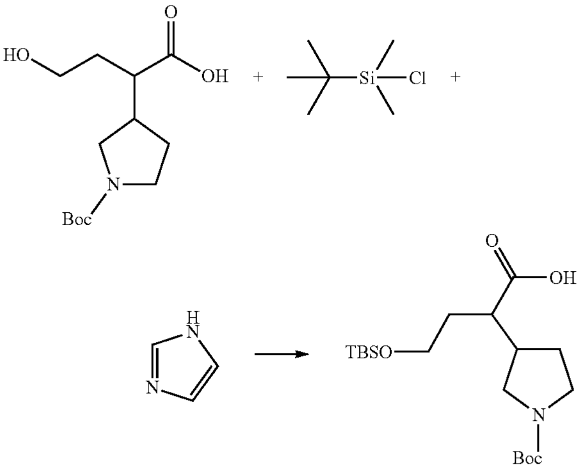

Tert-Butyldimethylsilylchloride (17.5 g, 76.83 mol) was added to a mixture of the product of step C of example 21 (17.5 g, 64.03 mmol) and imidazole (8.7 g, 128.05 mol) in N, N-dimethylformamide (300 mL). The reaction mixture was stirred at 30° C. for 5 hs under argon atmosphere, then poured into a separatory funnel containing 400 mL of brine and extracted 4 times with 200 mL of dichloromethane. The organic fractions were combined, dried over anhydrous $Na_2SO_4$, filtered, and concentrated under reduced pressure to give the crude product which was purified via flash chromatography eluting with dichloromethane and methanol (30:1) to give the product as a clear colorless oil (crude 14 g). MS (ESI, m/z): 388.3 $[M+H]^+$.

Step E: Preparation of tert-butyl 3-(11,11,12,12-tetramethyl-3,6-dioxo-4-(4-phenoxybenzoyl)-2,5,10-trioxa-11-silatridecan-7-yl)pyrrolidine-1-carboxylate

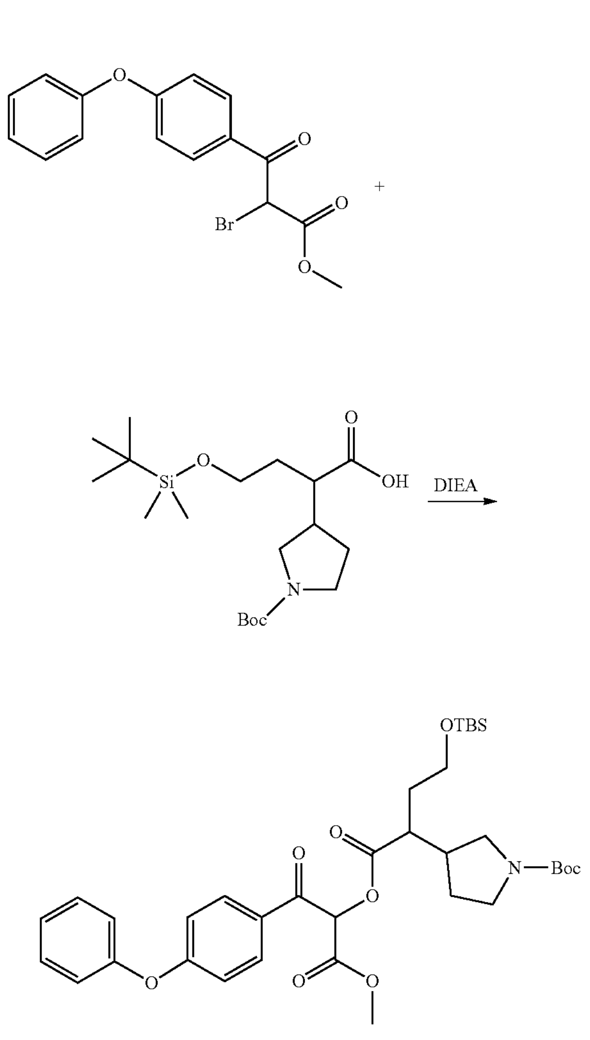

The product of step B (7.4 g, 21.08 mmol) of example 1 and the product of step D of example 21 (12.3 g, 31.62 mmol) were taken up in acetonitrile (250 mL), then N, N-diisopropylethylamine (5.5 g, 42.16 mmol) was added and the solution stirred at 30° C. for 3 hs. The solvent was removed by rotorary evaporation and the residue taken up in ethyl acetate, washed with 0.1 N HCl, and brine. The organic fractions were dried over anhydrous $Na_2SO_4$, filtered, and concentrated under reduced pressure to give the crude product which was purified via flash chromatography eluting with ethyl acetate and petroleum ether (1:20) to give the product as a clear colorless oil (6 g, 43%). $^1H$ NMR (600 MHz, $CDCl_3$) δ 7.98 (d, J=8.4 Hz, 2H), 7.42 (t, J=7.6 Hz, 2H), 7.24 (t, J=7.3 Hz, 1H), 7.09 (d, J=7.9 Hz, 2H), 7.01 (d, J=8.4 Hz, 2H), 6.25 (d, J=7.7 Hz, 1H), 3.79 (s, 3H), 3.73-3.56 (m, 3H), 3.52-3.43 (m, 1H), 3.24 (s, 1H), 3.09-2.89 (m, 1H), 2.63 (s, 1H), 2.52-2.35 (m, 1H), 2.05 (s, 1H), 1.93 (s, 1H), 1.87-1.71 (m, 1H), 1.45 (s, 9H), 1.26 (s, 1H), 0.87-0.84 (m, 6H), 0.04-(−0.03) (m, 6H). MS (ESI, m/z): 666.3 $[M+H]^+$.

Step F: Preparation of methyl 2-(1-(1-(tert-butoxycarbonyl)pyrrolidin-3-yl)-3-((tert-butyldimethylsilyl)oxy)propyl)-4-(4-phenoxyphenyl)-1H-imidazole-5-carboxylate

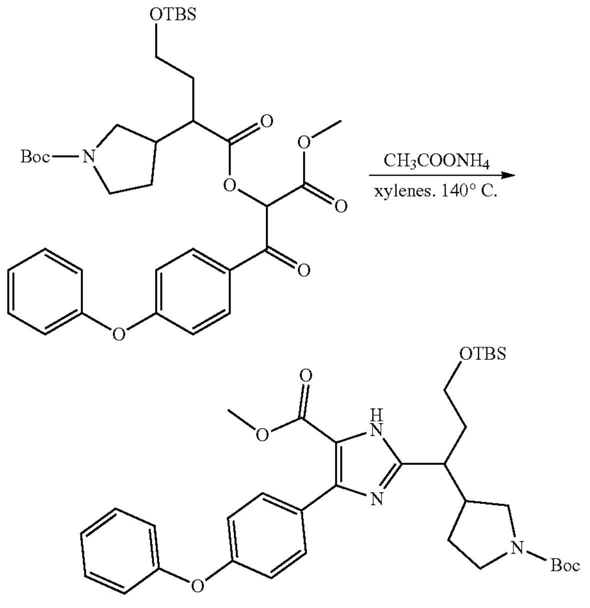

To a slurry of ammonium acetate (6 g, 9.15 mmol) in xylenes (40 mL) was added the product of step E of example 21 (8.5 g, 109.78 mmol). The mixture was stirred at 140° C. For 4 hours. The solution was cooled to room temperature and evaporated. The residue was dissolved in ethyl acetate and washed with saturated brine. The organic phase was dried over anhydrous $Na_2SO_4$, filtered and concentrated. The residue was purified by silica gel column chromatography with ethyl acetate and petroleum ether (1:20) to give the product as a clear colorless oil (2.5 g, 43%). $^1H$ NM R (600 MHz, $CDCl_3$) δ 7.89 (d, J=7.8 Hz, 2H), 7.29 (t, J=7.4 Hz, 2H), 7.06 (t, J 7.3 Hz, 1H), 7.00 (d, J=6.7 Hz, 4H), 3.79 (s, 3H), 3.68-3.57 (m, 2H), 3.46-3.32 (m, 3H), 3.17 (t, J=15.7 Hz, 1H), 2.99-2.83 (m, 3H), 2.64 (s, 1H), 1.90 (s, 3H), 1.75 (s, 2H), 1.42 (d, J=11.9 Hz, 9H), 1.38 (d, J=6.5 Hz, 2H), 0.86 (s, 9H), 0.00 (d, J=4.7 Hz, 6H). MS (ESI, m/z): 636.3 $[M+H]^+$.

Step G: Preparation of methyl 1-amino-2-(1-(1-(tert-butoxycarbonyl)pyrrolidin-3-yl)-3-((tert-butyldimethylsilyl)oxy)propyl)-4-(4-phenoxyphenyl)-1H-imidazole-5-carboxylate

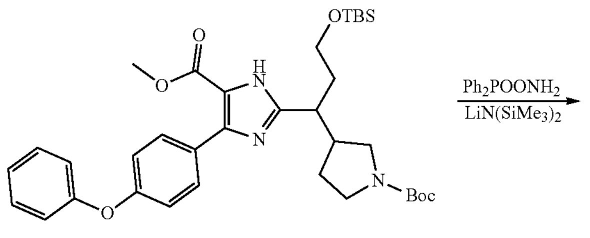

-continued

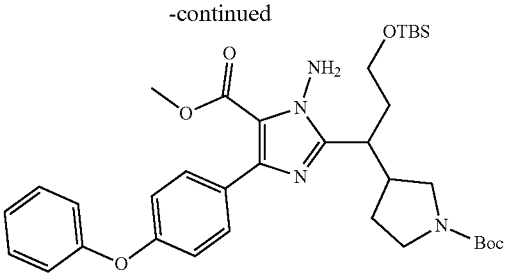

Lithium hexamethyldisilazane (6 mL of a 1 M solution in tetrahydrofuran, 5.89 mmol) was slowly added to the product of step F of example 21 (2.5 g, 3.93 mmol) in anhydrous N, N-dimethylformamide (30 mL) at 0° C. After the mixture was stirred for 30 min, O-(diphenylphosphinyl) hydroxylamine (1.8 g, 7.86 mmol) was added, followed by stirring at room temperature for 5 hs (in cases where the reaction mixture became too viscous, additional N, N-dimethylformamide was added). The reaction was quenched with water until a clear solution was formed and concentrated to dryness under reduced pressure. The residue was washed several times with ethyl acetate or dichloromethane. The combined organic fractions were concentrated in vacuo and purified by flash chromatography on silica gel with ethyl acetate and petroleum ether (1:3) to give the product as a clear colorless oil (1.5 g, 58%). $^1$H NMR (400 MHz, $CDCl_3$) δ 7.62-7.59 (m, 2H), 7.33 (t, J=7.0 Hz, 2H), 7.10 (t, J=7.4 Hz, 1H), 7.05-6.99 (m, 4H), 5.69-5.52 (m, 2H), 3.77 (s, 3H), 3.71-3.58 (m, 2H), 3.50-3.44 (m, 1H), 3.43-3.32 (m, 2H), 3.26-3.14 (m, 1H), 3.12-2.98 (m, 1H), 2.77-2.65 (m, 1H), 2.04 (s, 2H), 1.97-1.85 (m, 1H), 1.83-1.69 (m, 1H), 1.47-1.41 (m, 9H), 0.85 (s, 9H), 0.01-(−0.04) (m, 6H). MS (ESI, m/z): 651.3 $[M+H]^+$.

Step H: Preparation of methyl 1-amino-2-(1-(1-(tert-butoxycarbonyl)pyrrolidin-3-yl)-3-hydroxypropyl)-4-(4-phenoxyphenyl)-1H-imidazole-5-carboxylate

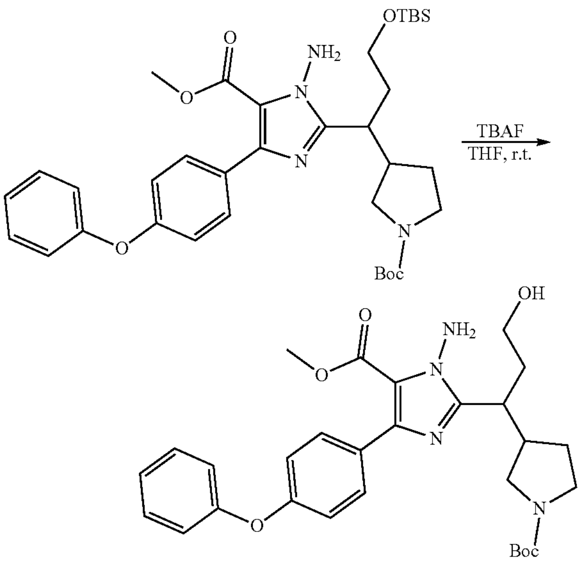

To a solution of the product of step G of example 21 (1.5 g, 2.30 mmol) in tetrahydrofuran (20 mL) was added a 1 M solution of tetrabutylammonium fluoride in tetrahydrofuran (2.5 mL, 2.5 mmol) at RT. The solution was stirred for 2 h and diluted with 100 mL ethyl acetate solution. The organic layer was separated and washed with $H_2O$ (3×200 mL). The water extract was washed with ethyl acetate solution (2×150 mL), and the organic layers were combined and dried over anhydrous $Na_2SO_4$. The solvent was evaporated in vacuo, and purified by flash chromatography on silica gel with dichloromethane and methanol (30:1) to give the product as a clear colorless oil (1.0 g, 80%). $^1$H NMR (600 MHz, $CDCl_3$) δ 7.64-7.55 (m, 2H), 7.32 (t, J=7.9 Hz, 2H), 7.10 (t, J=7.4 Hz, 1H), 7.05-6.96 (m, 4H), 5.74-5.60 (m, 2H), 3.76 (s, 3H), 3.70-3.53 (m, 2H), 3.49-3.23 (m, 4H), 3.19-3.13 (m, 1H), 3.07-3.01 (m, 1H), 2.88-2.69 (m, 1H), 2.06-1.90 (m, 2H), 1.80-1.69 (m, 1H). MS (ESI, m/z): 537.3 $[M+H]^+$.

Step I: Preparation of methyl 8-(1-(tert-butoxycarbonyl)pyrrolidin-3-yl)-2-(4-phenoxyphenyl)-5,6,7,8-tetrahydroimidazo[1,2-b]pyridazine-3-carboxylate

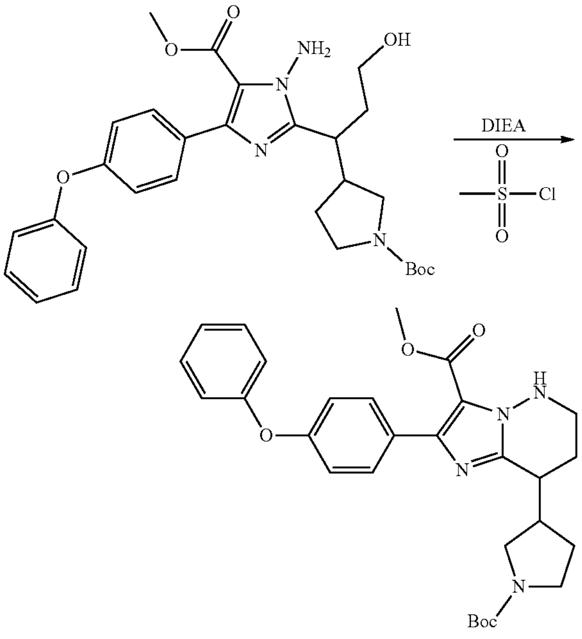

Methanesulfonyl chloride (320.2 mg, 2.80 mmol) was added via syringe into a stirred mixture of the product of step H of example 21 (1.0 g, 1.86 mmol) and N, N-diisopropylethylamine (481.7 mg, 3.37 mmol) in dichloromethane (10 ml) maintained at 0° C. The mixture was stirred at room temperature for 3 hs (TLC monitoring) and then partitioned between dichloromethane and water. The organic phase was dried and evaporated to afford a yellow oil. The crude intermediate was dissolved in tetrahydrofuran (10 mL), 1 M solution of tetrabutylammonium fluoride in tetrahydrofuran (2 mL, 2 mmol) and N, N-diisopropylethylamine (481.7 g, 3.37 mmol) was added to the mixture, which was stirred 3 hs, then partitioned between dichloromethane and water. The organic phase was dried and evaporated to afford a white solid, then passed through a column of silica gel with dichloromethane and methanol (30:1) to afford the desired product as a colorless oil (650 mg, 56%). $^1$H NMR (600 MHz, $CDCl_3$) δ 7.74-7.60 (m, 2H), 7.34 (t, J=7.9 Hz, 2H), 7.10 (dd, J=13.4, 6.0 Hz, 1H), 7.08-7.00 (m, 4H), 3.78 (s, 3H), 3.65-3.50 (m, 3H), 3.42-3.32 (m, 1H), 3.32-3.22 (m, 1H), 3.10 (t, J=10.0 Hz, 1H), 2.50 (d, J=4.8 Hz, 1H), 2.49-2.30 (m, 1H), 2.20-2.11 (m, 1H), 2.07-1.75 (m, 3H), 1.45 (s, 9H). MS (ESI, m/z): 519.3 $[M+H]^+$.

Step J: Preparation of 8-(1-(tert-butoxycarbonyl)pyrrolidin-3-yl)-2-(4-phenoxyphenyl)-5,6,7,8-tetrahydroimidazo[1,2-b]pyridazine-3-carboxylic acid

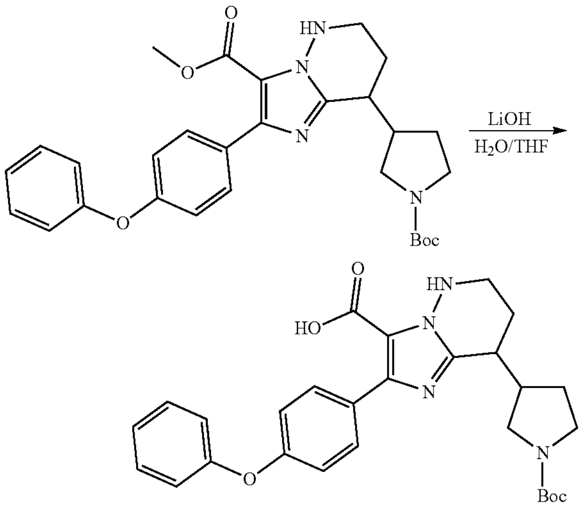

To a solution of the product of step I of example 21 (650 mg, 1.25 mmol) in tetrahydrofuran (10 mL)/water (3 mL) was added LiOH (150.1 mg, 6.27 mmol) in water (1 mL), the mixture was heated at 50° C. for 3 hs, and then cooled to r.t. The mixture acidified to pH 3-4 with concentrated HCl and then extracted with 3×100 mL of dichloromethane. The organic phase was washed with saturated brine and then dried over anhydrous $Na_2SO_4$. The organic phase was concentrated in vacuo to afford 600 mg crude product. The residue was used to next step. MS (ESI, m/z): 505.2 $[M+H]^+$.

Step K: Preparation of tert-butyl 3-(3-carbamoyl-2-(4-phenoxyphenyl)-5,6,7,8-tetrahydroimidazo[1,2-b]pyridazin-8-yl)pyrrolidine-1-carboxylate

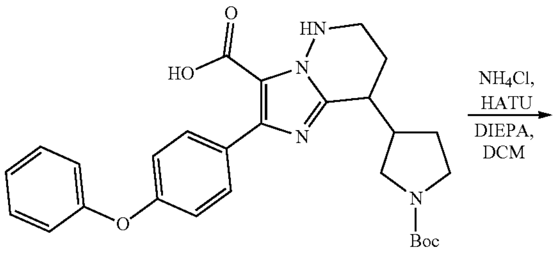

-continued

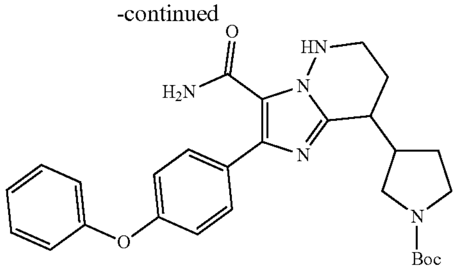

To the solution of the product of step J of example 21 (600 mg, 1.19 mmol) in dichloromethane (10 mL) was added N,N-diisopropylethylamine (614.7 mg, 4.76 mmol). After 5 min, $NH_4Cl$ (254.4 mg, 4.76 mmol) and HATU (678.2 mg, 1.78 mmol) was added. The reaction mixture was continued to stir at room temperature for 2 hs. Dichloromethane and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (40:1) to afford the desired product as a colorless oil (280 mg, 46%). $^1H$ NMR (600 MHz, $CDCl_3$) δ 7.60 (d, J=8.5 Hz, 2H), 7.33 (t, J=7.9 Hz, 2H), 7.11 (t, J=7.4 Hz, 1H), 7.01 (d, J=7.8 Hz, 4H), 6.87 (s, 1H), 5.80 (s, 1H), 3.59 (dd, J=13.2, 6.5 Hz, 1H), 3.54-3.48 (m, 1H), 3.42 (d, J=6.0 Hz, 1H), 3.32-3.22 (m, 2H), 3.11-3.06 (m, 2H), 2.71-2.52 (m, 1H), 2.34 (d, J=5.7 Hz, 2H), 2.13 (s, 1H), 1.95-1.80 (m, 2H), 1.43 (s, 11H). MS (ESI, m/z): 504.3 $[M+H]^+$.

Step L: Preparation of 2-(4-phenoxyphenyl)-8-(pyrrolidin-3-yl)-5,6,7,8-tetrahydroimidazo[1,2-b]pyridazine-3-carboxamide

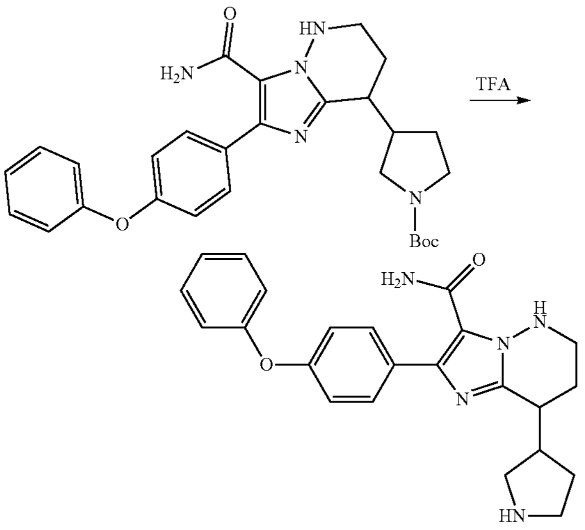

To a solution of the product of step K of example 21 (280 mg, 0.55 mmol) in dichloromethane (10 mL) was added $CF_3COOH$ (2 mL) at room temperature in reaction still. The mixture was stirred for 30 min, and concentrated under vacuum to get 540 mg crude. The residue was used to next step without further purification. MS (ESI, m/z): 404.2 $[M+H]^+$.

Step M: Preparation of 8-(1-acryloylpyrrolidin-3-yl)-2-(4-phenoxyphenyl)-5,6,7,8-tetrahydroimidazo[1,2-b]pyridazine-3-carboxamide

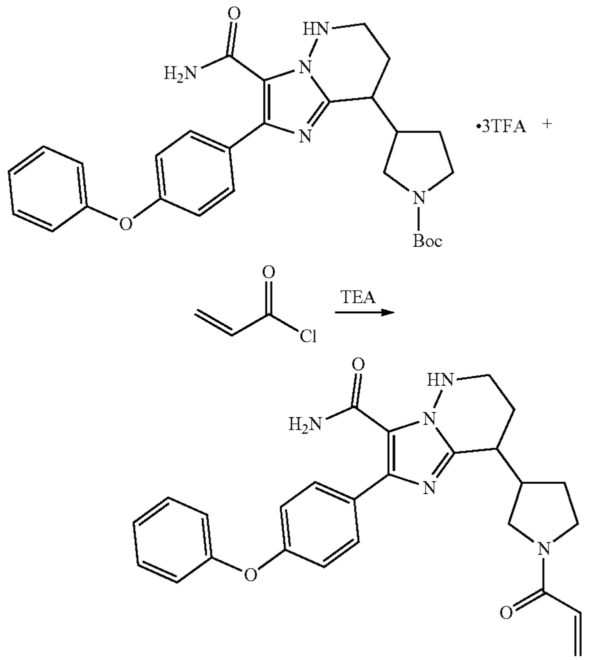

The mixture of the product of step L of example 21 (220.0 mg, 0.55 mmol) and triethylamine (220.7 mg, 2.18 mmol) in dichloromethane (5 mL) was cooled to −60° C. Then the solution of propenoyl chloride (49.5 mg, 0.55 mmol) in dichloromethane (1 mL) was added slowly, LC-MS was tracking, at the end of the reaction, 1 mL MeOH was added, the mixture was concentrated under vacuum to get 320 mg crude, and purified by flash chromatography on silica gel with dichloromethane and methanol (40:1) to get product as a white solid (48 mg, 21%). $^1$H NMR (400 MHz, $CDCl_3$) δ 7.64-7.55 (m, 2H), 7.37-7.32 (m, 2H), 7.12 (ddd, J=7.2, 5.1, 1.8 Hz, 1H), 7.03 (dt, J=5.0, 4.6 Hz, 4H), 6.42-6.28 (m, 2H), 5.93 (s, 1H), 5.69-5.61 (m, 1H), 3.89-3.66 (m, 2H), 3.49-3.28 (m, 3H), 3.27-3.15 (m, 1H), 3.13-2.96 (m, 1H), 2.86-2.63 (m, 1H), 2.36-2.25 (m, 1H), 2.23-2.02 (m, 2H), 1.92-1.83 (m, 1H). MS (ESI, m/z): 458.2 [M+H]$^+$.

Scheme II

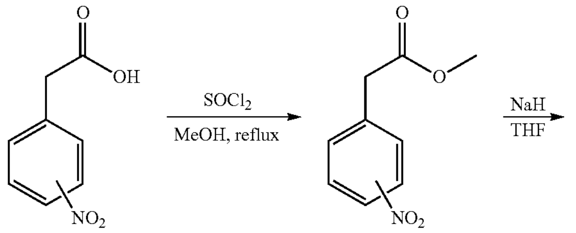

-continued

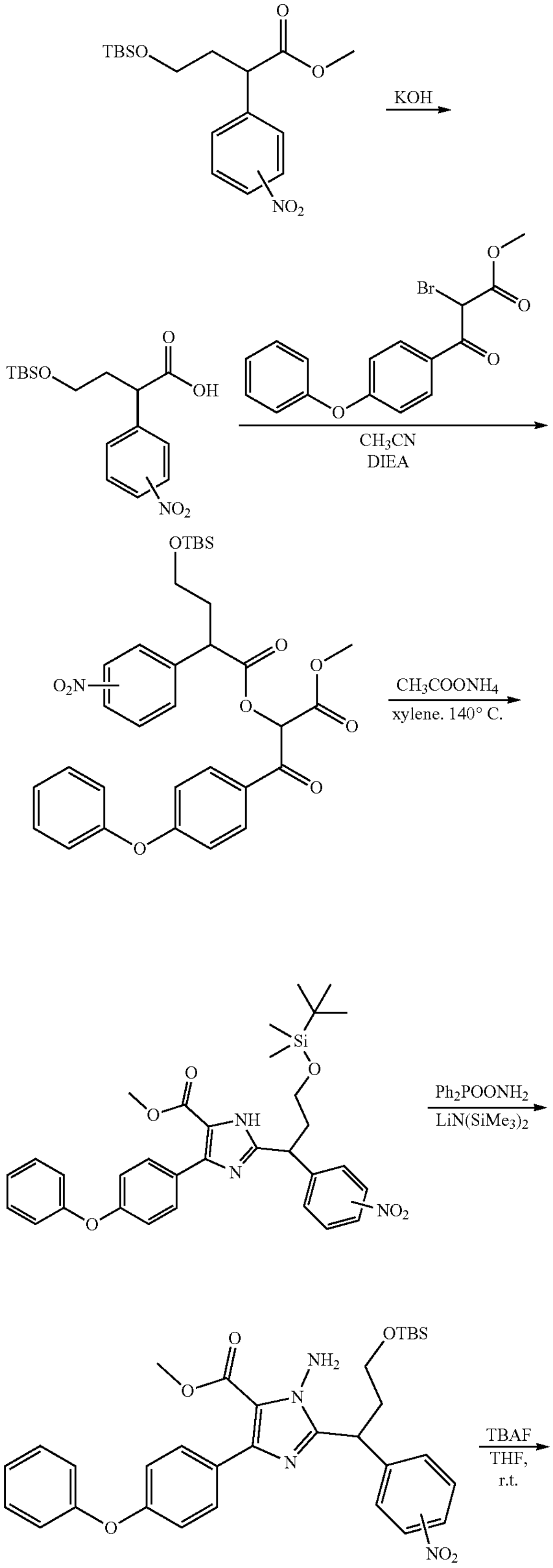

-continued

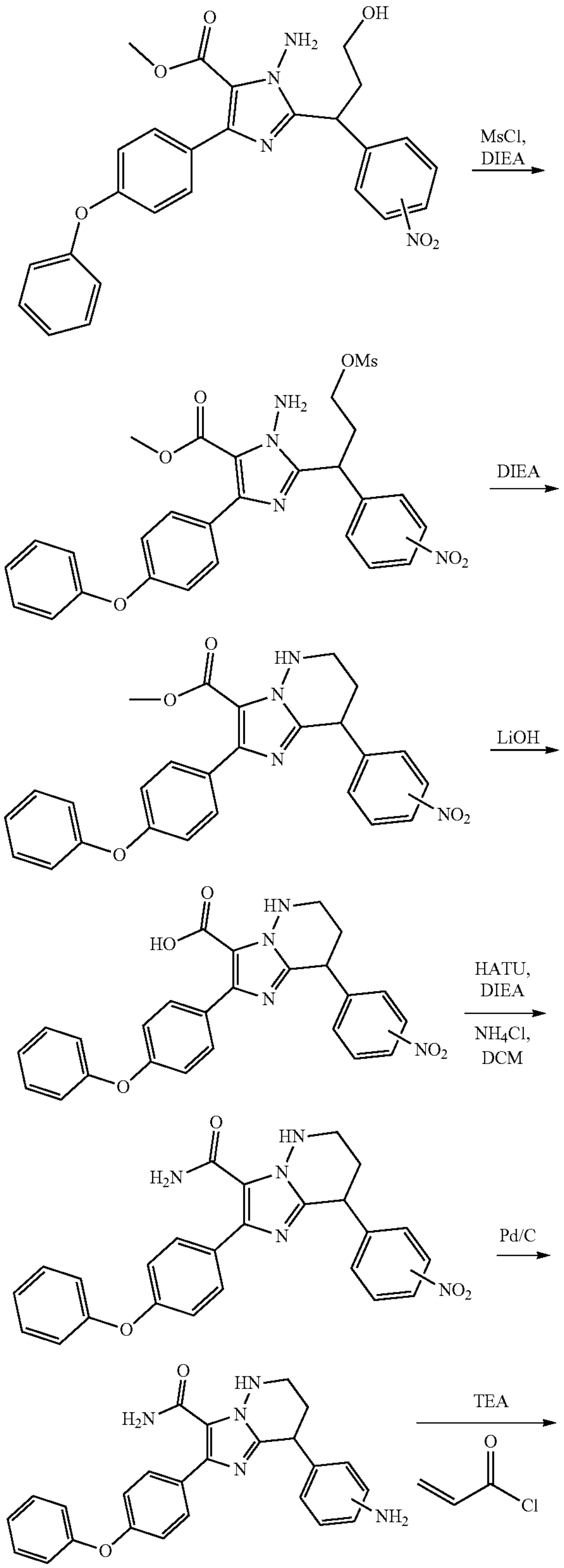

-continued

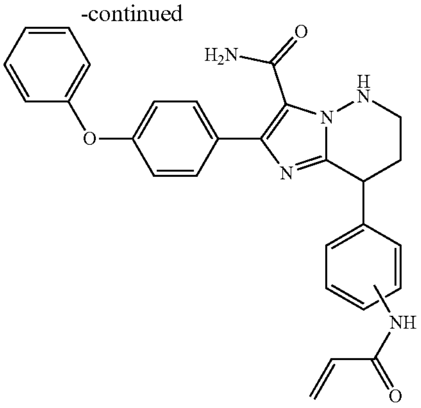

Example 22

Preparation of 8-(2-acrylamidophenyl)-2-(4-phenoxyphenyl)-5,6,7,8-tetrahydroimidazo[1,2-b]pyridazine-3-carboxamide

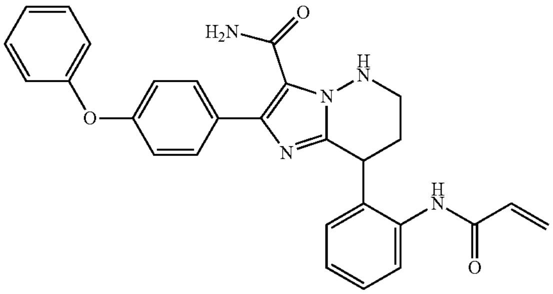 [SMILES: C=CC(=O)Nc1ccccc1C1CCNn2c1nc(-c1ccc(Oc3ccccc3)cc1)c2C(N)=O]

Experimental Section:

Step A: Preparation of methyl 2-(2-nitrophenyl)acetate

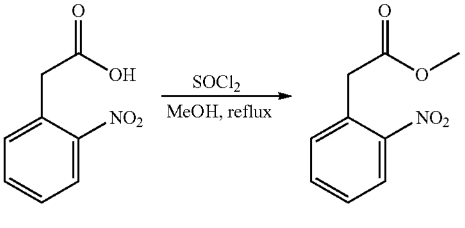

2-Nitrophenylacetic acid (300 g, 1.66 mol) was set stirring in 500 mL of methanol. Sulfurous dichloride (591.3 g, 4.97 mol) was added and the mixture heated to reflux. After 4 h the mixture was cooled and evaporated under reduced pressure to give a clear yellow oil. The oil was taken up in ethyl acetate and washed with saturated $NaHCO_3$. The organics were dried over anhydrous $Na_2SO_4$ and evaporated to give product as a clear orange liquid (320 g, 99%). $^1H$ NMR (400 MHz, $CDCl_3$) δ 8.13-8.07 (m, 1H), 7.63-7.56 (m, 1H), 7.50-7.44 (m, 1H), 7.39-7.34 (m, 1H), 4.03 (s, 2H), 3.70 (s, 3H). MS (ESI, m/z): 196.1 $[M+H]^+$.

Step B: Preparation of methyl 4-((tert-butyldimethylsilyl)oxy)-2-(2-nitrophenyl)butanoate

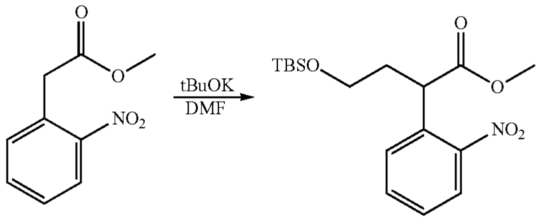

A solution of the product of step A of example 22 (100.0 g, 512.36 mmol) and t-BuOK (115.0 g, 1.02 mol) in N, N-dimethylformamide (1500 mL) was stirred at room temperature for 1 hs. Then (2-bromo-ethoxy)-tert-butyl-dimethyl-silane (196.1 g, 819.78 mmol) was added slowly at 0° C. to this solution. The mixture was stirred at room temperature overnight, then poured into water (500 mL). The aqueous phase was extracted with ethyl acetate (3×500 mL), and the organic layer was washed with saturated $NH_4Cl$ (500 mL), water (3×500 mL), brine (500 mL), dried with anhydrous $Na_2SO_4$, and evaporated to get crude product. It was purified by flash chromatography with ethyl acetate and petroleum ether (1:20) to obtain the desired product as a clear orange liquid (103 g, 56%). $^1$H NMR (600 MHz, $CDCl_3$) δ 7.91-7.87 (m, 1H), 7.59-7.54 (m, 1H), 7.52-7.49 (m, 1H), 7.44-7.38 (m, 1H), 4.39 (t, J=7.2 Hz, 1H), 3.68-3.64 (m, 4H), 3.54-3.50 (m, 1H), 2.47-2.41 (m, 1H), 2.06-1.95 (m, 1H), 0.86 (s, 9H), −0.00 (d, J=7.0 Hz, 6H). MS (ESI, m/z): 354.2 [M+H]$^+$.

Step C: Preparation of 4-((tert-butyldimethylsilyl)oxy)-2-(2-nitrophenyl)butanoic Acid

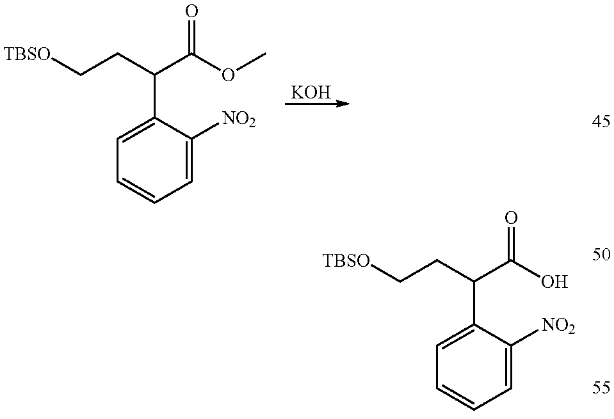

To a solution of the ester product of step B of example 22 (50 g, 5.7 mmol) in tetrahydrofuran (500 mL) was added a solution of aqueous 10% KOH (250 mL). The reaction mixture was stirred until complete consumption of the ester. Water was added and the reaction mixture was acidified to pH 5-6 with 1 M HCl. The mixture was extracted with ethyl acetate. The combined organic phases were washed with brine, dried over anhydrous $Na_2SO_4$ and concentrated in vacuo to get the product as a colorless oil (41 g, 85%), which was used for the next step without further purification. $^1$H NMR (600 MHz, $CDCl_3$) δ 7.96-7.92 (m, 1H), 7.61-7.56 (m, 1H), 7.52-7.48 (m, 1H), 7.47-7.40 (m, 1H), 4.42 (t, J=6.9 Hz, 1H), 3.73-3.67 (m, 1H), 3.54-3.51 (m, 1H), 2.52-2.43 (m, 1H), 2.07-1.97 (m, 1H), 0.86 (s, 9H), 0.00 (d, J=9.2 Hz, 6H). MS (ESI, m/z): 340.2 [M+H]$^+$.

Step D: Preparation of 1-methoxy-1,3-dioxo-3-(4-phenoxyphenyl)propan-2-yl 4-((tert-butyldimethylsilyl)oxy)-2-(2-nitrophenyl)butanoate

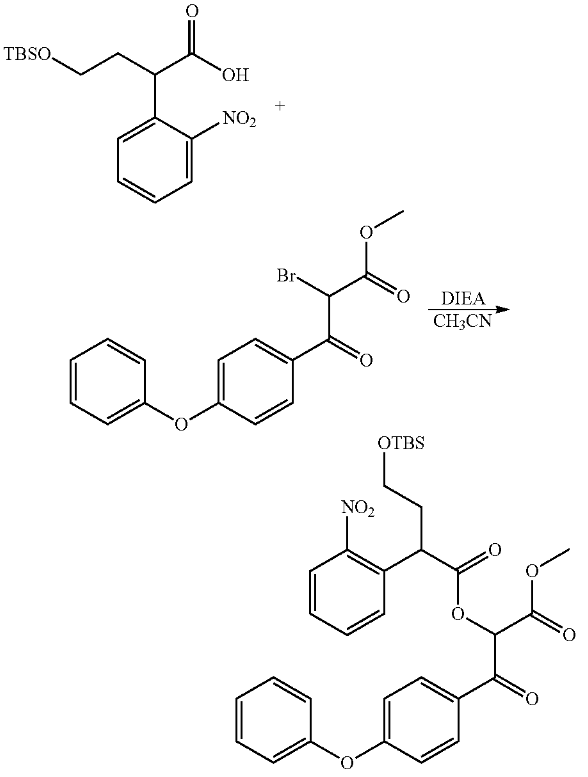

The product of step B (20.0 g, 57.28 mmol) of example 1 and the product of step C of example 22 (21.39 g, 63.00 mmol) were taken up in acetonitrile (250 mL), then N, N-diisopropylethylamine (11.1 mL, 85.92 mmol) was added and the solution stirred at 30° C. for 3 hs. The solvent was removed by rotorary evaporation and the residue taken up in ethyl acetate, washed with 0.1 N HCl, and brine. The organic fractions were dried over anhydrous $Na_2SO_4$, filtered, and concentrated under reduced pressure to give the crude product which was purified via flash chromatography eluting with ethyl acetate and petroleum ether (1:20) to give the product as a clear orange oil (23 g, 66%). $^1$H NMR (400 MHz, $CDCl_3$) δ 7.97-7.81 (m, 3H), 7.63-7.49 (m, 2H), 7.45-7.38 (m, 3H), 7.26-7.20 (m, 1H), 7.11-7.06 (m, 2H), 6.96-6.88 (m, 2H), 6.19 (d, J=1.9 Hz, 1H), 4.57 (t, J=7.1 Hz, 1H), 3.79-3.72 (m, 3H), 3.72-3.66 (m, 1H), 3.54-3.48 (m, 1H), 2.58-2.45 (m, 1H), 2.13-1.97 (m, 1H), 0.84 (t, J=2.1 Hz, 9H), −0.01-(−0.04) (m, 6H). MS (ESI, m/z): 608.2 [M+H]$^+$.

Step E: Preparation of methyl 2-(3-((tert-butyldimethylsilyl)oxy)-1-(2-nitrophenyl)propyl)-4-(4-phenoxyphenyl)-1H-imidazole-5-carboxylate

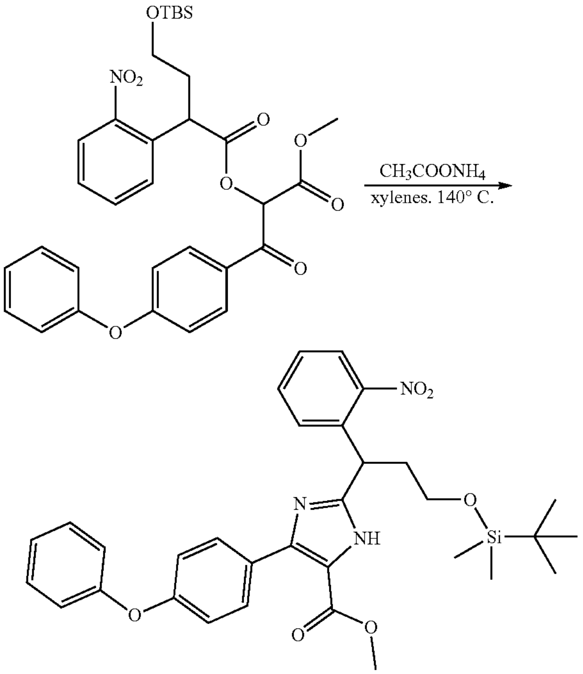

To a slurry of ammonium acetate (18.26 g, 236.95 mmol) in xylenes (50 mL) was added the product of step D of example 22 (12 g, 19.75 mmol). The mixture was stirred at 140° C. for 4 hs. The solution was cooled to room temperature and the solvent was evaporated. The residue was dissolved in ethyl acetate and washed with saturated brine. The organic phase was dried over anhydrous $Na_2SO_4$, filtered and concentrated. The residue was purified by silica gel column chromatography with ethyl acetate and petroleum ether (1:5) to give the product as a clear yellow oil (2.5 g, 21%). $^1H$ NMR (600 MHz, $CDCl_3$) δ 10.12 (s, 1H), 7.97 (d, J=8.5 Hz, 2H), 7.84 (d, J=8.0 Hz, 1H), 7.70 (d, J=7.8 Hz, 1H), 7.55 (t, J=7.6 Hz, 2H), 7.40-7.31 (m, 3H), 7.11 (t, J=7.4 Hz, 1H), 7.06-6.99 (m, 3H), 4.96 (t, J=7.2 Hz, 1H), 3.82 (s, 3H), 3.68-3.63 (m, 1H), 3.58-3.54 (m, 1H), 2.67-3.64 (m, 1H), 2.35-2.30 (m, 1H), 0.87 (s, 9H), 0.01-(−0.03) (m, 6H). MS (ESI, m/z): 588.3 $[M+H]^+$.

Step F: Preparation of methyl 1-amino-2-(3-((tert-butyldimethylsilyl)oxy)-1-(2-nitrophenyl)propyl)-4-(4-phenoxyphenyl)-1H-imidazole-5-carboxylate

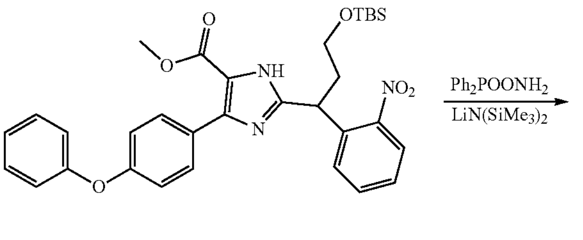

-continued

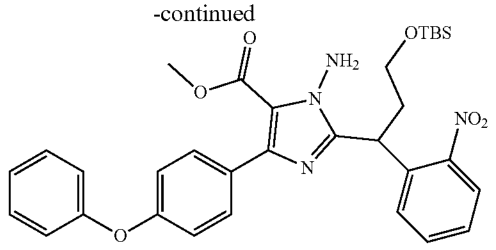

Lithium hexamethyldisilazane (6.3 mL of a 1 M solution in tetrahydrofuran, 2.77 mmol) was slowly added to the product of step E of example 22 (2.5 g, 4.25 mmol) in anhydrous N, N-dimethylformamide (10 mL) at 0° C. After the mixture was stirred for 30 min, O-(diphenylphosphinyl) hydroxylamine (1.98 g, 8.51 mmol) was added at 0° C., followed by stirring at room temperature for 4 hs (in cases where the reaction mixture became too viscous, additional N, N-dimethylformamide was added). The reaction was quenched with water until a clear solution was formed and concentrated to dryness under reduced pressure. The residue was washed several times with ethyl acetate or dichloromethane. The combined organic fractions were concentrated in vacuo and purified by flash chromatography on silica gel with ethyl acetate and petroleum ether (1:3) to give the product as a clear colorless oil (2.3 g, 89%). $^1H$ NMR (600 MHz, $CDCl_3$) δ 7.79-7.76 (m, 1H), 7.70-7.65 (m, 3H), 7.51-7.44 (m, 1H), 7.37-7.31 (m, 3H), 7.13-7.09 (m, 1H), 7.06-7.00 (m, 4H), 5.33-5.29 (m, 1H), 5.13 (s, 2H), 3.78-3.72 (m, 4H), 3.71-3.66 (m, 1H), 2.64-2.58 (m, 1H), 2.32-2.27 (m, 1H), 0.85 (s, 9H), 0.00-(−0.04) (m, 6H). MS (ESI, m/z): 603.3 $[M+H]^+$.

Step G: Preparation of methyl 1-amino-2-(3-hydroxy-1-(2-nitrophenyl)propyl)-4-(4-phenoxyphenyl)-1H-imidazole-5-carboxylate

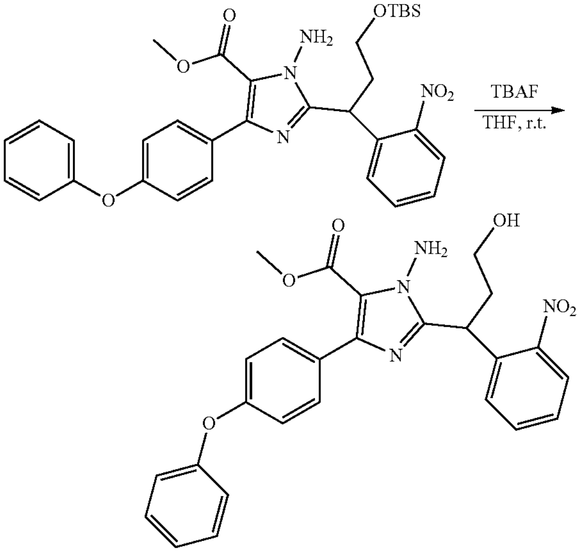

To a solution of the product of step F of example 22 (2.3 g, 3.82 mmol) in tetrahydrofuran (20 mL) was added a 1 M solution of tetrabutylammonium fluoride in tetrahydrofuran (10 mL, 10 mmol) at r.t. The solution was stirred for 2 hs and diluted with 100 mL ethyl acetate solution. The organic layer was separated and washed with $H_2O$ (3×100 mL). The water extract was washed with ethyl acetate solution (2×50 mL), and the organic layers were combined and dried over anhydrous $Na_2SO_4$. The solvent was evaporated in vacuo, and the residue was purified via flash chromatography eluting with ethyl acetate and petroleum ether (1:1) to give the product as a clear orange oil (1.3 g, 69%). $^1$H NMR (400 MHz, $CDCl_3$) δ 7.85 (d, J=7.9 Hz, 1H), 7.69-7.62 (m, 2H), 7.55-7.49 (m, 2H), 7.40-7.30 (m, 3H), 7.13 (t, J=7.4 Hz, 1H), 7.08-6.98 (m, 4H), 5.30 (dd, J=8.9, 5.0 Hz, 1H), 5.15 (s, 2H), 3.76 (s, 3H), 3.74-3.63 (m, 2H), 2.64-2.53 (m, 1H), 2.50-2.37 (m, 1H). MS (ESI, m/z): 489.2 $[M+H]^+$.

Step H: Preparation of methyl 1-amino-2-(3-((methylsulfonyl)oxy)-1-(2-nitrophenyl)propyl)-4-(4-phenoxyphenyl)-1H-imidazole-5-carboxylate

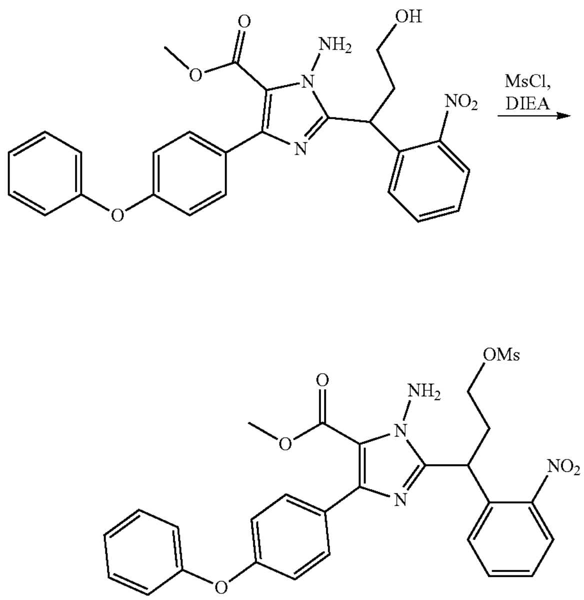

Methanesulfonyl chloride (365.7 mg, 3.19 mmol) was added via syringe into a stirred mixture of the product of step G of example 22 (1.3 g, 2.66 mmol) and N, N-diisopropylethylamine (687.9 mg, 5.32 mmol) in dichloromethane (3 ml) maintained at 0° C. The mixture was stirred at room temperature for 3 hs (TLC monitoring) and then partitioned between dichloromethane and water. The organic phase was dried and evaporated to afford a white solid which was passed through a column of silica gel with dichloromethane and methanol (40:1) to afford the desired product as a colorless oil (1.2 g, 79%). $^1$H NMR (600 MHz, $CDCl_3$) δ 7.85 (d, J=8.1 Hz, 1H), 7.69 (d, J=8.5 Hz, 2H), 7.61 (d, J=7.9 Hz, 1H), 7.51 (t, J=7.6 Hz, 1H), 7.40-7.33 (m, 3H), 7.13 (t, J=7.4 Hz, 1H), 7.08-7.02 (m, 4H), 5.37-5.31 (m, 1H), 5.10 (s, 2H), 4.43-4.34 (m, 2H), 3.75 (s, 3H), 3.03 (s, 3H), 2.92-2.83 (m, 1H), 2.60-2.50 (m, 1H). MS (ESI, m/z): 567.2 $[M+H]^+$.

Step I: Preparation of methyl 8-(2-nitrophenyl)-2-(4-phenoxyphenyl)-5,6,7,8-tetrahydroimidazo[1,2-b]pyridazine-3-carboxylate

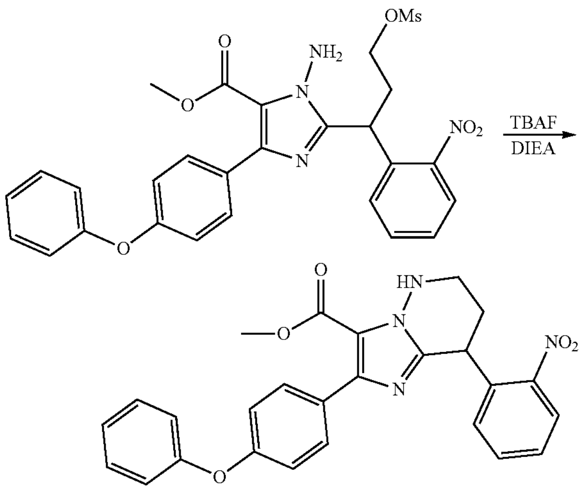

The crude the product of step H of example 22 (1.0 g, 1.76 mmol) was dissolved in anhydrous tetrahydrofuran (20 mL), N, N-diisopropylethylamine (456.2 mg, 3.5 mmol) and TBAF (4 mL, 1 mol/L tetrahydrofuran solution) were added, then heated to 30° C. for 3 hs, concentrated and purified by flash column chromatography with dichloromethane and methanol (40:1) to give the desired product (300 mg, 36%). $^1$H NMR (400 MHz, $CDCl_3$) δ 8.00 (dd, J=8.2, 1.3 Hz, 1H), 7.60-7.50 (m, 3H), 7.45-7.38 (m, 1H), 7.34-7.29 (m, 2H), 7.22 (t, J=3.4 Hz, 1H), 7.15-7.07 (m, 2H), 7.04-6.95 (m, 4H), 5.05 (t, J=7.4 Hz, 1H), 3.82 (s, 3H), 3.62-3.44 (m, 2H), 2.75-2.68 (m, 1H), 2.29-2.18 (m, 1H). MS (ESI, m/z): 471.2 $[M+H]^+$.

Step J: Preparation of 8-(2-nitrophenyl)-2-(4-phenoxyphenyl)-5,6,7,8-tetrahydroimidazo[1,2-b]pyridazine-3-carboxylic Acid

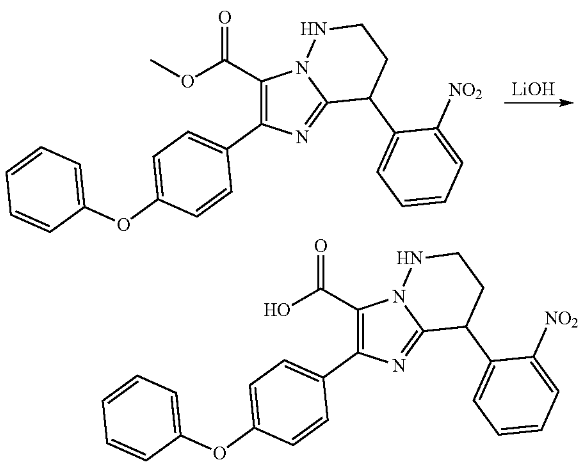

To a solution of the product of step I of example 22 (300 mg, 0.64 mmol) in tetrahydrofuran (10 mL) was added LiOH (76.6 mg, 3.19 mmol) in water (1 mL), the mixture was heated at 50° C. for 3 hs, then cooled to r.t. The mixture acidified to pH 3-4 with concentrated HCl and then extracted with 3×100 mL of dichloromethane. The organic phase was washed with saturated brine and then dried over anhydrous $Na_2SO_4$. The organic phase was concentrated in vacuo to afford 340 mg crude product. The residue was used to next step without further purification. MS (ESI, m/z): 457.2 $[M+H]^+$.

Step K: Preparation of 8-(2-nitrophenyl)-2-(4-phenoxyphenyl)-5,6,7,8-tetrahydroimidazo[1,2-b]pyridazine-3-carboxamide

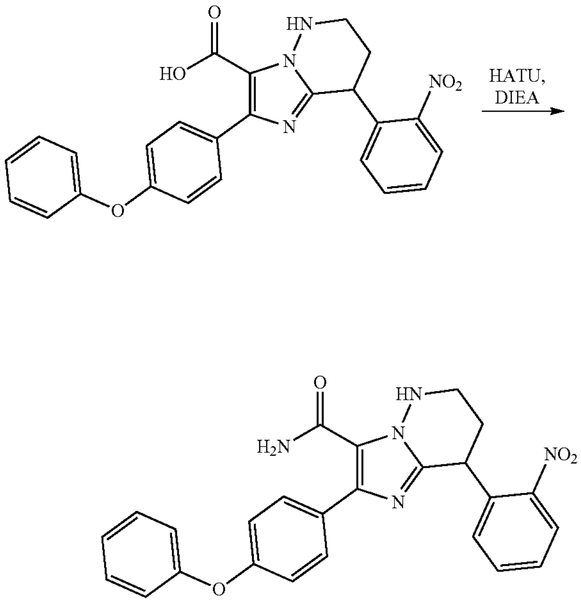

To the solution of the product of step J of example 22 (340 mg, 0.74 mmol) in dichloromethane (10 mL) was added N, N-diisopropylethylamine (385.1 mg, 2.98 mmol). After 5 min, $NH_4Cl$ (159.4 mg, 2.98 mmol) and HATU (424.8 mg, 1.12 mmol) was added. The reaction mixture was continued to stir at room temperature for 2 hs. Dichloromethane and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (40:1) to give product as an off-white solid (290 mg, 85%). $^1H$ NMR (600 MHz, $CDCl_3$) δ 7.96 (d, J=8.1 Hz, 1H), 7.56 (t, J=7.5 Hz, 1H), 7.52 (d, J=7.8 Hz, 2H), 7.41 (t, J=7.8 Hz, 11H), 7.32 (t, J=7.3 Hz, 2H), 7.22 (d, J=7.8 Hz, 1H), 7.11 (t, J=7.4 Hz, 1H), 7.04 (s, 1H), 6.98 (d, J=8.2 Hz, 4H), 6.78 (s, 1H), 5.65 (s, 1H), 4.97 (t, J=7.7 Hz, 1H), 3.56 (d, J=12.7 Hz, 1H), 3.47 (d, J=4.5 Hz, 1H), 2.74-2.62 (m, 1H), 2.28-2.21 (m, 1H). MS (ESI, m/z): 456.2 $[M+H]^+$.

Step L: Preparation of 8-(2-aminophenyl)-2-(4-phenoxyphenyl)-5,6,7,8-tetrahydroimidazo[1,2-b]pyridazine-3-carboxamide

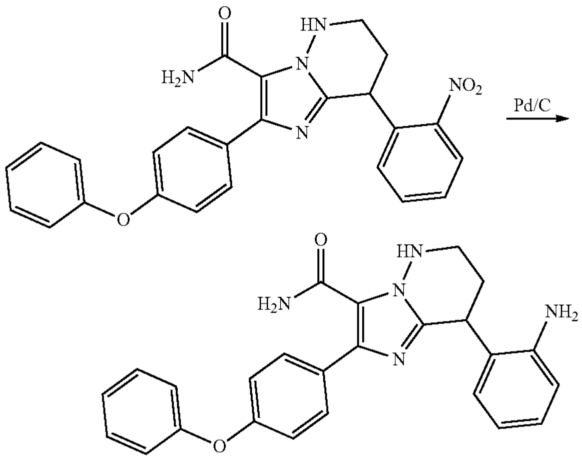

To a solution of the product of step K of example 22 (330 mg, crude) in MeOH (10 mL) was added 10% Pd/C (100 mg, 30%) at room temperature. The mixture was stirred for 3 hs under $H_2$. The mixture was cooled to r.t. The mixture was passed through Celite, and the solid was washed with ethyl acetate, and filtrate was concentrated under vacuum to get 300 mg crude. The residue was used to next step without further purification. MS (ESI, m/z): 426.2 $[M+H]^+$.

Step M: Preparation of 8-(2-acrylamidophenyl)-2-(4-phenoxyphenyl)-5,6,7,8-tetrahydroimidazo[1,2-b]pyridazine-3-carboxamide

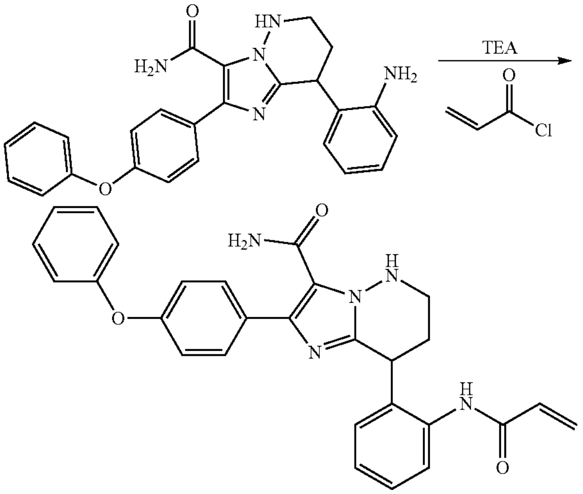

The mixture of the product of step L of example 22 (70 mg, 0.16 mmol) and triethylamine (33.36 mg, 0.33 mmol) in dichloromethane (2 mL) was cooled to −60° C. Then the solution of propenoyl chloride (19.36 mg, 0.21 mmol) in dichloromethane (1 mL) was added slowly, LC-MS was tracking, at the end of the reaction, 1 mL MeOH was added, the mixture was concentrated under vacuum to get crude product and purified by flash chromatography on silica gel with dichloromethane and methanol (40:1) to get product as a white solid (11 mg, 14%). $^1$H NMR (600 MHz, MeOD) δ 7.58 (d, J=8.2 Hz, 2H), 7.42 (d, J=7.8 Hz, 1H), 7.37-7.30 (m, 3H), 7.26 (t, J=7.5 Hz, 1H), 7.14-7.08 (m, 2H), 7.00 (d, J=8.0 Hz, 2H), 6.95 (d, J=8.3 Hz, 2H), 6.51-6.43 (m, 1H), 6.39-6.33 (m, 1H), 5.83-5.77 (m, 1H), 4.65 (t, J=7.4 Hz, 1H), 3.51-3.45 (m, 1H), 3.40-3.33 (m, 1H), 2.44-2.36 (m, 1H), 2.10-1.99 (m, 1H). MS (ESI, m/z): 480.2 [M+H]$^+$.

Example 23

8-(4-acrylamidophenyl)-2-(4-phenoxyphenyl)-5,6,7,8-tetrahydroimidazo[1,2-b]pyridazine-3-carboxamide

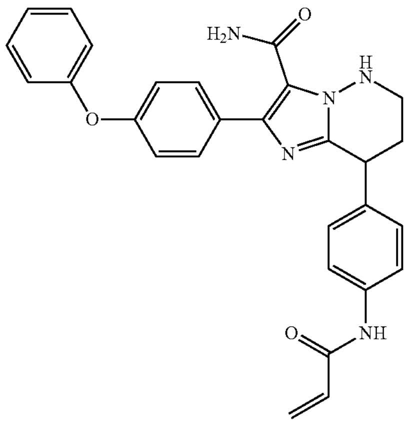 [SMILES: C=CC(=O)Nc1ccc(C2CCNn3c2nc(-c2ccc(Oc4ccccc4)cc2)c3C(N)=O)cc1]

Step A: Preparation of methyl 2-(4-nitrophenyl)acetate

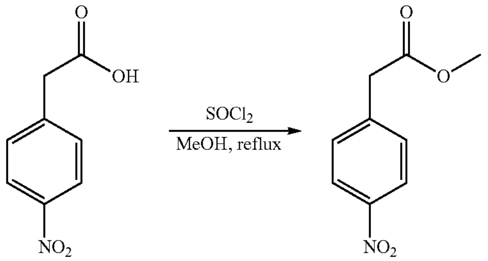

4-Nitrophenylacetic acid (240 g, 1.33 mol) was set stirring in 400 mL of methanol. Sulfurous dichloride (472.8 g, 3.98 mol) was added and the mixture heated to reflux. After 4 h the mixture was cooled and evaporated under reduced pressure to give a clear yellow oil. The oil was brought up in ethyl acetate and washed with saturated $NaHCO_3$. The organics were dried (anhydrous $Na_2SO_4$) and evaporated to give the ester as a clear orange liquid (256 g, 99%). MS (ESI, m/z): 196.1 [M+H]$^+$.

Step B: Preparation of methyl 4-((tert-butyldimethylsilyl)oxy)-2-(4-nitrophenyl)butanoate

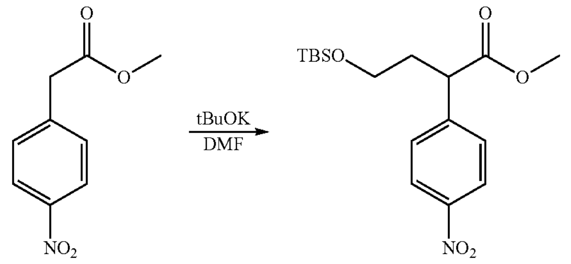

A solution of the product of step A of example 23 (100.0 g, 512.36 mmol) and t-BuOK (115.0 g, 1.02 mol) in N,N-dimethylformamide (1500 mL) was stirred at room temperature for 1 h. Then (2-bromo-ethoxy)-tert-butyl-dimethyl-silane (196.1 g, 819.78 mmol) was added slowly at 0° C. to this solution. The mixture was stirred at room temperature overnight and poured into water (500 mL). The aqueous phase was extracted with ethyl acetate (3×500 mL), and the organic layer was washed with saturated $NH_4Cl$ (500 mL), water (3×500 mL), brine (500 mL), dried with anhydrous $Na_2SO_4$, and evaporated to get crude product. It was purified by flash chromatography with ethyl acetate and petroleum ether (1:3) to obtain the desired product as a clear orange liquid (96 g, 53%). $^1$H NMR (600 MHz, $CDCl_3$) δ 8.17 (d, J=8.7 Hz, 2H), 7.47 (d, J=8.7 Hz, 2H), 3.97 (t, J=7.5 Hz, 1H), 3.66 (s, 3H), 3.64-3.59 (m, 1H), 3.47-3.43 (m, 1H), 2.38-2.29 (m, 1H), 1.96-1.90 (m, 1H), 0.88 (s, 9H), −0.01 (d, J=7.0 Hz, 6H). MS (ESI, m/z): 354.2 [M+H]$^+$.

Step C: Preparation of 4-((tert-butyldimethylsilyl)oxy)-2-(4-nitrophenyl)butanoic Acid

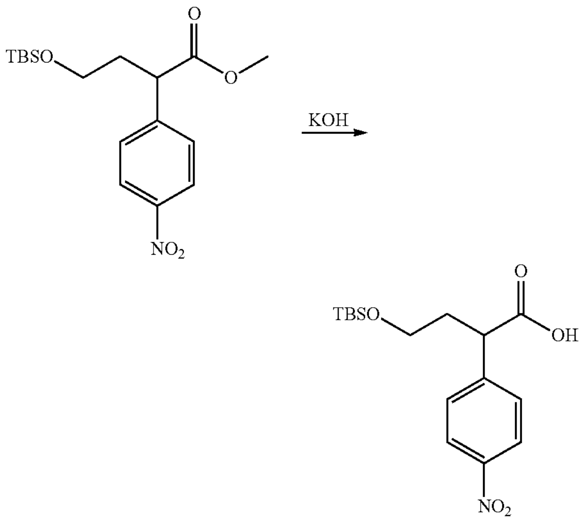

To a solution of the product of step B of example 23 (75 g, 8.55 mmol) in tetrahydrofuran (500 mL) was added a solution of aqueous 10% KOH (250 mL). The reaction mixture was stirred until complete consumption of the ester. Water was added and the reaction mixture was acidified to pH 5-6 with 1 M HCl. The mixture was extracted with ethyl acetate. The combined organic phases were washed with brine, dried over anhydrous $Na_2SO_4$ and concentrated in vacuo to get the product as a colorless oil (60 g, 81%), which was used for the next step without further purification. $^1H$ NMR (600 MHz, DMSO-d6) δ 12.66 (s, 1H), 8.22 (d, J=8.7 Hz, 2H), 7.58 (d, J=8.7 Hz, 2H), 3.86 (t, J=7.5 Hz, 1H), 3.60-3.56 (m, 1H), 3.50-3.46 (m, 1H), 2.30-2.19 (m, 1H), 1.94-1.84 (m, 1H), 0.86 (s, 9H), −0.01 (d, J=7.5 Hz, 6H). MS (ESI, m/z): 340.2 $[M+H]^+$.

Step D: Preparation of 1-methoxy-1,3-dioxo-3-(4-phenoxyphenyl)propan-2-yl 4-((tert-butyldimethylsilyl)oxy)-2-(4-nitrophenyl)butanoate

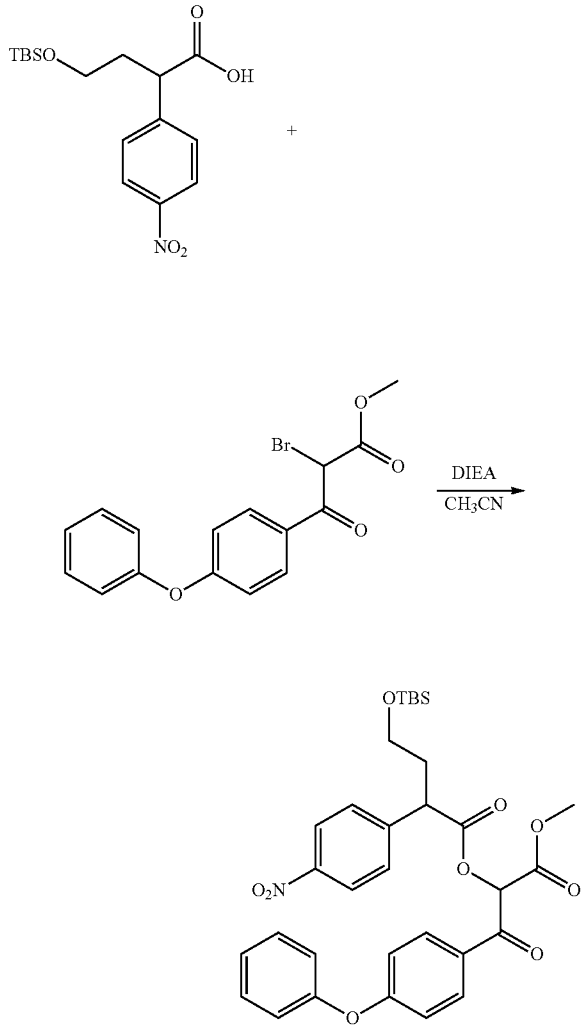

The product of step B (37.7 g, 105.96 mmol) of example 1 and the product of step C of example 23 (40.2 g, 127.16 mmol) were taken up in acetonitrile (250 mL), then N, N-diisopropylethylamine (20.5 g, 158.94 mmol) was added and the solution stirred at 30° C. for 3 hs. The solvent was removed by rotorary evaporation and the residue taken up in ethyl acetate, washed with 0.1 N HCl, and brine. The organic fractions were dried over anhydrous $Na_2SO_4$, filtered, and concentrated under reduced pressure to give the crude product which was purified via flash chromatography eluting with ethyl acetate and petroleum ether (1:20) to give the product as a clear orange oil (33.1 g, 51%). $^1H$ NMR (600 MHz, $CDCl_3$) δ 8.18 (d, J=8.4 Hz, 1H), 8.13 (d, J=8.4 Hz, 1H), 7.87 (d, J=8.6 Hz, 1H), 7.81 (d, J=8.6 Hz, 1H), 7.51 (d, J=8.4 Hz, 1H), 7.46 (d, J=8.4 Hz, 1H), 7.44-7.40 (m, 2H), 7.27-7.21 (m, 1H), 7.07 (t, J=8.8 Hz, 2H), 6.94 (d, J=8.6 Hz, 1H), 6.88 (d, J=8.6 Hz, 1H), 6.22 (d, J=5.5 Hz, 1H), 4.18-4.15 (m, 1H), 3.79-3.76 (m, 3H), 3.69-3.64 (m, 1H), 3.49-3.44 (m, 1H), 2.48-2.38 (m, 1H), 2.06-1.96 (m, 1H), 0.87 (d, J=9.6 Hz, 9H), 0.06-0.03 (m, 6H). MS (ESI, m/z): 608.2 $[M+H]^+$.

Step E: Preparation of methyl 2-(3-((tert-butyldimethylsilyl)oxy)-1-(4-nitrophenyl)propyl)-4-(4-phenoxyphenyl)-1H-imidazole-5-carboxylate

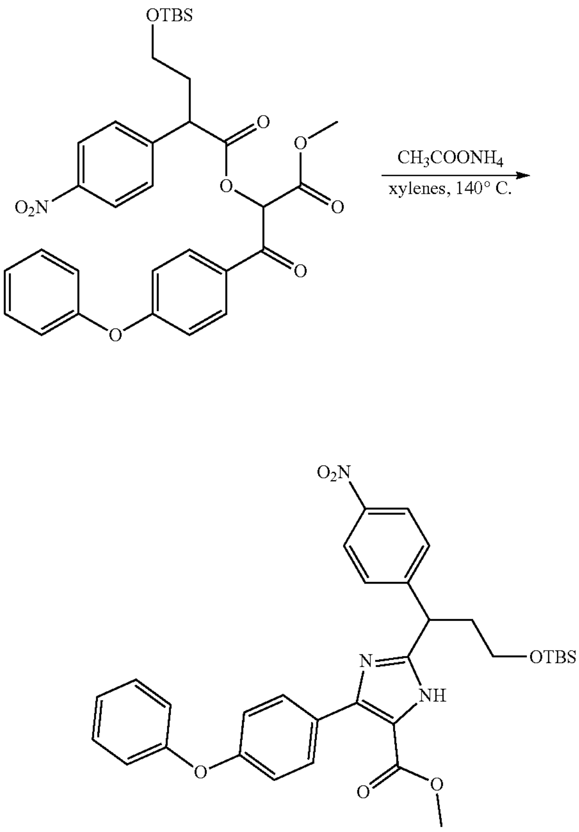

To a slurry of ammonium acetate (50.2 g, 651.60 mmol) in xylenes (350 mL) was added the product of step D of example 23 (33.0 g, 54.30 mmol). The mixture was stirred at 140° C. for 4 hs. The solution was cooled to room temperature and the solvent was evaporated. The residue was dissolved in ethyl acetate and washed with saturated brine. The organic phase was dried over anhydrous $Na_2SO_4$, filtered and concentrated. The residue was purified by silica gel column chromatography with ethyl acetate and petroleum ether (1:5) to give the product as a clear yellow oil (9.6 g, 30%). $^1H$ NMR (600 MHz, $CDCl_3$) δ 9.81 (s, 1H), 8.16 (d, J=8.4 Hz, 2H), 7.91 (d, J=8.4 Hz, 2H), 7.49 (d, J=8.4 Hz, 2H), 7.32 (t, J=7.8 Hz, 2H), 7.09 (t, J=7.5 Hz, 1H), 7.02 (t, J=7.3 Hz, 4H), 4.47 (t, J=7.3 Hz, 1H), 3.80 (s, 3H), 3.64-3.58 (m, 1H), 3.57-3.53 (m, 1H), 2.54-2.45 (m, 1H), 2.25-2.16 (m, 1H), 0.88 (s, 9H), 0.01 (d, J=7.1 Hz, 6H). MS (ESI, m/z): 588.3 $[M+H]^+$.

Step F: Preparation of methyl 1-amino-2-(3-((tert-butyldimethylsilyl)oxy)-1-(4-nitrophenyl)propyl)-4-(4-phenoxyphenyl)-1H-imidazole-5-carboxylate

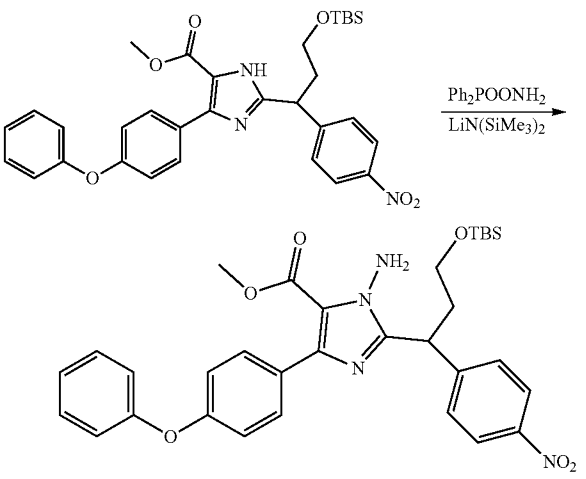

Lithium hexamethyldisilazane (24.5 mL of a 1 M solution in tetrahydrofuran, 24.49 mmol) was slowly added to the product of step E of example 23 (9.6 g, 16.33 mmol) in anhydrous N, N-dimethylformamide (100 mL) at 0° C. After the mixture was stirred for 30 min, O-(diphenylphosphinyl) hydroxylamine (7.3 g, 32.67 mmol) was added at 0° C., followed by stirring at room temperature for 3 hs (in cases where the reaction mixture became too viscous, additional N, N-dimethylformamide was added). The reaction was quenched with water until a clear solution was formed and concentrated to dryness under reduced pressure. The residue was washed several times with ethyl acetate or dichloromethane. The combined organic fractions were concentrated in vacuo and purified by flash chromatography on silica gel with ethyl acetate and petroleum ether (1:3) to give the product as a clear colorless oil (3.5 g, 35%). $^1H$ NMR (600 MHz, $CDCl_3$) δ 8.16 (d, J=8.3 Hz, 2H), 7.67 (d, J=8.4 Hz, 2H), 7.59 (d, J=8.3 Hz, 2H), 7.36 (t, J=7.6 Hz, 2H), 7.13 (t, J=7.4 Hz, 1H), 7.08-7.03 (m, 4H), 5.20 (s, 2H), 4.90 (t, J=7.7 Hz, 1H), 3.77 (s, 3H), 3.70-3.62 (m, 1H), 3.58-3.55 (m, 1H), 2.60-2.54 (m, 1H), 2.26-2.21 (m, 1H), 0.90 (s, 9H), 0.01 (d, J=6.8 Hz, 6H). MS (ESI, m/z): 603.3 $[M+H]^+$.

Step G: Preparation of methyl 1-amino-2-(3-hydroxy-1-(4-nitrophenyl)propyl)-4-(4-phenoxyphenyl)-1H-imidazole-5-carboxylate

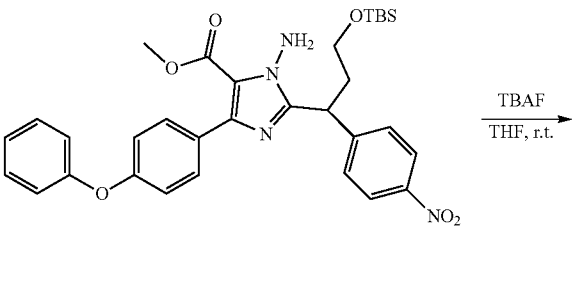

-continued

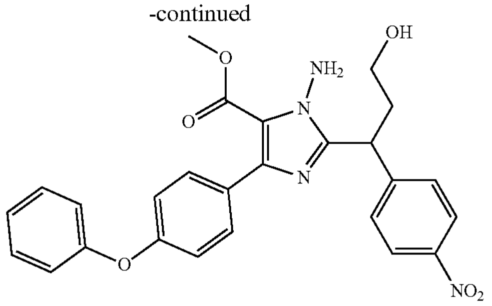

To a solution of the product of step F of example 23 (3.0 g, 4.98 mmol) in tetrahydrofuran (20 mL) was added a 1 M solution of tetrabutylammonium fluoride in tetrahydrofuran (5 mL, 5 mmol) at r.t. The solution was stirred for 2 hs and diluted with 100 mL ethyl acetate solution. The organic layer was separated and washed with $H_2O$ (3×100 mL). The water extract was washed with ethyl acetate solution (2×50 mL), and the organic layers were combined and dried over anhydrous $Na_2SO_4$. The solvent was evaporated in vacuo, and the residue was purified via flash chromatography eluting with ethyl acetate and petroleum ether (1:1) to give the product as a clear orange oil (2.3 g, 76%). $^1H$ NMR (400 MHz, $CDCl_3$) δ 8.13 (d, J=8.8 Hz, 2H), 7.65 (d, J=8.8 Hz, 2H), 7.53 (d, J=8.8 Hz, 2H), 7.38-7.30 (m, 2H), 7.11 (t, J=7.4 Hz, 1H), 7.07-6.99 (m, 4H), 4.92-4.83 (m, 1H), 3.75 (s, 3H), 3.60 (t, J=5.4 Hz, 2H), 2.56-2.48 (m, 1H), 2.36-2.22 (m, 1H). MS (ESI, m/z): 489.2 $[M+H]^+$.

Step H: Preparation of methyl 1-amino-2-(3-((methylsulfonyl)oxy)-1-(4-nitrophenyl)propyl)-4-(4-phenoxyphenyl)-1H-imidazole-5-carboxylate

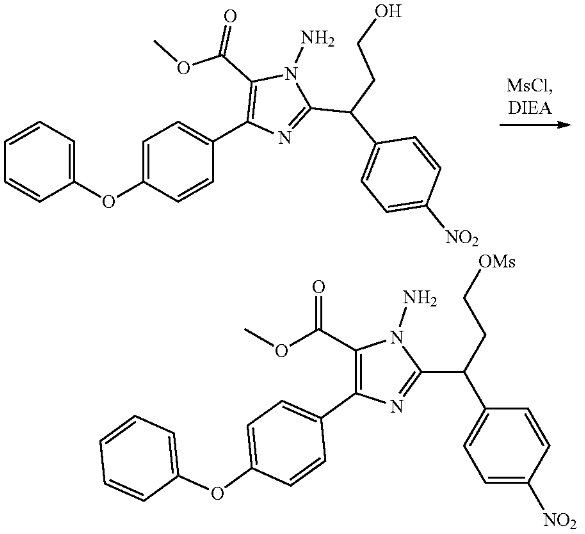

Methanesulfonyl chloride (809.0 mg, 7.06 mmol) was added via syringe into a stirred mixture of the product of step G of example 23 (2.3 g, 4.71 mmol) and N, N-diisopropylethylamine (1.22 g, 9.42 mmol) in dichloromethane (3 ml) maintained at 0° C. The mixture was stirred at room temperature for 3 hs (TLC monitoring) and then partitioned between dichloromethane and water. The organic phase was dried and evaporated to afford a white solid which was passed through a column of silica gel with dichloromethane and methanol (40:1) to afford the desired product as a colorless oil (2.1 g, 78%). $^1$H NMR (600 MHz, $CDCl_3$) δ 8.16 (d, J=8.3 Hz, 2H), 7.68 (d, J=8.3 Hz, 2H), 7.61 (d, J=8.3 Hz, 2H), 7.36 (t, J=7.7 Hz, 2H), 7.13 (t, J=7.4 Hz, 1H), 7.08-7.02 (m, 4H), 5.25 (s, 2H), 4.93-4.86 (m, 1H), 4.34-4.28 (m, 1H), 4.26-4.23 (m, 1H), 3.77 (s, 3H), 2.99 (s, 3H), 2.90-2.82 (m, 1H), 2.48-2.39 (m, 1H). MS (ESI, m/z): 567.2 $[M+H]^+$.

Step I: Preparation of methyl 8-(4-nitrophenyl)-2-(4-phenoxyphenyl)-5,6,7,8-tetrahydroimidazo[1,2-b]pyridazine-3-carboxylate

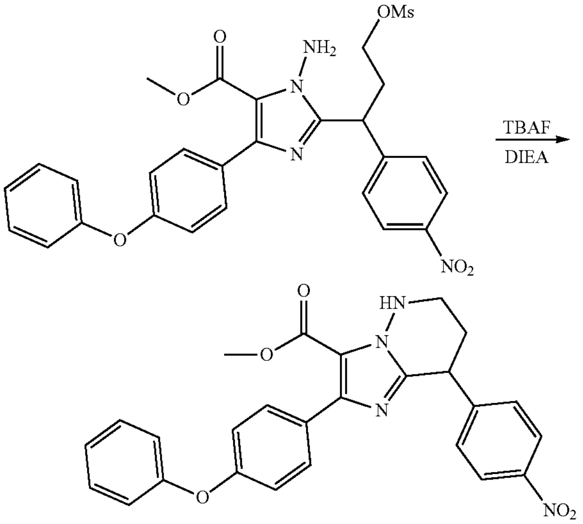

The crude the product of step H of example 23 (2.0 g, 3.53 mmol) was dissolved in anhydrous tetrahydrofuran (20 mL), N, N-diisopropylethylamine (912.5 mg, 7.06 mmol) and TBAF (4 mL, 1 mol/L tetrahydrofuran solution) were added, then heated to 30° C. for 3 hs, concentrated and purified by flash column chromatography with dichloromethane and methanol (30:1) to give the desired product (0.56 g, 37%). $^1$H NMR (400 MHz, $CDCl_3$) δ 8.16-8.10 (m, 2H), 7.70-7.63 (m, 2H), 7.39-7.31 (m, 4H), 7.17-7.09 (m, 1H), 7.08-7.01 (m, 4H), 5.51 (dd, J=4.5, 1.4 Hz, 1H), 4.06-3.99 (m, 1H), 3.87-3.80 (m, 1H), 3.78 (s, 3H), 1.96-1.86 (m, 2H). MS (ESI, m/z): 471.2 $[M+H]^+$.

Step J: Preparation of 8-(4-nitrophenyl)-2-(4-phenoxyphenyl)-5,6,7,8-tetrahydroimidazo[1,2-b]pyridazine-3-carboxylic Acid

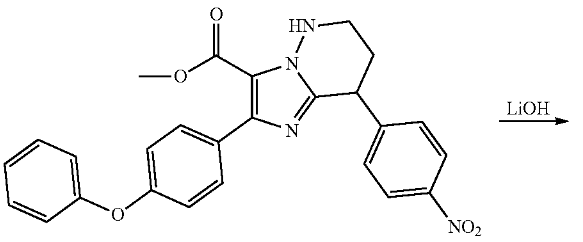

-continued

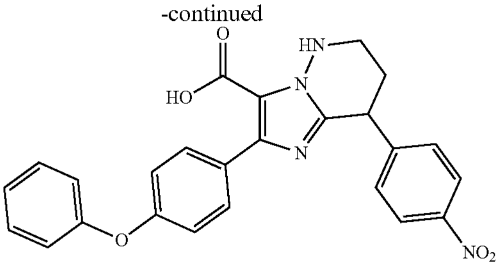

To a solution of the product of step I of example 23 (560 mg, 1.19 mmol) in tetrahydrofuran (10 mL) was added LiOH (142.5 mg, 5.95 mmol) in water (2 mL), the mixture was heated at 50° C. for 3 hs. Then cooled to r.t. The mixture acidified to pH 3-4 with concentrated HCl, then extracted with dichloromethane (3×100 mL). The organic phase was washed with saturated brine and then dried over anhydrous $Na_2SO_4$. The organic phase was concentrated in vacuo to afford 300 mg crude product. The residue was used to next step without further purification. MS (ESI, m/z): 457.2 $[M+H]^+$.

Step K: Preparation of 8-(4-nitrophenyl)-2-(4-phenoxyphenyl)-5,6,7,8-tetrahydroimidazo[1,2-b]pyridazine-3-carboxamide

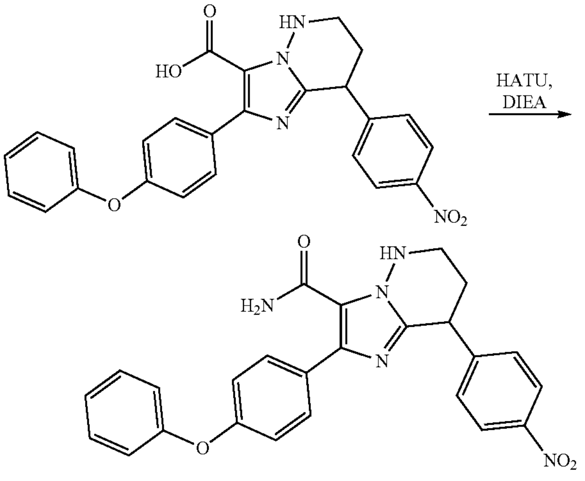

To the solution of the product of step J of example 23 (260 mg, 0.57 mmol) in dichloromethane (10 mL) was added N, N-diisopropylethylamine (294.5 mg, 2.28 mmol). After 5 min, $NH_4Cl$ (121.5 mg, 2.28 mmol) and HATU (324.8 mg, 0.85 mmol) were added. The reaction mixture was continued to stir at room temperature for 2 hs. Dichloromethane and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (40:1) to give product as an off-white solid (200 mg, 77%). $^1$H NMR (600 MHz, $CDCl_3$) δ 8.14 (d, J=8.5 Hz, 2H), 7.57 (d, J=8.3 Hz, 2H), 7.40-7.30 (m, 4H), 7.15 (t, J=7.4 Hz, 1H), 7.08 (d, J=8.3 Hz, 2H), 7.05 (d, J=8.0 Hz, 2H), 5.85 (s, 1H), 5.60 (s, 1H), 5.45 (s, 1H), 1.73 (t, J=6.0 Hz, 2H), 1.49 (t, J=6.0 Hz, 2H). MS (ESI, m/z): 456.2 $[M+H]^+$.

Step L: Preparation of 8-(4-aminophenyl)-2-(4-phenoxyphenyl)-5,6,7,8-tetrahydroimidazo[1,2-b]pyridazine-3-carboxamide

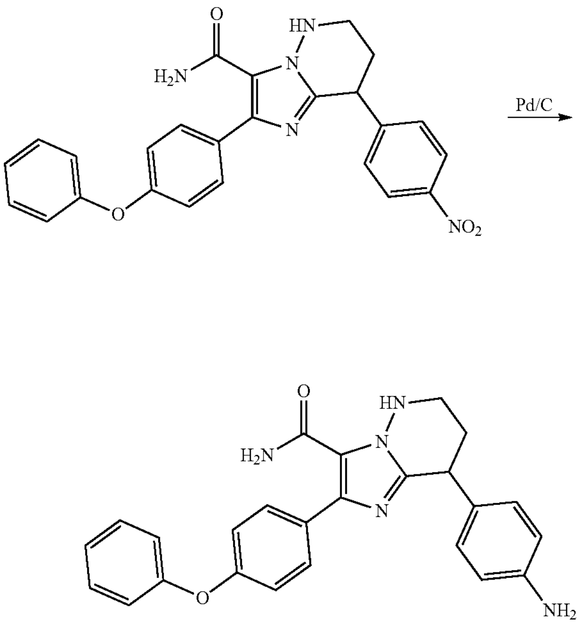

To a solution of the product of step K of example 23 (200 mg, crude) in MeOH (10 mL) was added Pd/C 10% (100 mg, 30%) at room temperature. The mixture was stirred for 3 hs under $H_2$. And then cooled to r.t. The mixture was passed through Celite, and the solid was washed with ethyl acetate, and filtrate was concentrated under vacuum to get 65 mg crude. The residue was used to next step without further purification. MS (ESI, m/z): 426.2 $[M+H]^+$.

Step M: Preparation of 8-(4-acrylamidophenyl)-2-(4-phenoxyphenyl)-5,6,7,8-tetrahydroimidazo[1,2-b]pyridazine-3-carboxamide

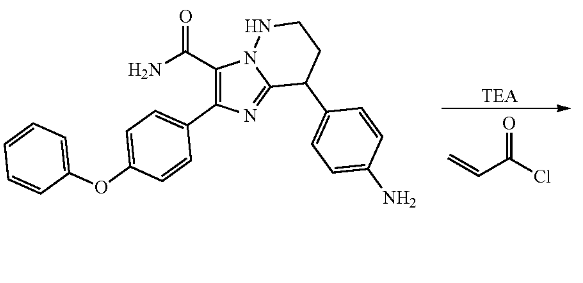

-continued

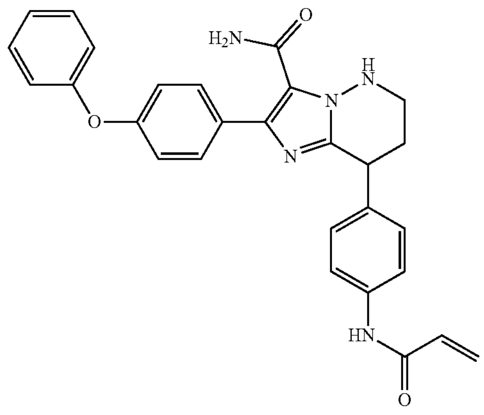

The mixture of the product of step L of example 23 (65 mg, 0.15 mmol) and triethylamine (23.2 mg, 0.23 mmol) in dichloromethane (5 mL) was cooled to −60° C. Then the solution of propenoyl chloride (13.8 mg, 0.15 mmol) in dichloromethane (1 mL) was added slowly, LC-MS was tracking, at the end of the reaction, 1 mL MeOH was added, the mixture was concentrated under vacuum to get crude product and purified by flash chromatography on silica gel with dichloromethane and methanol (40:1) to get product as a white solid (23 mg, 23%). $^1H$ NMR (600 MHz, MeOD) δ 7.58 (d, J=8.2 Hz, 2H), 7.42 (d, J=7.8 Hz, 1H), 7.38-7.31 (m, 3H), 7.26 (t, J=7.5 Hz, 1H), 7.11 (t, J=7.6 Hz, 2H), 7.00 (d, J=8.0 Hz, 2H), 6.95 (d, J=8.3 Hz, 2H), 6.47 (dd, J=16.9, 10.3 Hz, 1H), 6.36 (d, J=17.0 Hz, 1H), 5.80 (d, J=10.2 Hz, 1H), 4.65 (t, J=7.4 Hz, 1H), 3.48 (dd, J=13.6, 3.6 Hz, 1H), 3.40-3.33 (m, 1H), 2.44-2.36 (m, 1H), 2.10-1.99 (m, 1H). MS (ESI, m/z): 480.2 $[M+H]^+$.

Example 24

8-(1-cyanopiperidin-4-yl)-2-(4-phenoxyphenyl)-5,6,7,8-tetrahydroimidazo[1,2-b]pyridazine-3-carboxamide

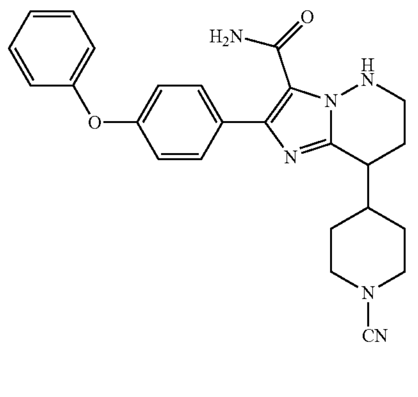 [SMILES: N#CN1CCC(C2CCNn3c2nc(-c2ccc(Oc4ccccc4)cc2)c3C(N)=O)CC1]

Preparation of 8-(1-cyanopiperidin-4-yl)-2-(4-phenoxyphenyl)-5,6,7,8-tetrahydroimidazo[1,2-b]pyridazine-3-carboxamide

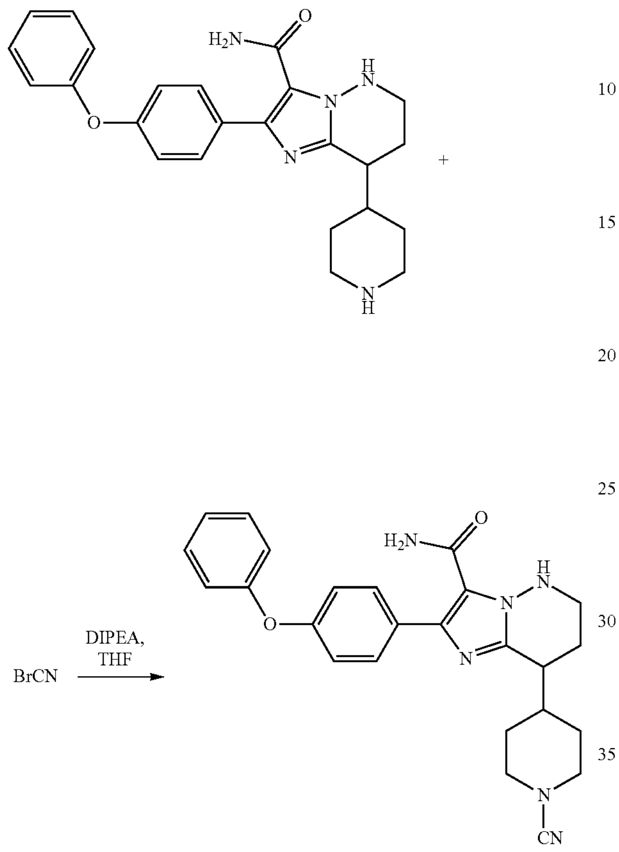

To the solution of the product (200.0 mg, 0.48 mmol) of step P of example 1 in tetrahydrofuran (20 mL) was added N, N-diisopropylethylamine (371.5 mg, 2.88 mmol). After BrCN (76.1 mg, 0.72 mmol) was added. The reaction mixture was continued to stir at room temperature for 8 hs. Dichloromethane and water were added. The layers were separated, and the aqueous phase was extracted with dichloromethane. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give product as an off-white solid (45 mg, 21%). $^1H$ NMR (600 MHz, $CDCl_3$) δ 7.58-7.53 (m, 2H), 7.39 (d, J=6.3 Hz, 1H), 7.38-7.33 (m, 2H), 7.14 (t, J=7.4 Hz, 1H), 7.07-7.03 (m, 4H), 6.05 (s, 1H), 5.57 (s, 1H), 3.50-3.42 (m, 3H), 3.38-3.31 (m, 1H), 3.13-3.03 (m, 3H), 2.38-2.33 (m, 1H), 2.11-2.07 (m, 1H), 1.98-1.90 (m, 1H), 1.79 (d, J=13.1 Hz, 1H), 1.69-1.60 (m, 2H), 1.52-1.49 (m, 1H). MS (ESI, m/z): 443.2 $[M+H]^+$.

Example 25

(E)-8-(1-(4-(dimethylamino)but-2-enoyl)piperidin-4-yl)-2-(4-phenoxyphenyl)-5,6,7,8-tetrahydroimidazo[1,2-b]pyridazine-3-carboxamide

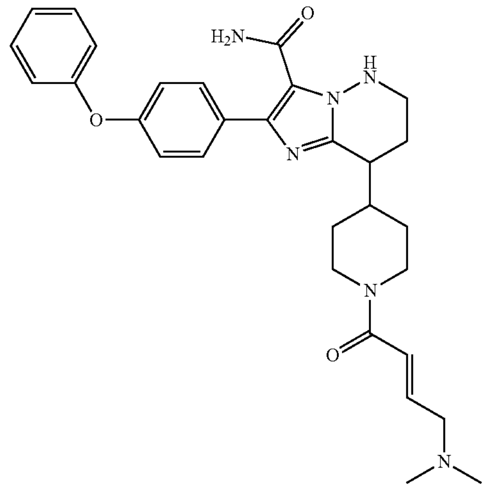

Preparation of (E)-8-(1-(4-(dimethylamino)but-2-enoyl)piperidin-4-yl)-2-(4-phenoxyphenyl)-5,6,7,8-tetrahydroimidazo[1,2-b]pyridazine-3-carboxamide

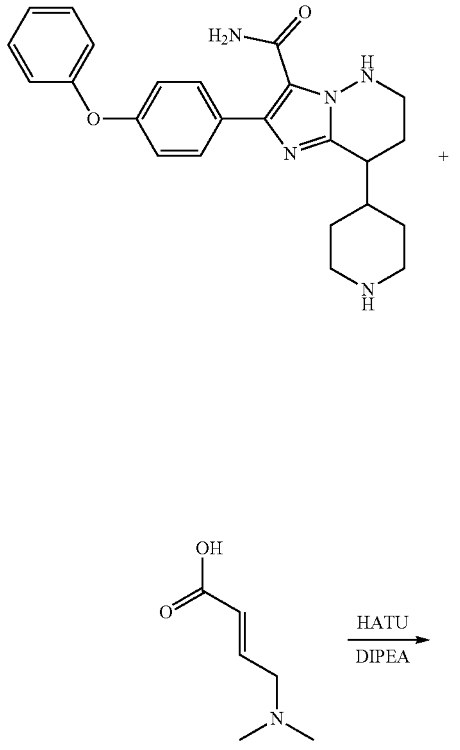

-continued

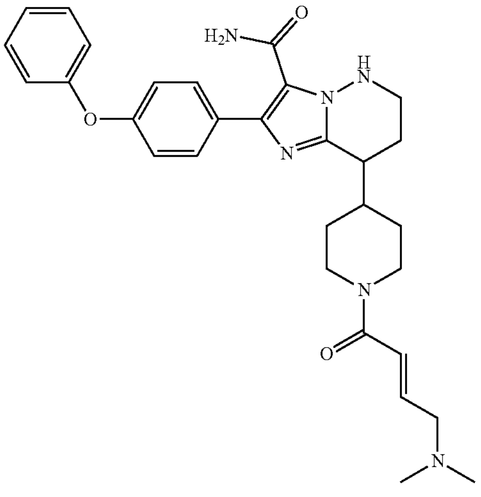 [SMILES: CN(C)C/C=C/C(=O)N1CCC(C2CCNn3c2nc(-c2ccc(Oc4ccccc4)cc2)c3C(N)=O)CC1]

To the solution of the product (200.0 mg, 0.48 mmol) of step P of example 1 in dry N, N-dimethylformamide (10 mL) was added N, N-diisopropylethylamine (371.5 mg, 2.88 mmol). After 5 min, (E)-4-(dimethylamino)but-2-enoic acid (68.1 mg, 0.52 mmol) and HATU (273.1 mg, 0.72 mmol) was added. The reaction mixture was continued to stir at room temperature for 2 hs. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (10:1) to give product as an off-white solid (31 mg, 12%). $^1H$ NMR (600 MHz, DMSO-d6) δ 7.81 (d, J=8.7 Hz, 2H), 7.40 (t, J=7.9 Hz, 2H), 7.14 (t, J=7.3 Hz, 1H), 7.04-6.97 (m, 4H), 6.59-6.57 (m, 2H), 4.54-4.45 (m, 2H), 4.15-3.99 (m, 2H), 3.31 (d, J=9.5 Hz, 1H), 3.17 (d, J=4.8 Hz, 3H), 3.03 (s, 2H), 2.87 (s, 2H), 2.54 (s, 6H), 2.51 (d, J=1.6 Hz, 2H), 2.24 (s, 2H). MS (ESI, m/z): 529.3 [M+H]$^+$.

Scheme III

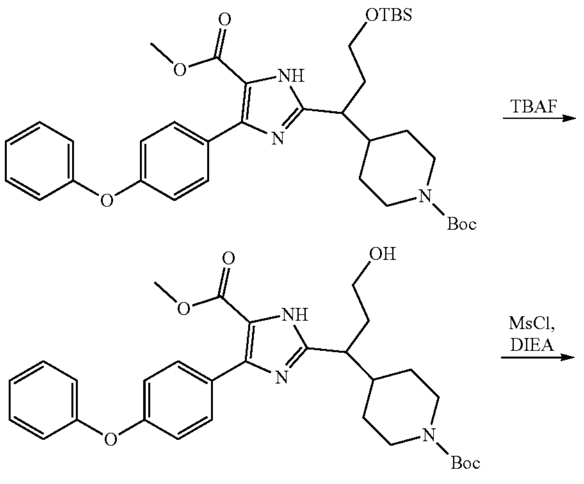

-continued

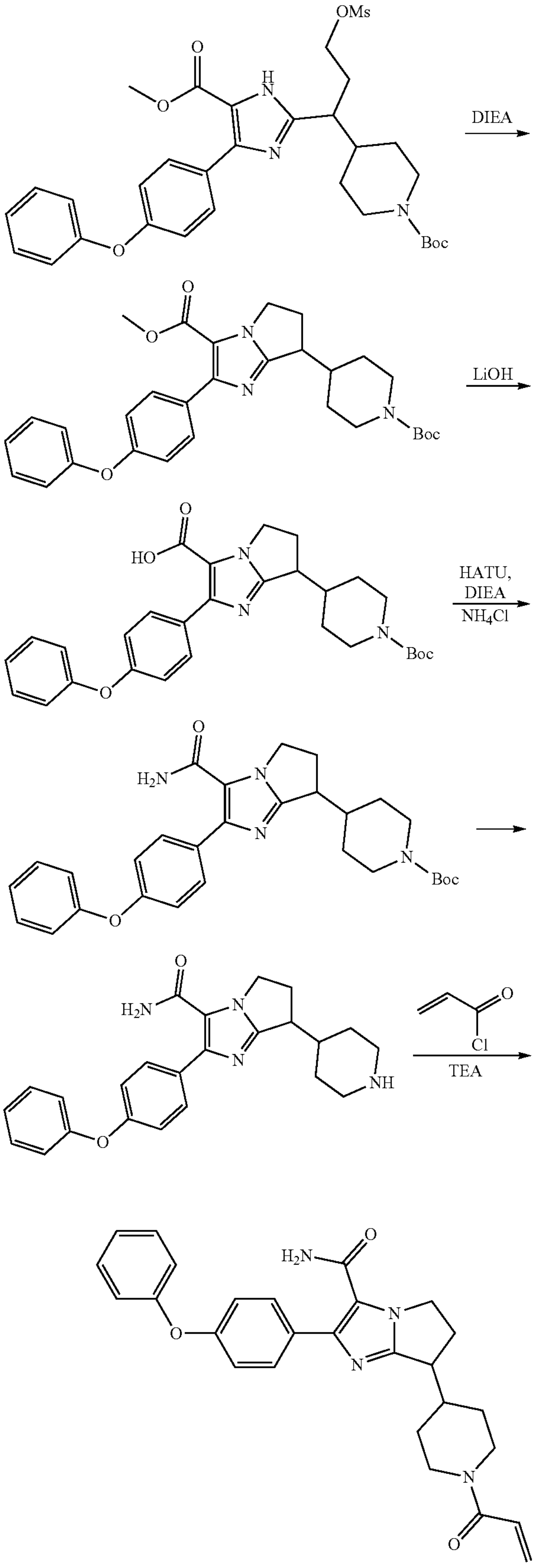

Example 26

7-(1-acryloylpiperidin-4-yl)-2-(4-phenoxyphenyl)-6,7-dihydro-5H-pyrrolo[1,2-a]imidazole-3-carboxamide

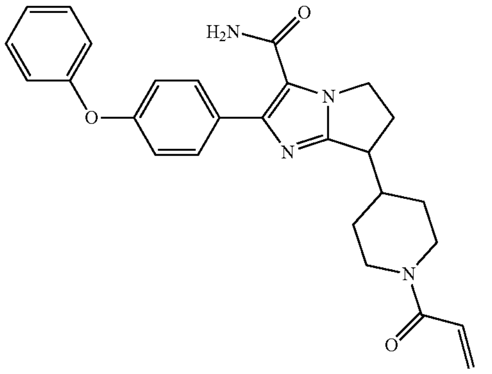 [SMILES: C=CC(=O)N1CCC(C2CCn3c2nc(-c2ccc(Oc4ccccc4)cc2)c3C(N)=O)CC1]

Step A: Preparation of tert-butyl 4-(3-hydroxy-1-(5-(methoxycarbonyl)-4-(4-phenoxyphenyl)-1H-imidazol-2-yl)propyl)piperidine-1-carboxylate

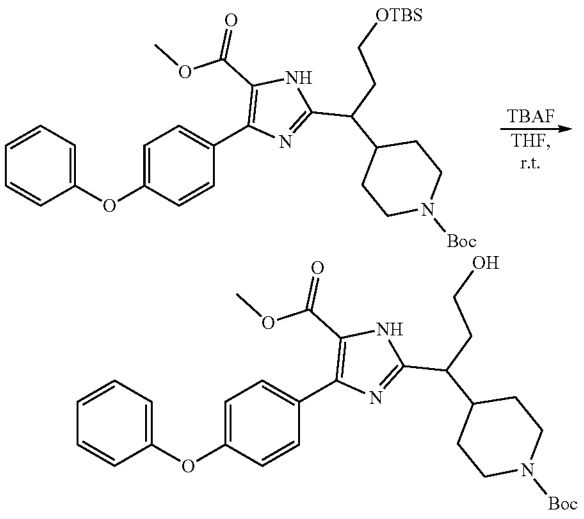

To a solution of the product of step I (3.4 g, 5.23 mmol) of example 1 in tetrahydrofuran (150 mL) was added a 1 M solution of tetrabutylammonium fluoride in tetrahydrofuran (8 mL, 7.84 mmol) at r.t. The solution was stirred for 2 hs and diluted with 100 mL ethyl acetate solution. The organic layer was separated and washed with $H_2O$ (3×200 mL). The water extract was washed with ethyl acetate solution (2×150 mL), and the organic layers were combined and dried over anhydrous $Na_2SO_4$. The solvent was evaporated in vacuo, and purified by flash chromatography on silica gel with dichloromethane and methanol (30:1) to give the product as a clear colorless oil (2.5 g, 89%). $^1H$ NMR (600 MHz, $CDCl_3$) δ 7.84 (d, J=6.1 Hz, 2H), 7.33 (t, J=7.7 Hz, 2H), 7.11 (d, J=6.6 Hz, 1H), 7.03-7.00 (m, 4H), 4.02 (s, 1H), 3.80 (s, 3H), 3.67-3.60 (m, 1H), 3.52-3.45 (m, 1H), 2.82 (s, 1H), 2.62 (s, 2H), 2.24-2.08 (m, 2H), 2.03-1.97 (m, 2H), 1.96-1.88 (m, 1H), 1.85-1.80 (m, 1H), 1.42 (s, 9H), 1.19-1.08 (m, 2H). MS (ESI, m/z): 536.3 [M+H]+.

Step B: Preparation of tert-butyl 4-(1-(5-(methoxycarbonyl)-4-(4-phenoxyphenyl)-1H-imidazol-2-yl)-3-((methylsulfonyl)oxy)propyl)piperidine-1-carboxylate

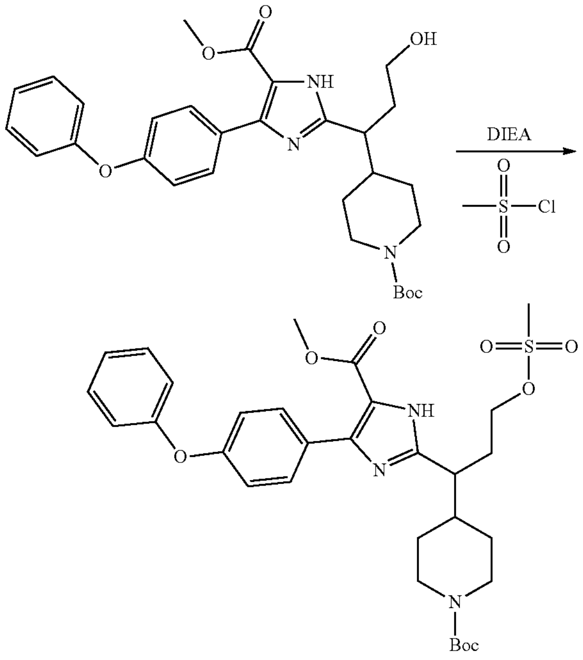

Methanesulfonyl chloride (801.9 mg, 7.00 mmol) was added via syringe into a stirred mixture of the product of step A (2.5 g, 4.67 mmol) of example 26 and N, N-diisopropylethylamine (1.2 g, 9.33 mmol) in dichloromethane (100 ml) maintained at 0° C. The mixture was stirred at room temperature for 3 h (TLC monitoring) and then partitioned between dichloromethane and water. The organic phase was dried, then evaporated to afford a white solid, the crude product was passed through a column of silica gel with dichloromethane and methanol (20:1) to afford the desired product as a colorless oil (1.6 g, 56%). MS (ESI, m/z): 614.2 [M+H]+.

Step C: Preparation of methyl 7-(1-(tert-butoxycarbonyl)piperidin-4-yl)-2-(4-phenoxyphenyl)-6,7-dihydro-5H-pyrrolo[1,2-a]imidazole-3-carboxylate

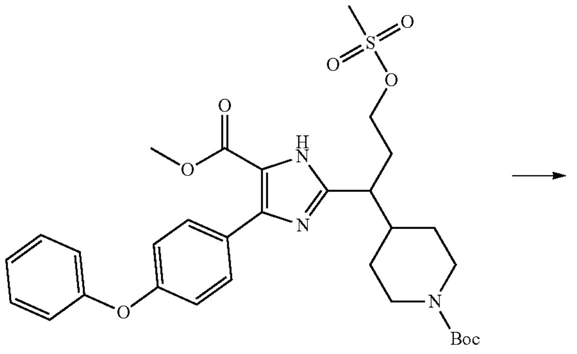

-continued

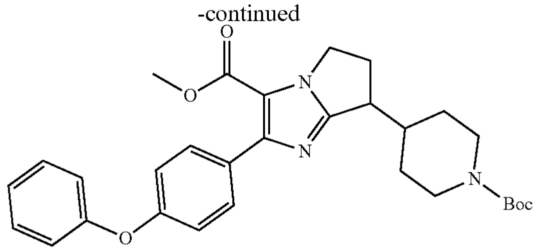

N, N-diisopropylethylamine (505.0 mg, 3.91 mmol) and 1 M solution of tetrabutylammonium fluoride in tetrahydrofuran (2.6 mL, 2.61 mmol) were added to the solution of the product of step B (1.6 g, 2.61 mmol) of example 26 in anhydrous tetrahydrofuran (20 mL), the mixture was heated to 50° C. for 2 hs, then cooled to r.t., concentrated and purified by flash column chromatography with dichloromethane and methanol (10:1) to give the desired product (1.1 g, 81%). $^{1}$H NMR (600 MHz, $CDCl_3$) δ 7.79 (d, J=8.6 Hz, 2H), 7.33 (t, J=7.9 Hz, 2H), 7.10 (t, J=7.3 Hz, 1H), 7.07-6.98 (m, 4H), 4.30-4.26 (m, 1H), 4.21-4.16 (m, 2H), 3.80 (s, 3H), 3.08 (s, 1H), 2.75-2.63 (m, 3H), 2.39-2.33 (m, 1H), 2.08 (s, 1H), 1.93 (s, 1H), 1.55 (s, 1H), 1.45 (s, 9H), 1.40-1.27 (m, 3H). MS (ESI, m/z): 518.3 $[M+H]^+$.

Step D: Preparation of 7-(1-(tert-butoxycarbonyl) piperidin-4-yl)-2-(4-phenoxyphenyl)-6,7-dihydro-5H-pyrrolo[1,2-a]imidazole-3-carboxylic Acid

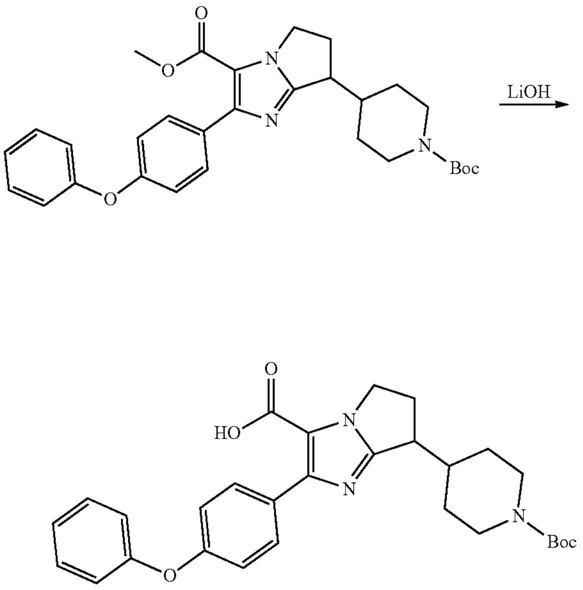

To a solution of the product of step C (1.1 g, 2.13 mmol) of example 26 in tetrahydrofuran (30 mL) was added LiOH (254.5 mg, 10.63 mmol) in water (5 mL), the mixture was heated at 50° C. for 3 hs. After cooled to r.t., The mixture was acidified to pH 3-4 with concentrated HCl and then extracted with dichloromethane (3×100 mL). The organic phase was washed with saturated brine and then dried over anhydrous $Na_2SO_4$. The organic phase was concentrated in vacuo to afford 1 g crude product. The residue was used to next step without further purification. MS (ESI, m/z): 504.2 $[M+H]^+$.

Step E: Preparation of tert-butyl 4-(3-carbamoyl-2-(4-phenoxyphenyl)-6,7-dihydro-5H-pyrrolo[1,2-a] imidazol-7-yl)piperidine-1-carboxylate

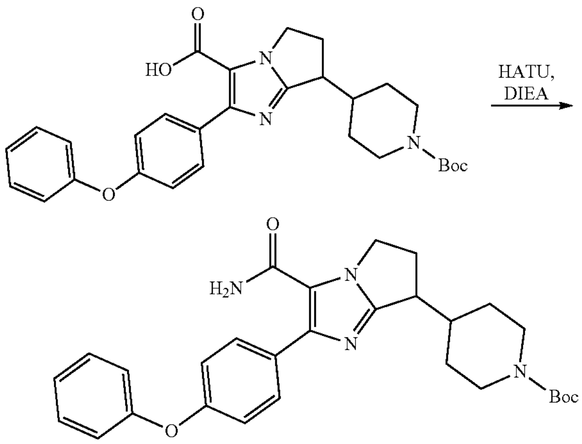

To the solution of the product of step D (300.0 mg, 0.59 mmol) of example 26 in dichloromethane (20 mL) was added N, N-diisopropylethylamine (308.0 mg, 2.38 mmol). After 5 min, $NH_4Cl$ (127.5 mg, 2.38 mmol) and HATU (339.8 mg, 0.89 mmol) was added. The reaction mixture was continued to stir at room temperature for 2 hs. Dichloromethane and water were added. The layers were separated, and the aqueous phase was extracted with dichloromethane. The combined organic phases were washed three times (3×100 mL) with brine solution. The organic phase was dried over anhydrous $Na_2SO_4$, filtered and concentrated. The residue was purified by chromatography with dichloromethane and methanol (40:1) to give product as an off-white solid (165 mg, 55%). $^{1}$H NMR (400 MHz, $CDCl_3$) δ 7.55 (d, J=8.3 Hz, 2H), 7.36 (t, J=7.7 Hz, 2H), 7.14 (t, J=7.3 Hz, 1H), 7.05 (t, J=8.8 Hz, 4H), 4.41-4.28 (m, 1H), 4.27-4.03 (m, 3H), 3.75-3.68 (m, 1H), 3.20-3.15 (m, 1H), 3.06 (d, J=6.7 Hz, 1H), 2.75-2.57 (m, 3H), 2.41-2.32 (m, 1H), 2.04 (s, 1H), 1.91 (s, 1H), 1.56 (d, J=12.5 Hz, 1H), 1.44 (s, 9H). MS (ESI, m/z): 503.3 $[M+H]^+$.

Step F: Preparation of 2-(4-phenoxyphenyl)-7-(piperidin-4-yl)-6,7-dihydro-5H-pyrrolo[1,2-a]imidazole-3-carboxamide

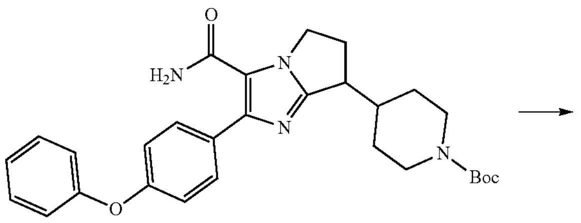

-continued

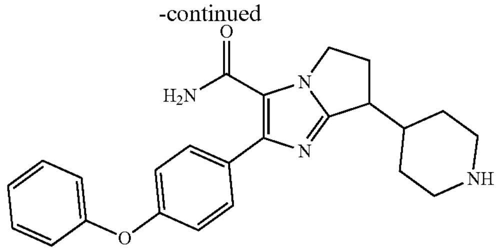

To a solution of the product of step E (165 mg, crude) of example 26 in EtOH (10 mL) was added $CF_3COOH$ (2 mL) at room temperature. The mixture was stirred for 3 hs, then concentrated under vacuum to get 116 mg crude product. The residue was used to next step without further purification. MS (ESI, m/z): 403.2 $[M+H]^+$.

Step G: Preparation of 7-(1-acryloylpiperidin-4-yl)-2-(4-phenoxyphenyl)-6,7-dihydro-5H-pyrrolo[1,2-a]imidazole-3-carboxamide

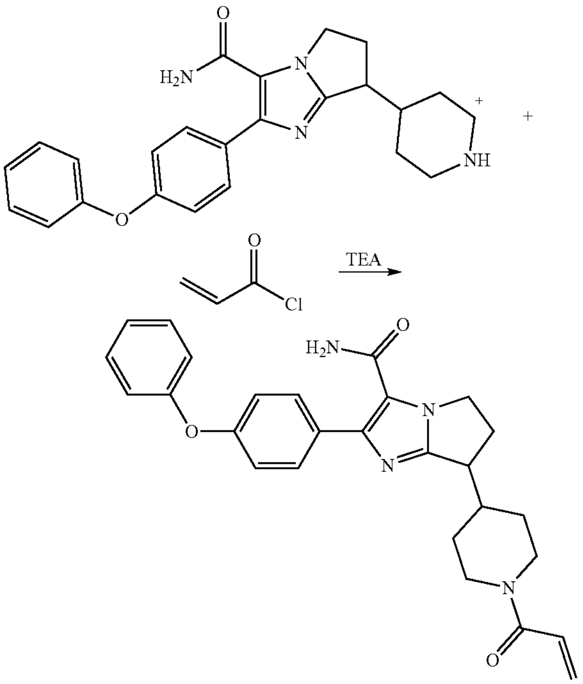

The mixture of the product of step F (116.0 mg, 0.28 mmol) of example 26 and triethylamine (116.7 mg, 1.15 mmol) in dichloromethane (10 mL) was cooled to 0° C., then the solution of propenoyl chloride (28.7 mg, 0.32 mmol) in dichloromethane (1 mL) was added slowly, LC-MS was tracking, at the end of the reaction, 1 mL MeOH was added, the mixture was concentrated under vacuum to get crude product. The residue was purified by flash chromatography on silica gel with dichloromethane and methanol (40:1) to get product as a white solid (69 mg, 52%). $^1H$ NMR (600 MHz, $CDCl_3$) δ 7.56 (d, J=8.4 Hz, 2H), 7.38-7.35 (m, 2H), 7.16-7.14 (m, 1H), 7.08-7.04 (m, 41H), 6.59-6.54 (m, 1H), 6.27-6.24 (m, 1H), 5.67-5.66 (m, 1H), 4.74 (s, 1H), 4.35 (s, 1H), 4.22 (s, 1H), 4.04 (s, 1H), 3.07-3.03 (m, 2H), 2.72-2.66 (m, 1H), 2.62 (s, 1H), 2.39-2.33 (m, 1H), 2.32-2.18 (m, 11H), 2.09-2.07 (m, 1H), 2.02-1.96 (m, 1H), 1.86 (s, 1H), 1.71-1.65 (m, 1H). MS (ESI, m/z): 457.2 $[M+H]^+$.

Scheme IV

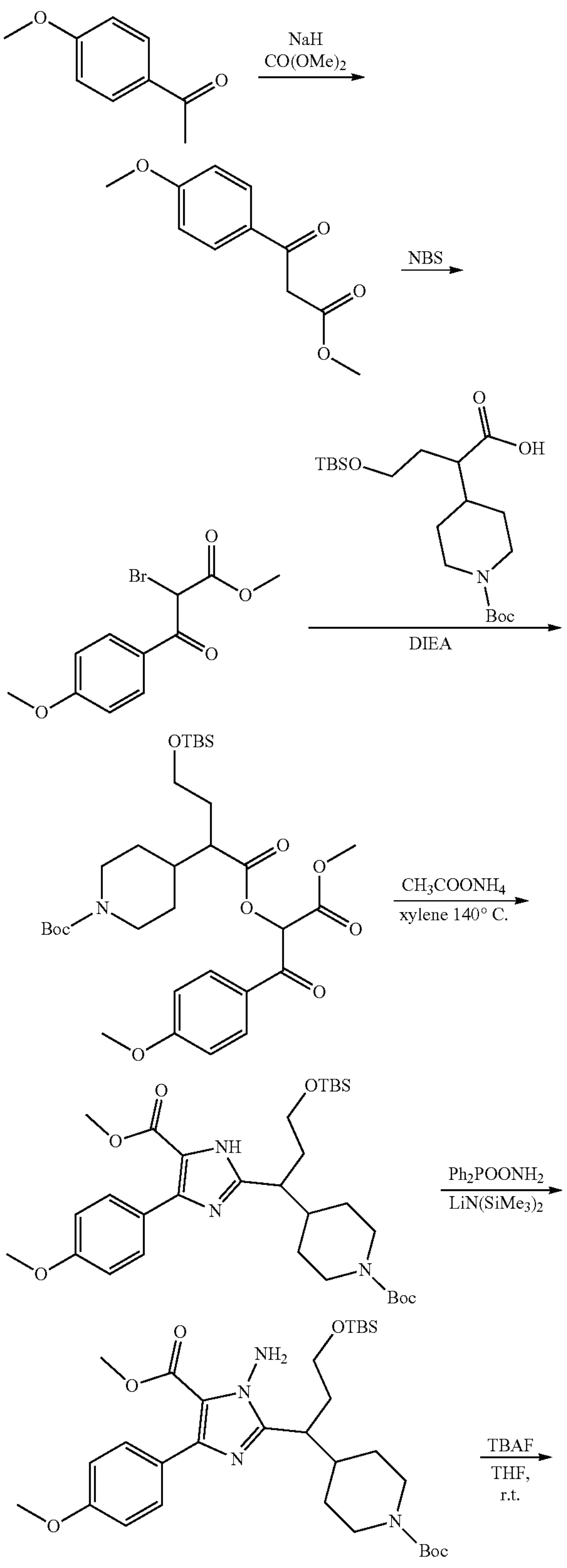

-continued
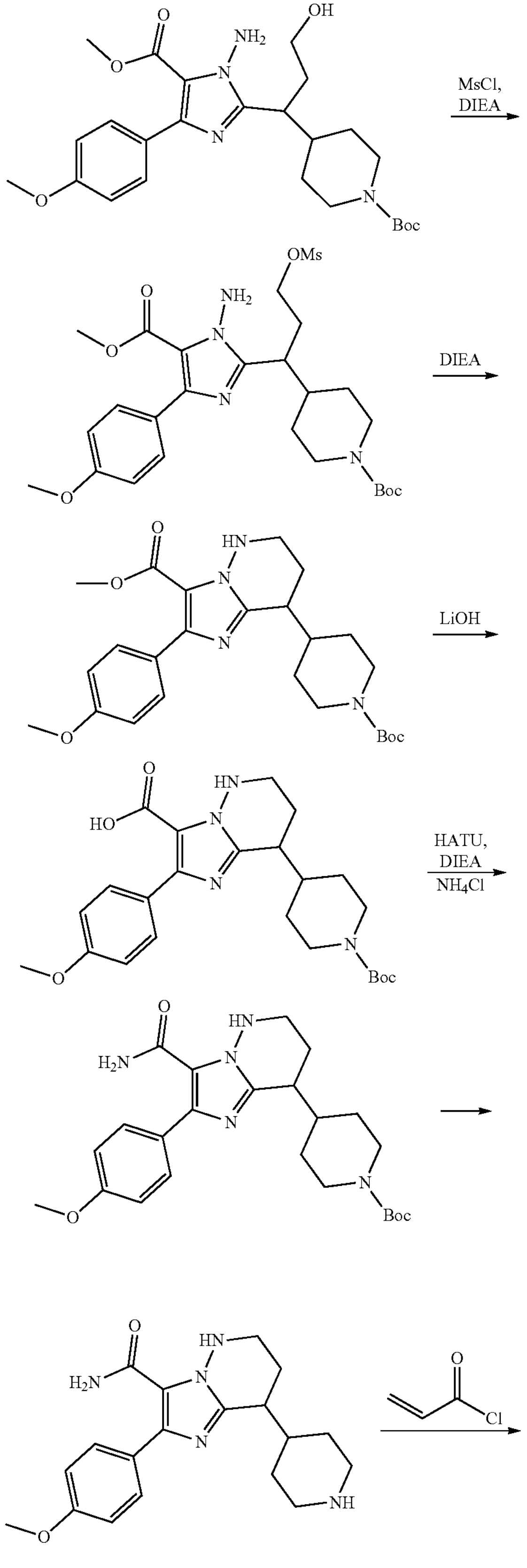
-continued
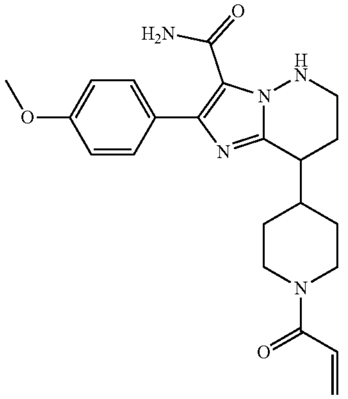 [SMILES: C=CC(=O)N1CCC(C2CCNn3c2nc(-c2ccc(OC)cc2)c3C(N)=O)CC1]
Example 27
8-(1-acryloylpiperidin-4-yl)-2-(4-methoxyphenyl)-5,6,7,8-tetrahydroimidazo[1,2-b]pyridazine-3-carboxamide
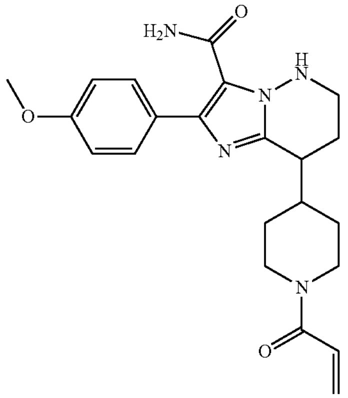 [SMILES: C=CC(=O)N1CCC(C2CCNn3c2nc(-c2ccc(OC)cc2)c3C(N)=O)CC1]
Step A: Preparation of methyl 2-bromo-3-(4-methoxyphenyl)-3-oxopropanoate
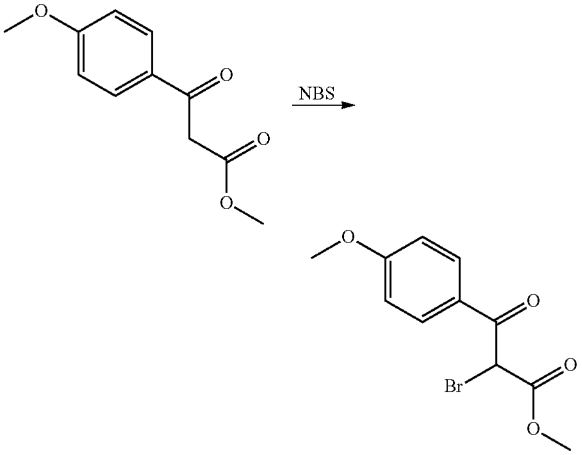

To a solution of methyl 3-(4-methoxyphenyl)-3-oxopropanoate (40.0 g, 192.11 mmol) in methyl tert-butyl ether (500 mL) was added N-bromosuccinimide (41.0 g, 230.53 mmol) and $CH_3COONH_4$ (2.9 g, 38.42 mmol). The reaction mixture was stirred for 3 hs at r.t. The mixture was washed with water (3×500 mL), then dried over anhydrous sodium sulfate. Evaporation of the solvent gave the crude product as oil, the crude residue was flash chromatographed with ethyl acetate and petroleum ether (1:10) to give product as yellow oil (48 g, 87%). $^1H$ NMR (600 MHz, $CDCl_3$) δ 7.93 (d, J=8.7 Hz, 2H), 6.92 (d, J=8.7 Hz, 2H), 5.65 (s, 1H), 3.84 (s, 3H), 3.77 (s, 3H). MS (ESI, m/z): 287.9 $[M+H]^+$.

Step B: Preparation of tert-butyl 4-(4-(4-methoxybenzoyl)-11,11,12,12-tetramethyl-3,6-dioxo-2,5,10-trioxa-11-silatridecan-7-yl) piperidine-1-carboxylate

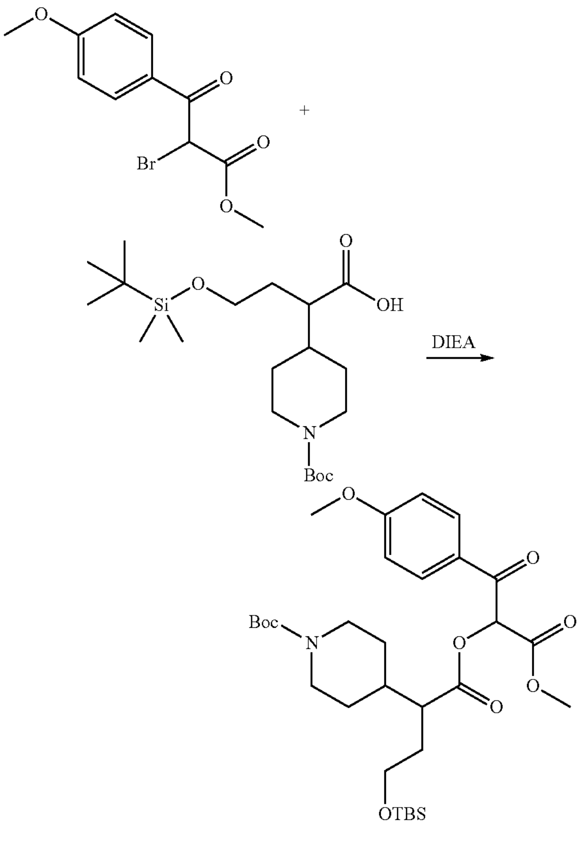

The product of step G (52.5 g, 130.61 mmol) of example 1 and the product of step A (25.0 g, 87.07 mmol) of example 27 were taken up in acetonitrile (400 mL), then N, N-diisopropylethylamine (22.5 g, 174.15 mmol) was added and the solution stirred at 30° C. for 3 hs. The solvent was removed by rotorary evaporation and the residue taken up in ethyl acetate, washed with 0.1 N HCl and brine. The organic fractions were dried over anhydrous $Na_2SO_4$, filtered, and concentrated under reduced pressure to give the crude product which was purified via flash chromatography with ethyl acetate and petroleum ether (1:10) to give the product as a clear colorless oil (43 g, 81%). $^1H$ NMR (600 MHz, $CDCl_3$) δ 7.96 (d, J=8.7 Hz, 2H), 6.94 (d, J=8.7 Hz, 2H), 6.25 (s, 1H), 4.22-3.97 (m, 2H), 3.87 (s, 3H), 3.76 (s, 3H), 3.72 (s, 2H), 3.65-3.61 (m, 1H), 3.58-3.50 (m, 1H), 2.75-2.51 (m, 3H), 1.83 (s, 2H), 1.62-1.60 (m, 1H), 1.43 (d, J=3.4 Hz, 9H), 1.33-1.17 (m, 2H), 0.85-0.82 (m, 9H), 0.01-(−0.04) (m, 6H). MS (ESI, m/z): 608.3 $[M+H]^+$.

Step C: Preparation of tert-butyl 4-(3-((tert-butyldimethylsilyl)oxy)-1-(5-(methoxycarbonyl)-4-(4-methoxyphenyl)-1H-imidazol-2-yl)propyl)piperidine-1-carboxylate

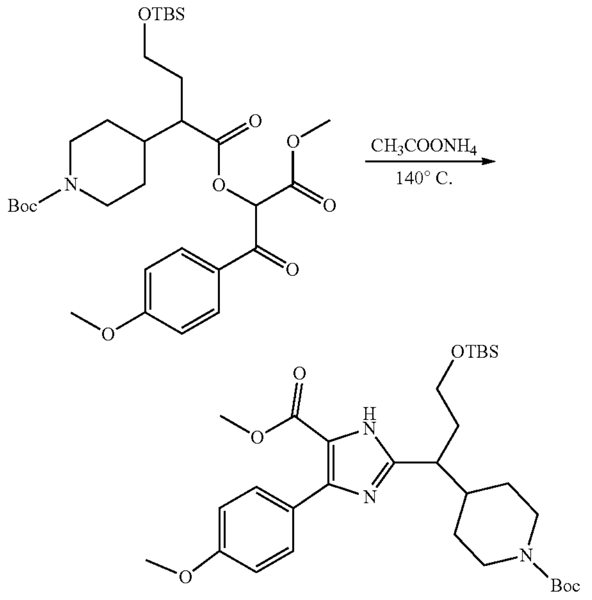

To a slurry of ammonium acetate (65.5 g, 848.94 mmol) in xylenes (400 mL) was added the product of step B (43.0 g, 70.75 mmol) of example 27. The mixture was stirred at 140° C. for 4 hours. The solution was cooled to room temperature and the solvent was evaporated. The residue was dissolved in ethyl acetate and washed with saturated brine. The organic phase was dried over anhydrous $Na_2SO_4$, filtered and concentrated. The residue was purified by silica gel column chromatography with ethyl acetate and petroleum ether (1:5) to give the product as a clear colorless oil (9 g, 21%). $^1H$ NMR (600 MHz, $CDCl_3$) δ 7.86-7.55 (m, 2H), 6.92 (d, J=8.3 Hz, 2H), 4.22-3.95 (m, 2H), 3.83-3.81 (m, 6H), 3.63-3.59 (m, 1H), 3.50-3.42 (m, 1H), 2.82-2.78 (m, 1H), 2.63-2.41 (m, 3H), 2.03-1.93 (m, 3H), 1.84-1.82 (m, 1H), 1.42 (s, 9H), 1.21-1.09 (m, 2H), 0.87 (s, 9H), 0.00 (s, 6H). MS (ESI, m/z): 588.3 $[M+H]^+$.

Step D: Preparation of tert-butyl 4-(1-(1-amino-5-(methoxycarbonyl)-4-(4-methoxyphenyl)-1H-imidazol-2-yl)-3-((tert-butyldimethylsilyl)oxy)propyl) piperidine-1-carboxylate

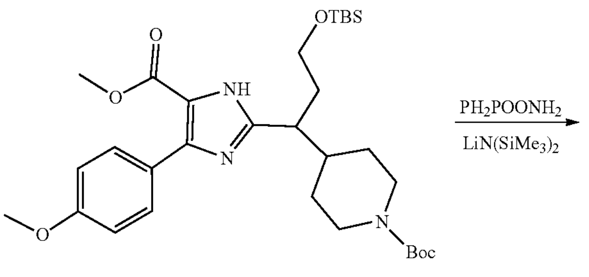

-continued

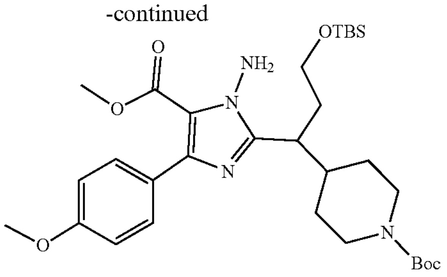

Lithium hexamethyldisilazane (23 mL of a 1 M solution in tetrahydrofuran, 22.96 mmol) was slowly added to the product of step C (9.1 g, 15.31 mmol) of example 27 in anhydrous N, N-dimethylformamide (150 mL) at 0° C. After the mixture was stirred for 30 min, O-(diphenylphosphinyl) hydroxylamine (7.1 g, 30.62 mmol) was added at 0° C., followed by stirring at room temperature for 4-6 hs (in cases where the reaction mixture became too viscous, additional N, N-dimethylformamide was added). The reaction was quenched with water until a clear solution was formed and concentrated to dryness under reduced pressure. The residue was washed several times with ethyl acetate or dichloromethane. The combined organic fractions were concentrated in vacuo and purified by flash chromatography on silica gel with ethyl acetate and petroleum ether (1:3) to give the product as a clear colorless oil (7.5 g, 81%). $^1$H NMR (400 MHz, $CDCl_3$) δ 7.57 (d, J=8.6 Hz, 2H), 6.91 (d, J=8.6 Hz, 2H), 5.57 (s, 2H), 4.11 (s, 1H), 4.00 (s, 1H), 3.82 (s, 3H), 3.76 (s, 3H), 3.63-3.57 (m, 1H), 3.36-3.30 (m, 2H), 2.78-2.53 (m, 2H), 2.04-1.97 (m, 2H), 1.98-1.86 (m, 2H), 1.43 (s, 9H), 1.38-1.33 (m, 1H), 1.29-1.19 (m, 2H), 0.85 (s, 9H), −0.01 (d, J=11.5 Hz, 6H). MS (ESI, m/z): 603.3 [M+H]$^+$.

Step E: Preparation of tert-butyl 4-(1-(1-amino-5-(methoxycarbonyl)-4-(4-methoxyphenyl)-1H-imidazol-2-yl)-3-hydroxypropyl)piperidine-1-carboxylate

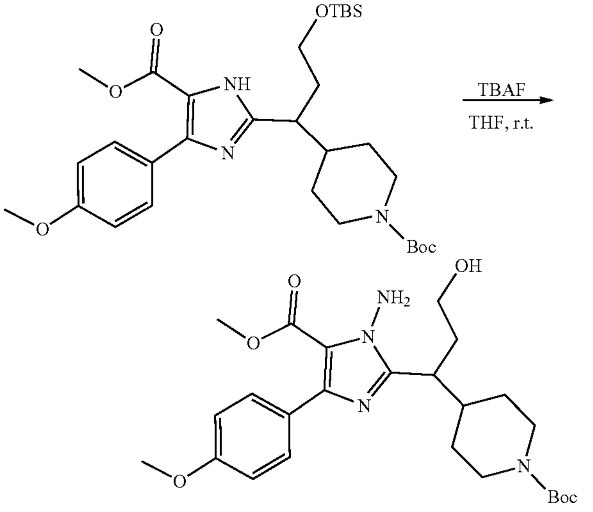

To a solution of the product of step D (7.5 g, 12.44 mmol) of example 27 in tetrahydrofuran (50 mL) was added a 1 M solution of tetrabutylammonium fluoride in tetrahydrofuran (13 mL, 12.44 mmol) at r.t. The solution was stirred for 2 hs and diluted with 100 mL ethyl acetate. The organic layer was separated and washed with $H_2O$ (3×200 mL). The water extract was washed with ethyl acetate (2×150 mL), and the organic layers were combined and dried over anhydrous $Na_2SO_4$. The solvent was evaporated in vacuo, and purified by flash chromatography on silica gel with dichloromethane and methanol (25:1) to give the product as a clear colorless oil (5 g, 82%). $^1$H NMR (400 MHz, $CDCl_3$) δ 7.56 (d, J=8.5 Hz, 2H), 6.90 (d, J=8.5 Hz, 2H), 5.53 (s, 2H), 4.11 (dd, J=14.0, 7.0 Hz, 1H), 4.00 (s, 1H), 3.82 (s, 3H), 3.76 (s, 3H), 3.57 (s, 1H), 3.40 (s, 1H), 3.29 (td, J=9.1, 5.2 Hz, 1H), 2.78-2.54 (m, 2H), 2.01 (dd, J=9.5, 5.3 Hz, 3H), 1.90 (s, 1H), 1.43 (s, 9H), 1.31 (d, J=11.8 Hz, 1H), 1.28-1.17 (m, 2H). MS (ESI, m/z): 489.3 [M+H]$^+$.

Step F: Preparation of methyl 8-(1-(tert-butoxycarbonyl)piperidin-4-yl)-2-(4-methoxyphenyl)-5,6,7,8-tetrahydroimidazo[1,2-b]pyridazine-3-carboxylate

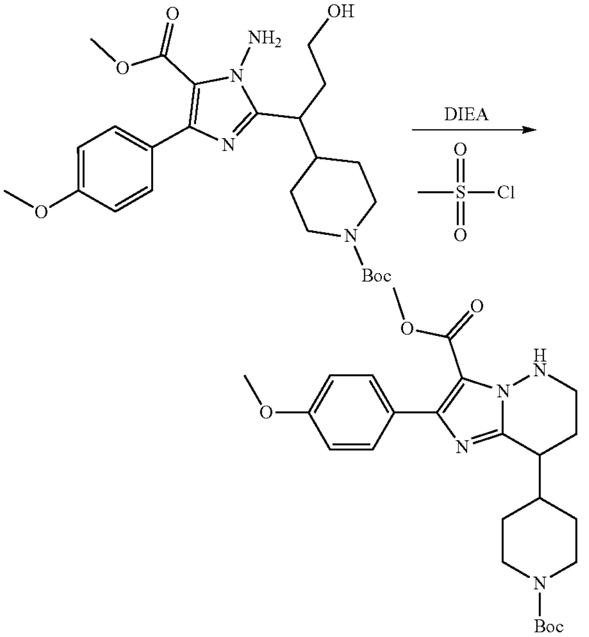

Methanesulfonyl chloride (2.3 g, 20.47 mmol) was added via syringe into a stirred mixture of the product of step E (5.0 g, 10.23 mmol) of example 27 and N, N-diisopropylethylamine (3.3 g, 25.58 mmol) in dichloromethane (50 ml) maintained at 0° C. The mixture was stirred at room temperature for 3 hs (TLC monitoring) and then partitioned between dichloromethane and water. The organic phase was dried and evaporated to afford an oil. The crude intermediate was dissolved in tetrahydrofuran (20 mL), 1 M solution of tetrabutylammonium fluoride in tetrahydrofuran (10 mL, 10.23 mmol) and N, N-diisopropylethylamine (3.3 g, 25.58 mmol) was added to the mixture, which was stirred 3 hs, then partitioned between dichloromethane and water. The organic phase was dried and evaporated to afford a white solid, then passed through a column of silica gel with dichloromethane and methanol (25:1) to afford the desired product as a colorless oil (2.0 g, 41%). $^1$H NMR (600 MHz, $CDCl_3$) δ 7.59 (d, J=8.7 Hz, 2H), 6.91 (d, J=8.7 Hz, 2H), 4.16 (s, 2H), 3.83 (s, 3H), 3.76 (s, 3H), 3.49-3.42 (m, 1H), 3.34-3.31 (m, 1H), 3.08 (s, 1H), 2.68 (s, 2H), 2.39 (s, 1H), 2.08-2.01 (m, 1H), 1.95-1.88 (m, 1H), 1.73 (d, J=12.5 Hz, 1H), 1.44 (s, 9H), 1.41 (d, J=9.4 Hz, 1H), 1.32 (s, 1H), 1.28 (s, 1H). MS (ESI, m/z): 471.3 $[M+H]^+$.

Step G: Preparation of 8-(1-(tert-butoxycarbonyl) piperidin-4-yl)-2-(4-methoxyphenyl)-5,6,7,8-tetrahydroimidazo[1,2-b]pyridazine-3-carboxylic Acid

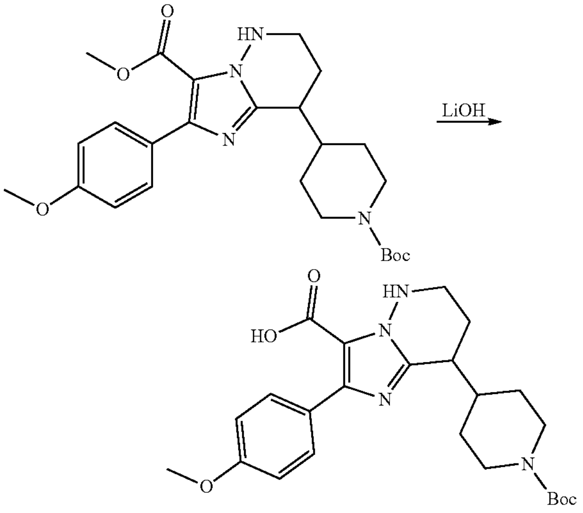

To a solution of the product of step F (2.0 g, 4.25 mmol) of example 27 in tetrahydrofuran (30 mL) was added LiOH (1.1 g, 42.50 mmol) in water (10 mL), the mixture was heated at 50° C. for 3 hs. Then cooled to r.t. The mixture acidified to pH 3-4 with concentrated HCl and then extracted with dichloromethane (3×100 mL). The organic phase was washed with saturated brine and then dried over anhydrous $Na_2SO_4$. The organic phase was concentrated in vacuo to afford 2.1 g crude product. The residue was used to next step without further purification. MS (ESI, m/z): 457.2 $[M+H]^+$.

Step H: Preparation of tert-butyl 4-(3-carbamoyl-2-(4-methoxyphenyl)-5,6,7,8-tetrahydroimidazo[1,2-b] pyridazin-8-yl)piperidine-1-carboxylate

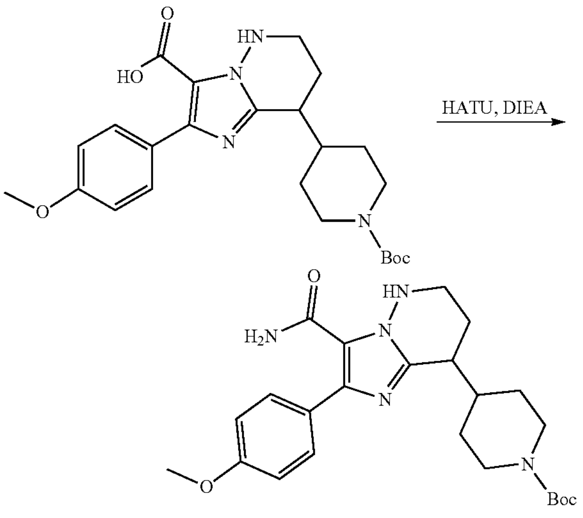

To the solution of the product of step G (1.0 g, 2.19 mmol) of example 27 in dichloromethane (30 mL) was added N,N-diisopropylethylamine (1.4 g, 10.95 mmol). After 5 min, $NH_4Cl$ (468.6 mg, 8.76 mmol) and HATU (1.3 g, 3.29 mmol) was added. The reaction mixture was continued to stir at room temperature for 2 h. Dichloromethane and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (40:1) to give product as an off-white solid (630 mg, 63%). $^1H$ NMR (600 MHz, $CDCl_3$) δ 7.51 (d, J=8.6 Hz, 2H), 6.96 (d, J=8.7 Hz, 2H), 4.16 (s, 2H), 3.83 (s, 3H), 3.45-3.37 (m, 1H), 3.36-3.27 (m, 1H), 3.11 (d, J=3.7 Hz, 1H), 2.69 (s, 2H), 2.39 (s, 1H), 2.07-2.01 (m, 1H), 1.97-1.88 (m, 1H), 1.71-1.69 (m, 1H), 1.44 (s, 9H), 1.43-1.41 (m, 1H), 1.36 (s, 1H), 1.32 (s, 1H). MS(ESI, m/z): 456.3 $[M+H]^+$.

Step I: Preparation of 2-(4-methoxyphenyl)-8-(piperidin-4-yl)-5,6,7,8-tetrahydroimidazo[1,2-b] pyridazine-3-carboxamide

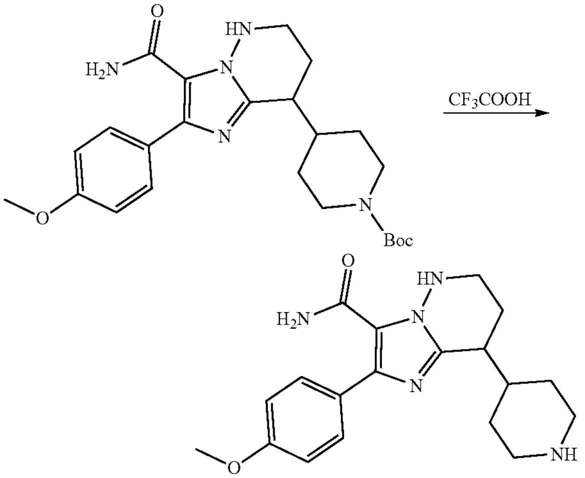

To a solution of the product of step H (630 mg, crude) of example 27 in EtOH (5 mL) was added $CF_3COOH$ (2 mL) at room temperature in reaction still. The mixture was stirred for 30 min. The mixture was concentrated under vacuum to get 6.5 g crude. The residue was used to next step without further purification. MS (ESI, m/z): 356.2 $[M+H]^+$.

Step J: Preparation of 8-(1-acryloylpiperidin-4-yl)-2-(4-methoxyphenyl)-5,6,7,8-tetrahydroimidazo[1,2-b]pyridazine-3-carboxamide

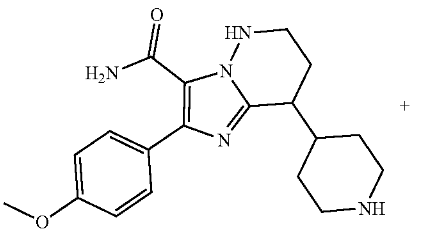

-continued

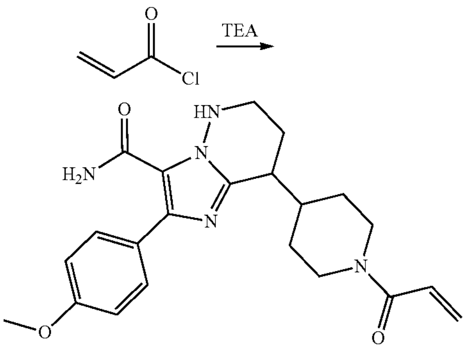

The mixture of the product of step I (150.0 mg, 0.42 mmol) of example 27 and triethylamine (213.5 mg, 2.11 mmol) in dichloromethane (30 mL) was cooled to −60° C. Then the solution of propenoyl chloride (30.5 mg, 0.33 mmol) in dichloromethane (1 mL) was added slowly, LC-MS was tracking, at the end of the reaction, 1 mL MeOH was added, the mixture was concentrated under vacuum to get crude product, and purified by flash chromatography on silica gel with dichloromethane and methanol (40:1) to get white solid (34 mg, 17%). $^{1}$H NMR (600 MHz, $CDCl_3$) δ 7.62-7.48 (m, 2H), 6.96 (d, J=8.6 Hz, 2H), 6.60-6.51 (m, 1H), 6.26-6.23 (m, 1H), 5.65 (d, J=10.5 Hz, 1H), 4.76-4.69 (m, 1H), 4.06-3.98 (m, 1H), 3.83 (s, 3H), 3.41-3.30 (m, 1H), 3.09-3.06 (m, 2H), 2.67-2.43 (m, 2H), 2.07-1.98 (m, 2H), 1.95-1.84 (m, 2H), 1.40 (s, 1H), 1.36 (s, 1H), 1.33-1.30 (m, 1H). MS (ESI, m/z): 410.2 [M+H]$^+$.

Scheme V

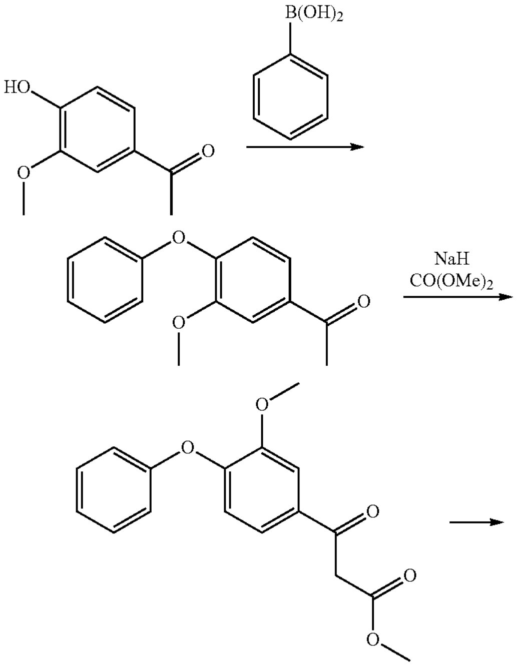

-continued

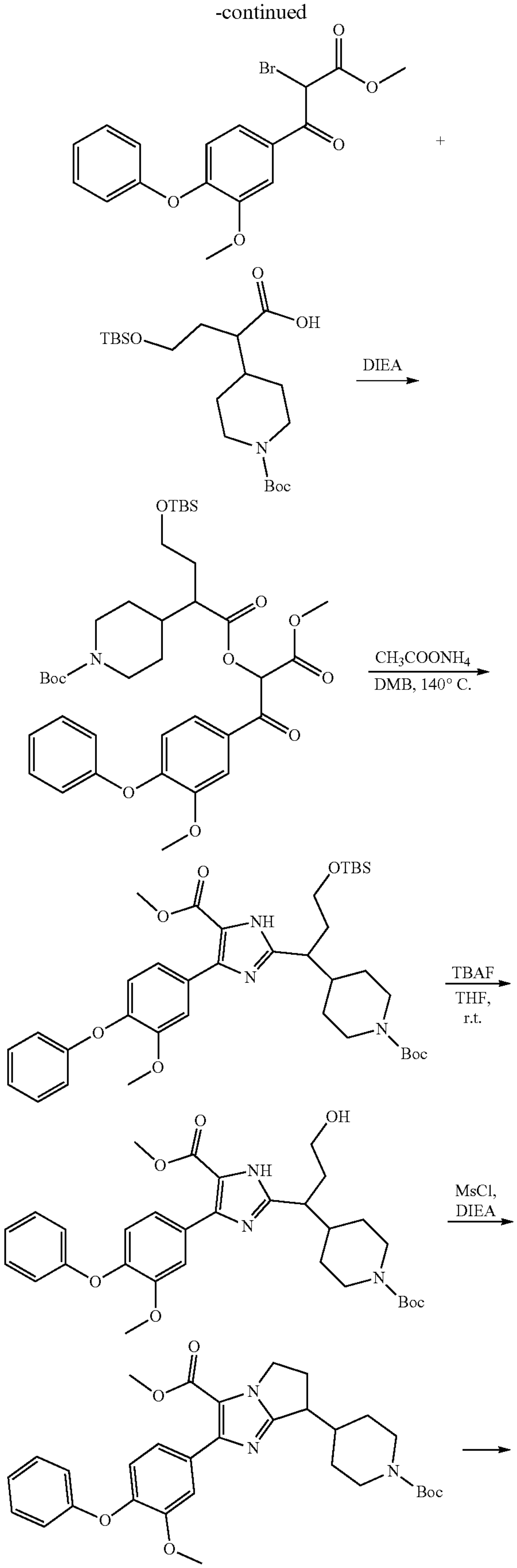

-continued

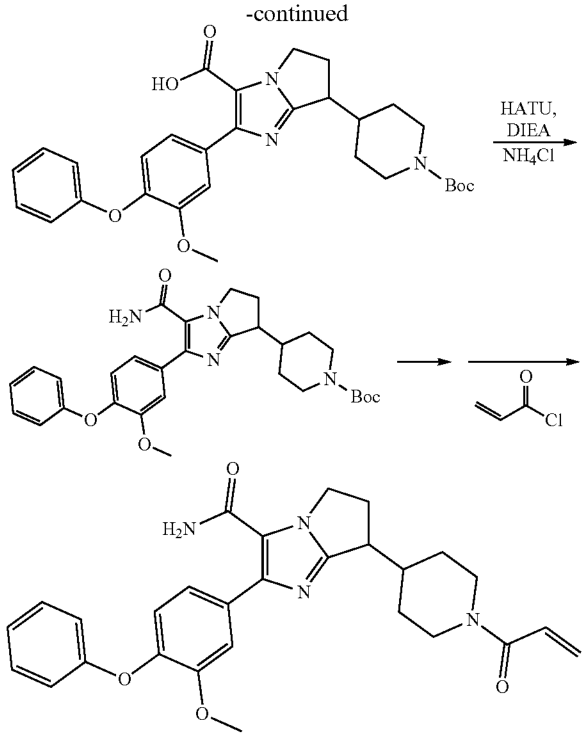

Example 28

7-(1-acryloylpiperidin-4-yl)-2-(3-methoxy-4-phenoxyphenyl)-6,7-dihydro-5H-pyrrolo[1,2-a]imidazole-3-carboxamide

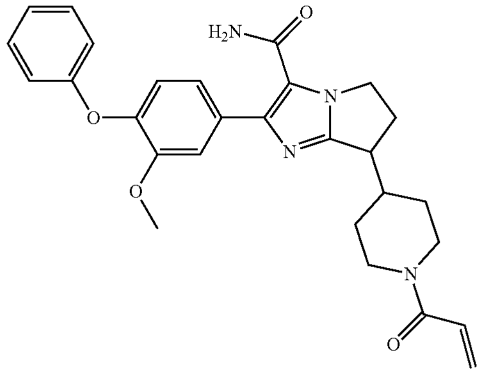 [SMILES: C=CC(=O)N1CCC(C2CCn3c2nc(-c2ccc(Oc4ccccc4)c(OC)c2)c3C(N)=O)CC1]

Step A: Preparation of 1-(3-methoxy-4-phenoxyphenyl)ethan-1-one

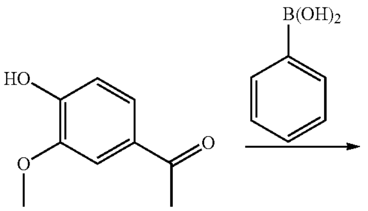

-continued

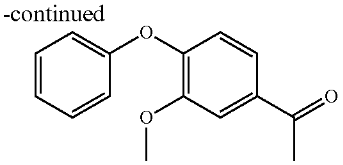

A slurry of 1-(4-hydroxy-3-methoxyphenyl)ethan-1-one (100.0 g, 601.77 mmol), phenylboronic acid (183.5 g, 1.5 mol), anhydrous $Cu(OAc)_2$ (218.6 g, 1.2 mol), and pyridine (95.2 g, 1.2 mol) in methylene chloride (2000 mL) was stirred at room temperature for 72 hs. Water was added, and the mixture was extracted with dichloromethane. Organic layers were combined and dried (anhydrous $Na_2SO_4$), and the solvent was removed. Products were obtained by chromatography with petroleum ether and ethyl acetate (40:1) to give product (53 g, 36%). $^1H$ NMR (400 MHz, $CDCl_3$) δ 7.64 (d, J=2.0 Hz, 1H), 7.49 (dd, J=8.3, 2.0 Hz, 1H), 7.39-7.32 (m, 2H), 7.18-7.11 (m, 1H), 7.06-7.00 (m, 2H), 6.87 (d, J=8.3 Hz, 1H), 3.93 (s, 3H), 2.58 (s, 3H). MS (ESI, m/z): 243.1 $[M+H]^+$.

Step B: Preparation of methyl 3-(3-methoxy-4-phenoxyphenyl)-3-oxopropanoate

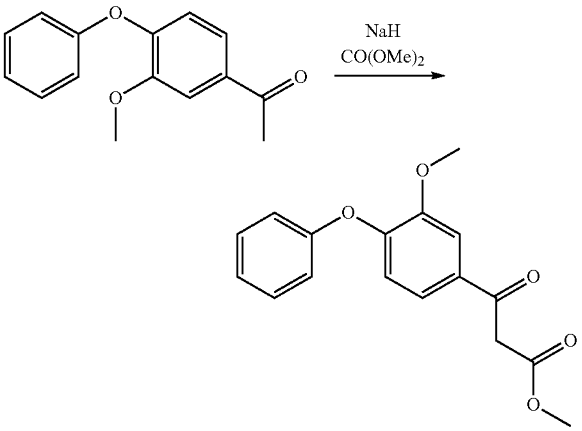

To a stirred suspension of NaH (60% dispersion in mineral oil; 17.5 g, 437.52 mmol) in toluene (100 mL) at 0° C. was added dropwise the solution of the product of step A (53.0 g, 218.76 mmol) of example 28 in toluene (100 mL). After 30 minutes, dimethylcarbonate (98.53 g, 1.09 mol) was added. The mixture was refluxing for 3 hs, then poured into water. 1 mol/L cooled glacial acetic acid was added dropwise until pH 6-7. The solvent tetrahydrofuran was evaporated, and the residue was diluted with saturated brine and extracted with ethyl acetate (3×2000 mL). The combined organic layer was washed with saturated brine, dried over anhydrous $Na_2SO_4$, filtered and concentrated. The residue was purified by chromatography with petroleum ether and ethyl acetate (20:1) to afford product as a yellow solid (35 g, 53%). $^1H$ NMR (600 MHz, $CDCl_3$) δ 7.63 (d, J=2.0 Hz, 1H), 7.44 (dd, J=8.4, 2.0 Hz, 1H), 7.38-7.34 (m, 2H), 7.16 (t, J=7.4 Hz, 1H), 7.06-7.01 (m, 2H), 6.84 (d, J=8.4 Hz, 1H), 3.93 (s, 3H), 3.74 (s, 3H). MS (ESI, m/z): 301.1 $[M+H]^+$.

Step C: Preparation of methyl 2-bromo-3-oxo-3-(4-phenoxyphenyl)propanoate

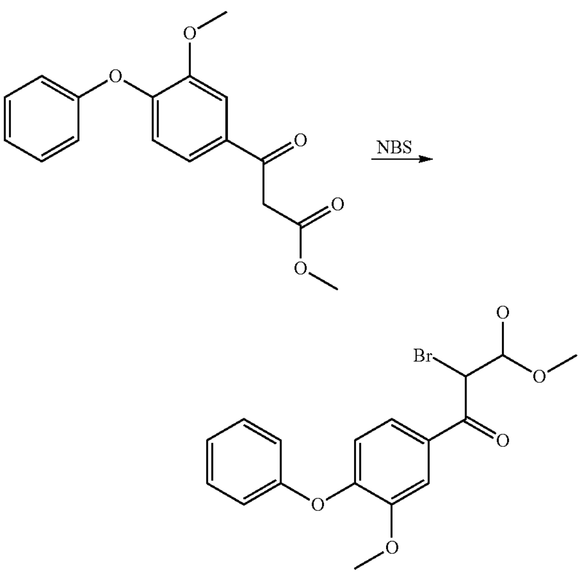

To a solution of the product of step B (30.0 g, 99.90 mmol) of example 28 in tert-butyl methyl ether (500 mL) was added N-bromosuccinimide (21.3 g, 119.88 mmol) and $CH_3COONH_4$ (3.8 g, 49.95 mmol). The reaction mixture was room temperature for 6 hs. Then the tert-butyl methyl ether was evaporated. The residue was diluted with ethyl acetate (1500 mL). The mixture was washed with aqueous 5% HCl (2×1000 mL) and water (500 mL), then dried over anhydrous sodium sulfate. Evaporation of the solvent gave the crude product as oil, the crude residue was flash chromatographed with ethyl acetate and petroleum ether (1:10) to get desired product as yellow oil (29 g, 76%). $^1H$ NMR (600 MHz, $CDCl_3$) δ 7.65 (d, J=2.0 Hz, 1H), 7.50 (dd, J=8.5, 2.1 Hz, 1H), 7.39-7.34 (m, 2H), 7.17 (t, J=7.4 Hz, 1H), 7.07-7.02 (m, 2H), 6.82 (d, J=8.4 Hz, 1H), 5.66 (s, 1H), 3.93 (s, 3H), 3.81 (s, 3H). MS (ESI, m/z): 380.0 $[M+H]^+$.

Step D: Preparation of tert-butyl 4-(4-(3-methoxy-4-phenoxybenzoyl)-11,11,12,12-tetramethyl-3,6-dioxo-2,5,10-trioxa-11-silatridecan-7-yl)piperidine-1-carboxylate

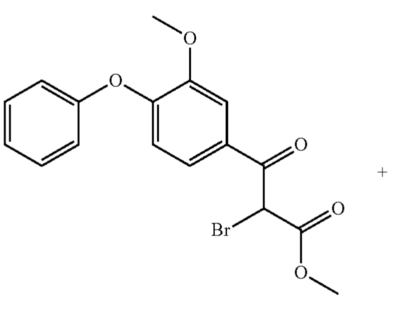

-continued

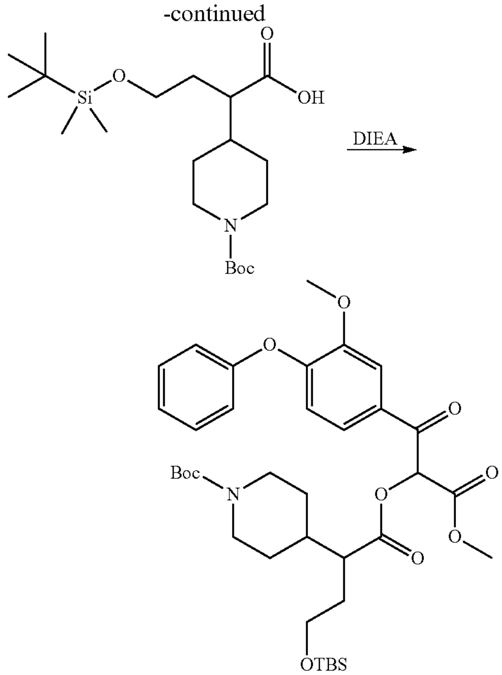

The product of step G (39.9 g, 99.42 mmol) of example 1 and the product of step C (29.0 g, 76.48 mmol) of example 28 were taken up in acetonitrile (400 mL), then N, N-diisopropylethylamine (14.8 g, 114.71 mmol) was added and the solution stirred at 30° C. for 3 hs. The solvent was removed by rotorary evaporation and the residue taken up in ethyl acetate, washed with brine. The organic fractions were dried over anhydrous $Na_2SO_4$, filtered, and concentrated under reduced pressure to give the crude product which was purified via flash chromatography with ethyl acetate and petroleum ether (1:10) to give the product as a clear colorless oil (49 g, 91%). $^1H$ NMR (600 MHz, $CDCl_3$) δ 7.63 (t, J=2.3 Hz, 1H), 7.52 (ddd, J=8.5, 6.5, 1.9 Hz, 1H), 7.34 (t, J=8.0 Hz, 2H), 7.15 (td, J=7.4, 0.9 Hz, 1H), 7.02 (d, J=8.3 Hz, 2H), 6.80 (dd, J=8.4, 1.2 Hz, 1H), 6.25 (d, J=5.4 Hz, 1H), 4.22-3.97 (m, 2H), 3.91 (s, 3H), 3.75 (s, 3H), 3.66-3.59 (m, 1H), 3.57-3.49 (m, 1H), 2.69-2.52 (m, 3H), 1.88-1.78 (m, 2H), 1.77-1.63 (m, 2H), 1.62-1.59 (m, 1H), 1.42 (s, 9H), 1.32-1.17 (m, 2H), 0.81 (d, J=18.8 Hz, 9H), 0.00-(−0.07) (m, 6H). MS (ESI, m/z): 700.3 $[M+H]^+$.

Step E: Preparation of tert-butyl 4-(3-((tert-butyldimethylsilyl)oxy)-1-(4-(3-methoxy-4-phenoxyphenyl)-5-(methoxycarbonyl)-1H-imidazol-2-yl)propyl)piperidine-1-carboxylate

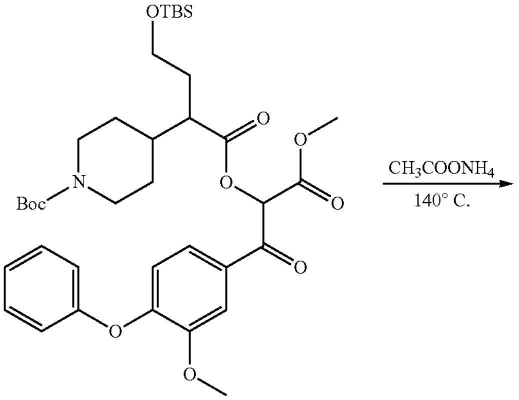

-continued

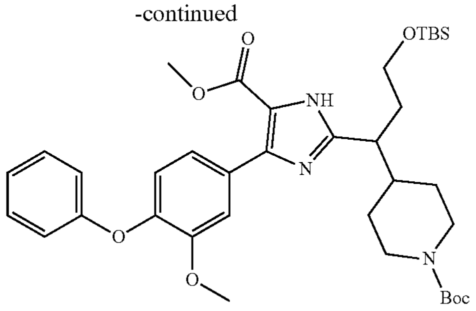

To a slurry of ammonium acetate (64.8 g, 840.10 mmol) in xylenes (500 mL) was added the product of step D (49.0 g, 70.01 mmol) of example 28. The mixture was stirred at 140° C. for 4 hours. The solution was cooled to room temperature and the solvent was evaporated. The residue was dissolved in ethyl acetate and washed with saturated brine. The organic phase was dried over anhydrous $Na_2SO_4$, filtered and concentrated. The residue was purified by silica gel column chromatography with ethyl acetate and petroleum ether (1:5) to give the product as a clear colorless oil (17.8 g, 37%). $^1H$ NMR (400 MHz, $CDCl_3$) δ 9.97 (s, 1H), 7.74 (d, J=1.6 Hz, 1H), 7.54 (dd, J=8.3, 1.8 Hz, 1H), 7.29 (t, J=7.9 Hz, 2H), 7.04 (t, J=7.3 Hz, 1H), 6.98 (d, J=8.1 Hz, 3H), 4.18-4.03 (m, 2H), 3.90 (s, 3H), 3.84 (s, 3H), 3.66-3.61 (m, 1H), 3.49-3.43 (m, 1H), 2.85-2.79 (m, 1H), 2.66 (d, J=12.6 Hz, 2H), 2.08-1.93 (m, 4H), 1.85 (d, J=12.8 Hz, 1H), 1.43 (s, 9H), 1.22-1.14 (m, 2H), 0.88 (s, 9H), 0.02 (d, J=3.8 Hz, 6H). MS (ESI, m/z): 680.4 $[M+H]^+$.

Step F: Preparation of tert-butyl 4-(3-hydroxy-1-(4-(3-methoxy-4-phenoxyphenyl)-5-(methoxycarbonyl)-1H-imidazol-2-yl)propyl)piperidine-1-carboxylate

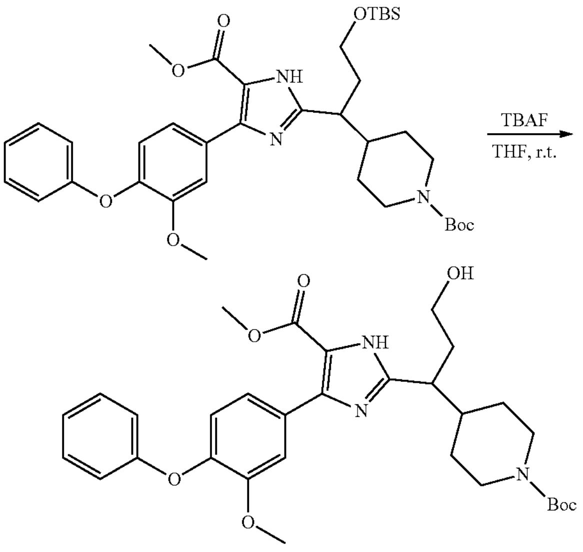

To a solution of the product of step E (5.0 g, 7.35 mmol) of example 28 in tetrahydrofuran (150 mL) was added a 1 M solution of tetrabutylammonium fluoride in tetrahydrofuran (15 mL, 14.70 mmol) at r.t. The solution was stirred for 2 hs and diluted with 100 mL ethyl acetate solution. The organic layer was separated and washed with $H_2O$ (3×200 mL). The water extract was washed with ethyl acetate solution (2×150 mL), and the organic layers were combined and dried over anhydrous $Na_2SO_4$. The solvent was evaporated in vacuo, and purified by flash chromatography on silica gel with dichloromethane and methanol (30:1) to give the product as a clear colorless oil (3.8 g, 91%). $^1H$ NMR (400 MHz, $CDCl_3$) δ 7.55 (s, 1H), 7.31 (d, J=6.4 Hz, 1H), 7.24-7.20 (m, 2H), 6.98 (t, J=7.4 Hz, 1H), 6.92-6.86 (m, 3H), 4.04-3.93 (m, 2H), 3.80 (s, 3H), 3.74 (s, 3H), 3.60-3.53 (m, 1H), 3.41 (d, J=6.6 Hz, 1H), 2.81-2.75 (m, 1H), 2.59 (s, 2H), 1.99-1.85 (m, 4H), 1.77-1.74 (m, 1H), 1.36 (s, 9H), 1.11-1.02 (m, 2H). MS (ESI, m/z): 566.3 $[M+H]^+$.

Step G: Preparation of tert-butyl 4-(1-(4-(3-methoxy-4-phenoxyphenyl)-5-(methoxycarbonyl)-1H-imidazol-2-yl)-3-((methylsulfonyl)oxy)propyl)piperidine-1-carboxylate

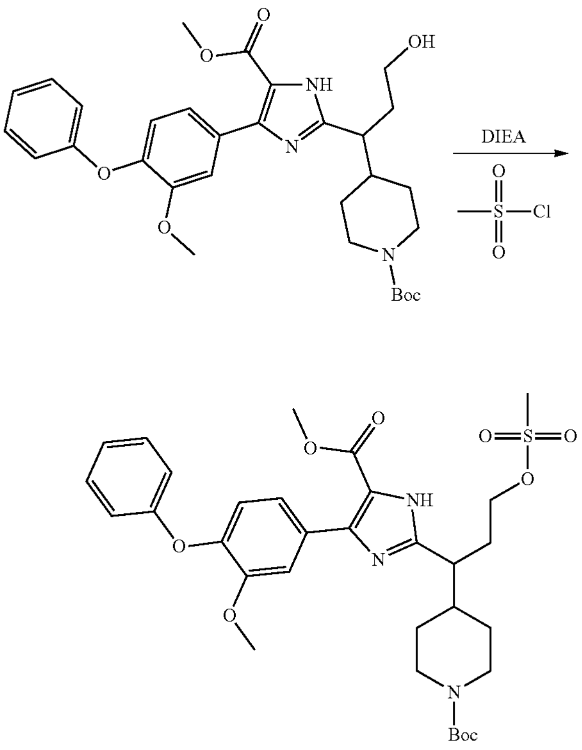

Methanesulfonyl chloride (1.54 g, 13.44 mmol) was added via syringe into a stirred mixture of the product of step F (3.8 g, 6.72 mmol) of example 28 and N, N-diisopropylethylamine (2.2 g, 16.79 mmol) in dichloromethane (100 ml) maintained at 0° C. The mixture was stirred at room temperature for 3 h (TLC monitoring) and then partitioned between dichloromethane and water. The organic phase was dried, then evaporated to afford a white solid, the crude product was passed through a column of silica gel with dichloromethane and methanol (20:1) to afford the desired product as a colorless oil (4.3 g, crude). MS (ESI, m/z): 644.3 $[M+H]^+$.

Step H: Preparation of methyl 7-(1-(tert-butoxycarbonyl)piperidin-4-yl)-2-(3-methoxy-4-phenoxyphenyl)-6,7-dihydro-5H-pyrrolo[1,2-a]imidazole-3-carboxylate

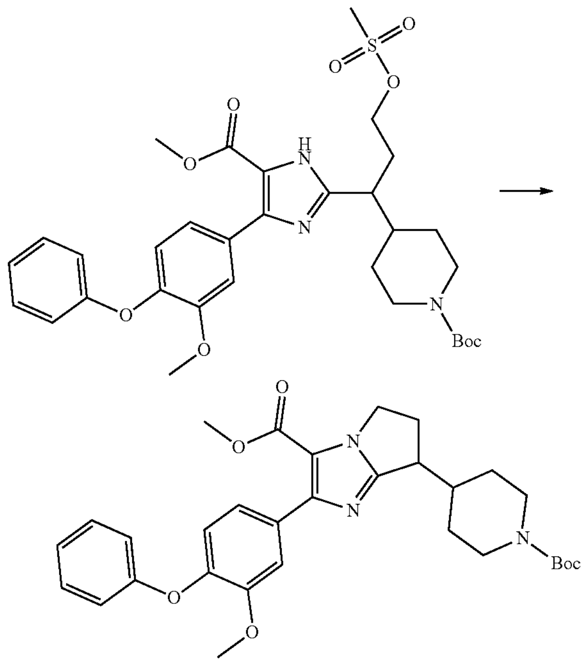

N, N-diisopropylethylamine (2.2 g, 16.79 mmol) and 1 M solution of tetrabutylammonium fluoride in tetrahydrofuran (6 mL, 6.72 mmol) were added to the solvent of the product of step G (4.3 g, crude) of example 28 in anhydrous tetrahydrofuran (20 mL), the mixture was heated to 50° C. for 2 hs, then cooled to r.t., concentrated and purified by flash column chromatography with dichloromethane and methanol (10:1) to give the desired product (1.6 g, 43%). $^1H$ NMR (400 MHz, $CDCl_3$) δ 7.57 (d, J=1.4 Hz, 1H), 7.41 (dd, J=8.3, 1.6 Hz, 1H), 7.32-7.26 (m, 2H), 7.04 (t, J=7.3 Hz, 1H), 6.98 (t, J=8.3 Hz, 3H), 4.32-4.09 (m, 4H), 3.89 (s, 3H), 3.81 (s, 3H), 3.10 (d, J=6.2 Hz, 1H), 2.74-2.65 (m, 3H), 2.44-2.31 (m, 1H), 2.09-2.06 (m, 1H), 1.96 (s, 1H), 1.56-1.53 (m, 1H), 1.45 (s, 9H), 1.38-128 (m, 2H). MS (ESI, m/z): 548.3 $[M+H]^+$.

Step I: Preparation of 7-(1-(tert-butoxycarbonyl)piperidin-4-yl)-2-(4-phenoxyphenyl)-6,7-dihydro-5H-pyrrolo[1,2-a]imidazole-3-carboxylic Acid

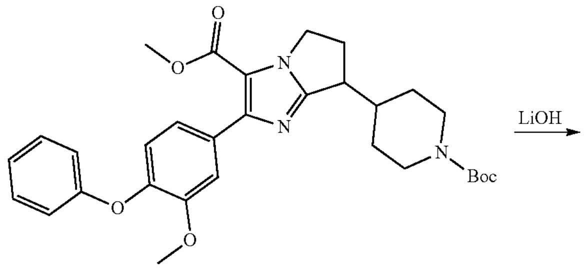

-continued

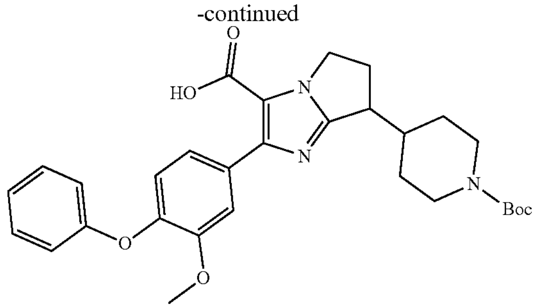

To a solution of the product of step H (1.6 g, 2.92 mmol) of example 28 in tetrahydrofuran (30 mL) was added LiOH (349.8 mg, 14.61 mmol) in water (5 mL), the mixture was heated at 50° C. for 3 hs. After cooled to r.t. The mixture was acidified to pH 3-4 with concentrated HCl and then extracted with dichloromethane (3×100 mL). The organic phase was washed with saturated brine and then dried over anhydrous $Na_2SO_4$. The organic phase was concentrated in vacuo to afford 1.5 g crude product. The residue was used to next step without further purification. MS (ESI, m/z): 534.2 [M+H]r.

Step J: Preparation of tert-butyl 4-(3-carbamoyl-2-(3-methoxy-4-phenoxyphenyl)-6,7-dihydro-5H-pyrrolo[1,2-a]imidazol-7-yl)piperidine-1-carboxylate

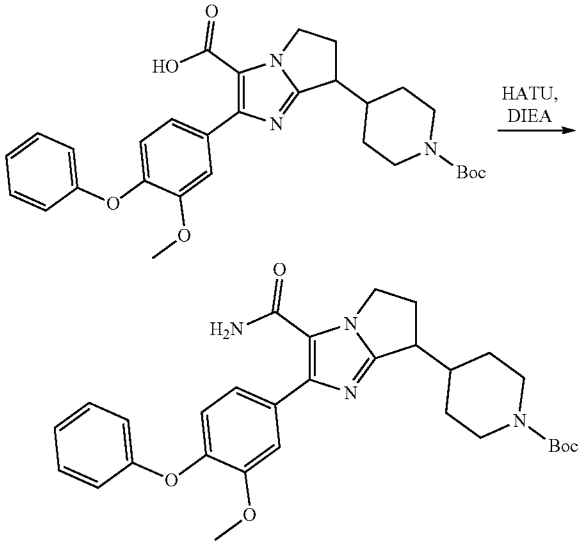

To the solution of the product of step I (1.5 g, 2.81 mmol) of example 28 in dichloromethane (20 mL) was added N, N-diisopropylethylamine (1.5 g, 11.24 mmol). After 5 min, $NH_4Cl$ (601.4 mg, 11.24 mmol) and HATU (1.6 g, 4.22 mmol) was added. The reaction mixture was continued to stir at room temperature for 2 hs. Dichloromethane and water were added. The layers were separated, and the aqueous phase was extracted with dichloromethane. The combined organic phases were washed with brine solution (3×100 mL). The organic phase was dried over anhydrous $Na_2SO_4$, filtered and concentrated. The residue was purified by chromatography with dichloromethane and methanol (40:1) to give product as an off-white solid (0.45 g, 30%). $^1H$ NMR (400 MHz, $CDCl_3$) δ 7.28-7.23 (m, 2H), 7.20-7.15 (m, 2H), 7.07-7.05 (m, 1H), 7.04-6.99 (m, 1H), 6.94-6.90 (m, 2H), 5.82-5.61 (m, 1H), 5.36 (s, 1H), 4.32-4.24 (m, 1H), 4.21-4.03 (m, 3H), 3.81 (s, 3H), 3.01 (d, J=7.0 Hz, 1H), 2.69-2.57 (m, 3H), 2.35-2.28 (m, 1H), 2.01-1.92 (m, 2H), 1.87 (s, 1H). MS (ESI, m/z): 533.3 [M+H]r.

Step K: Preparation of 2-(3-methoxy-4-phenoxy-phenyl)-7-(piperidin-4-yl)-6,7-dihydro-5H-pyrrolo[1,2-a]imidazole-3-carboxamide

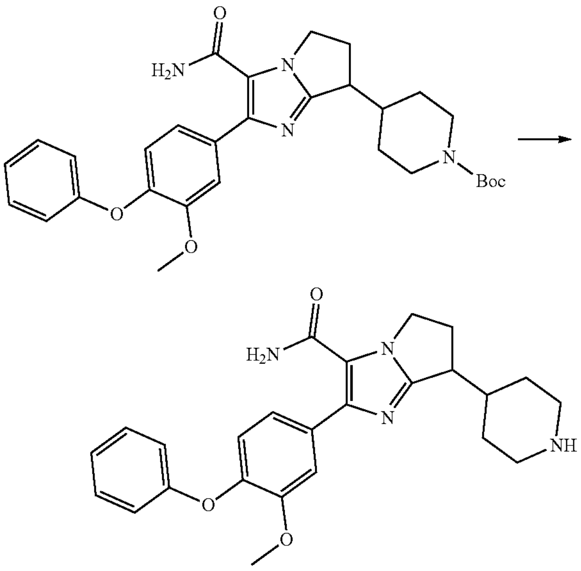

To a solution of the product of step J (450 mg, 0.84 mmol) of example 28 in EtOH (10 mL) was added $CF_3COOH$ (2 mL) at room temperature. The mixture was stirred for 3 hs, then concentrated under vacuum to get 116 mg crude product. The residue was used to next step without further purification. MS (ESI, m/z): 433.2 $[M+H]^+$.

Step L: Preparation of 7-(1-acryloylpiperidin-4-yl)-2-(3-methoxy-4-phenoxyphenyl)-6,7-dihydro-5H-pyrrolo[1,2-a]imidazole-3-carboxamide

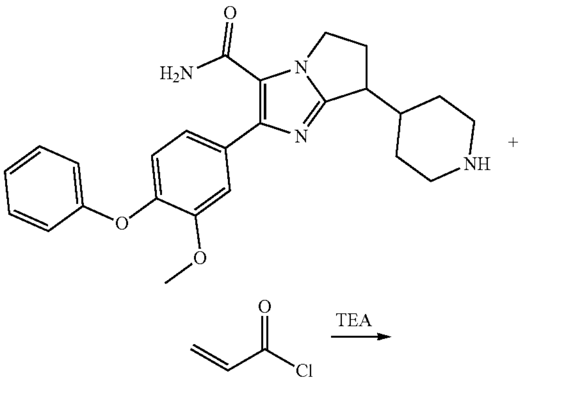

-continued

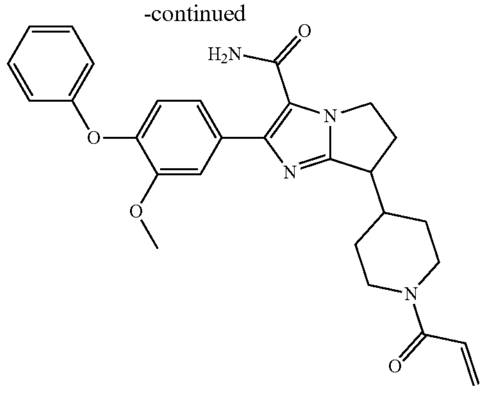

The mixture of the product of step K (200.0 mg, 0.46 mmol) of example 28 and triethylamine (233.4 mg, 2.30 mmol) in dichloromethane (10 mL) was cooled to 0° C., then the solution of propenoyl chloride (41.8 mg, 0.46 mmol) in dichloromethane (1 mL) was added slowly, LC-MS was tracking, at the end of the reaction, 1 mL MeOH was added, the mixture was concentrated under vacuum to get crude product. The residue was purified by flash chromatography on silica gel with dichloromethane and methanol (40:1) to get product as a white solid (43 mg, 19%). $^1$H NMR (400 MHz, $CDCl_3$) δ 7.31 (t, J=8.0 Hz, 2H), 7.22 (d, J=1.3 Hz, 1H), 7.14-7.04 (m, 2H), 7.00-6.96 (m, 3H), 6.59-6.53 (m, 1H), 6.27-6.22 (m, 1H), 5.68-5.63 (m, 1H), 4.73 (s, 1H), 4.35 (s, 1H), 4.23 (s, 1H), 4.04 (d, J=9.3 Hz, 1H), 3.87 (s, 3H), 3.11-3.01 (m, 2H), 2.74-2.56 (m, 2H), 2.40-2.31 (m, 1H), 2.15-1.93 (m, 2H), 1.68 (s, 1H), 1.45-1.32 (m, 2H). MS (ESI, m/z): 487.2 $[M+H]^+$.

Scheme VI

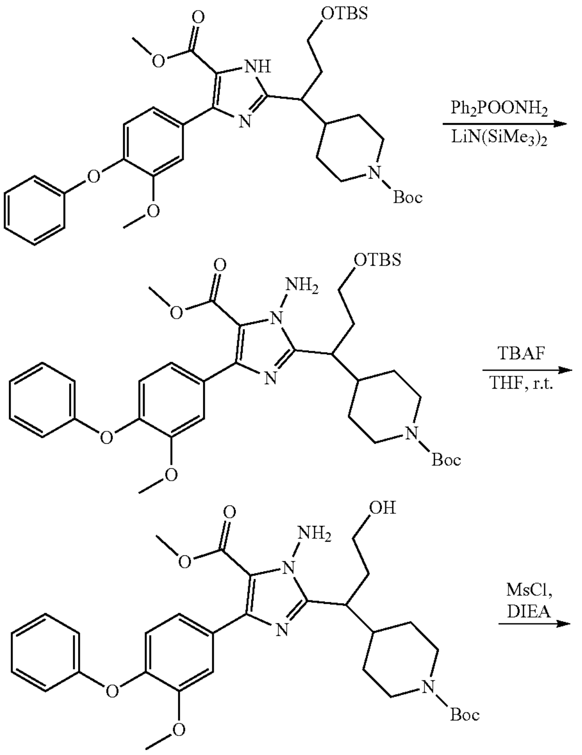

-continued
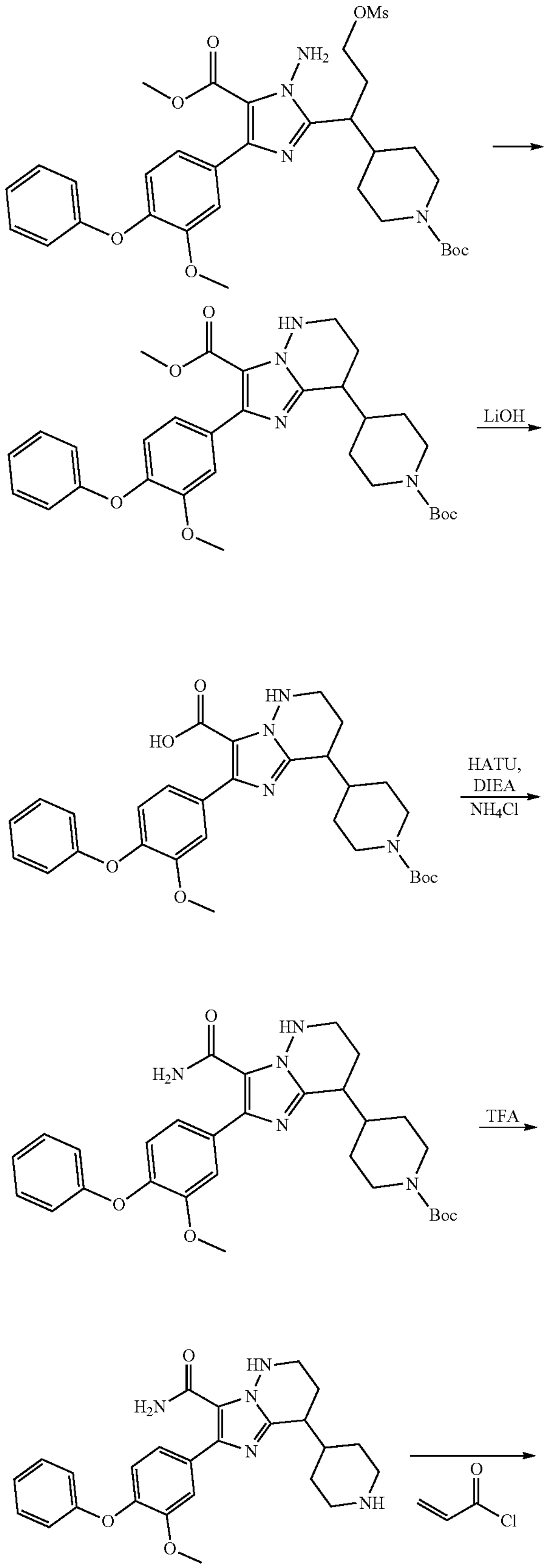
-continued
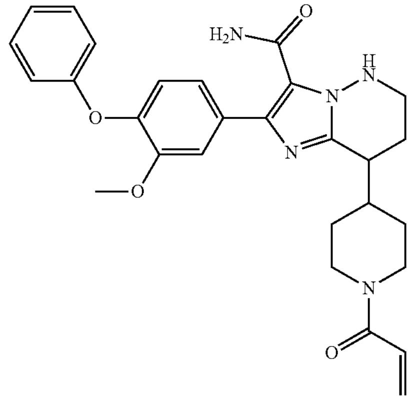
Example 29
8-(1-acryloylpiperidin-4-yl)-2-(3-methoxy-4-phenoxyphenyl)-5,6,7,8-tetrahydroimidazo[1,2-b]pyridazine-3-carboxamide
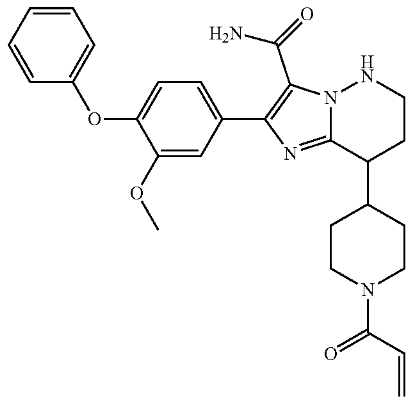 [SMILES: C=CC(=O)N1CCC(C2CCNn3c2nc(-c2ccc(Oc4ccccc4)c(OC)c2)c3C(N)=O)CC1]
Step A: Preparation of tert-butyl 4-(1-(1-amino-4-(3-methoxy-4-phenoxyphenyl)-5-(methoxycarbonyl)-1H-imidazol-2-yl)-3-((tert-butyldimethylsilyl)oxy)propyl)piperidine-1-carboxylate
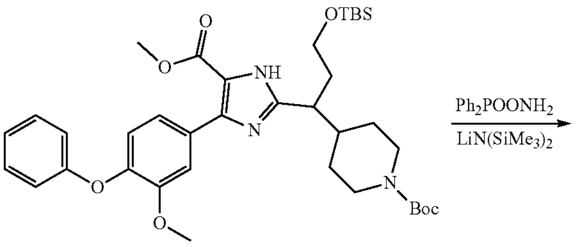

-continued

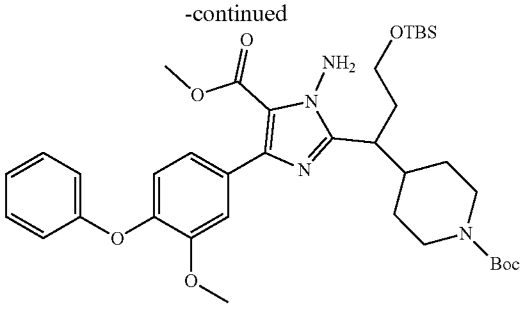

Lithium hexamethyldisilazane (11 mL of a 1 M solution in tetrahydrofuran, 11.03 mmol) was slowly added to the product of step D (5.0 g, 7.35 mmol) of example 28 in anhydrous N, N-dimethylformamide (150 mL) at 0° C. After the mixture was stirred for 30 min, O-(diphenylphosphinyl) hydroxylamine (3.4 g, 14.71 mmol) was added at 0° C., followed by stirring at room temperature for 4 hs (in cases where the reaction mixture became too viscous, additional N, N-dimethylformamide was added). The reaction was quenched with water until a clear solution was formed and concentrated to dryness under reduced pressure. The residue was washed several times with ethyl acetate or dichloromethane. The combined organic fractions were concentrated in vacuo and purified by flash chromatography on silica gel with acetate and petroleum to (1:3) to give the product as a clear colorless oil (3.2 g, 62%). $^1$H NMR (400 MHz, $CDCl_3$) δ 7.34 (d, J=1.8 Hz, 1H), 7.32-7.27 (m, 2H), 7.22 (dd, J=8.3, 1.9 Hz, 1H), 7.04 (t, J=7.4 Hz, 1H), 7.01-6.95 (m, 3H), 5.61 (s, 2H), 4.23-3.98 (m, 2H), 3.87 (s, 3H), 3.79 (s, 3H), 3.67-3.61 (m, 1H), 3.40-3.34 (m, 2H), 2.75-2.58 (m, 2H), 2.08-2.03 (m, 2H), 2.02-1.91 (m, 2H), 1.44 (s, 9H), 1.29-1.19 (m, 2H), 0.87 (s, 9H), 0.01 (d, J=11.1 Hz, 6H). MS (ESI, m/z): 695.4 $[M+H]^+$.

Step B: Preparation of tert-butyl 4-(1-(1-amino-4-(3-methoxy-4-phenoxyphenyl)-5-(methoxycarbonyl)-1H-imidazol-2-yl)-3-hydroxypropyl)piperidine-1-carboxylate

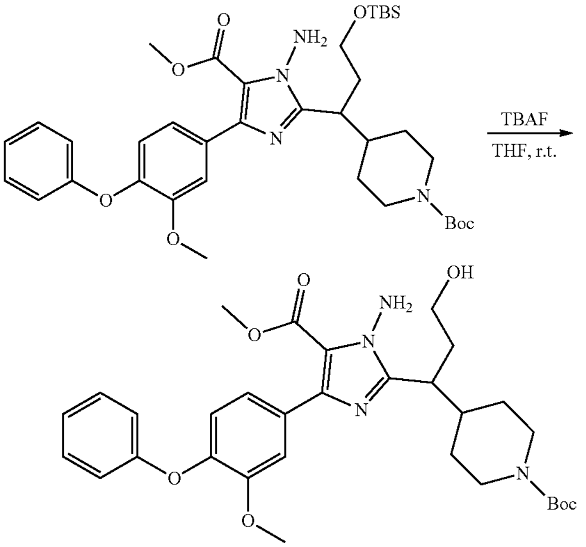

To a solution of the product of step A (3.2 g, 4.60 mmol) of example 29 tetrahydrofuran (50 mL) was added a 1 M solution of tetrabutylammonium fluoride in tetrahydrofuran (5 mL, 4.60 mmol) at r.t. The solution was stirred for 2 hs and diluted with 100 mL ethyl acetate solution. The organic layer was separated and washed with $H_2O$ (3×200 mL). The water extract was washed with ethyl acetate solution (2×150 mL), and the organic layers were combined and dried over anhydrous $Na_2SO_4$. The solvent was evaporated in vacuo, and purified by flash chromatography on silica gel with dichloromethane and methanol (25:1) to give the product as a clear colorless oil (2 g, 74%). $^1$H NMR (400 MHz, $CDCl_3$) δ 7.25-7.19 (m, 3H), 7.12 (dd, J=8.3, 1.9 Hz, 1H), 6.98 (t, J=7.4 Hz, 1H), 6.93-6.86 (m, 3H), 5.50 (s, 2H), 4.13-4.01 (m, 1H), 3.97-3.90 (m, 1H), 3.79 (s, 3H), 3.72 (s, 3H), 3.59-3.52 (m, 1H), 3.38-3.32 (m, 1H), 3.29-3.23 (m, 1H), 2.67-2.52 (m, 2H), 2.00-1.94 (m, 3H), 1.84 (d, J=12.7 Hz, 1H), 1.36 (s, 9H), 1.22-1.07 (m, 3H). MS (ESI, m/z): 581.3 $[M+H]^+$.

Step C: Preparation of methyl 8-(1-(tert-butoxycarbonyl)piperidin-4-yl)-2-(3-methoxy-4-phenoxyphenyl)-5,6,7,8-tetrahydroimidazo[1,2-b]pyridazine-3-carboxylate

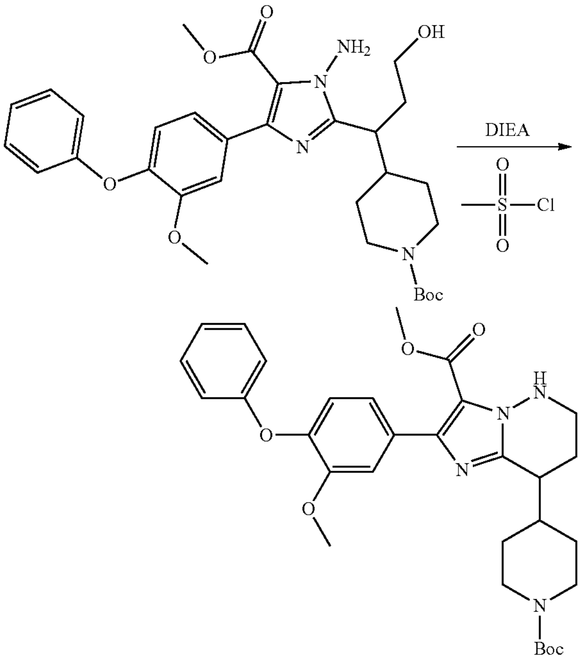

Methanesulfonyl chloride (789.0 mg, 6.98 mmol) was added via syringe into a stirred mixture of the product of step B (2.0 g, 3.44 mmol) of example 29 and N, N-diisopropylethylamine (890.3 mg, 6.98 mmol) in dichloromethane (50 ml) maintained at 0° C. The mixture was stirred at room temperature for 3 hs (TLC monitoring) and then partitioned between dichloromethane and water. The organic phase was dried and evaporated to afford an oil. The crude intermediate was dissolved in tetrahydrofuran (20 mL), 1 M solution of tetrabutylammonium fluoride in tetrahydrofuran (4 mL, 3.44 mmol) and N, N-diisopropylethylamine (890.3 mg, 6.98 mmol) was added to the mixture, which was stirred 3 hs, then partitioned between dichloromethane and water. The organic phase was dried and evaporated to afford a white solid, then passed through a column of silica gel with dichloromethane and methanol (25:1) to afford the desired product as a colorless oil (1.54 g, 79%). 1H NMR (400 MHz, $CDCl_3$) δ 7.35 (d, J=1.9 Hz, 1H), 7.32-7.28 (m, 2H), 7.22 (dd, J=8.3, 1.9 Hz, 1H), 7.05 (t, J=7.4 Hz, 1H), 7.01-6.96 (m, 3H), 4.16 (s, 2H), 3.87 (s, 3H), 3.79 (s, 3H), 3.50-3.44 (m, 1H), 3.38-3.31 (m, 1H), 3.14-3.08 (m, 1H), 2.74-2.66 (m, 2H), 2.42 (s, 1H), 2.10-2.02 (m, 2H), 1.98-1.91 (m, 1H), 1.75-1.72 (m, 1H), 1.44 (s, 9H), 1.37 (s, 1H), 1.33 (s, 1H). MS (ESI, m/z): 563.3 $[M+H]^+$.

Step D: Preparation of 8-(1-(tert-butoxycarbonyl) piperidin-4-yl)-2-(3-methoxy-4-phenoxyphenyl)-5,6,7,8-tetrahydroimidazo[1,2-b]pyridazine-3-carboxylic Acid

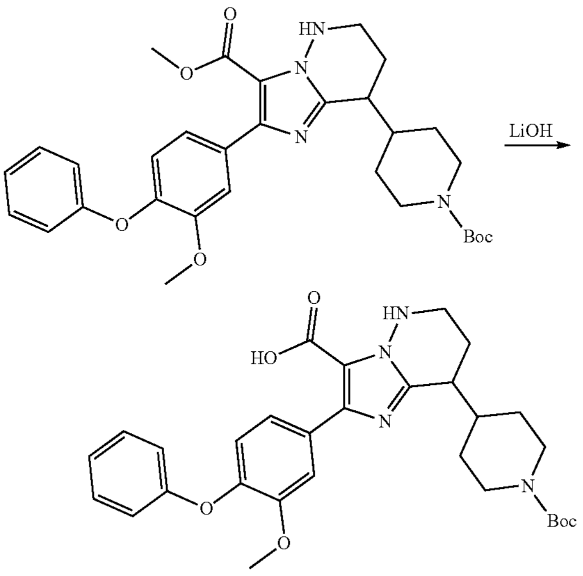

To a solution of the product of step C (1.5 g, 2.67 mmol) of example 29 in tetrahydrofuran (30 mL) was added LiOH (319.2 mg, 13.33 mmol) in water (10 mL), the mixture was heated at 50° C. for 3 hs. Then cooled to r.t. The mixture acidified to pH 3-4 with concentrated HCl and then extracted with of dichloromethane (3×100 mL). The organic phase was washed with saturated brine and then dried over anhydrous $Na_2SO_4$. The organic phase was concentrated in vacuo to afford 1.8 g crude product. The residue was used to next step without further purification. MS (ESI, m/z): 549.3 $[M+H]^+$.

Step E: Preparation of tert-butyl 4-(3-carbamoyl-2-(3-methoxy-4-phenoxyphenyl)-5,6,7,8-tetrahydroimidazo[1,2-b]pyridazin-8-yl)piperidine-1-carboxylate

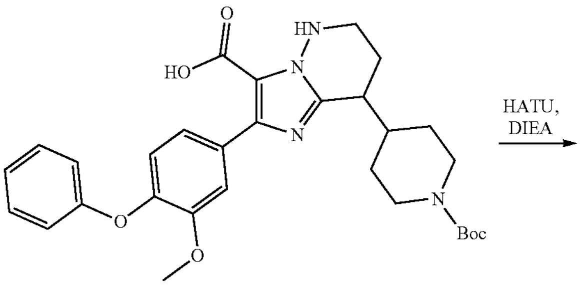

-continued

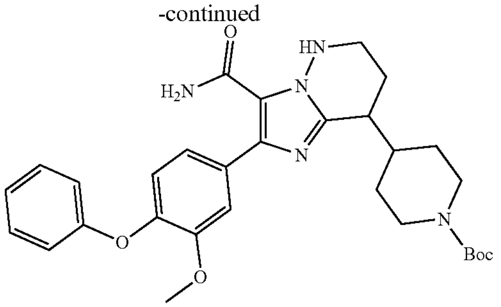

To the solution of the product of step D (1.0 g, 2.19 mmol) of example 29 in dichloromethane (30 mL) was added N,N-diisopropylethylamine (1.4 g, 10.95 mmol). After 5 min, $NH_4Cl$ (468.6 mg, 8.76 mmol) and HATU (1.3 g, 3.29 mmol) was added. The reaction mixture was continued to stir at room temperature for 2 hs. Dichloromethane and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (40:1) to give product as an off-white solid (1.4 g, 95%). $^1H$ NMR (600 MHz, $CDCl_3$) δ 7.31-7.28 (m, 3H), 7.16 (dd, J=8.2, 1.9 Hz, 1H), 7.06 (t, J=7.4 Hz, 1H), 7.00-6.94 (m, 3H), 4.17 (s, 2H), 3.86 (d, J=6.8 Hz, 3H), 3.43-3.41 (m, 1H), 3.33-3.29 (m, 1H), 3.11-3.08 (m, 1H), 2.71 (s, 2H), 2.46-2.34 (m, 1H), 2.18 (s, 1H), 2.10-1.98 (m, 1H), 1.98-1.85 (m, 1H), 1.72 (d, J=12.5 Hz, 1H), 1.44 (s, 9H), 1.38-1.33 (m, 1H), 1.30-1.22 (m, 1H). MS (ESI, m/z): 548.3 $[M+H]^+$.

Step F: Preparation of 2-(3-methoxy-4-phenoxyphenyl)-8-(piperidin-4-yl)-5,6,7,8-tetrahydroimidazo[1,2-b]pyridazine-3-carboxamide

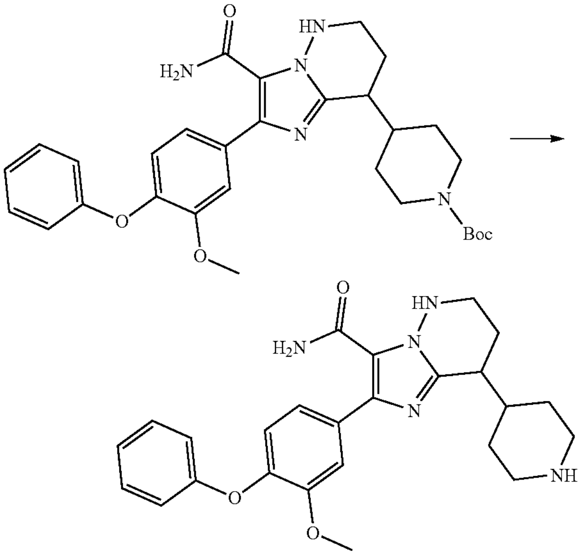

To a solution of the product of step E (1.4 g, 2.55 mmol) of example 29 in EtOH (5 mL) was added $CF_3COOH$ (2 mL) at room temperature in reaction still. The mixture was stirred for 30 min. The mixture was concentrated under vacuum to get 1.8 g crude. The residue was used to next step without further purification. MS (ESI, m/z): 448.2 $[M+H]^+$.

Step G: Preparation of 8-(1-acryloylpiperidin-4-yl)-2-(3-methoxy-4-phenoxyphenyl)-5,6,7,8-tetrahydro-imidazo[1,2-b]pyridazine-3-carboxamide

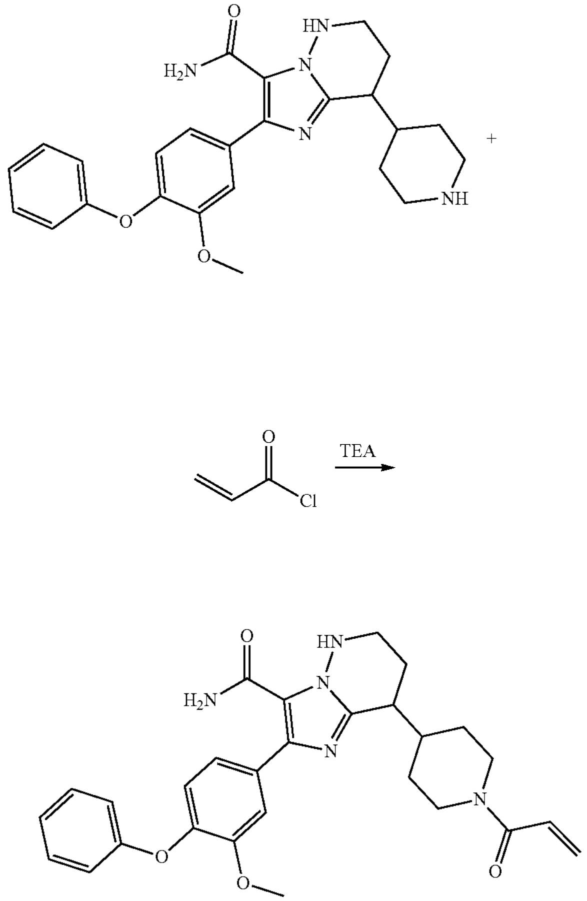

The mixture of the product of step F (200.0 mg, 0.45 mmol) of example 29 and triethylamine (180.9 mg, 1.79 mmol) in dichloromethane (30 mL) was cooled to −60° C., Then the solution of propenoyl chloride (40.5 mg, 0.45 mmol) in dichloromethane (1 mL) was added slowly, LC-MS was tracking, at the end of the reaction, 1 mL MeOH was added, the mixture was concentrated under vacuum to get crude product. and purified by flash chromatography on silica gel with dichloromethane and methanol (40:1) to get white solid (34 mg, 15%). $^1H$ NMR (600 MHz, $CDCl_3$) δ 7.32-7.29 (m, 2H), 7.24 (s, 1H), 7.14-7.11 (m, 1H), 7.07 (t, J=7.3 Hz, 1H), 6.99-6.97 (m, 3H), 6.60-6.53 (m, 1H), 6.28-6.22 (m, 1H), 5.66 (d, J=7.7 Hz, 1H), 4.78-4.70 (m, 1H), 4.12-3.97 (m, 1H), 3.87 (s, 3H), 3.43 (s, 1H), 3.35-3.31 (m, 1H), 3.18-3.03 (m, 2H), 2.66-2.60 (m, 1H), 2.55-2.48 (m, 1H), 2.06 (s, 1H), 1.93-1.87 (m, 2H), 1.82-1.75 (m, 1H), 1.57-1.53 (m, 1H), 1.50-1.44 (m, 1H). MS (ESI, m/z): 502.2 $[M+H]^+$.

TABLE I

The structure of representative compound

| Example No. | structure |
|---|---|
| 1 | 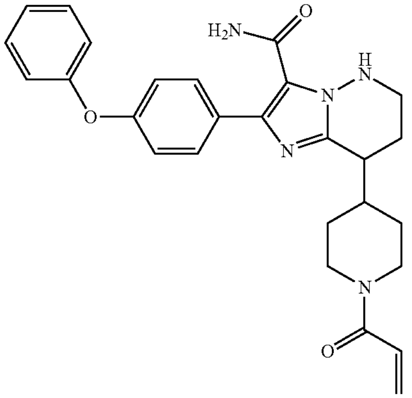 [SMILES: C=CC(=O)N1CCC(C2CCNn3c2nc(-c2ccc(Oc4ccccc4)cc2)c3C(N)=O)CC1] |
| 1a (peak1) | 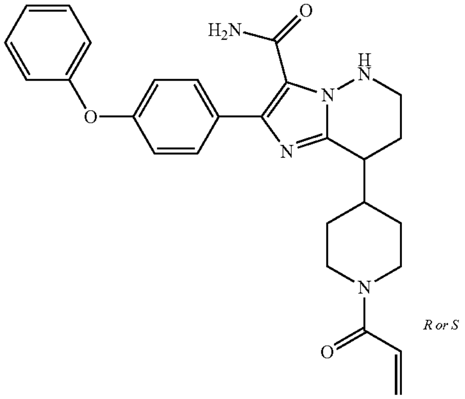<br>1a |
| 1b (peak2) | 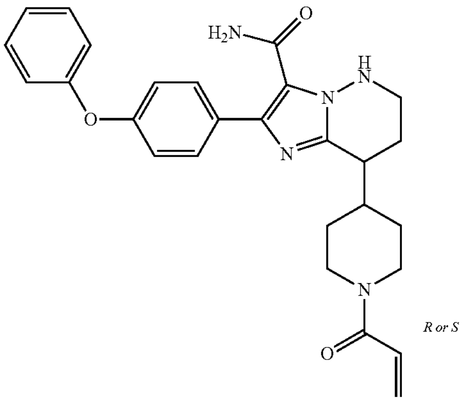<br>1b |

TABLE I-continued
| The structure of representative compound | |
|---|---|
| Example No. | structure |
| 2 | 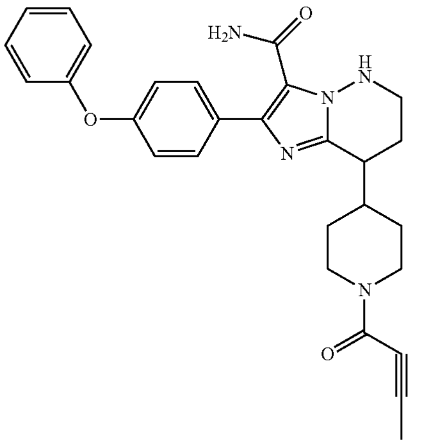 [SMILES: CC#CC(=O)N1CCC(C2CCNn3c2nc(-c2ccc(Oc4ccccc4)cc2)c3C(N)=O)CC1] |
| 3 | 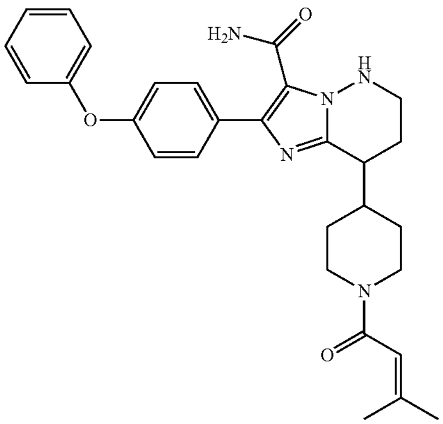 [SMILES: CC(C)=CC(=O)N1CCC(C2CCNn3c2nc(-c2ccc(Oc4ccccc4)cc2)c3C(N)=O)CC1] |
| 4 | 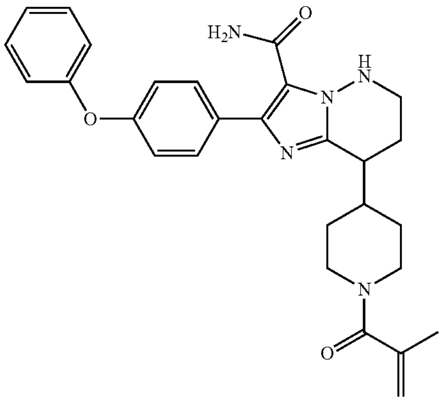 [SMILES: C=C(C)C(=O)N1CCC(C2CCNn3c2nc(-c2ccc(Oc4ccccc4)cc2)c3C(N)=O)CC1] |
TABLE I-continued
| The structure of representative compound | |
|---|---|
| Example No. | structure |
| 5 | 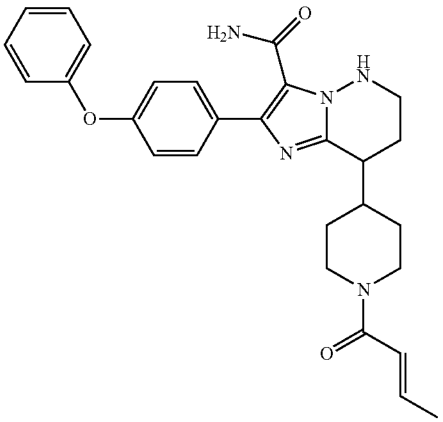 [SMILES: C/C=C/C(=O)N1CCC(C2CCNn3c2nc(-c2ccc(Oc4ccccc4)cc2)c3C(N)=O)CC1] |
| 6 | 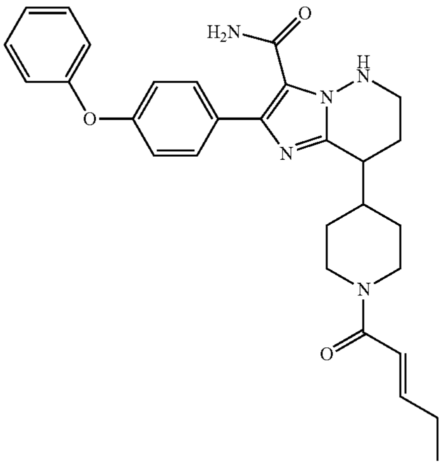 [SMILES: CC/C=C/C(=O)N1CCC(C2CCNn3c2nc(-c2ccc(Oc4ccccc4)cc2)c3C(N)=O)CC1] |
| 7 | 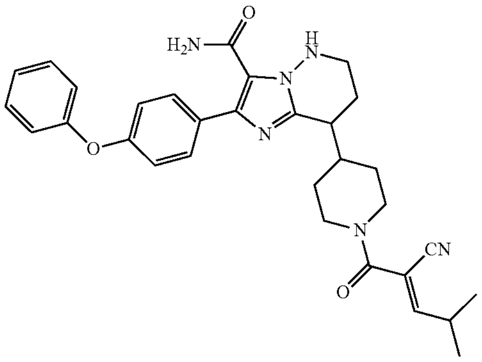 [SMILES: CC(C)/C=C(\C#N)C(=O)N1CCC(C2CCNn3c2nc(-c2ccc(Oc4ccccc4)cc2)c3C(N)=O)CC1] |

TABLE I-continued
The structure of representative compound
| Example No. | structure |
| --- | --- |
| 8 | 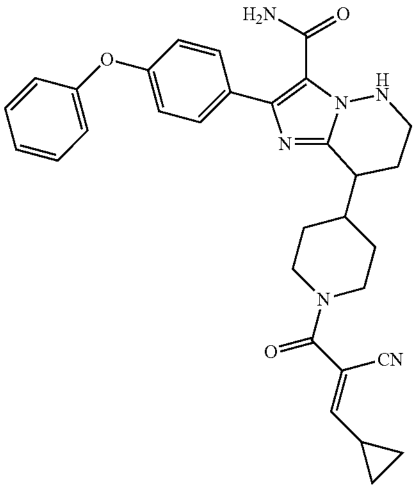 [SMILES: N#C/C(=C\C1CC1)C(=O)N1CCC(C2CCNn3c2nc(-c2ccc(Oc4ccccc4)cc2)c3C(N)=O)CC1] |
| 9 | 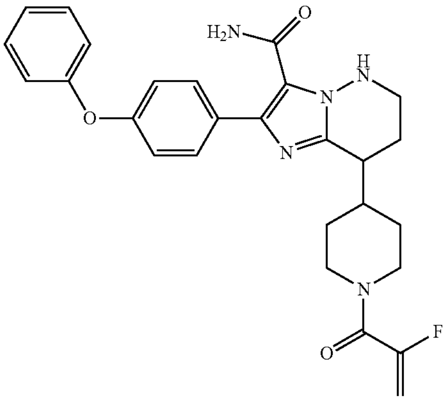 [SMILES: C=C(F)C(=O)N1CCC(C2CCNn3c2nc(-c2ccc(Oc4ccccc4)cc2)c3C(N)=O)CC1] |
| 10 | 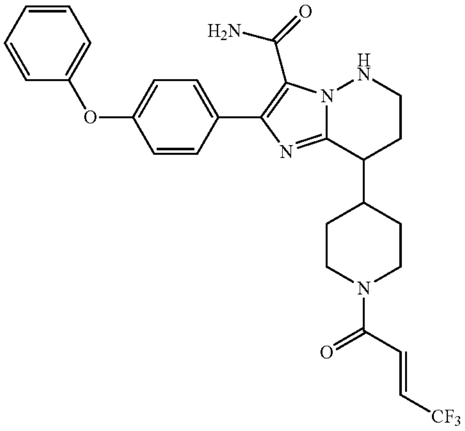 [SMILES: NC(=O)c1c(-c2ccc(Oc3ccccc3)cc2)nc2n1NCCC2C1CCN(C(=O)/C=C/C(F)(F)F)CC1] |
TABLE I-continued
The structure of representative compound
| Example No. | structure |
| --- | --- |
| 10a (peak1) | 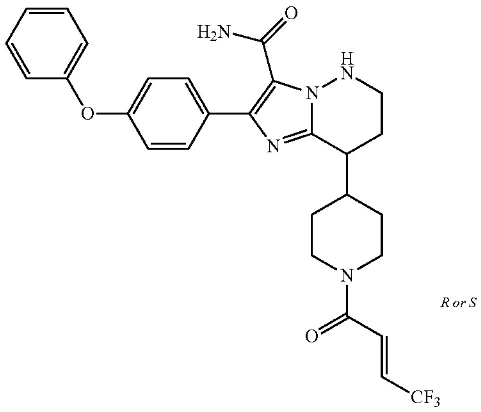<br>10a |
| 10b (peak2) | 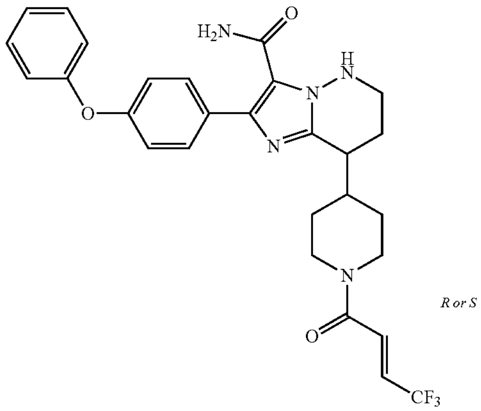<br>10b |
| 11 | 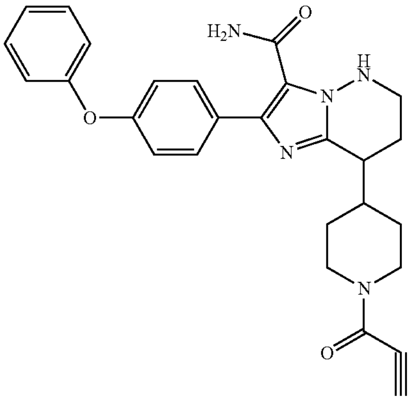 [SMILES: C#CC(=O)N1CCC(C2CCNn3c2nc(-c2ccc(Oc4ccccc4)cc2)c3C(N)=O)CC1] |

TABLE I-continued
The structure of representative compound
| Example No. | structure |
|---|---|
| 12 | 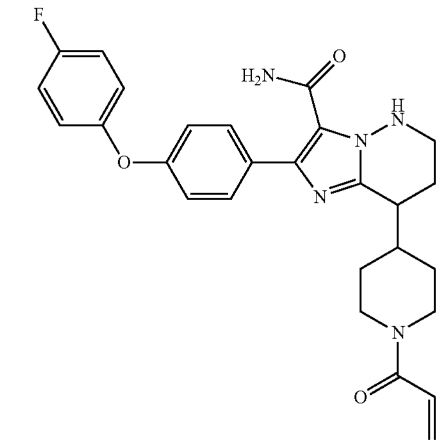 [SMILES: C=CC(=O)N1CCC(C2CCNn3c2nc(-c2ccc(Oc4ccc(F)cc4)cc2)c3C(N)=O)CC1] |
| 13 | 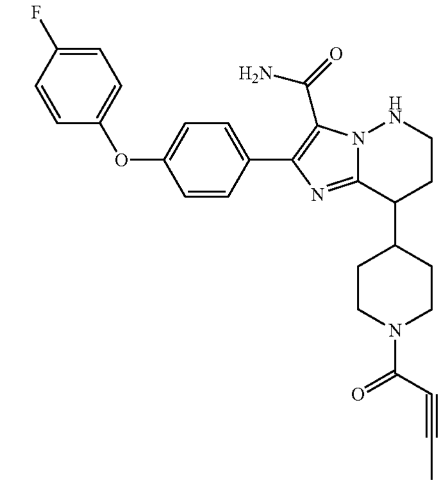 [SMILES: CC#CC(=O)N1CCC(C2CCNn3c2nc(-c2ccc(Oc4ccc(F)cc4)cc2)c3C(N)=O)CC1] |
| 14 | 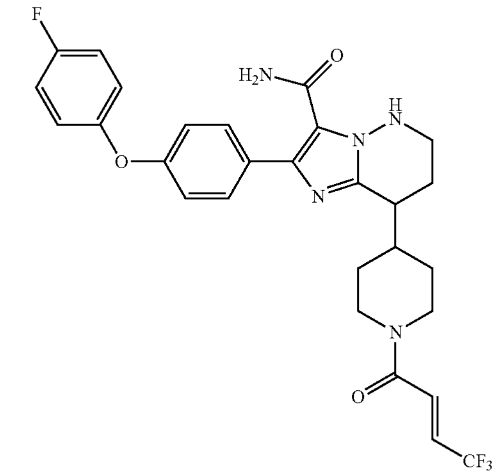 [SMILES: NC(=O)c1c(-c2ccc(Oc3ccc(F)cc3)cc2)nc2n1NCCC2C1CCN(C(=O)/C=C/C(F)(F)F)CC1] |
TABLE I-continued
The structure of representative compound
| Example No. | structure |
|---|---|
| 15 | 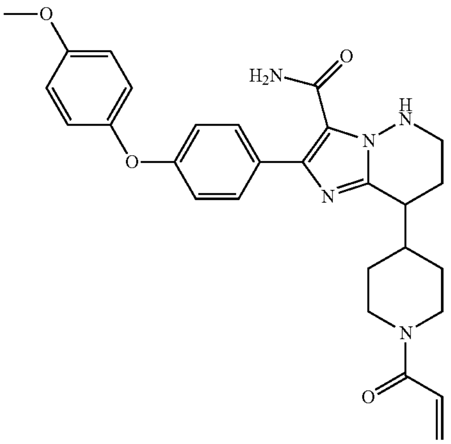 [SMILES: C=CC(=O)N1CCC(C2CCNn3c2nc(-c2ccc(Oc4ccc(OC)cc4)cc2)c3C(N)=O)CC1] |
| 16 | 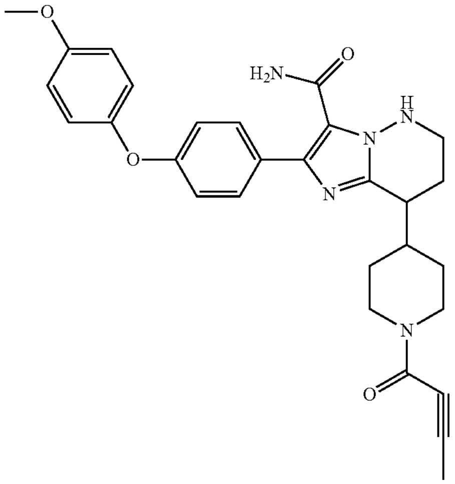 [SMILES: CC#CC(=O)N1CCC(C2CCNn3c2nc(-c2ccc(Oc4ccc(OC)cc4)cc2)c3C(N)=O)CC1] |
| 17 | 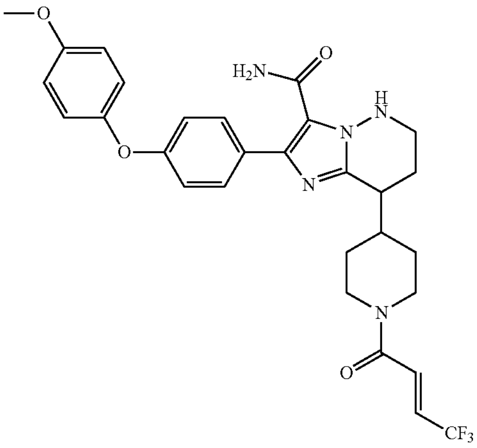 [SMILES: COc1ccc(Oc2ccc(-c3nc4n(c3C(N)=O)NCCC4C3CCN(C(=O)/C=C/C(F)(F)F)CC3)cc2)cc1] |

TABLE I-continued
| The structure of representative compound | |
|---|---|
| Example No. | structure |
| 18 | 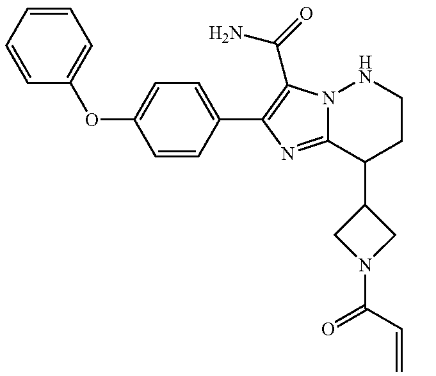 [SMILES: C=CC(=O)N1CC(C2CCNn3c2nc(-c2ccc(Oc4ccccc4)cc2)c3C(N)=O)C1] |
| 19 | 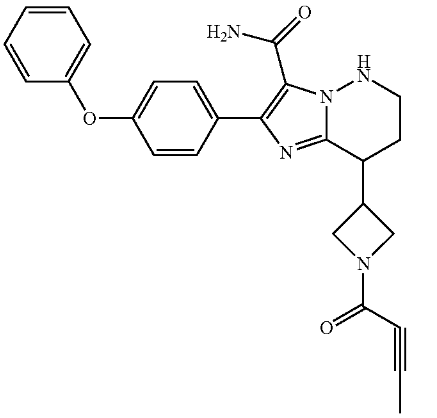 [SMILES: CC#CC(=O)N1CC(C2CCNn3c2nc(-c2ccc(Oc4ccccc4)cc2)c3C(N)=O)C1] |
| 20 | 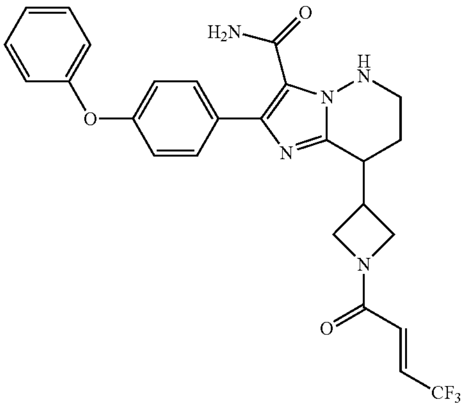 [SMILES: NC(=O)c1c(-c2ccc(Oc3ccccc3)cc2)nc2n1NCCC2C1CN(C(=O)/C=C/C(F)(F)F)C1] |
| 21 | 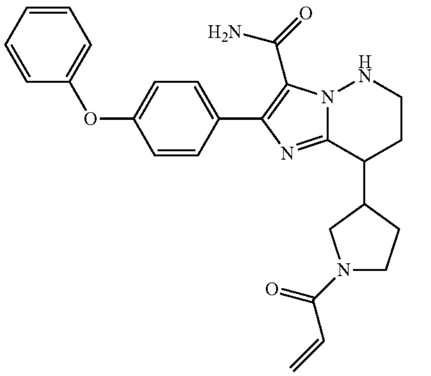 [SMILES: C=CC(=O)N1CCC(C2CCNn3c2nc(-c2ccc(Oc4ccccc4)cc2)c3C(N)=O)C1] |
| 22 | 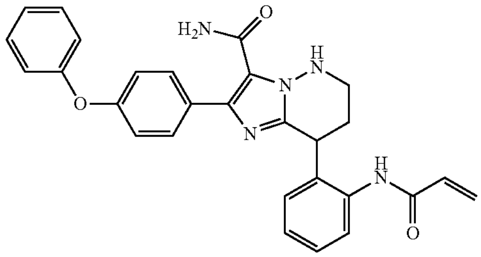 [SMILES: C=CC(=O)Nc1ccccc1C1CCNn2c1nc(-c1ccc(Oc3ccccc3)cc1)c2C(N)=O] |
| 23 | 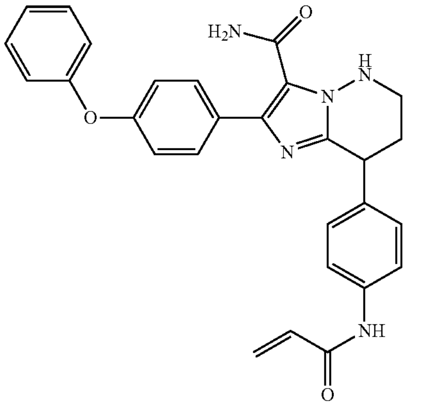 [SMILES: C=CC(=O)Nc1ccc(C2CCNn3c2nc(-c2ccc(Oc4ccccc4)cc2)c3C(N)=O)cc1] |
| 24 | 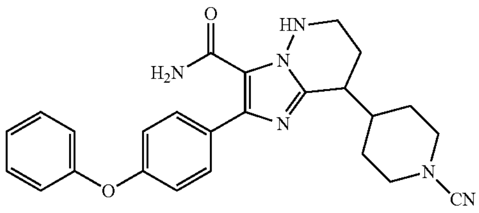 [SMILES: N#CN1CCC(C2CCNn3c2nc(-c2ccc(Oc4ccccc4)cc2)c3C(N)=O)CC1] |

TABLE I-continued

| The structure of representative compound | |
|---|---|
| Example No. | structure |
| 25 | 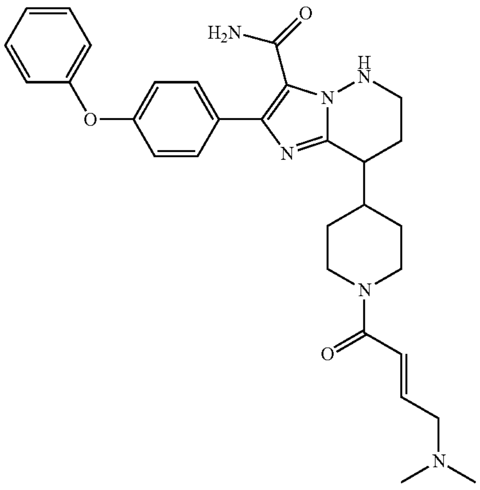 [SMILES: CN(C)C/C=C/C(=O)N1CCC(C2CCNn3c2nc(-c2ccc(Oc4ccccc4)cc2)c3C(N)=O)CC1] |
| 26 | 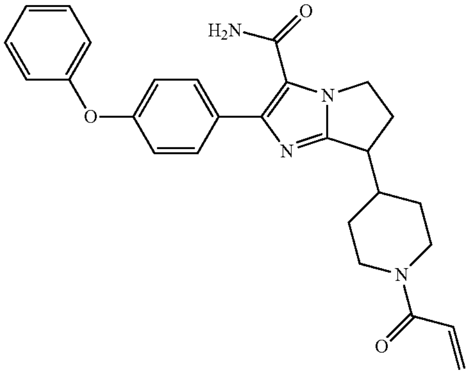 [SMILES: C=CC(=O)N1CCC(C2CCn3c2nc(-c2ccc(Oc4ccccc4)cc2)c3C(N)=O)CC1] |
| 27 | 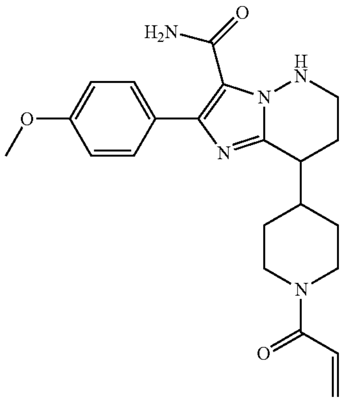 [SMILES: C=CC(=O)N1CCC(C2CCNn3c2nc(-c2ccc(OC)cc2)c3C(N)=O)CC1] |

TABLE I-continued

| The structure of representative compound | |
|---|---|
| Example No. | structure |
| 28 | 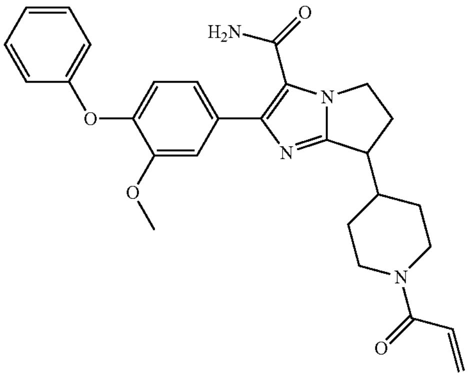 [SMILES: C=CC(=O)N1CCC(C2CCn3c2nc(-c2ccc(Oc4ccccc4)c(OC)c2)c3C(N)=O)CC1] |
| 29 | 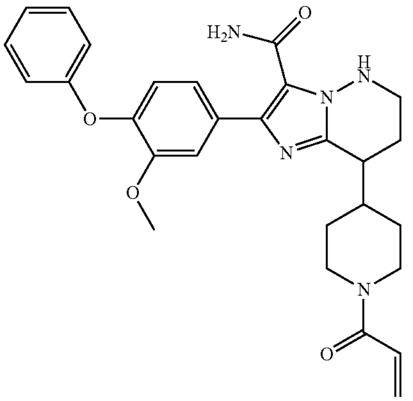 [SMILES: C=CC(=O)N1CCC(C2CCNn3c2nc(-c2ccc(Oc4ccccc4)c(OC)c2)c3C(N)=O)CC1] |

BTK, EGFR, BMX, or ITK Inhibitory Assay

Procedure for BTK, BMX, EGFR and ITK Inhibitory Assay:

Kinase inhibitory activities of compounds were evaluated using the Enzyme-linked immunosorbent assay (ELISA). The kinase enzyme of BTK, BMX, EGFR and ITK were purchased from Carna Bioscience (Kobe, Japan). A total of 10 ng/mL antiphosphotyrosine (PY713) antibody (abcam, Cambridge Science Park, UK) was precoated in 96-well ELISA plates. The kinase enzymes in each reaction well were set to BTK (101.25 ng/mL), BMX (90 ng/mL), EGFR (90 ng/mL) or ITK (120 ng/mL) and incubated with indicated compounds in 1× reaction buffer (50 mmol/L HEPES pH 7.4, 20 mmol/L $MgCl_2$, 0.1 mmol/L $MnCl_2$, 1 mmol/L DTT) containing 20 μmol/L (the final concentration of substrate in ITK reaction was 30 μmol/L) substrate ($NH_2$-ETVYSEVRK-biotin) at 25° C. for 1 h. Then, a total of 3 μmol/L ATP was added and the reaction was continued for 2 hrs. The products of reaction were transferred into 96-well ELISA plates containing antibody and incubated at 25° C. for 30 min. After incubation, the wells were washed with PBS and then incubated with horseradish peroxidase (IRP)-conjugated streptavidin. The wells were visualized using 3,3',5,5'-tetramethylbenzidine (TMB), and chromogenic reaction was ended with 2 mol/L $H_2SO_4$, the absorbance was read with a multimode plate reader (PerkinElmer, USA) at 450 nm. IC50 values and curve fits were obtained using Prism (GraphPad Software).

TABLE II

| BTK inhibition of representative compounds | |
|---|---|
| Example No. | BTK ($IC_{50}$, nM) |
| 1 | 4.6 |
| 1a (peak 1)a | 2.6 |
| 1b (peak 2)a | 28.9 |
| 2 | 76.4 |
| 8 | 284.7 |
| 10 | 8.2 |
| 10a (peak 1) | 6.7 |
| 10b (peak 2) | 61.8 |
| 11 | 8.2 |
| 12 | 49.4 |
| 13 | 121.6 |
| 14 | 61.5 |
| 15 | 42.6 |
| 16 | 777.8 |
| 17 | 211.9 |
| 18 | 37.4 |
| 19 | 230.1 |
| 20 | 8.0 |
| 21 | 131.6 |
| 22 | 5.4 |
| 25 | 184.6 |
| 26 | 8.4 |
| 27 | 241.8 |
| 28 | 10.7 |
| 29 | 46.5 |

TABLE III

Selectivity for BTK and BMX inhibition of representative compounds

| Example No. | BTK ($IC_{50}$, nM) | BMX ($IC_{50}$, nM) | Selectivity Ratio |
|---|---|---|---|
| 1 | 4.6 | 26.7 | 5.80 |
| 1a (peak 1) | 2.6 | 15.3 | 5.88 |
| 1b (peak 2) | 28.9 | 53.9 | 1.86 |
| 10 | 8.2 | 49.5 | 6.04 |
| 10a (peak 1) | 6.7 | 20.9 | 3.12 |
| 10b (peak 2) | 61.8 | 143.6 | 2.32 |
| 11 | 8.2 | 22.8 | 2.78 |
| 20 | 8.0 | 70.3 | 8.79 |
| 22 | 5.4 | 64.5 | 11.94 |
| 26 | 8.4 | 31.11 | 3.70 |
| 28 | 10.7 | 80.33 | 7.51 |

TABLE IV

Selectivity for BTK and EGFR inhibition of representative compounds

| Example No. | BTK ($IC_{50}$, nM) | EGFR ($IC_{50}$, nM) | Selectivity Ratio |
|---|---|---|---|
| 1 | 4.6 | 89.6 | 19.48 |
| 1a (peak 1) | 2.6 | 5.2 | 2.00 |
| 1b (peak 2) | 28.9 | 169.8 | 5.87 |
| 10 | 8.2 | 1930 | 235.36 |
| 10a (peak 1) | 6.7 | 2448 | 365.37 |
| 10b (peak 2) | 61.8 | 39475 | 638.75 |
| 11 | 8.2 | 28.15 | 3.43 |
| 20 | 8.0 | 3244 | 405.5 |
| 22 | 5.4 | 16.49 | 3.05 |
| 26 | 8.4 | 81.91 | 9.75 |
| 28 | 10.7 | 381.6 | 35.66 |

TABLE V

Selectivity for BTK and ITK inhibition of representative compounds

| Example No. | BTK ($IC_{50}$, nM) | ITK ($IC_{50}$, nM) | Selectivity Ratio |
|---|---|---|---|
| 1 | 4.6 | 13550 | 2945 |
| 1a (peak 1) | 2.6 | 482.7 | 185.6 |
| 1b (peak 2) | 28.9 | >30000 | >1038 |
| 10 | 8.2 | 10778 | 1314 |
| 10a (peak 1 ) | 6.7 | 2020 | 301.5 |
| 10b (peak 2) | 61.8 | >30000 | >485.4 |
| 11 | 8.2 | 224.7 | 27.40 |
| 20 | 8.0 | 8645 | 1080.6 |
| 22 | 5.4 | 27867 | 5160.6 |
| 26 | 8.4 | 4664 | 555.2 |
| 28 | 10.7 | >30000 | >2803.7 |

Cell Antiproliferative Activity Assay

Cell antiproliferative activity was evaluated by the CellTiter-Glo (Promega, USA) assay. Make 1000× compounds solution in DMSO, add 1 μl 1000× compounds to 49 μl growth medium to make 20× compounds. Dilute cell suspensions in growth medium to desired density and 95 μl were taken to 96-well plate. Add 5 μl 20× compounds into 96-well plate according to the plate map. Final DMSO concentration in each well was 0.1%. Then the cell was incubated at 37° C., 5% $CO_2$ for 72 hs. Equilibrate the assay plate to room temperature before measurement. Add 20 μl of CellTiter-Glo© Reagent into each well. Mix contents for 2 minutes on an orbital shaker to induce cell lysis. Incubate at room temperature for 10 minutes to stabilize luminescent signal. Record luminescence using EnVision Multilabel Reader (PerkinElmer). Cell viability (CV %) was calculated relative to vehicle (DMSO) treated control wells using following formula: Cell viability (%)=(RLU compound−RLU blank)/(RLU control−RLU blank)*100%. The IC50 values were calculated using GraphPad Prism 6.0 software, fitting to a 4-parameter equation to generate concentration response curves. All assays were conducted with three parallel samples and three repetitions.

TABLE VI cell growth inhibition of representative compounds

| | Cell Growth $IC_{50}$ (nM) | | | |
|---|---|---|---|---|
| Example No. | TMD8 | Ramos | MOLM-13 | 293T |
| 1 | 12.3 | — | — | 573384 |
| 1a (peak 1) | 5.4 | — | — | 8447 |
| 1b (peak 2) | 101.6 | — | — | 5237 |
| 10 | 51.6 | 2762 | — | 45297 |
| 10a (peak 1) | 16.5 | 1268 | 3148 | 1014 |
| 10b (peak 2) | 256.8 | 6442 | — | 1908 |
| 11 | — | 725.4 | 1103 | — |
| 20 | — | 294.4 | 1359 | — |

PK Properties Assay

Six SD rats were divided into two groups, and compound was administered by gavage and tail vein injection. The intravenous injection group was administered 2 min, 5 min, 15 min, 30 min, 1 h, 2 h, 4 h, 6 h, 8 h, and 12 h after administration. 0.25 mL of blood samples were collected from the posterior orbital venous plexus at 5 min, 15 min, 30 min, 1 h, 2 h, 4 h, 6 h, 8 h, 12 h, and 24 h after administration. LC-MS/MS method was used to determine the concentration of compound in plasma samples from SD rats, and the pharmacokinetic parameters were calculated using WinNolin software.

TABLE VII

| PK properties representative compounds | | | | | | | |
|---|---|---|---|---|---|---|---|
| | iv (5 mg/kg)[a] | | | po (5 mg/kg)[b] | | | |
| Example No. | $T_{1/2}$ (h) | CL (mL/min/kg) | $V_d$ (L/kg) | $T_{1/2}$ (h) | $C_{max}$ (ng/mL) | AUC (h · ng/mL) | F (%) |
| 1a (peak 1) | 0.41 | 27 | 0.959 | 1.41 | 923.0 | 3433 | 52.91 |
| 10a (peak 1) | 0.31 | 59.8 | 1.603 | 1.45 | 703.3 | 1392 | 47.17 |

[a]Dosed using 5 mg/kg solution (20% water, 80% PEG400),
[b]Dosed using 5 mg/kg solution (20% water, 80% PEG400),
n = 3 respectively.

What is claimed is:

1. A compound represented by Formula I:

I

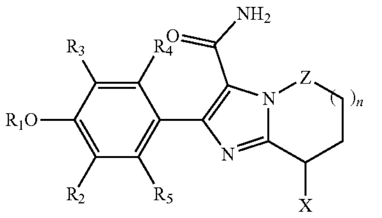

or a pharmaceutically acceptable salt, stereoisomer, or tautomer thereof, wherein:

$R^1$ is $C_{1-6}$ alkyl or aryl;

wherein the $C_{1-6}$ alkyl is optionally substituted with one or more substituents independently selected from the group consisting of halogen, $OC_{1-6}$ alkyl, and $C_{3-6}$ cycloalkyl; and wherein the aryl is optionally substituted with one or more substituents independently selected from the group consisting of halogen, CN, $C_{1-4}$ fluoroalkyl, and $OC_{1-6}$ alkyl;

$R_2$ is H, halogen, CN, $C_{1-6}$ alkyl, $C_{1-4}$ fluoroalkyl, $OC_{1-6}$ alkyl, or $C_{3-6}$ cycloalkyl;

$R_3$ is H, halogen, CN, $C_{1-6}$ alkyl, $C_{1-4}$ fluoroalkyl, $OC_{1-6}$ alkyl, or $C_{3-6}$ cycloalkyl;

$R_4$ is H, halogen, CN, $C_{1-6}$ alkyl, $C_{1-4}$ fluoroalkyl, $OC_{1-6}$ alkyl, or $C_{3-6}$ cycloalkyl;

$R_5$ is H, halogen, CN, $C_{1-6}$ alkyl, $C_{1-4}$ fluoroalkyl, $OC_{1-6}$ alkyl, or $C_{3-6}$ cycloalkyl;

Z is $—CH_2—$ or —NH—;

X is $—(CH_2)_mNR_6Y$, a nitrogen-containing 4- to 8-membered heterocyclyl, a nitrogen-containing spirocyclic heterocyclyl, aryl, or heteroaryl;

wherein the heterocyclyl is substituted on one or more nitrogen atom(s) with one or more independently selected Y substituents;

wherein the aryl is substituted with one or more substituents independently selected from the group consisting of halogen, CN, $C_{1-4}$ fluoroalkyl, $NR_6Y$, and $OC_{1-6}$ alkyl; and wherein the heteroaryl is substituted with one or more substituents independently selected from the group consisting of halogen, CN, $C_{1-4}$ fluoroalkyl, $NR_6Y$, and $OC_{1-6}$ alkyl;

each $R_6$ is independently H or $C_{1-6}$ alkyl, wherein each $C_{1-6}$ alkyl is optionally and independently substituted with one or more substituents independently selected from the group consisting of halogen and $OC_{1-6}$ alkyl;

each Y is independently CN, C(O)P, S(O)P, or $S(O)_2P$;

each P is independently $CR_7{=}CR_8R_9$ or $C{\equiv}CR_x$;

each $R_x$ is independently H, CN, halogen, $C_{1-6}$ alkyl, $(CH_2)_mNR_{10}R_{11}$, $OC_{1-6}$ alkyl, $C_{3-6}$ cycloalkyl, or phenyl, wherein each $C_{1-6}$ alkyl is optionally and independently substituted with one or more substituents independently selected from the group consisting of halogen and OH;

each $R_7$ is independently H, halogen, CN, $C_{1-6}$ alkyl, or $C_{3-6}$ cycloalkyl;

wherein each $C_{1-6}$ alkyl is optionally and independently substituted with one or more substituents independently selected from the group consisting of F, OH, and $OC_{1-6}$ alkyl; and wherein each $C_{3-6}$ cycloalkyl is optionally and independently substituted with one or more F substituents;

each $R_8$ is independently H, halogen, CN, $C_{1-6}$ alkyl, $C_{2-6}$ alkenyl, $C_{3-6}$ cycloalkyl, aryl, or heteroaryl;

wherein each $C_{1-6}$ alkyl is optionally and independently substituted with one or more substituents independently selected from the group consisting of halogen, $NR_{10}R_{11}$, OH, $OC_{1-6}$ alkyl, phenyl, naphthalenyl, and heteroaryl;

wherein each $C_{2-6}$ alkenyl is optionally and independently substituted with one or more substituents independently selected from the group consisting of halogen, $NR_{10}R_{11}$, OH, $OC_{1-6}$ alkyl, aryl, and heteroaryl;

wherein each $C_{3-6}$ cycloalkyl is optionally and independently substituted with one or more independently selected halogen substituents; and wherein each aryl or heteroaryl is optionally and independently substituted with one or more substituents independently selected from the group consisting of halogen, CN, $C_{1-6}$ alkyl, and $OC_{1-6}$ alkyl;

each $R_9$ is independently H, halogen, CN, $C_{1-6}$ alkyl, $C_{2-6}$ alkenyl, $C_{3-6}$ cycloalkyl, aryl, or heteroaryl;

wherein each $C_{1-6}$ alkyl is optionally and independently substituted with one or more substituents independently selected from the group consisting of halogen, $NR_{10}R_{11}$, OH, $OC_{1-6}$ alkyl, phenyl, naphthalenyl, and heteroaryl;

wherein each $C_{2-6}$ alkenyl is optionally and independently substituted with one or more substituents independently selected from the group consisting of halogen, $NR_{10}R_{11}$, OH, $OC_{1-6}$ alkyl, aryl, and heteroaryl;

wherein each $C_{3-6}$ cycloalkyl is optionally and independently substituted with one or more independently selected halogen substituents; and wherein each aryl or heteroaryl is optionally and independently substituted with one or more substituents independently selected from the group consisting of halogen, CN, $C_{1-6}$ alkyl, and $OC_{1-6}$ alkyl;

each $R_{10}$ is independently H, $C_{1-6}$ alkyl, or $C_{3-6}$ cycloalkyl;

each $R_{11}$ is independently H, $C_{1-6}$ alkyl, or $C_{3-6}$ cycloalkyl; or any $R_{10}$ and $R_{11}$, together with the nitrogen atom to which they are bonded, independently forms a 4- to 6-membered heterocycloalkyl;

each m is independently 1, 2, or 3; and n is 0, 1, 2, or 3.

2. The compound according to claim 1, or a pharmaceutically acceptable salt, stereoisomer, or tautomer thereof, wherein:

$R_1$ is $C_{1-6}$ alkyl or

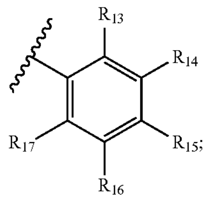

$R_{13}$ is H, halogen, CN, $C_{1-4}$ fluoroalkyl, or $OC_{1-6}$ alkyl;

$R_{14}$ is H, halogen, CN, $C_{1-4}$ fluoroalkyl, or $OC_{1-6}$ alkyl;

$R_{15}$ is H, halogen, CN, $C_{1-4}$ fluoroalkyl, or $OC_{1-6}$ alkyl;

$R_{16}$ is H, halogen, CN, $C_{1-4}$ fluoroalkyl, or $OC_{1-6}$ alkyl; and $R_{17}$ is H, halogen, CN, $C_{1-4}$ fluoroalkyl, or $OC_{1-6}$ alkyl.

3. The compound according to claim 1, or a pharmaceutically acceptable salt, stereoisomer, or tautomer thereof, wherein:

R is

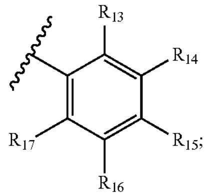

$R_{13}$ is H, halogen, CN, or $C_{1-4}$ fluoroalkyl;

$R_{14}$ is H, halogen, CN, or $C_{1-4}$ fluoroalkyl;

$R_{15}$ is H, halogen, CN, or $C_{1-4}$ fluoroalkyl;

$R_{16}$ is H, halogen, CN, or $C_{1-4}$ fluoroalkyl; and $R_{17}$ is H, halogen, CN, or $C_{1-4}$ fluoroalkyl.

4. The compound according to claim 3, or a pharmaceutically acceptable salt, stereoisomer, or tautomer thereof, wherein:

$R_{13}$ is H;

$R_{14}$ is H;

$R_{15}$ is H, F, Cl, Br, CN, or $CF_3$;

$R_{16}$ is H; and $R_{17}$ is H.

5. The compound according to claim 4, or a pharmaceutically acceptable salt, stereoisomer, or tautomer thereof, wherein $R_{15}$ is H.

6. The compound according to claim 1, or a pharmaceutically acceptable salt, stereoisomer, or tautomer thereof, wherein:

$R_2$ is $OC_{1-6}$ alkyl; or $R_3$ is $OC_{1-6}$ alkyl.

7. The compound according to claim 1, or a pharmaceutically acceptable salt, stereoisomer, or tautomer thereof, wherein Z is $-CH_2-$.

8. The compound according to claim 1, or a pharmaceutically acceptable salt, stereoisomer, or tautomer thereof, wherein Z is —NH—.

9. The compound according to claim 1, or a pharmaceutically acceptable salt, stereoisomer, or tautomer thereof, wherein:

X is:

$-(CH_2)_mNR_6Y$,

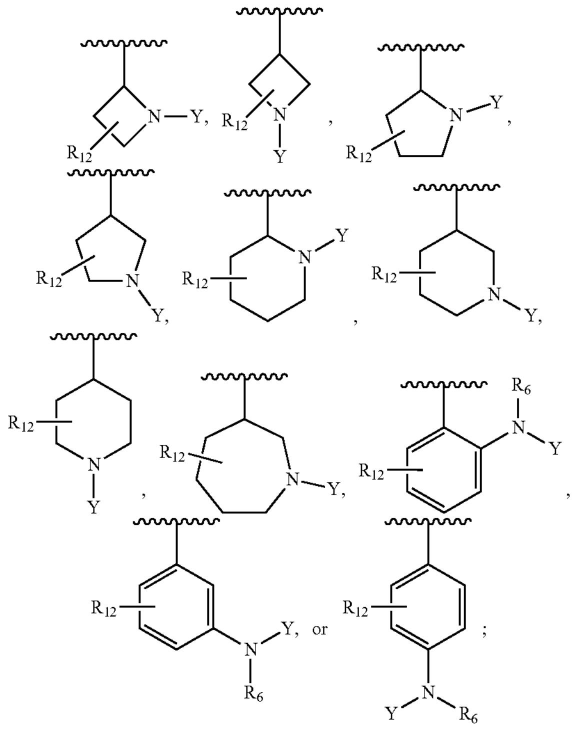

and each $R_{12}$ is independently H, F, $C_{1-4}$ fluoroalkyl, or $OC_{1-6}$ alkyl.

10. The compound according to claim 1, or a pharmaceutically acceptable salt, stereoisomer, or tautomer thereof, wherein n is 0 or 1.

11. The compound according to claim 1, or a pharmaceutically acceptable salt, stereoisomer, or tautomer thereof, wherein:

$R_2$ is H;

$R_3$ is H;

$R_4$ is H;

$R_5$ is H; and each $R_6$ is independently H.

12. The compound according to claim 1, or a pharmaceutically acceptable salt, stereoisomer, or tautomer thereof, wherein:

X is:

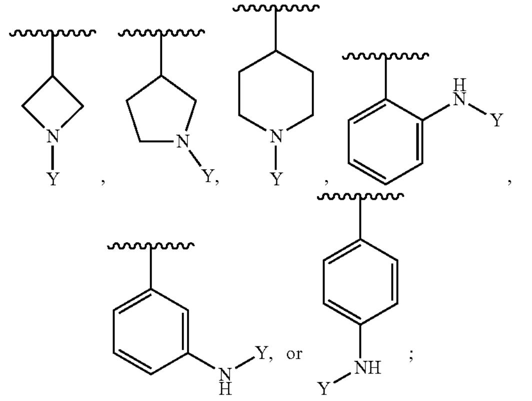

Y is CN or C(O)P;

P is $CR_7{=}CR_8R_9$ or $C{\equiv}CR_x$;

$R_x$ is H, $C_{1-6}$ alkyl, or $C_{3-6}$ cycloalkyl, wherein the $C_{1-6}$ alkyl is optionally substituted with one or more independently selected halogen substituents;

$R_7$ is H, halogen, CN, or $C_{1-6}$ alkyl, wherein the $C_{1-6}$ alkyl is optionally substituted with one or more F substituents;

$R_8$ is H, halogen, $C_{1-6}$ alkyl, or $C_{3-6}$ cycloalkyl, wherein the $C_{1-6}$ alkyl is optionally substituted with one or more substituents independently selected from the group consisting of halogen and $NR_{10}R_{11}$;

$R_9$ is H, halogen, $C_{1-6}$ alkyl, or $C_{3-6}$ cycloalkyl, wherein the $C_{1-6}$ alkyl is optionally substituted with one or more substituents independently selected from the group consisting of halogen and $NR_{10}R_{11}$;

each $R_{10}$ is independently $C_{1-6}$ alkyl; and each $R_{11}$ is independently $C_{1-6}$ alkyl.

13. The compound according to claim 1, or a pharmaceutically acceptable salt, stereoisomer, or tautomer thereof, wherein:

X is:

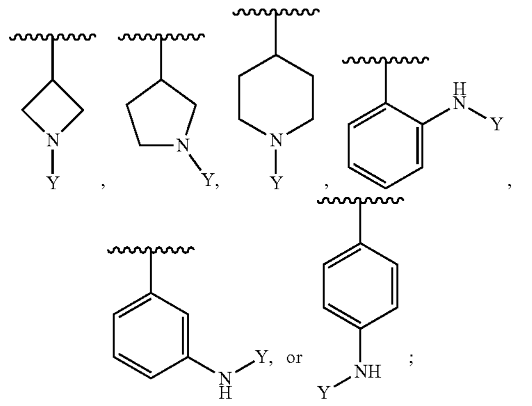

Y is C(O)P;

P is $CR_7{=}CR_8R_9$ or $C{\equiv}CR_x$;

$R_x$ is H or $CH_3$;

$R_7$ is H, F, or CN;

$R_8$ is H or $CF_3$; and $R_9$ is H or $CF_3$.

14. The compound according to claim 1, or a pharmaceutically acceptable salt, stereoisomer, or tautomer thereof, wherein:

$R_1$ is

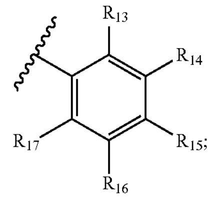

$R_{13}$ is H, F, Cl, Br, CN, $CF_3$, or $OCH_3$;

$R_{14}$ is H, F, Cl, Br, CN, $CF_3$, or $OCH_3$;

$R_{15}$ is H, F, Cl, Br, CN, $CF_3$, or $OCH_3$;

$R_{16}$ is H, F, Cl, Br, CN, $CF_3$, or $OCH_3$;

$R_{17}$ is H, F, Cl, Br, CN, $CF_3$, or $OCH_3$;

$R_2$ is H or $OCH_3$;

$R_3$ is H;

$R_4$ is H;

$R_5$ is H;

Z is $-CH_2-$;

X is:

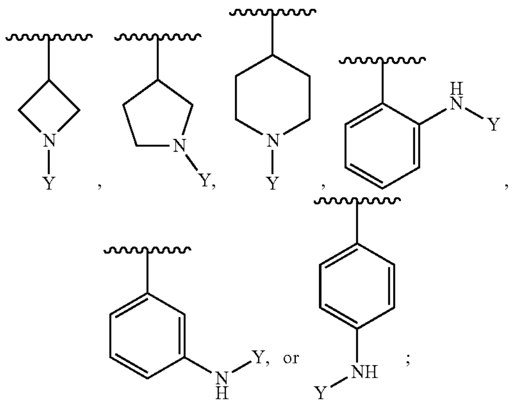

Y is C(O)P;

P is $CR_7{=}CR_8R_9$ or $C{\equiv}CR_x$;

$R_x$ is H, $CH_3$, $CF_3$, $(CH_2)_mNR_{10}R_{11}$, or cyclopropyl;

$R_7$ is H, halogen, or CN;

$R_8$ is H, $CH_3$, $CF_3$, $C_{1-6}$ alkylene-$NR_{10}R_{11}$, or cyclopropyl;

$R_9$ is H, $CH_3$, $CF_3$, $C_{1-6}$ alkylene-$NR_{10}R_{11}$, or cyclopropyl;

each $R_{10}$ is independently $C_{1-6}$ alkyl;

each $R_{11}$ is independently $C_{1-6}$ alkyl; and n is 0.

15. The compound according to claim 1, or a pharmaceutically acceptable salt, stereoisomer, or tautomer thereof, wherein:

$R_1$ is phenyl;

$R_2$ is H or $OCH_3$;

$R_3$ is H;

$R_4$ is H;

$R_5$ is H; and

Z is $-CH_2-$.

16. The compound according to claim 1, or a pharmaceutically acceptable salt, stereoisomer, or tautomer thereof, wherein:

$R_1$ is phenyl;
$R_2$ is H or $OCH_3$;
$R_3$ is H;
$R_4$ is H;
$R_5$ is H;
Z is —NH—;
X is:
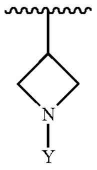, 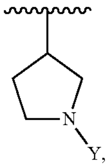 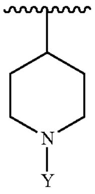, 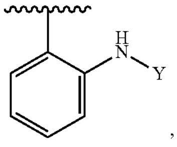,
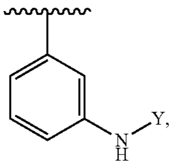 or 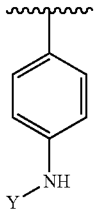;
$R_7$ is H, halogen, or CN;
$R_8$ is H, $CH_3$, $CF_3$, or cyclopropyl;
$R_9$ is H, $CH_3$, $CF_3$, or cyclopropyl; and
n is 1.
17. The compound according to claim 1, wherein the compound is selected from the group consisting of:
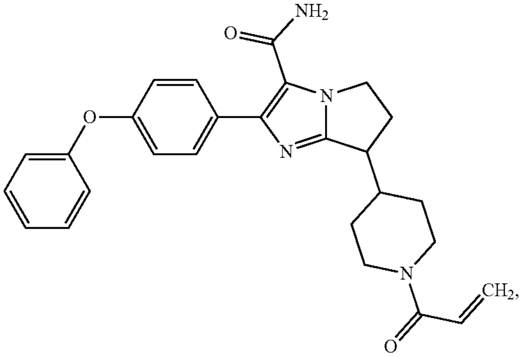
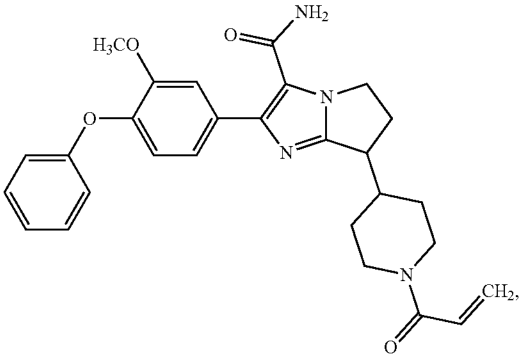
-continued
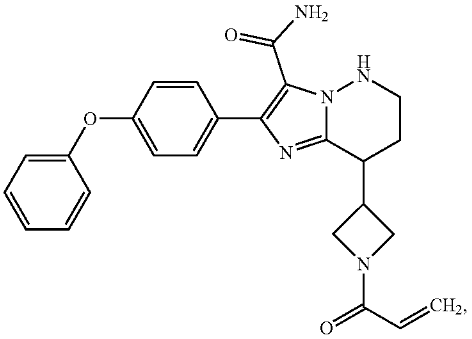
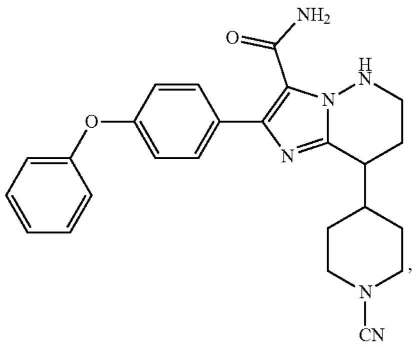
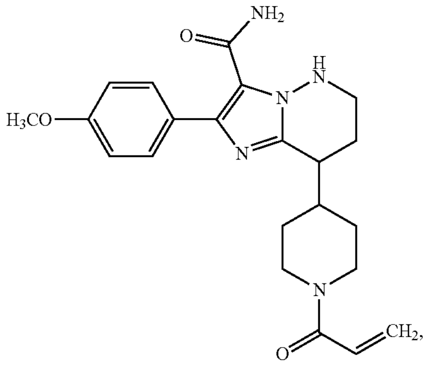
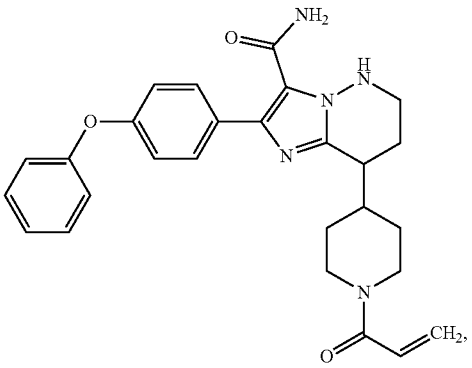

-continued
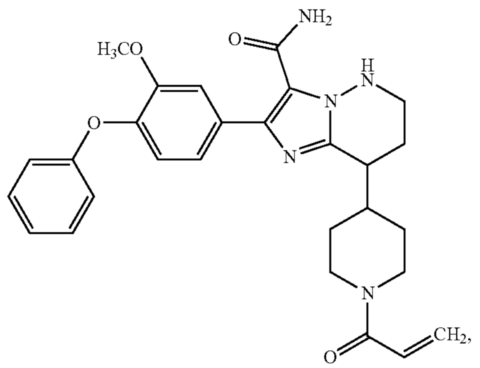
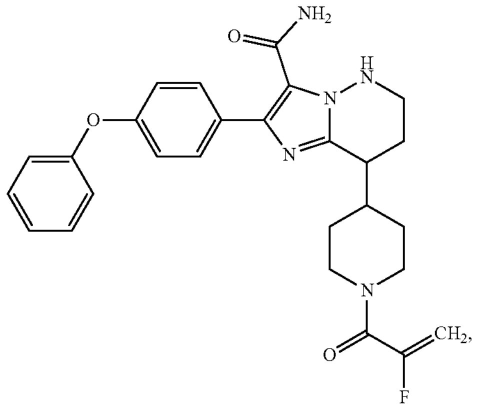
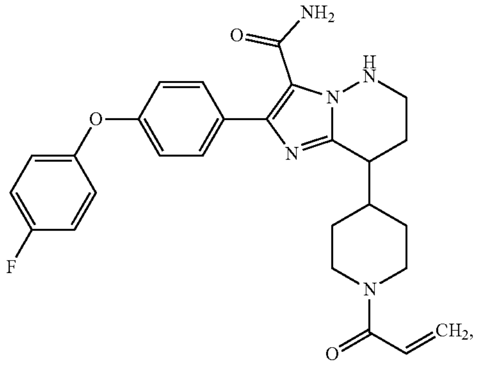
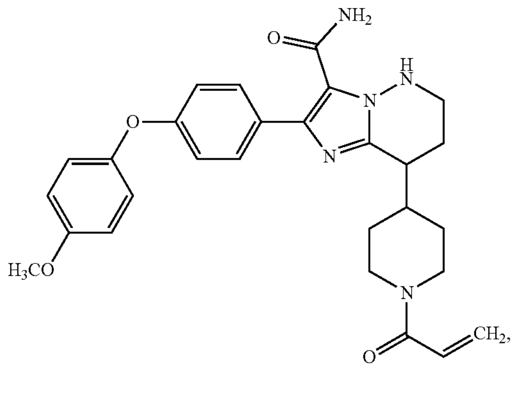
-continued
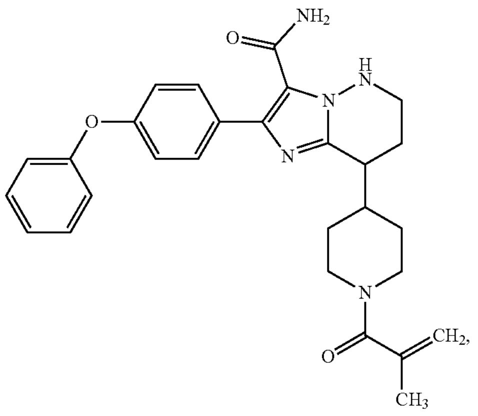
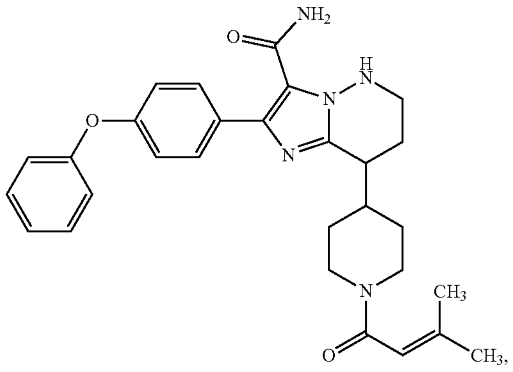
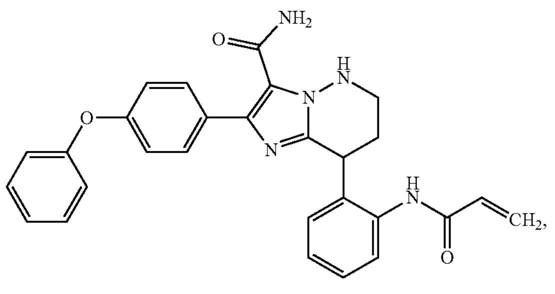
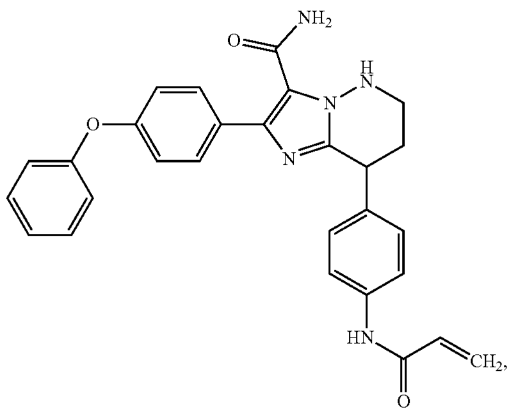

-continued
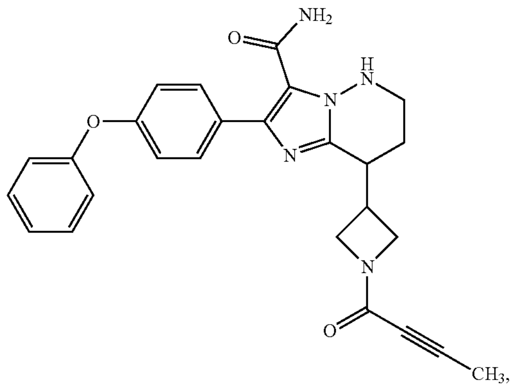
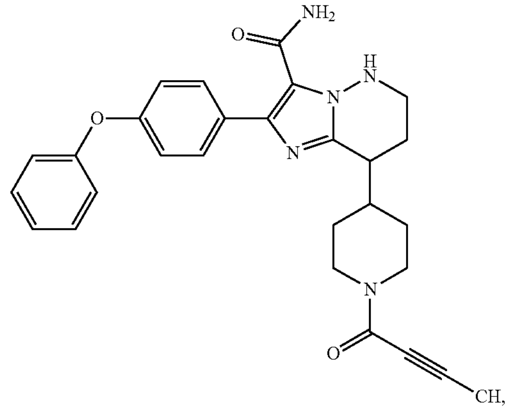
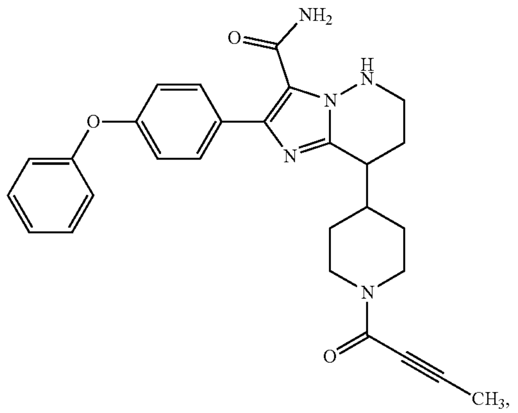
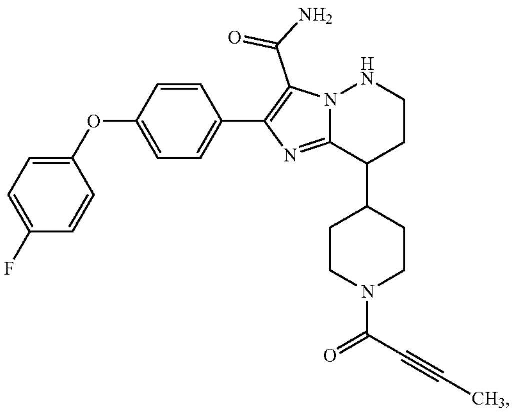
and
-continued
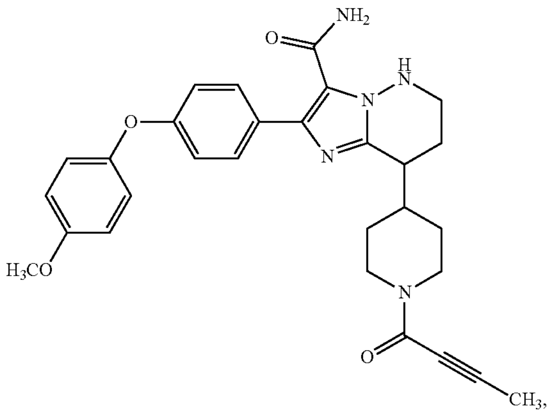
or a pharmaceutically acceptable salt, stereoisomer, or tautomer thereof.
18. The compound according to claim 1, wherein the compound is selected from the group consisting of:
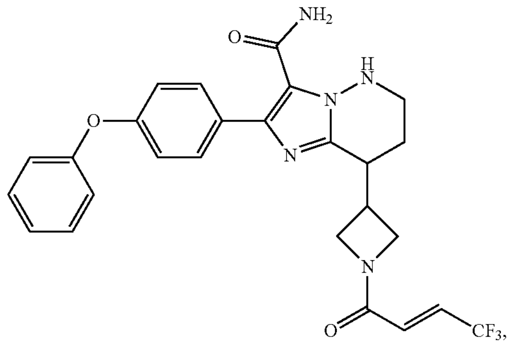
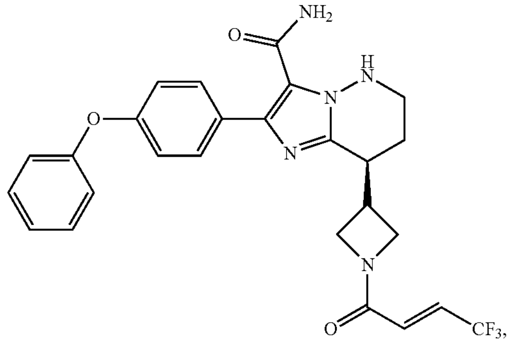
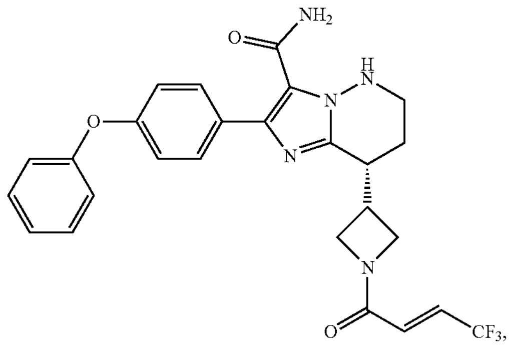

-continued
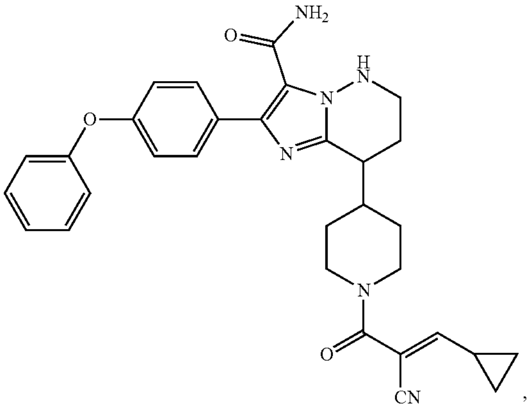
,
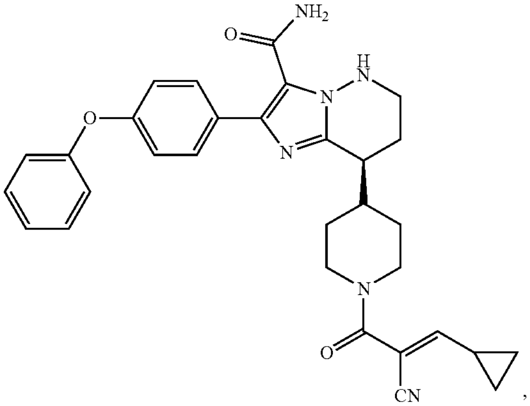
,
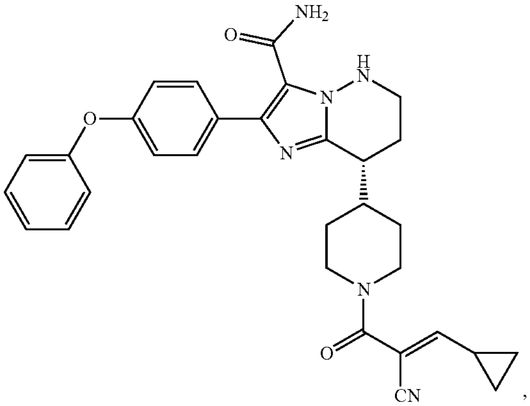
,
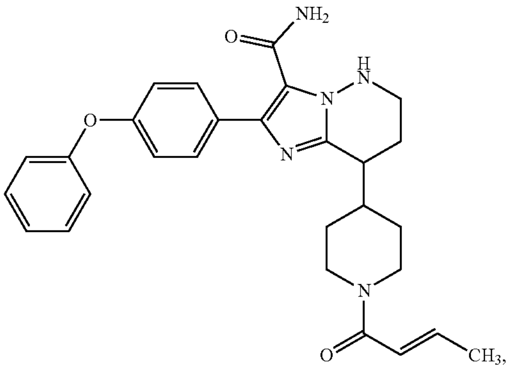
-continued
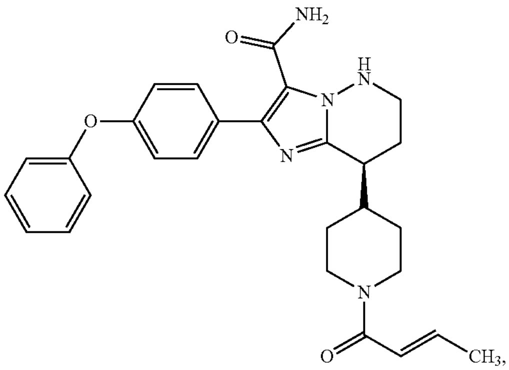
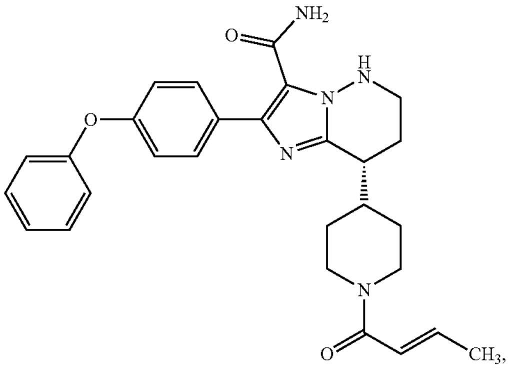
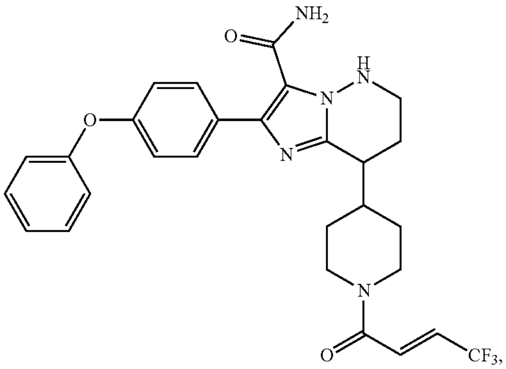
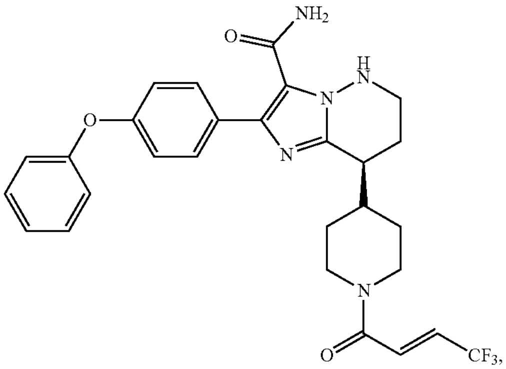

-continued
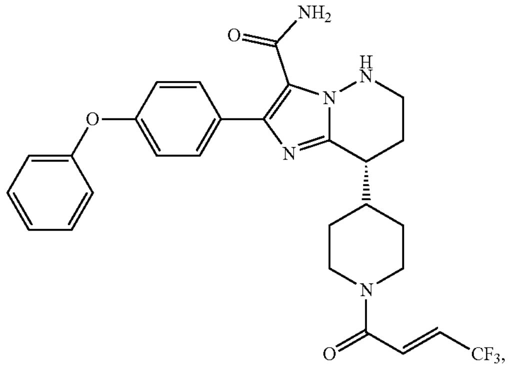
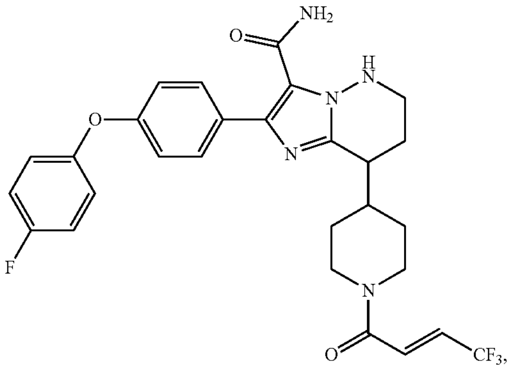
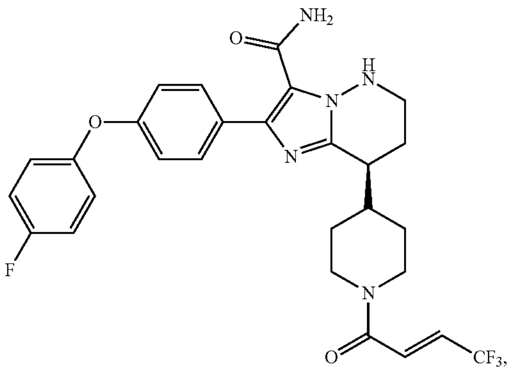
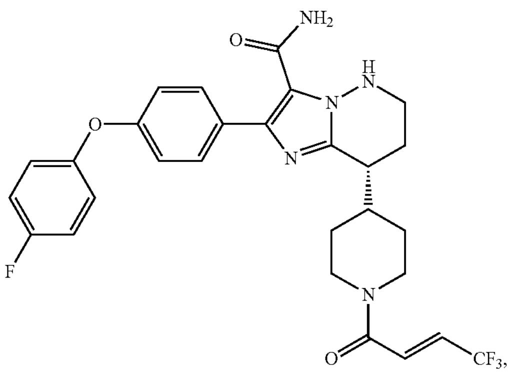
-continued
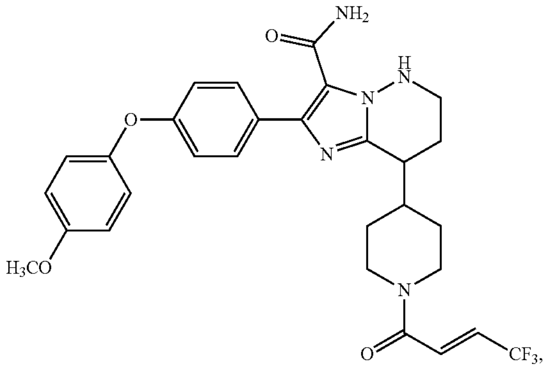
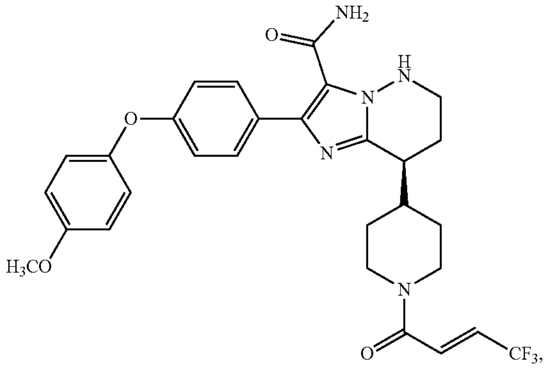
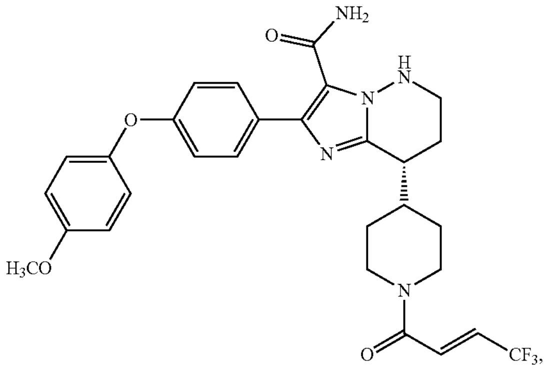
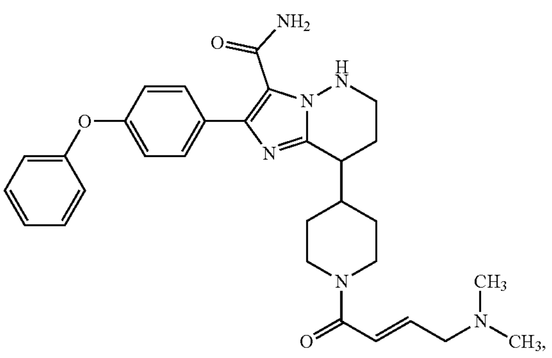

-continued
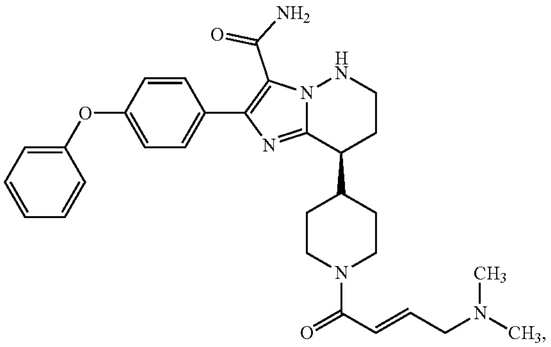
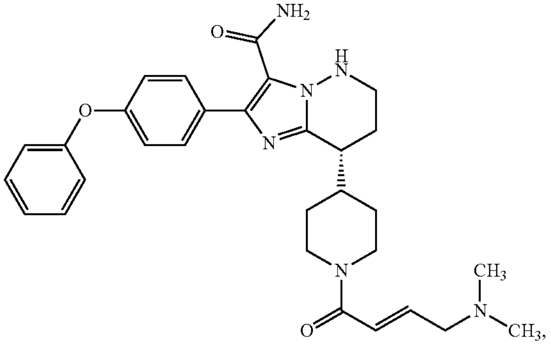
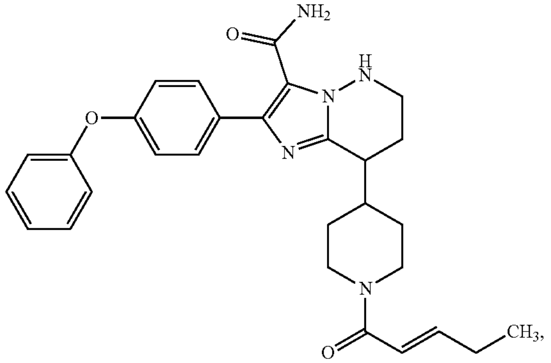
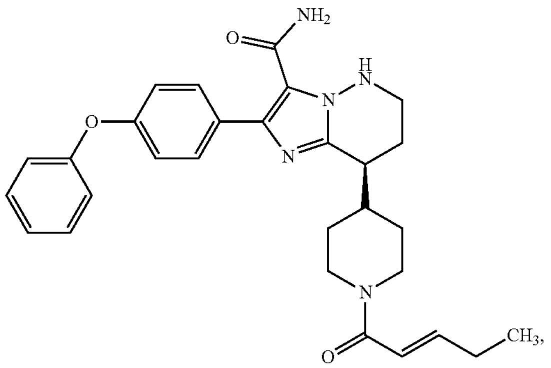
-continued
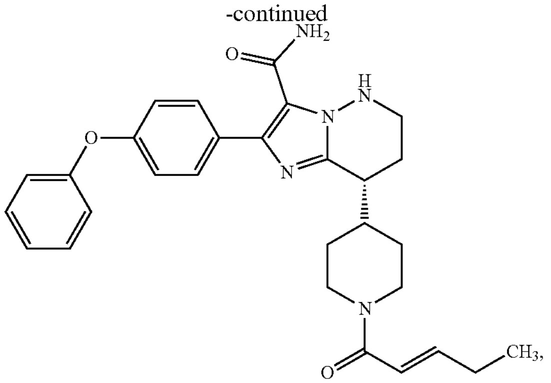
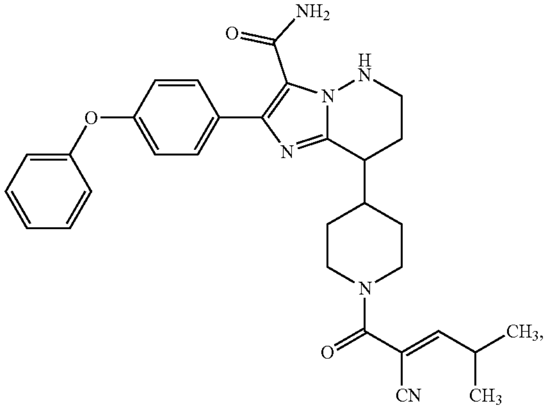
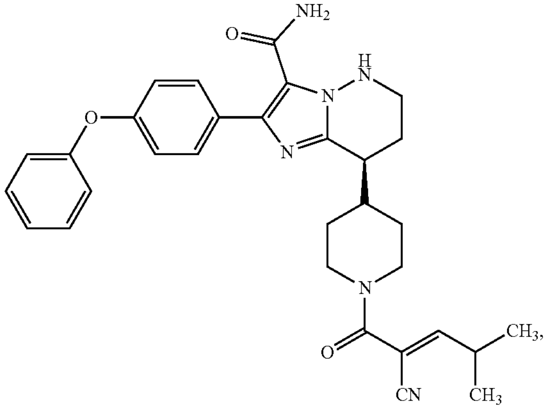
and
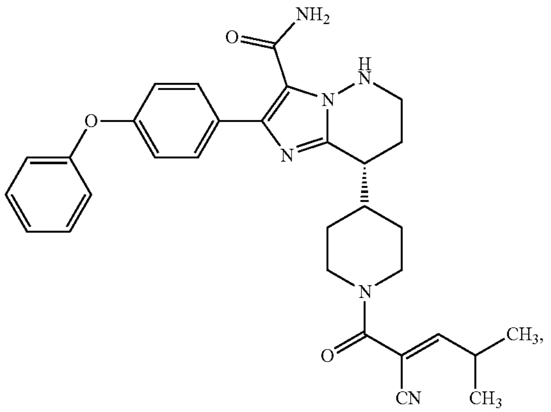 [SMILES: CC(C)/C=C(\C#N)C(=O)N1CCC([C@H]2CCNn3c2nc(-c2ccc(Oc4ccccc4)cc2)c3C(N)=O)CC1]
or a pharmaceutically acceptable salt or tautomer thereof.
19. A pharmaceutical composition comprising a pharmaceutically acceptable carrier and an effective amount of the compound according to claim 1, or a pharmaceutically acceptable salt, stereoisomer, or tautomer thereof.

20. A method for inhibiting Bruton's tyrosine kinase activity (BTK) activity in a subject in need thereof, wherein the method comprises administering to the subject an effective amount of the compound according to claim 1, or a pharmaceutically acceptable salt, stereoisomer, or tautomer thereof.

21. The method according to claim 20, wherein the subject suffers from a BTK-mediated disease or disorder selected from the group consisting of an allergy, an autoimmune disease, a cancer, and an inflammatory disease.

22. The method according to claim 21, wherein the allergy, autoimmune disease, cancer, or inflammatory disease is selected from the group consisting of asthma, central nervous system lymphoma, chronic lymphocytic leukemia, Crohn's disease, diffused large B cell lymphoma, follicular lymphoma, large B cell lymphoma, lupus, erythematosus, mantle cell lymphoma, multiple sclerosis, ocular lymphoma, psoriasis, rheumatoid arthritis, splenic marginal zone lymphoma, urticaria, and Waldenstrom's macroglobulinemia.

23. The method according to claim 2, wherein the central nervous system lymphoma is primary central nervous system lymphoma.

* * * * *